(12) United States Patent
Banner et al.

(10) Patent No.: US 8,673,894 B2
(45) Date of Patent: Mar. 18, 2014

(54) 2,5,6,7-TETRAHYDRO-[1,4]OXAZEPIN-3-YLAMINE OR 2,3,6,7-TETRAHYDRO-[1,4]OXAZEPIN-5-YLAMINE COMPOUNDS

(75) Inventors: David Banner, Basel (CH); Wolfgang Guba, Muellheim (DE); Hans Hilpert, Muenchenstein (CH); Roland Humm, Auggen (DE); Harald Mauser, Birsfelden (CH); Alexander V. Mayweg, Basel (CH); Robert Narquizian, Zaessingue (FR); Eoin Power, Blackrock (IE); Mark Rogers-Evans, Bottmingen (CH); Didier Rombach, Mulhouse (FR); Thomas Woltering, Freiburg (DE); Wolfgang Wostl, Grenzach-Wyhlen (DE)

(73) Assignee: Hoffmann-La Roche Inc., Nutley, NJ (US)

( * ) Notice: Subject to any disclaimer, the term of this patent is extended or adjusted under 35 U.S.C. 154(b) by 188 days.

(21) Appl. No.: 13/096,059

(22) Filed: Apr. 28, 2011

(65) Prior Publication Data
US 2011/0312937 A1 Dec. 22, 2011

(30) Foreign Application Priority Data
May 7, 2010 (EP) .................................. 10162340

(51) Int. Cl.
*A61P 25/28* (2006.01)
*A61K 31/553* (2006.01)
*C07D 267/10* (2006.01)
*C07D 413/12* (2006.01)
*C07D 417/12* (2006.01)

(52) U.S. Cl.
USPC ............ 514/211.01; 514/211.09; 514/211.15; 540/544; 540/552

(58) Field of Classification Search
USPC ........... 514/211.01, 211.09, 211.15; 540/544, 540/552
See application file for complete search history.

(56) References Cited

U.S. PATENT DOCUMENTS

2011/0021520 A1* 1/2011 Badiger et al. ............. 514/233.2

FOREIGN PATENT DOCUMENTS

EP 2147914 1/2010

OTHER PUBLICATIONS

Hussain et al., "Molecular & Cellular Neuroscience" 16:609-619 ( 2000).
Desnues et al., "Clinical & Vaccine Immunology" 13:170-178 ( 2006).
Vassar et al., "Science" 286:735-741 ( 1999).
Li et al., "Aging Cell" 5:153-165 ( 2006).
Zimmet et al., "Nature" 414:782-787 ( 2001).
Luo et al., "National Neurosceince" 4:231-232 ( 2001).
Merten et al., "Zeitschrift fur Kardiologue" 93:855-863 ( 2004).
Greenberg et al., "Annals of Neurology" 57:664-678 ( 2005).
Kondoh et al., "Breast Cancer Research Treatment" 78:37-44 ( 2003).
Basset et al., "Scandinavian Journal of Immunology" 51:307-311 ( 2000).
Hodges et al., "Human Molecular Genetics" 15:965-977 ( 2006).
Wild et al., "Diabetes Care" 27:1047-1053 ( 2004).
Hedlund et al., "Cancer Research" 68:388-394 ( 2008).
Kuhn et al., "J. Biol. Chem." 282:11982-11995 ( 2007).
Hoffmeister et al., "Journal of the Pancreas" 10:501-506 ( 2009).
Kiljanski et al., "Thyroid" 15:645-652 ( 2005).
"PCT International Search Report PCT/EP2011/056990 dated Jul. 4, 2011".
Talantov et al., "Clinical Cancer Research" 11:7234-7242 ( 2005).
Kim et al., "Neurobiology of Disease" 22:346-356 ( 2006).
Prentki et al., "J. Clin. Investig." 116:1802-1812 ( 2006).
Vattemi et al., "Lancet" 358:1962-1964 ( 2001).
Gatchel et al., "Proceedings of the National Academy of Sciences USA" 105:1291-1296 ( 2008).
Benedikt et al., "Science" 296:352-356 ( 2002).
Lagos et al., "Blood" 109:1550-1558 ( 2007).
Kihara et al., "Proceedings of the National Academy of Sciences USA" 106:21807-21812 ( 2009)
Selkoe, D., "Annual Review in Cell Biology" 10:373-403 ( 1994).
Roberds et al., "Human Mol. Genet" 10:1317-1324 ( 2001).
Fukui et al., "Cell Metabolism" 2:373-384 ( 2005).
McConlogue et al., "J. Biol. Chem." 282:26326-26334 ( 2007).
Toegel et al., "Osteoarthritis Cartilage" 18:240-248 ( 2010).
Maugeri et al., "Srp Arh Celok Lek—Abstract" 138:50-52 ( 2010).
Barbiero et al., "Experimental Neurology" 182:335-345 ( 2003).

(Continued)

*Primary Examiner* — Brenda Coleman

(57) ABSTRACT

This invention relates to compounds of the formula

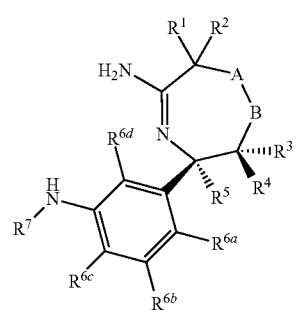

wherein A, B and $R^1$ to $R^7$ are as described below, or to pharmaceutically acceptable salts thereof. These compounds are BACE1 and/or BACE2 inhibitors and can be used as medicaments for the therapeutic and/or prophylactic treatment of diseases such as Alzheimer's disease, diabetes, particularly type 2 diabetes, and other metabolic disorders.

17 Claims, No Drawings

(56) References Cited

OTHER PUBLICATIONS

Akpinar et al., "Cell Metabolism" 2:385-397 (2005).
Koistinen et al., "Muscle & Nerve" 34:444-450 (2006).
Lichtenthaler et al., "J. Biol. Chem." 278:48713-48719 (2003).
Woodard-Grice et al., "J. Biol. Chem." 283:26364-26373 (2008).
Sugimoto et al., "J. Biol. Chem." 282:34896-34903 (2007).
Baggio et al., "Annu. Rev. Med." 57:265-281 (2006).
Grewal et al., "Molecular & Cellular Biology" 26:4970-4981 (2006).
Huang et al., Organic Letters 3(21):3417-3419 (2001).
Ostermann et al., J. Mol. Biol. 355:249-261 (2006).
Doyle et al., Adv. Synth. Catal. 343(1):112-117 (2001).
Tang et al., J. Org. Chem. 64:12-13 (1999).
Gruninger-Leitch et al., J. of Biol. Chemistry 277(7):4687-4693 (2002).
Hardy et al., Science 297(5580):353-356 (Jul 19, 2002).
Finzi et al., Ultrastructural Pathology 32(6):246-251 (2008).
Haight et al., J. Org. Chem. 68:8092-8096 (2003).
Gaetjens et al., Chem. Eur. Journal 9:4924-4935 (2003).
Cheng et al., Biochemical Pharmacology 22:3099-3108 (1973).
Brockhaus et al., Neuro Report 9(7):1481-1486 (1998).
Zhang et al., Biorg. & Med. Chem. Letters 14:6011-6016 (2004).
Lemoine et al., Bioorg. & Med. Chem. Letters 20:4753-4756 (2010).
Doyle et al., Adv. Synth. Catal. 343(3):299-302 (2001).
Doyle et al., Organic Letters 2(8):1145-1147 (2000).
Sun et al., J. Org. Chem. 62(24):8604-8608 (1997).

* cited by examiner

2,5,6,7-TETRAHYDRO-[1,4]OXAZEPIN-3-YLAMINE OR 2,3,6,7-TETRAHYDRO-[1,4]OXAZEPIN-5-YLAMINE COMPOUNDS

PRIORITY TO RELATED APPLICATION(S)

This application claims the benefit of European Patent Application No 10162340.3, filed May 7, 2010, which is hereby incorporated by reference in its entirety.

FIELD OF THE INVENTION

The compounds of the present invention have Asp2 (β-secretase, BACE1 or Memapsin-2) inhibitory activity and may therefore be used in the therapeutic and/or prophylactic treatment of diseases and disorders characterized by elevated β-amyloid levels and/or β-amyloid oligomers and/or β-amyloid plaques and further deposits, particularly Alzheimer's disease. Furthermore, the formation, or formation and deposition, of β-amyloid plaques in, on or around neurological tissue (e.g., the brain) is inhibited by such compounds by blocking the Aβ production from APP or an APP fragment. In addition, the compounds of the present invention have BACE2 inhibitory activity and can therefore be used in the therapeutic and/or prophylactic treatment of diseases and disorders such as type 2 diabetes and other metabolic disorders.

BACKGROUND OF THE INVENTION

Alzheimer's disease (AD) is a neurodegenerative disorder of the central nervous system and the leading cause of a progressive dementia in the elderly population. Its clinical symptoms are impairment of memory, cognition, temporal and local orientation, judgment and reasoning but also severe emotional disturbances. There are currently no treatments available which can prevent the disease or its progression or stably reverse its clinical symptoms. AD has become a major health problem in all societies with high life expectancies and also a significant economic burden for their health systems.

AD is characterized by two major pathologies in the central nervous system (CNS), the occurrence of amyloid plaques and neurofibrillar tangles (Hardy et al., The amyloid hypothesis of Alzheimer's disease: progress and problems on the road to therapeutics, *Science*. Jul. 19, 2002; 297(5580):353-6, Selkoe, Cell biology of the amyloid beta-protein precursor and the mechanism of Alzheimer's disease, *Annu Rev Cell Biol*. 1994; 10:373-403). Both pathologies are also commonly observed in patients with Down's syndrome (trisomy 21), which also develop AD-like symptoms in early life. Neurofibrillar tangles are intracellular aggregates of the microtubule-associated protein tau (MAPT). Amyloid plaques occur in the extracellular space; their principal components are Aβ-peptides. The latter are a group of proteolytic fragments derived from the β-amyloid precursor protein (APP) by a series of proteolytic cleavage steps. Several forms of APP have been identified of which the most abundant are proteins of 695, 751 and 770 amino acids length. They all arise from a single gene through differential splicing. The Aβ-peptides are derived from the same domain of the APP but differ at their N- and C-termini, the main species are of 40 and 42 amino-acid length. There are several lines of evidence which strongly suggest that aggregated Aβ-peptides are the essential molecules in the pathogenesis of AD: 1) amyloid plaques formed of Aβ-peptides are invariably part of the AD pathology; 2) Aβ-peptides are toxic for neurons; 3) in Familial Alzheimer's Disease (FAD) the mutations in the disease genes APP, PSN1, PSN2 lead to increased levels of Aβ-peptides and early brain amyloidosis; 4) transgenic mice which express such FAD genes develop a pathology which bears many resemblances to the human disease. Aβ-peptides are produced from APP through the sequential action of 2 proteolytic enzymes termed β- and γ-secretase. β-Secretase cleaves first in the extracellular domain of APP approximately 28 amino acids outside of the trans-membrane domain (TM) to produce a C-terminal fragment of APP containing the TM- and the cytoplasmatic domain (CTFβ). CTFβ is the substrate for γ-secretase which cleaves at several adjacent positions within the TM to produce the Aβ peptides and the cytoplasmic fragment. The γ-secretase is a complex of at least four different proteins, its catalytic subunit is very likely a presenilin protein (PSEN1, PSEN2). The β-secretase (BACE1, Asp2; BACE stands for β-site APP-cleaving enzyme) is an aspartyl protease which is anchored into the membrane by a transmembrane domain (Vassar et al., Beta-secretase cleavage of Alzheimer's amyloid precursor protein by the transmembrane aspartic protease BACE, *Science*. Oct. 22, 1999; 286(5440): 735). It is expressed in many tissues of the human organism but its level is especially high in the CNS. Genetic ablation of the BACE1 gene in mice has clearly shown that its activity is essential for the processing of APP which leads to the generation of Aβ-peptides, in the absence of BACE1 no Aβ-peptides are produced (Luo et al., Mice deficient in BACE1, the Alzheimer's beta-secretase, have normal phenotype and abolished beta-amyloid generation, *Nat Neurosci*. March 2001; 4(3):231-2, Roberds et al., BACE knockout mice are healthy despite lacking the primary beta-secretase activity in brain: implications for Alzheimer's disease therapeutics, *Hum Mol Genet. Jun.* 1, 2001; 10(12): 1317-24). Mice which have been genetically engineered to express the human APP gene and which form extensive amyloid plaques and Alzheimer's disease like pathologies during aging fail to do so when β-secretase activity is reduced by genetic ablation of one of the BACE1 alleles (McConlogue et al., Partial reduction of BACE1 has dramatic effects on Alzheimer plaque and synaptic pathology in APP Transgenic Mice. *J Biol Chem. Sep.* 7, 2007; 282(36):26326). It is thus presumed that inhibitors of BACE1 activity can be useful agents for therapeutic intervention in AD.

Type 2 diabetes (T2D) is caused by insulin resistance and inadequate insulin secretion from pancreatic β-cells leading to poor blood-glucose control and hyperglycemia (M Prentki & C J Nolan, "Islet beta-cell failure in type 2 diabetes." J. Clin. Investig. 2006, 116(7), 1802-1812). Patients with T2D have an increased risk of microvascular and macrovascular disease and a range of related complications including diabetic nephropathy, retinopathy and cardiovascular disease. In 2000, an estimated 171 million people had the condition with the expectation that this figure will double by 2030 (S Wild, G Roglic, A Green, R. Sicree & H King, "Global prevalence of diabetes", Diabetes Care 2004, 27(5), 1047-1053), making the disease a major healthcare problem. The rise in prevalence of T2D is associated with an increasingly sedentary lifestyle and high-energy food intake of the world's population (P Zimmet, KGMM Alberti & J Shaw, "Global and societal implications of the diabetes epidemic" Nature 2001, 414, 782-787).

β-Cell failure and consequent dramatic decline in insulin secretion and hyperglycemia marks the onset of T2D. Most current treatments do not prevent the loss of β-cell mass characterizing overt T2D. However, recent developments with GLP-1 analogues, gastrin and other agents show that preservation and proliferation of β-cells is possible to achieve, leading to an improved glucose tolerance and slower progression to overt T2D (L L Baggio & D J Drucker, "Therapeutic approaches to preserve islet mass in type 2 diabetes", Annu Rev. Med. 2006, 57, 265-281).

Tmem27 has been identified as a protein promoting beta-cell proliferation (P Akpinar, S Kuwajima, J Krützfeldt, M Stoffel, "Tmem27: A cleaved and shed plasma membrane protein that stimulates pancreatic β cell proliferation", Cell Metab. 2005, 2, 385-397) and insulin secretion (K Fukui, Q Yang, Y Cao, N Takahashi et al., "The HNF-1 target Collectrin controls insulin exocytosis by SNARE complex formation", Cell Metab. 2005, 2, 373-384). Tmem27 is a 42 kDa membrane glycoprotein which is constitutively shed from the surface of β-cells, resulting from a degradation of the full-length cellular Tmem27. Overexpression of Tmem27 in a transgenic mouse increases β-cell mass and improves glucose tolerance in a diet-induced obesity DIO model of diabetes. Furthermore, siRNA knockout of Tmem27 in a rodent β-cell proliferation assay (e.g. using INS1e cells) reduces the proliferation rate, indicating a role for Tmem27 in control of β-cell mass.

In the same proliferation assay, BACE2 inhibitors also increase proliferation. However, BACE2 inhibition combined with Tmem27 siRNA knockdown results in low proliferation rates. Therefore, it is concluded that BACE2 is the protease responsible for the degradation of Tmem27. Furthermore, in vitro, BACE2 cleaves a peptide based on the sequence of Tmem27. The closely related protease BACE1 does not cleave this peptide and selective inhibition of BACE1 alone does not enhance proliferation of β-cells.

The close homolog BACE2 is a membrane-bound aspartyl protease and is co-localized with Tmem27 in human pancreatic β-cells (G Finzi, F Franzi, C Placidi, F Acquati et al., "BACE2 is stored in secretory granules of mouse and rat pancreatic beta cells", Ultrastruct Pathol. 2008, 32(6), 246-251). It is also known to be capable of degrading APP (I Hussain, D Powell, D Howlett, G Chapman et al., "ASP1 (BACE2) cleaves the amyloid precursor protein at the β-secretase site" Mol Cell Neurosci. 2000, 16, 609-619), IL-1R2 (P Kuhn, E Marjaux, A Imhof, B De Strooper et al., "Regulated intramembrane proteolysis of the interleukin-1 receptor II by alpha-, beta-, and gamma-secretase" J. Biol. Chem. 2007, 282(16), 11982-11995) and ACE2. The capability to degrade ACE2 indicates a possible role of BACE2 in the control of hypertension.

Inhibition of BACE2 is therefore proposed as a treatment for T2D with the potential to preserve and restore β-cell mass and stimulate insulin secretion in pre-diabetic and diabetic patients Inhibitors of BACE1 and/or BACE2 can in addition be used to treat the following diseases: IBM (inclusion body myositis) (Vattemi G. et al., Lancet. Dec. 8, 2001; 358(9297): 1962-4), Down's Syndrome (Barbiero L. et al, Exp Neurol. August 2003; 182(2):335-45), Wilson's Disease (Sugimoto I. et al., J Biol Chem. Nov. 30, 2007; 282(48):34896-903), Whipple's disease (Desnues B. et al., Clin Vaccine Immunol. February 2006; 13(2):170-8), SpinoCerebellar Ataxia 1 and SpinoCerebellar Ataxia 7 (Gatchel J. R. et al., *Proc Natl Acad Sci USA* Jan. 29, 2008; 105(4):1291-6), Dermatomyositis (Greenberg S. A. et al., Ann Neurol. May 2005; 57(5):664-78 and Greenberg S. A. et al., *Neurol* May 2005; 57(5):664-78), Kaposi Sarcoma (Lagos D. et al, Blood, Feb. 15, 2007; 109 (4):1550-8), Glioblastoma multiforme (E-MEXP-2576, http://www.ebi.ac.uk/microarray-as/aer/result?queryFor=PhysicalArrayDesign&aAccession=A-MEXP-258), Rheumatoid arthritis (Ungethuem U. et al, GSE2053), Amyotrophic lateral sclerosis (Koistinen H. et al., Muscle Nerve. October 2006; 34(4):444-50 and Li Q. X. et al, Aging Cell. April 2006; 5(2):153-65), Huntington's Disease (Kim Y. J. et al., Neurobiol Dis. May 2006; 22(2):346-56. Epub Jan. 19, 2006 and Hodges A. et al., Hum Mol Genet. Mar. 15, 2006; 15(6):965-77. Epub Feb. 8, 2006), Multiple Mieloma (Kihara Y. et al, Proc Natl Acad Sci USA. Dec. 22, 2009; 106(51):21807-12), Malignant melanoma (Talantov D. et al, Clin Cancer Res. Oct. 15, 2005; 11(20):7234-42), Sjogren syndrome (Basset C. et al., Scand J Immunol. March 2000; 51(3):307-11), Lupus erythematosus (Grewal P. K. et al, Mol Cell Biol. July 2006; 26(13):4970-81), Macrophagic myofasciitis, juvenile idiopathic arthritis, granulomatous arthritis, Breast cancer (Hedlund M. et al, Cancer Res. Jan. 15, 2008; 68(2):388-94 and Kondoh K. et al., Breast Cancer Res Treat. March 2003; 78(1):37-44), Gastrointestinal diseases (Hoffmeister A. et al, JOP. Sep. 4, 2009; 10(5):501-6), Autoimmune/inflammatory diseases (Woodard-Grice A. V. et al., J Biol Chem. Sep. 26, 2008; 283(39):26364-73. Epub Jul. 23, 2008), Rheumatoid Arthritis (Toegel S. et al, Osteoarthritis Cartilage. February 2010; 18(2):240-8. Epub Sep. 22, 2009), Inflammatory reactions (Lichtenthaler S. F. et al., J Biol Chem. Dec. 5, 2003; 278(49):48713-9. Epub Sep. 24, 2003), Arterial Thrombosis (Merten M. et al., Z Kardiol. November 2004; 93(11):855-63), Cardiovascular diseases such as Myocardial infarction and stroke (Maugeri N. et al., Srp Arh Celok Lek. January 2010; 138 Suppl 1:50-2) and Graves disease (Kiljański J. et al, Thyroid. July 2005; 15(7): 645-52).

SUMMARY OF THE INVENTION

The present invention relates to compounds of the formula

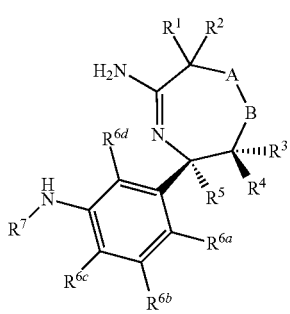

I wherein A, B and $R^1$ to $R^7$ are as described below, and to pharmaceutically acceptable salts thereof.

The present invention also relates to a pharmaceutical composition comprising a compound of formula I and a pharmaceutically acceptable carrier and/or adjuvant.

The present invention further relates to the manufacture of compounds of the present invention, medicaments comprising the compounds of the present invention, the production of such medicaments as well as the use of the compounds of the present invention in the treatment or prevention of diseases such as Alzheimer's disease and type 2 diabetes.

DETAILED DESCRIPTION OF THE INVENTION

Unless otherwise indicated, the following definitions are set forth to illustrate and define the meaning and scope of the various terms used to describe the invention.

The term "halogen" refers to fluoro, chloro, bromo and iodo, with fluoro, chloro and bromo being of particular interest. More particularly, halogen refers to fluoro and chloro.

The term "lower alkyl" or "$C_{1-7}$-alkyl", alone or in combination, signifies a straight-chain or branched-chain alkyl group with 1 to 7 carbon atoms, in particular a straight or branched-chain alkyl group with 1 to 6 carbon atoms and more particularly a straight or branched-chain alkyl group with 1 to 4 carbon atoms. Examples of straight-chain and branched $C_{1-7}$ alkyl groups are methyl, ethyl, propyl, isopropyl, butyl, isobutyl, tert.-butyl, the isomeric pentyls, the isomeric hexyls and the isomeric heptyls, in particular methyl and ethyl.

The term "lower alkoxy" or "$C_{1-7}$-alkoxy" refers to the group R'—O—, wherein R' is lower alkyl and the term "lower alkyl" has the previously given significance. Examples of lower alkoxy groups are methoxy, ethoxy, n-propoxy, isopropoxy, n-butoxy, isobutoxy, sec.-butoxy and tert.-butoxy, preferably methoxy and ethoxy.

The term "cycloalkyl" or "$C_{3-7}$-cycloalkyl" denotes a saturated carbocyclic group containing from 3 to 7 carbon atoms, such as cyclopropyl, cyclobutyl, cyclopentyl, cyclohexyl or cycloheptyl. In particular, cycloalkyl means cyclopropyl, cyclobutyl and cyclopentyl.

The term "lower halogenalkyl" or "halogen-$C_{1-7}$-alkyl" refers to lower alkyl groups as defined above wherein at least one of the hydrogen atoms of the lower alkyl group is replaced by a halogen atom, particularly fluoro or chloro, more particularly fluoro. Among the lower halogenalkyl groups are trifluoromethyl, difluoromethyl, trifluoroethyl, 2,2-difluoroethyl, fluoromethyl and chloromethyl, with trifluoromethyl or difluoromethyl being of particular interest.

The term "lower halogenalkoxy" or "halogen-$C_{1-7}$-alkoxy" refers to lower alkoxy groups as defined above wherein at least one of the hydrogen atoms of the lower alkoxy group is replaced by a halogen atom, particularly fluoro or chloro, more particularly fluoro. Among the halogenated lower alkoxy groups are trifluoromethoxy, 2,2,2-trifluoroethoxy, difluoromethoxy, fluormethoxy and chloromethoxy, with trifluoromethoxy and 2,2,2-trifluoroethoxy being of particular interest.

The term "lower hydroxyalkyl" or "hydroxy-$C_{1-7}$-alkyl" refers to lower alkyl groups as defined above wherein at least one of the hydrogen atoms of the lower alkyl group is replaced by a hydroxy group. Among the lower hydroxyalkyl groups are hydroxymethyl or hydroxyethyl.

The term "$C_{1-7}$-alkoxy-$C_{1-7}$-alkyl" or "lower alkoxy-lower alkyl" refers to lower alkyl groups as defined above wherein at least one of the hydrogen atoms of the lower alkyl group is replaced by a lower alkoxy group. Among the lower alkoxy-lower alkyl groups are methoxy-methyl or methoxy-ethyl.

The term "oxo" means the group "=O" bound to a ring atom.

The term "cyano", alone or in combination with other groups, refers to N≡C—(NC—).

The term "hydroxy", alone or in combination with other groups, refers to —OH.

The term "aryl" refers to an aromatic monocyclic or multicyclic ring system having 6 to 14 carbon atoms, in particular 6 to 10 carbon atoms. Exemplary aryl groups are phenyl and naphthyl. In particular, aryl means phenyl.

The term "heteroaryl" refers to an aromatic or partly unsaturated 5- or 6-membered ring which comprises at least one heteroatom selected from nitrogen, oxygen and/or sulphur, and can in addition comprise one or three atoms selected from nitrogen, oxygen and/or sulphur, such as pyridyl, pyrazinyl, pyrimidinyl, pyridazinyl, 6-oxo-1,6-dihydropyridazinyl, 5-oxo-4,5-dihydropyrazinyl, pyrrolyl, furyl, thienyl, oxazolyl, isoxazolyl, oxadiazolyl, thiadiazolyl, tetrazolyl, pyrazolyl, imidazolyl, triazolyl and thiazolyl. The term "heteroaryl" further refers to bicyclic aromatic or partly unsaturated groups comprising two 5- or 6-membered rings, in which one or both rings can contain one, two or three atoms selected from nitrogen, oxygen or sulphur, such as quinolinyl, isoquinolinyl, cinnolinyl, pyrazolo[1,5-a]pyridyl, imidazo[1,2-a]pyridyl, pyrrolo[2,3-b]pyridinyl, thieno[3,2-b]pyridyl, thieno[2,3-c]pyridyl, quinoxalinyl, benzo[b]thienyl, benzothiazolyl, benzotriazolyl, indolyl, indazolyl and 3,4-dihydro-1H-isoquinolinyl. In particular, heteroaryl groups are thienyl, oxazolyl, isoxazolyl, thiazolyl, pyrazolyl, imidazolyl, pyridyl, pyrimidinyl, pyrazinyl, 6-oxo-1,6-dihydropyridazinyl, 5-oxo-4,5-dihydropyrazinyl, imidazo[1,2-a]pyridyl, benzo[b]thienyl, pyrrolo[2,3-b]pyridinyl, thieno[3,2-b]pyridyl, thieno[2,3-c]pyridyl, quinolinyl and isoquinolinyl, more particularly oxazolyl, pyrazolyl, pyridyl and pyrimidinyl and most particularly pyridyl.

The terms "salt with formic acid" and "formate" are used interchangeably.

Compounds of formula I can form pharmaceutically acceptable salts. The term "pharmaceutically acceptable salts" refers to those salts which retain the biological effectiveness and properties of the free bases or free acids, which are not biologically or otherwise undesirable. Preferably, the pharmaceutically acceptable salts of the compounds of formula I are the acid addition salts with physiologically compatible mineral acids, such as hydrochloric acid, sulfuric acid, sulfurous acid or phosphoric acid; or with organic acids, such as methanesulfonic acid, ethanesulfonic acid, p-toluenesulfonic acid, formic acid, acetic acid, propionic acid, glycolic acid, pyruvic acid, oxylic acid, lactic acid, trifluoroacetic acid, citric acid, fumaric acid, maleic acid, malonic acid, tartaric acid, benzoic acid, cinnamic acid, mandelic acid, succinic acid or salicylic acid. In addition, pharmaceutically acceptable salts may be prepared from addition of an inorganic base or an organic base to the free acid. Salts derived from an inorganic base include, but are not limited to, the sodium, potassium, lithium, ammonium, calcium, magnesium salts and the like. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polymine resins and the like. The compound of formula I can also be present in the form of zwitterions. Particularly preferred pharmaceutically acceptable salts of compounds of formula I are the acid addition salts such as the hydrochloride salts, the formate salts or trifluoroacetate salts.

The term "pharmaceutically acceptable salts" refers to salts that are suitable for use in contact with the tissues of humans and animals. Examples of suitable salts with inorganic and organic acids are, but are not limited to acetic acid, citric acid, formic acid, fumaric acid, hydrochloric acid, lactic acid, maleic acid, malic acid, methane-sulfonic acid, nitric acid, phosphoric acid, p-toluenesulphonic acid, succinic acid, sulfuric acid, sulphuric acid, tartaric acid, trifluoroacetic acid and the like. The terms "pharmaceutically acceptable carrier" and "pharmaceutically acceptable auxiliary substance" refer to carriers and auxiliary substances such as diluents or excipients that are compatible with the other ingredients of the formulation.

The term "pharmaceutical composition" encompasses a product comprising specified ingredients in pre-determined amounts or proportions, as well as any product that results, directly or indirectly, from combining specified ingredients in specified amounts. Preferably it encompasses a product comprising one or more active ingredients, and an optional carrier comprising inert ingredients, as well as any product that results, directly or indirectly, from combination, complexation or aggregation of any two or more of the ingredients, or from dissociation of one or more of the ingredients, or from other types of reactions or interactions of one or more of the ingredients.

The term "inhibitor" denotes a compound which competes with, reduces or prevents the binding of a particular ligand to particular receptor or which reduces or prevents the inhibition of the function of a particular protein.

The term "half maximal inhibitory concentration" ($IC_{50}$) denotes the concentration of a particular compound required for obtaining 50% inhibition of a biological process in vitro. $IC_{50}$ values can be converted logarithmically to $pIC_{50}$ values ($-\log IC_{50}$), in which higher values indicate exponentially greater potency. The $IC_{50}$ value is not an absolute value but depends on experimental conditions e.g. concentrations employed. The $IC_{50}$ value can be converted to an absolute inhibition constant (Ki) using the Cheng-Prusoff equation (Biochem. Pharmacol. (1973) 22:3099). The term "inhibition constant" (Ki) denotes the absolute binding affinity of a particular inhibitor to a receptor. It is measured using competition binding assays and is equal to the concentration where the particular inhibitor would occupy 50% of the receptors if no competing ligand (e.g. a radioligand) was present. Ki values can be converted logarithmically to pKi values ($-\log$ Ki), in which higher values indicate exponentially greater potency.

"Therapeutically effective amount" means an amount of a compound that, when administered to a subject for treating a disease state, is sufficient to effect such treatment for the disease state. The "therapeutically effective amount" will vary depending on the compound, disease state being treated, the severity or the disease treated, the age and relative health of the subject, the route and form of administration, the judgment of the attending medical or veterinary practitioner, and other factors.

The term "as defined herein" and "as described herein" when referring to a variable incorporates by reference the broad definition of the variable as well as preferred, more preferred and most preferred definitions, if any.

The terms "treating", "contacting" and "reacting" when referring to a chemical reaction means adding or mixing two or more reagents under appropriate conditions to produce the indicated and/or the desired product. It should be appreciated that the reaction which produces the indicated and/or the desired product may not necessarily result directly from the combination of two reagents which were initially added, i.e., there may be one or more intermediates which are produced in the mixture which ultimately leads to the formation of the indicated and/or the desired product. The term "aromatic" denotes the conventional idea of aromaticity as defined in the literature, in particular in IUPAC—Compendium of Chemical Terminology, 2nd, A. D. McNaught & A. Wilkinson (Eds). Blackwell Scientific Publications, Oxford (1997).

The term "pharmaceutically acceptable excipient" denotes any ingredient having no therapeutic activity and being non-toxic such as disintegrators, binders, fillers, solvents, buffers, tonicity agents, stabilizers, antioxidants, surfactants or lubricants used in formulating pharmaceutical products.

The compounds of formula I can also be solvated, e.g., hydrated. The solvation can be effected in the course of the manufacturing process or can take place e.g. as a consequence of hygroscopic properties of an initially anhydrous compound of formula I (hydration). The term "pharmaceutically acceptable salts" also includes physiologically acceptable solvates.

"Isomers" are compounds that have identical molecular formulae but that differ in the nature or the sequence of bonding of their atoms or in the arrangement of their atoms in space. Isomers that differ in the arrangement of their atoms in space are termed "stereoisomers". Stereoisomers that are not mirror images of one another are termed "diastereoisomers", and stereoisomers that are non-superimposable mirror images are termed "enantiomers", or sometimes optical isomers. A carbon atom bonded to four non-identical substituents is termed a "chiral center". Whenever a chiral carbon is present in a chemical structure, it is intended that all stereoisomers associated with that chiral carbon are encompassed by the structure.

All separate embodiments may be combined.

The present invention relates to compounds of the formula

I wherein

A is O and B is —$CR^8R^9$—; or

B is O and A is —$CR^8R^9$;

$R^1$ is selected from the group consisting of hydrogen, $C_{1-7}$-alkyl and $C_{3-7}$-cycloalkyl;

$R^2$ is selected from the group consisting of hydrogen, $C_{1-7}$-alkyl and $C_{3-7}$-cycloalkyl;

$R^3$ is selected from the group consisting of hydrogen, halogen, $C_{1-7}$-alkyl and $C_{3-7}$-cycloalkyl;

$R^4$ is selected from the group consisting of hydrogen, halogen, $C_{1-7}$-alkyl and $C_{3-7}$-cycloalkyl;

$R^5$ is $C_{1-7}$-alkyl or $C_{3-7}$-cycloalkyl;

or $R^3$ and $R^5$ together with the C atom to which they are attached form a cyclopropyl ring;

$R^{6a}$, $R^{6b}$, $R^{6c}$ and $R^{6d}$ independently from each other are selected from the group consisting of hydrogen, $C_{1-7}$-alkyl, halogen and halogen-$C_{1-7}$-alkyl;

$R^7$ is —(CO)—$R^{10}$ or $R^{11}$, wherein $R^{10}$ is selected from the group consisting of aryl, said aryl being unsubstituted or substituted by one, two or three groups selected from the group consisting of $C_{1-7}$-alkyl, halogen, halogen-$C_{1-7}$-alkyl, $C_{1-7}$-alkoxy, halogen-$C_{1-7}$-alkoxy, cyano, hydroxy-$C_{1-7}$-alkyl, oxo and phenyl, heteroaryl, said heteroaryl being unsubstituted or substituted by one, two or three groups selected from the group consisting of $C_{1-7}$-alkyl, halogen, halogen-$C_{1-7}$-alkyl, $C_{1-7}$-alkoxy, halogen-$C_{1-7}$-alkoxy, cyano, hydroxy-$C_{1-7}$-alkyl, oxo and phenyl, $C_{1-7}$-alkyl, halogen-$C_{1-7}$-alkyl, $C_{3-7}$-cycloalkyl, said cycloalkyl being unsubstituted or substituted by one, two, three or four groups selected from the group consisting of $C_{1-7}$-alkyl, halogen or halogen-$C_{1-7}$-alkyl, and $C_{1-7}$-alkoxy-$C_{1-7}$-alkyl;

$R^{11}$ is selected from the group consisting of $C_{1-7}$-alkyl, and $C_{3-7}$-cycloalkyl, said cycloalkyl being unsubstituted or substituted by one, two, three or four groups selected from the group consisting of $C_{1-7}$-alkyl, halogen and halogen-$C_{1-7}$-alkyl, and $R^8$ and $R^9$ are independently from each other selected from hydrogen, $C_{1-7}$-alkyl and $C_{3-7}$-cycloalkyl;

or pharmaceutically acceptable salts thereof.

In a further embodiment, the invention relates to a compound of formula I, wherein A is O and B is —$CR^8R^9$—.

In a further embodiment, the invention relates to a compound of formula I, wherein B is O and A is —$CR^8R^9$—.

In a further embodiment, the invention relates to a compound of formula I, wherein $R^1$ and $R^2$ are independently from each other hydrogen or $C_{1-7}$-alkyl. Particularly, the invention relates to compounds of formula I, wherein $R^1$ and $R^2$ are independently from each other hydrogen or methyl. More particularly, $R^1$ and $R^2$ are hydrogen.

In a further embodiment, the invention relates to a compound of formula I, wherein $R^1$ is hydrogen.

In a further embodiment, the invention relates to a compound of formula I, wherein $R^1$ is $C_{1-7}$-alkyl.

In a further embodiment, the invention relates to a compound of formula I, wherein $R^1$ is methyl.

In a further embodiment, the invention relates to a compound of formula I, wherein $R^2$ is hydrogen.

In a further embodiment, the invention relates to a compound of formula I, wherein $R^2$ is $C_{1-7}$-alkyl.

In a further embodiment, the invention relates to a compound of formula I, wherein $R^2$ is methyl.

In a further embodiment, the invention relates to a compound of formula I, wherein $R^3$ and $R^4$ are both fluoro, A is O and B is $CH_2$.

In a further embodiment, the invention relates to a compound of formula I, wherein $R^3$ and $R^4$ are independently from each other selected from the group consisting of hydrogen, halogen, and $C_{1-7}$-alkyl. In particular, $R^3$ and $R^4$ are independently from each other hydrogen or fluoro.

In a further embodiment, the invention relates to a compound of formula I, wherein $R^3$ is hydrogen.

In a further embodiment, the invention relates to a compound of formula I, wherein $R^3$ is halogen.

In a further embodiment, the invention relates to a compound of formula I, wherein $R^3$ is fluoro.

In a further embodiment, the invention relates to a compound of formula I, wherein $R^4$ is hydrogen.

In a further embodiment, the invention relates to a compound of formula I, wherein $R^4$ is halogen.

In a further embodiment, the invention relates to a compound of formula I, wherein $R^4$ is fluoro.

In a further embodiment, the invention relates to a compound of formula I, wherein $R^3$ and $R^4$ are hydrogen. Another group of compounds particular interest are compounds of formula I, wherein $R^3$ and $R^4$ are fluoro.

In a further embodiment, the invention relates to a compound of formula I, wherein $R^5$ is $C_{1-7}$-alkyl, particularly methyl or ethyl. A further group of compounds of formula I of the present invention are those, wherein $R^3$ and $R^5$ together with the C atom to which they are attached form a cyclopropyl ring.

In a further embodiment, the invention relates to a compound of formula I, wherein $R^5$ is $C_{1-7}$-alkyl.

In a further embodiment, the invention relates to a compound of formula I, wherein $R^5$ is methyl.

In a further embodiment, the invention relates to a compound of formula I, wherein $R^5$ is ethyl.

In a further embodiment, the invention relates to a compound of formula I, wherein $R^3$ and $R^5$ together are cyclopropyl.

In a further embodiment, the invention relates to a compound of formula I, wherein $R^{6a}$, $R^{6b}$, $R^{6c}$ and $R^{6d}$ are selected from hydrogen or halogen. In particular, the invention refers to compounds of formula I, wherein $R^{6a}$ is hydrogen or fluoro and $R^{6b}$, $R^{6c}$ and $R^{6d}$ are hydrogen. The invention further relates to compounds of formula I, wherein $R^{6a}$ is fluoro and $R^{6b}$, $R^{6c}$ and $R^{6d}$ are hydrogen.

In a further embodiment, the invention relates to a compound of formula I, wherein $R^{6a}$ is hydrogen.

In a further embodiment, the invention relates to a compound of formula I, wherein $R^{6a}$ is halogen.

In a further embodiment, the invention relates to a compound of formula I, wherein $R^{6a}$ is fluoro.

In a further embodiment, the invention relates to a compound of formula I, wherein $R^{6b}$ is hydrogen.

In a further embodiment, the invention relates to a compound of formula I, wherein $R^{6c}$ is hydrogen.

In a further embodiment, the invention relates to a compound of formula I, wherein $R^{6c}$ is halogen.

In a further embodiment, the invention relates to a compound of formula I, wherein $R^{6c}$ is fluoro.

In a further embodiment, the invention relates to a compound of formula I, wherein $R^{6d}$ is hydrogen.

In a further embodiment, the invention relates to a compound of formula I, wherein $R^7$ is —(CO)—$R^{10}$ and $R^{10}$ is selected from the group consisting of aryl, said aryl being unsubstituted or substituted by one, two or three groups selected from the group consisting of $C_{1-7}$-alkyl, halogen, halogen-$C_{1-7}$-alkyl, $C_{1-7}$-alkoxy, halogen-$C_{1-7}$-alkoxy, cyano, hydroxy-$C_{1-7}$-alkyl, oxo and phenyl, heteroaryl, said heteroaryl being unsubstituted or substituted by one, two or three groups selected from the group consisting of $C_{1-7}$-alkyl, halogen, halogen-$C_{1-7}$-alkyl, $C_{1-7}$-alkoxy, halogen-$C_{1-7}$-alkoxy, cyano, hydroxy-$C_{1-7}$-alkyl, oxo and phenyl, $C_{1-7}$-alkyl, halogen-$C_{1-7}$-alkyl, $C_{3-7}$-cycloalkyl, said cycloalkyl being unsubstituted or substituted by one, two, three or four groups selected from the group consisting of $C_{1-7}$-alkyl, halogen or halogen-$C_{1-7}$-alkyl, and $C_{1-7}$-alkoxy-$C_{1-7}$-alkyl.

In a further embodiment, the invention relates to a compound of formula I, wherein $R^7$ is —(CO)—$R^{10}$ and $R^{10}$ is selected from the group consisting of heteroaryl, said heteroaryl being unsubstituted or substituted by one, two or three groups selected from the group consisting of $C_{1-7}$-alkyl, halogen, halogen-$C_{1-7}$-alkyl, $C_{1-7}$-alkoxy, halogen-$C_{1-7}$-alkoxy, cyano, hydroxy-$C_{1-7}$-alkyl, oxo and phenyl, halogen-$C_{1-7}$-alkyl, $C_{3-7}$-cycloalkyl, said cycloalkyl being unsubstituted or substituted by one, two, three or four groups selected from the group consisting of $C_{1-7}$-alkyl, halogen or halogen-$C_{1-7}$-alkyl, and $C_{1-7}$-alkoxy-$C_{1-7}$-alkyl.

In a further embodiment, the invention relates to a compound of formula I, wherein $R^{10}$ is heteroaryl, said heteroaryl being unsubstituted or substituted by one, two or three groups selected from the group consisting of $C_{1-7}$-alkyl, halogen, halogen-$C_{1-7}$-alkyl, $C_{1-7}$-alkoxy, halogen-$C_{1-7}$-alkoxy, cyano, hydroxy-$C_{1-7}$-alkyl, oxo and phenyl.

In a further embodiment, the invention relates to a compound of formula I, wherein $R^{10}$ is heteroaryl selected from the group consisting of thienyl, oxazolyl, isoxazolyl, thiazolyl, pyrazolyl, imidazolyl, pyridyl, pyrimidinyl, pyrazinyl, 6-oxo-1,6-dihydropyridazinyl, 5-oxo-4,5-dihydropyrazinyl, imidazo[1,2-a]pyridyl, benzo[b]thienyl, pyrrolo[2,3-b]pyridinyl, thieno[3,2-b]pyridyl, thieno[2,3-c]pyridyl, quinolinyl and isoquinolinyl, said heteroaryl being unsubstituted or substituted by one, two or three groups selected from the group consisting of $C_{1-7}$-alkyl, halogen, halogen-$C_{1-7}$-alkyl, $C_{1-7}$-alkoxy, halogen-$C_{1-7}$-alkoxy, cyano, hydroxy-$C_{1-7}$-alkyl, oxo and phenyl.

In a further embodiment, the invention relates to a compound of formula I, wherein $R^{10}$ is heteroaryl selected from the group consisting of oxazolyl, pyrazolyl, pyridyl, and pyrimidinyl, said heteroaryl being unsubstituted or substituted by one, two or three groups selected from the group consisting of $C_{1-7}$-alkyl, halogen, halogen-$C_{1-7}$-alkyl, $C_{1-7}$-alkoxy, halogen-$C_{1-7}$-alkoxy, cyano, hydroxy-$C_{1-7}$-alkyl, oxo and phenyl.

In a further embodiment, the invention relates to a compound of formula I, wherein $R^{10}$ is pyridyl, said pyridyl being unsubstituted or substituted by one, two or three groups selected from the group consisting of $C_{1-7}$-alkyl, halogen, halogen-$C_{1-7}$-alkyl, $C_{1-7}$-alkoxy, halogen-$C_{1-7}$-alkoxy, and cyano.

In a further embodiment, the invention relates to a compound of formula I, wherein $R^{10}$ is $C_{3-7}$-cycloalkyl, said cycloalkyl being unsubstituted or substituted by one, two, three or four groups selected from the group consisting of $C_{1-7}$-alkyl, halogen and halogen-$C_{1-7}$-alkyl.

In a further embodiment, the invention relates to a compound of formula I, wherein $R^{10}$ is halogen-$C_{1-7}$-alkyl or $C_{1-7}$-alkoxy-$C_{1-7}$-alkyl.

In a further embodiment, the invention relates to a compound of formula I, wherein $R^7$ is $R^{11}$ and $R^{11}$ is selected from the group consisting of $C_{1-7}$-alkyl and $C_{3-7}$-cycloalkyl, said cycloalkyl being unsubstituted or substituted by one, two, three or four groups selected from the group consisting of $C_{1-7}$-alkyl, halogen and halogen-$C_{1-7}$-alkyl. In particular, $R^{11}$ is $C_{3-7}$-cycloalkyl, said cycloalkyl being unsubstituted or substituted by one, two, three or four groups selected from the group consisting of $C_{1-7}$-alkyl, halogen and halogen-$C_{1-7}$-alkyl.

In a further embodiment, the invention relates to a compound of formula I, wherein $R^8$ and $R^9$ are hydrogen.

In a further embodiment, the invention relates to a compound of formula I, wherein $R^7$ is —(CO)—$R^{10}$.

In a further embodiment, the invention relates to a compound of formula I, wherein $R^{10}$ is 1,2,4-thiadiazol-3-yl, 1H-imidazol-4-yl, 1H-pyrazol-3-yl, 1H-pyrazol-5-yl, cyclobutanyl, cyclopropanyl, isoxazol-3-yl, oxazol-4-yl, pyrazin-2-yl, pyridazin-3-yl, pyridin-2-yl, pyrimidin-2-yl, thiazol-4-yl or thiophen-2-yl.

In a further embodiment, the invention relates to a compound of formula I, wherein $R^{10}$ is heteroaryl or heteroaryl substituted by cyano, halogen, $C_{1-7}$-alkyl, halogen-$C_{1-7}$-alkyl, halogen-$C_{1-7}$-alkoxy or $C_{1-7}$-alkoxy.

In a further embodiment, the invention relates to a compound of formula I, wherein $R^{10}$ is 1,2,4-thiadiazol-3-yl substituted by chloro; 1H-imidazol-4-yl substituted by methyl; 1H-pyrazol-3-yl substituted by chloro, methyl, ethyl, difluoromethyl or 2,2,2-trifluoroethyl; 1H-pyrazol-5-yl substituted by methyl or ethyl; isoxazol-3-yl substituted by methyl; oxazol-4-yl substituted by methyl, ethyl or trifluoromethyl; pyrazin-2-yl substituted by chloro, difluoromethyl, trifluoromethyl, methoxy, fluoromethoxy, 2-fluoroethoxy, 2,2-difluoroethoxy or 2,2,2-trifluoroethoxy; pyridazin-3-yl, pyridin-2-yl, pyridin-2-yl substituted by cyano, one or two chloro, one or two fluoro, methyl, difluoromethyl, trifluoromethyl, methoxy, isopropoxy, fluoromethoxy, difluoromethoxy, 2,2,3,3-tetrafluoropropoxy, 2,2-difluoroethoxy or 2,2,2-trifluoroethoxy; pyrimidin-2-yl substituted by chloro; thiazol-4-yl substituted by chloro or thiophen-2-yl substituted by one or two chloro.

In a further embodiment, the invention relates to a compound of formula I, wherein $R^{10}$ is $C_{3-7}$-cycoalkyl substituted by halogen-$C_{1-7}$-alkyl or halogen.

In a further embodiment, the invention relates to a compound of formula I, wherein $R^{10}$ is cyclobutanyl substituted by trifluoromethyl or cyclopropanyl substituted by trifluoromethyl or one or two fluoro.

In a further embodiment, the invention relates to a compound of formula I, wherein $R^{10}$ is $C_{1-7}$-alkyl substituted by $C_{1-7}$-alkoxyl or halogen.

In a further embodiment, the invention relates to a compound of formula I, wherein $R^{10}$ is ethyl substituted by methoxy or one, two or three fluoro.

In a further embodiment, the invention relates to a compound of formula I, wherein $R^{10}$ is 5-chloro-pyridin-2-yl, 1-(difluoromethyl)-1H-pyrazol-3-yl, 1-methoxy-ethyl, 1-methyl-1H-pyrazol-3-yl, 1-trifluoromethyl-cyclobutanyl-, 1-trifluoromethyl-cyclopropanyl-, 2,2,2-trifluoroethyl, 2,2-difluoro-cyclopropanyl, 2-chlorothiazol-4-yl, 2-methyl-5-(trifluoromethyl)oxazol-4-yl, 2-methyloxazol-4-yl, 3-(trifluoromethylpyridin-2-yl, 3,5-dichloro-pyridin-2-yl, 3,5-difluoro-pyridin-2-yl, 3-chloro-5-cyano-pyridin-2-yl, 3-chloro-5-fluoro-pyridin-2-yl, 3-chloro-5-trifluoromethyl-pyridin-2-yl, 3-chloro-pyridin-2-yl, 3-ethyl-4-methyl-1H-pyrazol-5-yl, 3-fluoro-5-(trifluoromethyl)-pyridin-2-yl, 3-fluoro-pyridin-2-yl, 3-trifluoromethyl-pyrinin-2-yl, 4,5-dichlorothiophen-2-yl, 4-chloro-1-(2,2,2-trifluoroethyl)-1H-pyrazol-3-yl, 4-chloro-1-(difluoromethyl)-1H-pyrazol-3-yl, 4-chloro-1-ethyl-1H-pyrazol-3-yl, 4-chloro-1H-pyrazol-3-yl, 4-chloro-1-methyl-1H-pyrazol-3-yl, 4-methyl-1H-pyrazol-3-yl, 4-methylisoxazol-3-yl, 5-(2,2,2-trifluoro-ethoxy)-pyridin-2-yl, 5-(2,2,3,3-tetrafluoropropoxy)-pyridin-2-yl, 5-(2,2-difluoroethoxy)-pyrazin-2-yl, 5-(2-fluoroethoxy)-pyrazin-2-yl, 5-(difluoromethyl)-pyrazin-2-yl, 5-(difluoromethyl)-pyridin-2-yl, 5-(ethoxymethyl)-pyridin-2-yl, 5-(fluoromethoxy)-pyrazin-2-yl, 5-(fluoromethoxy)-pyridin-2-yl, 5-(trifluoromethyl)-pyrazin-2-yl, 5-chloro-1,2,4-thiadiazol-3-yl, 5-chloro-3-methyl-pyridin-2-yl, 5-chloropyrazin-2-yl, 5-chloro-pyridin-2-yl, 5-chloropyrimidine-2-yl, 5-chloro-pyrimidin-2-yl, 5-cyano-pyridin-2-yl, 5-difluoromethoxy-pyridin-2-yl, 5-ethyloxazol-4-yl, 5-fluoro-3-methyl-pyridin-2-yl, 5-fluoro-pyridin-2-yl, 5-isopropoxy-pyridin-2-yl, 5-methoxy-pyrazin-2-yl, 5-methoxy-pyridin-2-yl, 5-methyl-1H-imidazol-4-yl, 5-methyl-oxazol-4-yl, 5-methyl-pyridin-2-yl, 6-(2,2,2-trifluoroethoxy)-pyrazin-2-yl, ethyl-acetyl-pyridin-2-yl, pyridazin-3-yl or pyridin-2-yl.

In a further embodiment, the invention relates to a compound of formula I, wherein $R^{10}$ is 5-chloro-pyridin-2-yl.

In a further embodiment, the invention relates to a compound of formula I, wherein $R^{10}$ is 1-(difluoromethyl)-1H-pyrazol-3-yl.

In a further embodiment, the invention relates to a compound of formula I, wherein $R^{10}$ is 1-methoxy-ethyl.

In a further embodiment, the invention relates to a compound of formula I, wherein $R^{10}$ is 1-methyl-1H-pyrazol-3-yl.

In a further embodiment, the invention relates to a compound of formula I, wherein $R^{10}$ is 1-trifluoromethyl-cyclobutanyl.

In a further embodiment, the invention relates to a compound of formula I, wherein $R^{10}$ is 2,2,2-trifluoro-ethyl.

In a further embodiment, the invention relates to a compound of formula I, wherein $R^{10}$ is 1-trifluoromethyl-cyclopropanyl.

In a further embodiment, the invention relates to a compound of formula I, wherein $R^{10}$ is 2,2-difluoro-cyclopropanyl.

In a further embodiment, the invention relates to a compound of formula I, wherein $R^{10}$ is 2-chlorothiazol-4-yl.

In a further embodiment, the invention relates to a compound of formula I, wherein $R^{10}$ is 2-methyl-5-(trifluoromethyl)oxazol-4-yl.

In a further embodiment, the invention relates to a compound of formula I, wherein $R^{10}$ is 2-methyloxazol-4-yl.

In a further embodiment, the invention relates to a compound of formula I, wherein $R^{10}$ is 3-(trifluoromethyl)-pyridin-2-yl.

In a further embodiment, the invention relates to a compound of formula I, wherein $R^{10}$ is 3,5-dichloro-pyridin-2-yl.

In a further embodiment, the invention relates to a compound of formula I, wherein $R^{10}$ is 3,5-difluoro-pyridin-2-yl.

In a further embodiment, the invention relates to a compound of formula I, wherein $R^{10}$ is 3-chloro-5-cyano-pyridin-2-yl.

In a further embodiment, the invention relates to a compound of formula I, wherein $R^{10}$ is 3-chloro-5-fluoro-pyridin-2-yl.

In a further embodiment, the invention relates to a compound of formula I, wherein $R^{10}$ is 3-chloro-5-trifluoromethyl-pyridin-2-yl.

In a further embodiment, the invention relates to a compound of formula I, wherein $R^{10}$ is 3-chloro-pyridin-2-yl.

In a further embodiment, the invention relates to a compound of formula I, wherein $R^{10}$ is 3-ethyl-4-methyl-1H-pyrazol-5-yl.

In a further embodiment, the invention relates to a compound of formula I, wherein $R^{10}$ is 3-fluoro-5-(trifluoromethyl)-pyridin-2-yl.

In a further embodiment, the invention relates to a compound of formula I, wherein $R^{10}$ is 3-fluoro-5-(trifluoromethyl)-pyridin-2-yl.

In a further embodiment, the invention relates to a compound of formula I, wherein $R^{10}$ is 3-fluoro-pyridin-2-yl.

In a further embodiment, the invention relates to a compound of formula I, wherein $R^{10}$ is 3-trifluoromethyl-pyridin-2-yl.

In a further embodiment, the invention relates to a compound of formula I, wherein $R^{10}$ is 4,5-dichlorothiophen-2-yl.

In a further embodiment, the invention relates to a compound of formula I, wherein $R^{10}$ is 4-chloro-1-(2,2,2-trifluoroethyl)-1H-pyrazol-3-yl.

In a further embodiment, the invention relates to a compound of formula I, wherein $R^{10}$ is 4-chloro-1-(difluoromethyl)-1H-pyrazol-3-yl.

In a further embodiment, the invention relates to a compound of formula I, wherein $R^{10}$ is 4-chloro-1-ethyl-1H-pyrazol-3-yl.

In a further embodiment, the invention relates to a compound of formula I, wherein $R^{10}$ is 4-chloro-1H-pyrazol-3-yl.

In a further embodiment, the invention relates to a compound of formula I, wherein $R^{10}$ is 4-chloro-1-methyl-1H-pyrazol-3-yl.

In a further embodiment, the invention relates to a compound of formula I, wherein $R^{10}$ is 4-methyl-1H-pyrazol-3-yl.

In a further embodiment, the invention relates to a compound of formula I, wherein $R^{10}$ is 4-methylisoxazol-3-yl.

In a further embodiment, the invention relates to a compound of formula I, wherein $R^{10}$ is 5-(2,2,2-trifluoro-ethoxy)-pyridin-2-yl.

In a further embodiment, the invention relates to a compound of formula I, wherein $R^{10}$ is 5-(2,2,3,3-tetrafluoropropoxy)-pyridin-2-yl.

In a further embodiment, the invention relates to a compound of formula I, wherein $R^{10}$ is 5-(2,2-difluoroethoxy)-pyrazin-2-yl.

In a further embodiment, the invention relates to a compound of formula I, wherein $R^{10}$ is 5-(2-fluoroethoxy)-pyrazin-2-yl.

In a further embodiment, the invention relates to a compound of formula I, wherein $R^{10}$ is 5-(difluoromethyl)-pyrazin-2-yl.

In a further embodiment, the invention relates to a compound of formula I, wherein $R^{10}$ is 5-(difluoromethyl)-pyridin-2-yl.

In a further embodiment, the invention relates to a compound of formula I, wherein $R^{10}$ is 5-(ethoxymethyl)-pyridin-2-yl.

In a further embodiment, the invention relates to a compound of formula I, wherein $R^{10}$ is 5-(fluoromethoxy)-pyrazin-2-yl.

In a further embodiment, the invention relates to a compound of formula I, wherein $R^{10}$ is 5-(fluoromethoxy)-pyridin-2-yl.

In a further embodiment, the invention relates to a compound of formula I, wherein $R^{10}$ is 5-(trifluoromethyl)-pyrazin-2-yl.

In a further embodiment, the invention relates to a compound of formula I, wherein $R^{10}$ is 5-chloro-1,2,4-thiadiazol-3-yl.

In a further embodiment, the invention relates to a compound of formula I, wherein $R^{10}$ is 5-chloro-3-methyl-pyridin-2-yl.

In a further embodiment, the invention relates to a compound of formula I, wherein $R^{10}$ is 5-chloropyrazin-2-yl.

In a further embodiment, the invention relates to a compound of formula I, wherein $R^{10}$ is 5-chloro-pyridin-2-yl.

In a further embodiment, the invention relates to a compound of formula I, wherein $R^{10}$ is 5-chloropyrimidine-2-yl.

In a further embodiment, the invention relates to a compound of formula I, wherein $R^{10}$ is 5-cyano-pyridin-2-yl.

In a further embodiment, the invention relates to a compound of formula I, wherein $R^{10}$ is 5-difluoromethoxy-pyridin-2-yl.

In a further embodiment, the invention relates to a compound of formula I, wherein $R^{10}$ is 5-ethyl-oxazol-4-yl.

In a further embodiment, the invention relates to a compound of formula I, wherein $R^{10}$ is 5-fluoro-3-methyl-pyridin-2-yl.

In a further embodiment, the invention relates to a compound of formula I, wherein $R^{10}$ is 5-fluoro-pyridin-2-yl.

In a further embodiment, the invention relates to a compound of formula I, wherein $R^{10}$ is 5-isopropoxy-pyridin-2-yl.

In a further embodiment, the invention relates to a compound of formula I, wherein $R^{10}$ is 5-methoxy-pyrazin-2-yl.

In a further embodiment, the invention relates to a compound of formula I, wherein $R^{10}$ is 5-methoxy-pyridin-2-yl.

In a further embodiment, the invention relates to a compound of formula I, wherein $R^{10}$ is 5-methoxy-pyridin-2-yl.

In a further embodiment, the invention relates to a compound of formula I, wherein $R^{10}$ is 5-methyl-1H-imidazol-4-yl.

In a further embodiment, the invention relates to a compound of formula I, wherein $R^{10}$ is 5-methyl-oxazol-4-yl.

In a further embodiment, the invention relates to a compound of formula I, wherein $R^{10}$ is 5-methyl-pyridin-2-yl.

In a further embodiment, the invention relates to a compound of formula I, wherein $R^{10}$ is 6-(2,2,2-trifluoroethoxy)-pyrazin-2-yl.

In a further embodiment, the invention relates to a compound of formula I, wherein $R^{10}$ is ethyl-acetyl-pyridin-2-yl.

In a further embodiment, the invention relates to a compound of formula I, wherein $R^{10}$ is pyridazin-3-yl.

In a further embodiment, the invention relates to a compound of formula I, wherein $R^{10}$ is pyridin-2-yl.

In a further embodiment, the invention relates to a compound of formula I, wherein $R^7$ is $R^{11}$.

In a further embodiment, the invention relates to a compound of formula I, wherein $R^{11}$ is $C_{3-7}$-cycloalkyl.

In a further embodiment, the invention relates to a compound of formula I, wherein $R^{11}$ is cyclopentyl In a further embodiment, the invention relates to a compound of formula I selected from the group consisting of
5-Chloro-pyridine-2-carboxylic acid [3-((1SR,7RS)-3-amino-5-oxa-2-aza-bicyclo[5.1.0]oct-2-en-1-yl)-4-fluoro-phenyl]-amide,
R)-5-(5-Cyclopentylamino-2-fluoro-phenyl)-6-fluoro-5-ethyl-2,5,6,7-tetrahydro-[1,4]oxazepin-3-ylamine,
(5R,6R)-5-(5-(cyclopentylamino)-2-fluorophenyl)-6-fluoro-5-methyl-2,5,6,7-tetrahydro-1,4-oxazepin-3-amine,
(R)-5-(5-(cyclopentylamino)-2-fluorophenyl)-6,6-difluoro-5-methyl-2,5,6,7-tetrahydro-1,4-oxazepin-3-amine,
(R)-ethyl 6-(3-(3-amino-6,6-difluoro-5-methyl-2,5,6,7-tetrahydro-1,4-oxazepin-5-yl)-4-fluorophenylcarbamoyl) nicotinate formate,
(R)-N-(3-(3-amino-5-ethyl-6,6-difluoro-2,5,6,7-tetrahydro-1,4-oxazepin-5-yl)-4-fluorophenyl)picolinamide,
(R)-N-(3-(3-amino-5-ethyl-6,6-difluoro-2,5,6,7-tetrahydro-1,4-oxazepin-5-yl)-4-fluorophenyl)-3-chloropicolinamide,
(R)-N-(3-(3-amino-5-ethyl-6,6-difluoro-2,5,6,7-tetrahydro-1,4-oxazepin-5-yl)-4-fluorophenyl)-3-(trifluoromethyl)picolinamide,
(R)-N-(3-(3-amino-5-ethyl-6,6-difluoro-2,5,6,7-tetrahydro-1,4-oxazepin-5-yl)-4-fluorophenyl)-5-fluoropicolinamide,
(R)-N-(3-(3-amino-5-ethyl-6,6-difluoro-2,5,6,7-tetrahydro-1,4-oxazepin-5-yl)-4-fluorophenyl)-5-cyanopicolinamide,
(R)-N-(3-(3-amino-5-ethyl-6,6-difluoro-2,5,6,7-tetrahydro-1,4-oxazepin-5-yl)-4-fluorophenyl)-5-chloropyrimidine-2-carboxamide,
(R)-N-(3-(3-amino-5-ethyl-6,6-difluoro-2,5,6,7-tetrahydro-1,4-oxazepin-5-yl)-4-fluorophenyl)pyridazine-3-carboxamide,
(R)-N-(3-(3-amino-5-ethyl-6,6-difluoro-2,5,6,7-tetrahydro-1,4-oxazepin-5-yl)-4-fluorophenyl)-5-chloropicolinamide,
(R)-N-(3-(3-amino-5-ethyl-6,6-difluoro-2,5,6,7-tetrahydro-1,4-oxazepin-5-yl)-4-fluorophenyl)-3,5-dichloropicolinamide,
(R)-N-(3-(3-amino-5-ethyl-6,6-difluoro-2,5,6,7-tetrahydro-1,4-oxazepin-5-yl)-4-fluorophenyl)-3-chloro-5-fluoropicolinamide,
(R)-N-(3-(3-amino-5-ethyl-6,6-difluoro-2,5,6,7-tetrahydro-1,4-oxazepin-5-yl)-4-fluorophenyl)-4-chloro-1-methyl-1H-pyrazole-3-carboxamide,
(R)-N-(3-(3-amino-5-ethyl-6,6-difluoro-2,5,6,7-tetrahydro-1,4-oxazepin-5-yl)-4-fluorophenyl)-4-chloro-1H-pyrazole-3-carboxamide,
(R)-N-(3-(3-amino-5-ethyl-6,6-difluoro-2,5,6,7-tetrahydro-1,4-oxazepin-5-yl)-4-fluorophenyl)-5-methyloxazole-4-carboxamide,
(R)-N-(3-(3-amino-5-ethyl-6,6-difluoro-2,5,6,7-tetrahydro-1,4-oxazepin-5-yl)-4-fluorophenyl)-4-chloro-1-ethyl-1H-pyrazole-3-carboxamide,
(R)-N-(3-(3-amino-5-ethyl-6,6-difluoro-2,5,6,7-tetrahydro-1,4-oxazepin-5-yl)-4-fluorophenyl)-4-methyl-1H-pyrazole-3-carboxamide,
(R)-N-(3-(3-amino-5-ethyl-6,6-difluoro-2,5,6,7-tetrahydro-1,4-oxazepin-5-yl)-4-fluorophenyl)-3-ethyl-4-methyl-1H-pyrazole-5-carboxamide,
(R)-N-(3-(3-amino-5-ethyl-6,6-difluoro-2,5,6,7-tetrahydro-1,4-oxazepin-5-yl)-4-fluorophenyl)-5-methyl-1H-imidazole-4-carboxamide,
(R)-N-(3-(3-amino-5-ethyl-6,6-difluoro-2,5,6,7-tetrahydro-1,4-oxazepin-5-yl)-4-fluorophenyl)-5-fluoro-3-methylpicolinamide,
(R)-N-(3-(3-amino-5-ethyl-6,6-difluoro-2,5,6,7-tetrahydro-1,4-oxazepin-5-yl)-4-fluorophenyl)-4-chloro-1-(difluoromethyl)-1H-pyrazole-3-carboxamide,
(R)-N-(3-(3-amino-6,6-difluoro-5,7,7-trimethyl-2,5,6,7-tetrahydro-1,4-oxazepin-5-yl)-4-fluorophenyl)-5-chloropicolinamide,
(R)-N-(3-(3-amino-6,6-difluoro-5,7,7-trimethyl-2,5,6,7-tetrahydro-1,4-oxazepin-5-yl)-4-fluorophenyl)-5-cyanopicolinamide,
(R)-N-(3-(3-amino-6,6-difluoro-5-methyl-2,5,6,7-tetrahydro-1,4-oxazepin-5-yl)-4-fluorophenyl)-5-chloropicolinamide,
(R)-N-(3-(3-amino-6,6-difluoro-5-methyl-2,5,6,7-tetrahydro-1,4-oxazepin-5-yl)-4-fluorophenyl)-3-fluoropicolinamide formate,
(R)-N-(3-(3-amino-6,6-difluoro-5-methyl-2,5,6,7-tetrahydro-1,4-oxazepin-5-yl)-4-fluorophenyl)-5-fluoropicolinamide formate,
(R)-N-(3-(3-amino-6,6-difluoro-5-methyl-2,5,6,7-tetrahydro-1,4-oxazepin-5-yl)-4-fluorophenyl)-5-cyanopicolinamide formate,
(R)-N-(3-(3-amino-6,6-difluoro-5-methyl-2,5,6,7-tetrahydro-1,4-oxazepin-5-yl)-4-fluorophenyl)-5-chloro-3-methylpicolinamide formate,
(R)-N-(3-(3-amino-6,6-difluoro-5-methyl-2,5,6,7-tetrahydro-1,4-oxazepin-5-yl)-4-fluorophenyl)-3,5-difluoropicolinamide formate,
(R)-N-(3-(3-amino-6,6-difluoro-5-methyl-2,5,6,7-tetrahydro-1,4-oxazepin-5-yl)-4-fluorophenyl)picolinamide formate,
(R)-N-(3-(3-amino-6,6-difluoro-5-methyl-2,5,6,7-tetrahydro-1,4-oxazepin-5-yl)-4-fluorophenyl)-3-chloropicolinamide formate,
(R)-N-(3-(3-amino-6,6-difluoro-5-methyl-2,5,6,7-tetrahydro-1,4-oxazepin-5-yl)-4-fluorophenyl)-3-(trifluoromethyl)picolinamide formate,
(R)-N-(3-(3-amino-6,6-difluoro-5-methyl-2,5,6,7-tetrahydro-1,4-oxazepin-5-yl)-4-fluorophenyl)-5-chloropyrazine-2-carboxamide formate,
(R)-N-(3-(3-amino-6,6-difluoro-5-methyl-2,5,6,7-tetrahydro-1,4-oxazepin-5-yl)-4-fluorophenyl)-3,5-dichloropicolinamide formate, (R)-N-(3-(3-amino-6,6-difluoro-5-methyl-2,5,6,7-tetrahydro-1,4-oxazepin-5-yl)-4-fluorophenyl)-3-chloro-5-fluoropicolinamide formate, (R)-N-(3-(3-amino-6,6-difluoro-5-methyl-2,5,6,7-tetrahydro-1,4-oxazepin-5-yl)-4-fluorophenyl)-4-chloro-1-methyl-1H-pyrazole-3-carboxamide formate, (R)-N-(3-(3-amino-6,6-difluoro-5-methyl-2,5,6,7-tetrahydro-1,4-oxazepin-5-yl)-4-fluorophenyl)-2-methyloxazole-4-carboxamide formate, (R)-N-(3-(3-amino-6,6-difluoro-5-methyl-2,5,6,7-tetrahydro-1,4-oxazepin-5-yl)-4-fluorophenyl)-1-methyl-1H-pyrazole-3-carboxamide formate, (R)-N-(3-(3-amino-6,6-difluoro-5-methyl-2,5,6,7-tetrahydro-1,4-oxazepin-5-yl)-4-fluorophenyl)-1-(difluoromethyl)-1H-pyrazole-3-carboxamide formate, (R)-N-(3-(3-amino-6,6-difluoro-5-methyl-2,5,6,7-tetrahydro-1,4-oxazepin-5-yl)-4-fluorophenyl)-5-(difluoromethoxy)picolinamide formate, (R)-N-(3-(3-amino-6,6-difluoro-5-methyl-2,5,6,7-tetrahydro-1,4-oxazepin-5-yl)-4-fluorophenyl)-5-(2,2,2-trifluoroethoxy)picolinamide formate, (R)-N-(3-(3-amino-6,6-difluoro-5-methyl-2,5,6,7-tetrahydro-1,4-oxazepin-5-yl)-4-fluorophenyl)-5-(2,2,3,3-tetrafluoropropoxy)picolinamide formate, (R)-N-(3-(3-amino-6,6-difluoro-5-methyl-2,5,6,7-tetrahydro-1,4-oxazepin-5-yl)-4-fluorophenyl)-3-chloro-5-cyanopicolinamide formate, (R)-N-(3-(3-amino-6,6-difluoro-5-methyl-2,5,6,7-tetrahydro-1,4-oxazepin-5-yl)-4-fluorophenyl)-5-(ethoxymethyl)picolinamide formate, (R)-N-(3-(3-amino-6,6-difluoro-5-methyl-2,5,6,7-tetrahydro-1,4-oxazepin-5-yl)-4-fluorophenyl)-3-(2,2,2-trifluoroethoxy)picolinamide, (R)-N-(3-(3-amino-6,6-difluoro-5-methyl-2,5,6,7-tetrahydro-1,4-oxazepin-5-yl)-4-fluorophenyl)-5-(2,2-difluoroethoxy)picolinamide formate, (R)-N-(3-(3-amino-6,6-difluoro-5-methyl-2,5,6,7-tetrahydro-1,4-oxazepin-5-yl)-4-fluorophenyl)-2-chlorothiazole-4-carboxamide formate, (R)-N-(3-(3-amino-6,6-difluoro-5-methyl-2,5,6,7-tetrahydro-1,4-oxazepin-5-yl)-4-fluorophenyl)-5-isopropoxypicolinamide formate, (R)-N-(3-(3-amino-6,6-difluoro-5-methyl-2,5,6,7-tetrahydro-1,4-oxazepin-5-yl)-4-fluorophenyl)-5-(fluoromethoxy)picolinamide formate, (R)-N-(3-(3-amino-6,6-difluoro-5-methyl-2,5,6,7-tetrahydro-1,4-oxazepin-5-yl)-4-fluorophenyl)-5-(2-fluoroethoxy)pyrazine-2-carboxamide formate, (R)-N-(3-(3-amino-6,6-difluoro-5-methyl-2,5,6,7-tetrahydro-1,4-oxazepin-5-yl)-4-fluorophenyl)-4,5-dichlorothiophene-2-carboxamide formate, (R)-N-(3-(3-amino-6,6-difluoro-5-methyl-2,5,6,7-tetrahydro-1,4-oxazepin-5-yl)-4-fluorophenyl)-5-chloro-1,2,4-thiadiazole-3-carboxamide formate, (R)-N-(3-(3-amino-6,6-difluoro-5-methyl-2,5,6,7-tetrahydro-1,4-oxazepin-5-yl)-4-fluorophenyl)-5-(2,2-difluoroethoxy)pyrazine-2-carboxamide formate, (R)-N-(3-(3-amino-6,6-difluoro-5-methyl-2,5,6,7-tetrahydro-1,4-oxazepin-5-yl)-4-fluorophenyl)-3-fluoro-5-(trifluoromethyl)picolinamide formate, (R)-N-(3-(3-amino-6,6-difluoro-5-methyl-2,5,6,7-tetrahydro-1,4-oxazepin-5-yl)-4-fluorophenyl)-6-(2,2,2-trifluoroethoxy)pyrazine-2-carboxamide formate, (R)-N-(3-(3-amino-6,6-difluoro-5-methyl-2,5,6,7-tetrahydro-1,4-oxazepin-5-yl)-4-fluorophenyl)-5-methoxypicolinamide formate, (R)-N-(3-(3-amino-6,6-difluoro-5-methyl-2,5,6,7-tetrahydro-1,4-oxazepin-5-yl)-4-fluorophenyl)-5-methylpicolinamide formate, (R)-N-(3-(3-amino-6,6-difluoro-5-methyl-2,5,6,7-tetrahydro-1,4-oxazepin-5-yl)-4-fluorophenyl)-4-chloro-1-ethyl-1H-pyrazole-3-carboxamide, (R)-N-(3-(3-amino-6,6-difluoro-5-methyl-2,5,6,7-tetrahydro-1,4-oxazepin-5-yl)-4-fluorophenyl)-4-chloro-1H-pyrazole-3-carboxamide, (R)-N-(3-(3-amino-6,6-difluoro-5-methyl-2,5,6,7-tetrahydro-1,4-oxazepin-5-yl)-4-fluorophenyl)-4-methyl-1H-pyrazole-3-carboxamide, (R)-N-(3-(3-amino-6,6-difluoro-5-methyl-2,5,6,7-tetrahydro-1,4-oxazepin-5-yl)-4-fluorophenyl)-5-methyloxazole-4-carboxamide, (R)-N-(3-(3-amino-6,6-difluoro-5-methyl-2,5,6,7-tetrahydro-1,4-oxazepin-5-yl)-4-fluorophenyl)-5-ethyloxazole-4-carboxamide, (R)-N-(3-(3-amino-6,6-difluoro-5-methyl-2,5,6,7-tetrahydro-1,4-oxazepin-5-yl)-4-fluorophenyl)-5-(trifluoromethyl)pyrazine-2-carboxamide formate, (R)-N-(3-(3-amino-6,6-difluoro-5-methyl-2,5,6,7-tetrahydro-1,4-oxazepin-5-yl)-4-fluorophenyl)-5-(fluoromethoxy)pyrazine-2-carboxamide formate, (R)-N-(3-(3-amino-6,6-difluoro-5-methyl-2,5,6,7-tetrahydro-1,4-oxazepin-5-yl)-4-fluorophenyl)-4-methylisoxazole-3-carboxamide, (R)-N-(3-(3-amino-6,6-difluoro-5-methyl-2,5,6,7-tetrahydro-1,4-oxazepin-5-yl)-4-fluorophenyl)-5-(difluoromethyl)pyrazine-2-carboxamide formate, (R)-N-(3-(3-amino-6,6-difluoro-5-methyl-2,5,6,7-tetrahydro-1,4-oxazepin-5-yl)-4-fluorophenyl)-4-chloro-1-(2,2,2-trifluoroethyl)-1H-pyrazole-3-carboxamide, (R)-N-(3-(3-amino-6,6-difluoro-5-methyl-2,5,6,7-tetrahydro-1,4-oxazepin-5-yl)-4-fluorophenyl)-3-ethyl-4-methyl-1H-pyrazole-5-carboxamide, (R)-N-(3-(3-amino-6,6-difluoro-5-methyl-2,5,6,7-tetrahydro-1,4-oxazepin-5-yl)-4-fluorophenyl)-5-(difluoromethyl)picolinamide formate, (R)-N-(3-(3-amino-6,6-difluoro-5-methyl-2,5,6,7-tetrahydro-1,4-oxazepin-5-yl)-4-fluorophenyl)-5-methoxypyrazine-2-carboxamide formate, (R)-N-(3-(3-amino-6,6-difluoro-5-methyl-2,5,6,7-tetrahydro-1,4-oxazepin-5-yl)-4-fluorophenyl)-2-methyl-5-(trifluoromethyl)oxazole-4-carboxamide, (R)-N-(3-(3-amino-6,6-difluoro-5-methyl-2,5,6,7-tetrahydro-1,4-oxazepin-5-yl)-4-fluorophenyl)-4-chloro-1-(difluoromethyl)-1H-pyrazole-3-carboxamide, (R)-N-(3-(5-amino-3-methyl-2,3,6,7-tetrahydro-1,4-oxazepin-3-yl)-4-fluorophenyl)-5-chloropicolinamide, (R)-N-(3-(5-amino-3-methyl-2,3,6,7-tetrahydro-1,4-oxazepin-3-yl)-4-fluorophenyl)-3-chloro-5-(trifluoromethyl)picolinamide, (R)-N-(3-(5-amino-3-methyl-2,3,6,7-tetrahydro-1,4-oxazepin-3-yl)-4-fluorophenyl)-5-cyanopicolinamide, (R)-N-(5-(3-amino-6,6-difluoro-5,7,7-trimethyl-2,5,6,7-tetrahydro-1,4-oxazepin-5-yl)-2,4-difluorophenyl)-5-cyanopicolinamide, (R)-N-(5-(3-amino-6,6-difluoro-5,7,7-trimethyl-2,5,6,7-tetrahydro-1,4-oxazepin-5-yl)-2,4-difluorophenyl)-5-chloropicolinamide,

[3-((S)-3-amino-5-methyl-2,5,6,7-tetrahydro-[1,4]oxazepin-5-yl)-4-fluoro-phenyl]-amide, 1-Trifluoromethyl-cyclobutanecarboxylic acid [3-((S)-3-amino-5-methyl-2,5,6,7-tetrahydro-[1,4]oxazepin-5-yl)-4-fluoro-phenyl]-amide, 1-Trifluoromethyl-cyclopropanecarboxylic acid [3-((S)-3-amino-5-methyl-2,5,6,7-tetrahydro-[1,4]oxazepin-5-yl)-4-fluoro-phenyl]-amide,
1-Trifluoromethyl-cyclopropanecarboxylic acid [3-((R)-3-amino-6,6-difluoro-5-methyl-2,5,6,7-tetrahydro-[1,4]oxazepin-5-yl)-4-fluoro-phenyl]-amide formate,
1-Trifluoromethyl-cyclopropanecarboxylic acid [3-((S)-3-amino-5,7,7-trimethyl-2,5,6,7-tetrahydro-[1,4]oxazepin-5-yl)-4-fluoro-phenyl]-amide,
2,2-Difluoro-cyclopropanecarboxylic acid [3-((S)-3-amino-5,7,7-trimethyl-2,5,6,7-tetrahydro-[1,4]oxazepin-5-yl)-4-fluoro-phenyl]-amide,
2,2-Difluoro-cyclopropanecarboxylic acid [3-((S)-3-amino-5-methyl-2,5,6,7-tetrahydro-[1,4]oxazepin-5-yl)-4-fluoro-phenyl]-amide,
3,5-Dichloro-pyridine-2-carboxylic acid [3-((S)-3-amino-5-ethyl-2,5,6,7-tetrahydro-[1,4]oxazepin-5-yl)-4-fluoro-phenyl]-amide,
3,5-Dichloro-pyridine-2-carboxylic acid [3-((S)-3-amino-5-methyl-2,5,6,7-tetrahydro-[1,4]oxazepin-5-yl)-4-fluoro-phenyl]-amide,
3-Chloro-5-trifluoromethyl-pyridine-2-carboxylic acid [3-((1S,7R)-3-amino-5-oxa-2-aza-bicyclo[5.1.0]oct-2-en-1-yl)-phenyl]-amide; trifluoro-acetate salt,
3-Chloro-5-trifluoromethyl-pyridine-2-carboxylic acid [3-((S)-3-amino-5-methyl-2,5,6,7-tetrahydro-[1,4]oxazepin-5-yl)-4-fluoro-phenyl]-amide,
3-Chloro-5-trifluoromethyl-pyridine-2-carboxylic acid [3-((R)-3-amino-6,6-difluoro-5-methyl-2,5,6,7-tetrahydro-[1,4]oxazepin-5-yl)-4-fluoro-phenyl]-amide,
3-Chloro-5-trifluoromethyl-pyridine-2-carboxylic acid [3-((S)-3-amino-5,7,7-trimethyl-2,5,6,7-tetrahydro-[1,4]oxazepin-5-yl)-4-fluoro-phenyl]-amide,
3-Fluoro-pyridine-2-carboxylic acid [3-((S)-3-amino-5-methyl-2,5,6,7-tetrahydro-[1,4]oxazepin-5-yl)-4-fluoro-phenyl]-amide (formate salt),
5-(2,2,2-Trifluoro-ethoxy)-pyridine-2-carboxylic acid [3-((S)-3-amino-5-methyl-2,5,6,7-tetrahydro-[1,4]oxazepin-5-yl)-4-fluoro-phenyl]-amide,
5-(2,2,2-Trifluoro-ethoxy)-pyridine-2-carboxylic acid [3-((1SR,7RS)-3-amino-5-oxa-2-aza-bicyclo[5.1.0]oct-2-en-1-yl)-4-fluoro-phenyl]-amide,
5-(2,2,2-Trifluoro-ethoxy)-pyridine-2-carboxylic acid [3-((1SR,7RS)-3-amino-5-oxa-2-aza-bicyclo[5.1.0]oct-2-en-1-yl)-phenyl]-amide,
5-(2,2,2-Trifluoro-ethoxy)-pyridine-2-carboxylic acid [3-((S)-3-amino-5,7,7-trimethyl-2,5,6,7-tetrahydro-[1,4]oxazepin-5-yl)-4-fluoro-phenyl]-amide,
5-Chloro-pyridine-2-carboxylic acid [3-((1SR,7RS)-3-amino-5-oxa-2-aza-bicyclo[5.1.0]oct-2-en-1-yl)-phenyl]-amide,
5-Chloro-pyridine-2-carboxylic acid [3-((S)-3-amino-5,7,7-trimethyl-2,5,6,7-tetrahydro-[1,4]oxazepin-5-yl)-4-fluoro-phenyl]-amide,
5-Chloro-pyridine-2-carboxylic acid [3-((5S,7S)-3-amino-5-methyl-7-phenyl-2,5,6,7-tetrahydro-[1,4]oxazepin-5-yl)-4-fluoro-phenyl]-amide,
5-Chloro-pyridine-2-carboxylic acid [3-((S)-3-amino-2,2,5-trimethyl-2,5,6,7-tetrahydro-[1,4]oxazepin-5-yl)-4-fluoro-phenyl]-amide,
5-Chloro-pyridine-2-carboxylic acid [3-((S)-3-amino-5-ethyl-2,5,6,7-tetrahydro-[1,4]oxazepin-5-yl)-4-fluoro-phenyl]-amide,
5-Chloro-pyridine-2-carboxylic acid [3-((S)-3-amino-5-methyl-2,5,6,7-tetrahydro-[1,4]oxazepin-5-yl)-4-fluoro-phenyl]-amide (formate salt),
5-Chloro-pyrimidine-2-carboxylic acid [3-((R)-3-amino-6,6-difluoro-5-methyl-2,5,6,7-tetrahydro-[1,4]oxazepin-5-yl)-4-fluoro-phenyl]-amide,
5-Difluoromethoxy-pyridine-2-carboxylic acid [3-((S)-3-amino-5,7,7-trimethyl-2,5,6,7-tetrahydro-[1,4]oxazepin-5-yl)-4-fluoro-phenyl]-amide,
5-Fluoro-pyridine-2-carboxylic acid [3-((5S,7S)-3-amino-5-methyl-7-phenyl-2,5,6,7-tetrahydro-[1,4]oxazepin-5-yl)-4-fluoro-phenyl]-amide,
5-Fluoro-pyridine-2-carboxylic acid [3-((S)-3-amino-2,2,5-trimethyl-2,5,6,7-tetrahydro-[1,4]oxazepin-5-yl)-4-fluoro-phenyl]-amide,
5-Fluoro-pyridine-2-carboxylic acid [3-((S)-3-amino-5-ethyl-2,5,6,7-tetrahydro-[1,4]oxazepin-5-yl)-4-fluoro-phenyl]-amide,
5-Fluoro-pyridine-2-carboxylic acid [3-(3-amino-2,2,5-trimethyl-2,5,6,7-tetrahydro-[1,4]oxazepin-5-yl)-4-fluoro-phenyl]-amide,
N-(3-((5R,6R)-3-amino-6-fluoro-5-methyl-2,5,6,7-tetrahydro-1,4-oxazepin-5-yl)-4-fluorophenyl)-5-chloropicolinamide,
N-(3-((5R,6R)-3-amino-6-fluoro-5-methyl-2,5,6,7-tetrahydro-1,4-oxazepin-5-yl)-4-fluorophenyl)-5-fluoropicolinamide,
N-(3-((5R,6R)-3-amino-6-fluoro-5-methyl-2,5,6,7-tetrahydro-1,4-oxazepin-5-yl)-4-fluorophenyl)-5-cyanopicolinamide,
N-(3-((5R,6R)-3-amino-6-fluoro-5-methyl-2,5,6,7-tetrahydro-1,4-oxazepin-5-yl)-4-fluorophenyl)-3-(2,2,2-trifluoroethoxy)picolinamide,
N-(3-((5R,6R)-3-amino-6-fluoro-5-methyl-2,5,6,7-tetrahydro-1,4-oxazepin-5-yl)-4-fluorophenyl)-4-chloro-1-(difluoromethyl)-1H-pyrazole-3-carboxamide,
N-(3-((R)-3-amino-6,6-difluoro-5-methyl-2,5,6,7-tetrahydro-1,4-oxazepin-5-yl)-4-fluorophenyl)-2,2-difluorocyclopropanecarboxamide formate,
N-(3-((R)-3-amino-6,6-difluoro-5-methyl-2,5,6,7-tetrahydro-1,4-oxazepin-5-yl)-4-fluorophenyl)-2-methoxypropanamide formate,
N-[3-((S)-3-Amino-5,7,7-trimethyl-2,5,6,7-tetrahydro-[1,4]oxazepin-5-yl)-4-fluoro-phenyl]-3,3,3-trifluoro-propionamide, and
Pyridine-2-carboxylic acid [3-((S)-3-amino-5-methyl-2,5,6,7-tetrahydro-[1,4]oxazepin-5-yl)-4-fluoro-phenyl]-amide.

In a further embodiment, the invention relates to a compound of formula I selected from the group consisting of:
5-chloro-pyridine-2-carboxylic acid [3-((1SR,7RS)-3-amino-5-oxa-2-aza-bicyclo[5.1.0]oct-2-en-1-yl)-4-fluoro-phenyl]-amide,
5-(2,2,2-trifluoro-ethoxy)-pyridine-2-carboxylic acid [3-((1SR,7RS)-3-amino-5-oxa-2-aza-bicyclo[5.1.0]oct-2-en-1-yl)-4-fluoro-phenyl]-amide,
5-chloro-pyridine-2-carboxylic acid [3-((1SR,7RS)-3-amino-5-oxa-2-aza-bicyclo[5.1.0]oct-2-en-1-yl)-phenyl]-amide,
5-(2,2,2-trifluoro-ethoxy)-pyridine-2-carboxylic acid [3-((1SR,7RS)-3-amino-5-oxa-2-aza-bicyclo[5.1.0]oct-2-en-1-yl)-phenyl]-amide,
5-chloro-pyridine-2-carboxylic acid [3-((S)-3-amino-5-methyl-2,5,6,7-tetrahydro-[1,4]oxazepin-5-yl)-4-fluoro-phenyl]-amide,
3-fluoro-pyridine-2-carboxylic acid [3-((S)-3-amino-5-methyl-2,5,6,7-tetrahydro-[1,4]oxazepin-5-yl)-4-fluoro-phenyl]-amide, pyridine-2-carboxylic acid [3-((S)-3-amino-5-methyl-2,5,6,7-tetrahydro-[1,4]oxazepin-5-yl)-4-fluoro-phenyl]-amide,
3,5-dichloro-pyridine-2-carboxylic acid [3-((S)-3-amino-5-methyl-2,5,6,7-tetrahydro-[1,4]oxazepin-5-yl)-4-fluoro-phenyl]-amide,
[3-((S)-3-amino-5-methyl-2,5,6,7-tetrahydro-[1,4]oxazepin-5-yl)-4-fluoro-phenyl]-amide,
5-chloro-pyridine-2-carboxylic acid [3-((S)-3-amino-5,7,7-trimethyl-2,5,6,7-tetrahydro-[1,4]oxazepin-5-yl)-4-fluoro-phenyl]-amide,
5-difluoromethoxy-pyridine-2-carboxylic acid [3-((S)-3-amino-5,7,7-trimethyl-2,5,6,7-tetrahydro-[1,4]oxazepin-5-yl)-4-fluoro-phenyl]-amide,
5-(2,2,2-trifluoro-ethoxy)-pyridine-2-carboxylic acid [3-((S)-3-amino-5-methyl-2,5,6,7-tetrahydro-[1,4]oxazepin-5-yl)-4-fluoro-phenyl]-amide,
5-fluoro-pyridine-2-carboxylic acid [3-((S)-3-amino-5-ethyl-2,5,6,7-tetrahydro-[1,4]oxazepin-5-yl)-4-fluoro-phenyl]-amide,
5-chloro-pyridine-2-carboxylic acid [3-((S)-3-amino-5-ethyl-2,5,6,7-tetrahydro-[1,4]oxazepin-5-yl)-4-fluoro-phenyl]-amide,
3,5-dichloro-pyridine-2-carboxylic acid [3-((S)-3-amino-5-ethyl-2,5,6,7-tetrahydro-[1,4]oxazepin-5-yl)-4-fluoro-phenyl]-amide,
3-chloro-5-trifluoromethyl-pyridine-2-carboxylic acid [3-((S)-3-amino-5-methyl-2,5,6,7-tetrahydro-[1,4]oxazepin-5-yl)-4-fluoro-phenyl]-amide,
1-trifluoromethyl-cyclopropanecarboxylic acid [3-((S)-3-amino-5-methyl-2,5,6,7-tetrahydro-[1,4]oxazepin-5-yl)-4-fluoro-phenyl]-amide,
5-(2,2,2-trifluoro-ethoxy)-pyridine-2-carboxylic acid [3-((S)-3-amino-5,7,7-trimethyl-2,5,6,7-tetrahydro-[1,4]oxazepin-5-yl)-4-fluoro-phenyl]-amide,
2,2-difluoro-cyclopropanecarboxylic acid [3-((S)-3-amino-5,7,7-trimethyl-2,5,6,7-tetrahydro-[1,4]oxazepin-5-yl)-4-fluoro-phenyl]-amide,
1-trifluoromethyl-cyclopropanecarboxylic acid [3-((S)-3-amino-5,7,7-trimethyl-2,5,6,7-tetrahydro-[1,4]oxazepin-5-yl)-4-fluoro-phenyl]-amide,
3-chloro-5-trifluoromethyl-pyridine-2-carboxylic acid [3-((S)-3-amino-5,7,7-trimethyl-2,5,6,7-tetrahydro-[1,4]oxazepin-5-yl)-4-fluoro-phenyl]-amide,
N-[3-((S)-3-amino-5,7,7-trimethyl-2,5,6,7-tetrahydro-[1,4]oxazepin-5-yl)-4-fluoro-phenyl]-3,3,3-trifluoro-propionamide,
2,2-difluoro-cyclopropanecarboxylic acid [3-((S)-3-amino-5-methyl-2,5,6,7-tetrahydro-[1,4]oxazepin-5-yl)-4-fluoro-phenyl]-amide,
1-trifluoromethyl-cyclobutanecarboxylic acid [3-((S)-3-amino-5-methyl-2,5,6,7-tetrahydro-[1,4]oxazepin-5-yl)-4-fluoro-phenyl]-amide,
3-chloro-5-trifluoromethyl-pyridine-2-carboxylic acid [3-((R)-3-amino-6,6-difluoro-5-methyl-2,5,6,7-tetrahydro-[1,4]oxazepin-5-yl)-4-fluoro-phenyl]-amide,
(R)-N-(3-(3-amino-6,6-difluoro-5-methyl-2,5,6,7-tetrahydro-1,4-oxazepin-5-yl)-4-fluorophenyl)-5-chloropicolinamide,
(R)-N-(3-(3-amino-6,6-difluoro-5-methyl-2,5,6,7-tetrahydro-1,4-oxazepin-5-yl)-4-fluorophenyl)-3-fluoropicolinamide,
5-fluoro-pyridine-2-carboxylic acid [3-(3-amino-2,2,5-trimethyl-2,5,6,7-tetrahydro-[1,4]oxazepin-5-yl)-4-fluoro-phenyl]-amide,
(R)-N-(3-(3-amino-6,6-difluoro-5-methyl-2,5,6,7-tetrahydro-1,4-oxazepin-5-yl)-4-fluorophenyl)-5-fluoropicolinamide,
(R)-N-(3-(3-amino-6,6-difluoro-5-methyl-2,5,6,7-tetrahydro-1,4-oxazepin-5-yl)-4-fluorophenyl)-5-cyanopicolinamide,
(R)-N-(3-(3-amino-6,6-difluoro-5-methyl-2,5,6,7-tetrahydro-1,4-oxazepin-5-yl)-4-fluorophenyl)-5-chloro-3-methylpicolinamide,
(R)-N-(3-(3-amino-6,6-difluoro-5-methyl-2,5,6,7-tetrahydro-1,4-oxazepin-5-yl)-4-fluorophenyl)-3,5-difluoropicolinamide,
(R)-N-(3-(3-amino-6,6-difluoro-5-methyl-2,5,6,7-tetrahydro-1,4-oxazepin-5-yl)-4-fluorophenyl)-1-(trifluoromethyl)cyclopropanecarboxamide,
N-(3-((R)-3-amino-6,6-difluoro-5-methyl-2,5,6,7-tetrahydro-1,4-oxazepin-5-yl)-4-fluorophenyl)-2,2-difluorocyclopropanecarboxamide,
(R)-N-(3-(3-amino-6,6-difluoro-5-methyl-2,5,6,7-tetrahydro-1,4-oxazepin-5-yl)-4-fluorophenyl)picolinamide,
(R)-N-(3-(3-amino-6,6-difluoro-5-methyl-2,5,6,7-tetrahydro-1,4-oxazepin-5-yl)-4-fluorophenyl)-3-chloropicolinamide,
(R)-N-(3-(3-amino-6,6-difluoro-5-methyl-2,5,6,7-tetrahydro-1,4-oxazepin-5-yl)-4-fluorophenyl)-3-(trifluoromethyl)picolinamide,
(R)-N-(3-(3-amino-6,6-difluoro-5-methyl-2,5,6,7-tetrahydro-1,4-oxazepin-5-yl)-4-fluorophenyl)-5-chloropyrazine-2-carboxamide,
(R)-N-(3-(3-amino-6,6-difluoro-5-methyl-2,5,6,7-tetrahydro-1,4-oxazepin-5-yl)-4-fluorophenyl)-3,5-dichloropicolinamide,
(R)-N-(3-(3-amino-6,6-difluoro-5-methyl-2,5,6,7-tetrahydro-1,4-oxazepin-5-yl)-4-fluorophenyl)-3-chloro-5-fluoropicolinamide,
(R)-N-(3-(3-amino-6,6-difluoro-5-methyl-2,5,6,7-tetrahydro-1,4-oxazepin-5-yl)-4-fluorophenyl)-4-chloro-1-methyl-1H-pyrazole-3-carboxamide,
(R)-N-(3-(3-amino-6,6-difluoro-5-methyl-2,5,6,7-tetrahydro-1,4-oxazepin-5-yl)-4-fluorophenyl)-2-methyloxazole-4-carboxamide,
(R)-N-(3-(3-amino-6,6-difluoro-5-methyl-2,5,6,7-tetrahydro-1,4-oxazepin-5-yl)-4-fluorophenyl)-1-methyl-1H-pyrazole-3-carboxamide,
(R)-N-(3-(3-amino-6,6-difluoro-5-methyl-2,5,6,7-tetrahydro-1,4-oxazepin-5-yl)-4-fluorophenyl)-1-(difluoromethyl)-1H-pyrazole-3-carboxamide,
5-chloro-pyridine-2-carboxylic acid [3-((R)-5-amino-3-methyl-2,3,6,7-tetrahydro-[1,4]oxazepin-3-yl)-4-fluoro-phenyl]-amide,
5-chloro-pyrimidine-2-carboxylic acid [3-((R)-3-amino-6,6-difluoro-5-methyl-2,5,6,7-tetrahydro-[1,4]oxazepin-5-yl)-4-fluoro-phenyl]-amide,
5-chloro-pyridine-2-carboxylic acid [3-((S)-3-amino-2,2,5-trimethyl-2,5,6,7-tetrahydro-[1,4]oxazepin-5-yl)-4-fluoro-phenyl]-amide,
(R)-N-(3-(3-amino-6,6-difluoro-5-methyl-2,5,6,7-tetrahydro-1,4-oxazepin-5-yl)-4-fluorophenyl)-5-(difluoromethoxy)picolinamide,
(R)-N-(3-(3-amino-6,6-difluoro-5-methyl-2,5,6,7-tetrahydro-1,4-oxazepin-5-yl)-4-fluorophenyl)-5-(2,2,2-trifluoroethoxy)picolinamide,
5-fluoro-pyridine-2-carboxylic acid [3-((S)-3-amino-2,2,5-trimethyl-2,5,6,7-tetrahydro-[1,4]oxazepin-5-yl)-4-fluoro-phenyl]-amide, 3-chloro-5-trifluoromethyl-pyridine-2-carboxylic acid [3-((R)-3-amino-5-oxa-2-aza-bicyclo[5.1.0]oct-2-en-1-yl)-phenyl]-amide, 3-chloro-5-trifluoromethyl-pyridine-2-carboxylic acid [3-((R)-5-amino-3-methyl-2,3,6,7-tetrahydro-[1,4]oxazepin-3-yl)-4-fluoro-phenyl]-amide, 5-cyano-pyridine-2-carboxylic acid [3-((R)-5-amino-3-methyl-2,3,6,7-tetrahydro-[1,4]oxazepin-3-yl)-4-fluoro-phenyl]-amide, (R)-N-(3-(3-amino-6,6-difluoro-5-methyl-2,5,6,7-tetrahydro-1,4-oxazepin-5-yl)-4-fluorophenyl)-5-(2,2,3,3-tetrafluoropropoxy)picolinamide, N-(3-((R)-3-amino-6,6-difluoro-5-methyl-2,5,6,7-tetrahydro-1,4-oxazepin-5-yl)-4-fluorophenyl)-2-methoxypropanamide, (R)-N-(3-(3-amino-6,6-difluoro-5-methyl-2,5,6,7-tetrahydro-1,4-oxazepin-5-yl)-4-fluorophenyl)-3-chloro-5-cyanopicolinamide, (R)-N-(3-(3-amino-6,6-difluoro-5-methyl-2,5,6,7-tetrahydro-1,4-oxazepin-5-yl)-4-fluorophenyl)-5-(ethoxymethyl)picolinamide, (R)-ethyl 6-(3-(3-amino-6,6-difluoro-5-methyl-2,5,6,7-tetrahydro-1,4-oxazepin-5-yl)-4-fluorophenylcarbamoyl) nicotinate formate, (R)-N-(3-(3-amino-6,6-difluoro-5-methyl-2,5,6,7-tetrahydro-1,4-oxazepin-5-yl)-4-fluorophenyl)-3-(2,2,2-trifluoroethoxy)picolinamide, (R)-N-(3-(3-amino-6,6-difluoro-5-methyl-2,5,6,7-tetrahydro-1,4-oxazepin-5-yl)-4-fluorophenyl)-5-(2,2-difluoroethoxy)picolinamide, N-(3-((5R,6R)-3-amino-6-fluoro-5-methyl-2,5,6,7-tetrahydro-1,4-oxazepin-5-yl)-4-fluorophenyl)-5-chloropicolinamide, N-(3-((5R,6R)-3-amino-6-fluoro-5-methyl-2,5,6,7-tetrahydro-1,4-oxazepin-5-yl)-4-fluorophenyl)-5-fluoropicolinamide, N-(3-((5R,6R)-3-amino-6-fluoro-5-methyl-2,5,6,7-tetrahydro-1,4-oxazepin-5-yl)-4-fluorophenyl)-5-cyanopicolinamide, (R)-5-(5-(cyclopentylamino)-2-fluorophenyl)-6,6-difluoro-5-methyl-2,5,6,7-tetrahydro-1,4-oxazepin-3-amine, (5R,6R)-5-(5-(cyclopentylamino)-2-fluorophenyl)-6-fluoro-5-methyl-2,5,6,7-tetrahydro-1,4-oxazepin-3-amine, and pharmaceutically acceptable salts thereof.

In a further embodiment, the invention relates to a compound of formula I selected from the group consisting of 5-chloro-pyridine-2-carboxylic acid [3-((S)-3-amino-5-methyl-2,5,6,7-tetrahydro-[1,4]oxazepin-5-yl)-4-fluoro-phenyl]-amide, 3-fluoro-pyridine-2-carboxylic acid [3-((S)-3-amino-5-methyl-2,5,6,7-tetrahydro-[1,4]oxazepin-5-yl)-4-fluoro-phenyl]-amide, pyridine-2-carboxylic acid [3-((S)-3-amino-5-methyl-2,5,6,7-tetrahydro-[1,4]oxazepin-5-yl)-4-fluoro-phenyl]-amide, 3,5-dichloro-pyridine-2-carboxylic acid [3-((S)-3-amino-5-methyl-2,5,6,7-tetrahydro-[1,4]oxazepin-5-yl)-4-fluoro-phenyl]-amide,

[3-((S)-3-amino-5-methyl-2,5,6,7-tetrahydro-[1,4]oxazepin-5-yl)-4-fluoro-phenyl]-amide, 5-chloro-pyridine-2-carboxylic acid [3-((S)-3-amino-5,7,7-trimethyl-2,5,6,7-tetrahydro-[1,4]oxazepin-5-yl)-4-fluoro-phenyl]-amide, 5-fluoro-pyridine-2-carboxylic acid [3-((S)-3-amino-5-ethyl-2,5,6,7-tetrahydro-[1,4]oxazepin-5-yl)-4-fluoro-phenyl]-amide, 3,5-dichloro-pyridine-2-carboxylic acid [3-((S)-3-amino-5-ethyl-2,5,6,7-tetrahydro-[1,4]oxazepin-5-yl)-4-fluoro-phenyl]-amide, 3-chloro-5-trifluoromethyl-pyridine-2-carboxylic acid [3-((S)-3-amino-5-methyl-2,5,6,7-tetrahydro-[1,4]oxazepin-5-yl)-4-fluoro-phenyl]-amide, 3-chloro-5-trifluoromethyl-pyridine-2-carboxylic acid [3-((S)-3-amino-5,7,7-trimethyl-2,5,6,7-tetrahydro-[1,4]oxazepin-5-yl)-4-fluoro-phenyl]-amide, 3-chloro-5-trifluoromethyl-pyridine-2-carboxylic acid [3-((R)-3-amino-6,6-difluoro-5-methyl-2,5,6,7-tetrahydro-[1,4]oxazepin-5-yl)-4-fluoro-phenyl]-amide, (R)-N-(3-(3-amino-6,6-difluoro-5-methyl-2,5,6,7-tetrahydro-1,4-oxazepin-5-yl)-4-fluorophenyl)-5-chloropicolinamide, (R)-N-(3-(3-amino-6,6-difluoro-5-methyl-2,5,6,7-tetrahydro-1,4-oxazepin-5-yl)-4-fluorophenyl)-5-fluoropicolinamide, (R)-N-(3-(3-amino-6,6-difluoro-5-methyl-2,5,6,7-tetrahydro-1,4-oxazepin-5-yl)-4-fluorophenyl)-5-cyanopicolinamide, (R)-N-(3-(3-amino-6,6-difluoro-5-methyl-2,5,6,7-tetrahydro-1,4-oxazepin-5-yl)-4-fluorophenyl)-5-chloro-3-methylpicolinamide, (R)-N-(3-(3-amino-6,6-difluoro-5-methyl-2,5,6,7-tetrahydro-1,4-oxazepin-5-yl)-4-fluorophenyl)-3,5-difluoropicolinamide, (R)-N-(3-(3-amino-6,6-difluoro-5-methyl-2,5,6,7-tetrahydro-1,4-oxazepin-5-yl)-4-fluorophenyl)picolinamide, (R)-N-(3-(3-amino-6,6-difluoro-5-methyl-2,5,6,7-tetrahydro-1,4-oxazepin-5-yl)-4-fluorophenyl)-3-chloropicolinamide, (R)-N-(3-(3-amino-6,6-difluoro-5-methyl-2,5,6,7-tetrahydro-1,4-oxazepin-5-yl)-4-fluorophenyl)-3,5-dichloropicolinamide, (R)-N-(3-(3-amino-6,6-difluoro-5-methyl-2,5,6,7-tetrahydro-1,4-oxazepin-5-yl)-4-fluorophenyl)-3-chloro-5-fluoropicolinamide, (R)-N-(3-(3-amino-6,6-difluoro-5-methyl-2,5,6,7-tetrahydro-1,4-oxazepin-5-yl)-4-fluorophenyl)-4-chloro-1-methyl-1H-pyrazole-3-carboxamide, (R)-N-(3-(3-amino-6,6-difluoro-5-methyl-2,5,6,7-tetrahydro-1,4-oxazepin-5-yl)-4-fluorophenyl)-2-methyloxazole-4-carboxamide, (R)-N-(3-(3-amino-6,6-difluoro-5-methyl-2,5,6,7-tetrahydro-1,4-oxazepin-5-yl)-4-fluorophenyl)-1-methyl-1H-pyrazole-3-carboxamide, (R)-N-(3-(3-amino-6,6-difluoro-5-methyl-2,5,6,7-tetrahydro-1,4-oxazepin-5-yl)-4-fluorophenyl)-1-(difluoromethyl)-1H-pyrazole-3-carboxamide, 5-chloro-pyridine-2-carboxylic acid [3-((S)-3-amino-2,2,5-trimethyl-2,5,6,7-tetrahydro-[1,4]oxazepin-5-yl)-4-fluoro-phenyl]-amide, 5-fluoro-pyridine-2-carboxylic acid [3-((S)-3-amino-2,2,5-trimethyl-2,5,6,7-tetrahydro-[1,4]oxazepin-5-yl)-4-fluoro-phenyl]-amide, (R)-N-(3-(3-amino-6,6-difluoro-5-methyl-2,5,6,7-tetrahydro-1,4-oxazepin-5-yl)-4-fluorophenyl)-5-(2,2,3,3-tetrafluoropropoxy)picolinamide, (R)-N-(3-(3-amino-6,6-difluoro-5-methyl-2,5,6,7-tetrahydro-1,4-oxazepin-5-yl)-4-fluorophenyl)-3-chloro-5-cyanopicolinamide, N-(3-((5R,6R)-3-amino-6-fluoro-5-methyl-2,5,6,7-tetrahydro-1,4-oxazepin-5-yl)-4-fluorophenyl)-5-chloropicolinamide, N-(3-((5R,6R)-3-amino-6-fluoro-5-methyl-2,5,6,7-tetrahydro-1,4-oxazepin-5-yl)-4-fluorophenyl)-5-fluoropicolinamide, and pharmaceutically acceptable salts thereof.

In a further embodiment, the invention relates to a compound of formula I selected from the group consisting of
3-chloro-5-trifluoromethyl-pyridine-2-carboxylic acid [3-((R)-3-amino-6,6-difluoro-5-methyl-2,5,6,7-tetrahydro-[1,4]oxazepin-5-yl)-4-fluoro-phenyl]-amide,
(R)-N-(3-(3-amino-6,6-difluoro-5-methyl-2,5,6,7-tetrahydro-1,4-oxazepin-5-yl)-4-fluorophenyl)-5-chloropicolinamide,
(R)-N-(3-(3-amino-6,6-difluoro-5-methyl-2,5,6,7-tetrahydro-1,4-oxazepin-5-yl)-4-fluorophenyl)-5-fluoropicolinamide,
(R)-N-(3-(3-amino-6,6-difluoro-5-methyl-2,5,6,7-tetrahydro-1,4-oxazepin-5-yl)-, 4-fluorophenyl)-5-cyanopicolinamide,
(R)-N-(3-(3-amino-6,6-difluoro-5-methyl-2,5,6,7-tetrahydro-1,4-oxazepin-5-yl)-4-fluorophenyl)-5-(2,2,3,3-tetrafluoropropoxy)picolinamide,
(R)-N-(3-(3-amino-6,6-difluoro-5-methyl-2,5,6,7-tetrahydro-1,4-oxazepin-5-yl)-4-fluorophenyl)-3-chloro-5-cyanopicolinamide, and pharmaceutically acceptable salts thereof.

In a further embodiment, the invention relates to a compound of formula I selected from the group consisting of
5-Chloro-pyridine-2-carboxylic acid [3-((S)-3-amino-5-methyl-2,5,6,7-tetrahydro-[1,4]oxazepin-5-yl)-4-fluoro-phenyl]-amide formate, (R)-N-(3-(3-amino-6,6-difluoro-5-methyl-2,5,6,7-tetrahydro-1,4-oxazepin-5-yl)-4-fluorophenyl)-5-chloropicolinamide, (R)-N-(3-(3-amino-6,6-difluoro-5-methyl-2,5,6,7-tetrahydro-1,4-oxazepin-5-yl)-4-fluorophenyl)-5-fluoropicolinamide formate, (R)-N-(3-(3-amino-6,6-difluoro-5-methyl-2,5,6,7-tetrahydro-1,4-oxazepin-5-yl)-4-fluorophenyl)-5-cyanopicolinamide formate, (R)-N-(3-(3-amino-6,6-difluoro-5-methyl-2,5,6,7-tetrahydro-1,4-oxazepin-5-yl)-4-fluorophenyl)-5-chloro-3-methylpicolinamide formate, (R)-N-(3-(3-amino-6,6-difluoro-5-methyl-2,5,6,7-tetrahydro-1,4-oxazepin-5-yl)-4-fluorophenyl)-3,5-difluoropicolinamide formate, (R)-N-(3-(3-amino-6,6-difluoro-5-methyl-2,5,6,7-tetrahydro-1,4-oxazepin-5-yl)-4-fluorophenyl)picolinamide formate, (R)-N-(3-(3-amino-6,6-difluoro-5-methyl-2,5,6,7-tetrahydro-1,4-oxazepin-5-yl)-4-fluorophenyl)-3-chloropicolinamide formate, (R)-N-(3-(3-amino-6,6-difluoro-5-methyl-2,5,6,7-tetrahydro-1,4-oxazepin-5-yl)-4-fluorophenyl)-3,5-dichloropicolinamide formate, (R)-N-(3-(3-amino-6,6-difluoro-5-methyl-2,5,6,7-tetrahydro-1,4-oxazepin-5-yl)-4-fluorophenyl)-3-chloro-5-fluoropicolinamide formate, (R)-N-(3-(3-amino-6,6-difluoro-5-methyl-2,5,6,7-tetrahydro-1,4-oxazepin-5-yl)-4-fluorophenyl)-4-chloro-1-methyl-1H-pyrazole-3-carboxamide formate, (R)-N-(3-(3-amino-6,6-difluoro-5-methyl-2,5,6,7-tetrahydro-1,4-oxazepin-5-yl)-4-fluorophenyl)-2-methyloxazole-4-carboxamide formate, (R)-N-(3-(3-amino-6,6-difluoro-5-methyl-2,5,6,7-tetrahydro-1,4-oxazepin-5-yl)-4-fluorophenyl)-1-methyl-1H-pyrazole-3-carboxamide formate, (R)-N-(3-(3-amino-6,6-difluoro-5-methyl-2,5,6,7-tetrahydro-1,4-oxazepin-5-yl)-4-fluorophenyl)-1-(difluoromethyl)-1H-pyrazole-3-carboxamide formate, (R)-N-(3-(3-amino-6,6-difluoro-5-methyl-2,5,6,7-tetrahydro-1,4-oxazepin-5-yl)-4-fluorophenyl)-5-(2,2,2-trifluoroethoxy)picolinamide formate, (R)-N-(3-(3-amino-6,6-difluoro-5-methyl-2,5,6,7-tetrahydro-1,4-oxazepin-5-yl)-4-fluorophenyl)-5-(2,2,3,3-tetrafluoropropoxy)picolinamide formate, (R)-N-(3-(3-amino-6,6-difluoro-5-methyl-2,5,6,7-tetrahydro-1,4-oxazepin-5-yl)-4-fluorophenyl)-3-chloro-5-cyanopicolinamide formate, (R)-N-(3-(5-amino-3-methyl-2,3,6,7-tetrahydro-1,4-oxazepin-3-yl)-4-fluorophenyl)-5-cyanopicolinamide, [3-((S)-3-amino-5-methyl-2,5,6,7-tetrahydro-[1,4]oxazepin-5-yl)-4-fluoro-phenyl]-amide, 3,5-Dichloro-pyridine-2-carboxylic acid [3-((S)-3-amino-5-ethyl-2,5,6,7-tetrahydro-[1,4]oxazepin-5-yl)-4-fluoro-phenyl]-amide, 3,5-Dichloro-pyridine-2-carboxylic acid [3-((S) -3-amino-5-methyl-2,5,6,7-tetrahydro-[1,4]oxazepin-5-yl)-4-fluoro-phenyl]-amide, 3-Chloro-5-trifluoromethyl-pyridine-2-carboxylic acid [3-((S)-3-amino-5-methyl-2,5,6,7-tetrahydro-[1,4]oxazepin-5-yl)-4-fluoro-phenyl]-amide, 3-Chloro-5-trifluoromethyl-pyridine-2-carboxylic acid [3-((R)-3-amino-6,6-difluoro-5-methyl-2,5,6,7-tetrahydro-[1,4]oxazepin-5-yl)-4-fluoro-phenyl]-amide, 3-Chloro-5-trifluoromethyl-pyridine-2-carboxylic acid [3-((S)-3-amino-5,7,7-trimethyl-2,5,6,7-tetrahydro-[1,4]oxazepin-5-yl)-4-fluoro-phenyl]-amide, 3-Fluoro-pyridine-2-carboxylic acid [3-((S)-3-amino-5-methyl-2,5,6,7-tetrahydro-[1,4]oxazepin-5-yl)-4-fluoro-phenyl]-amide (formate salt), 5-Chloro-pyridine-2-carboxylic acid [3-((S)-3-amino-5,7,7-trimethyl-2,5,6,7-tetrahydro-[1,4]oxazepin-5-yl)-4-fluoro-phenyl]-amide, 5-Chloro-pyridine-2-carboxylic acid [3-((S)-3-amino-2,2,5-trimethyl-2,5,6,7-tetrahydro-[1,4]oxazepin-5-yl)-4-fluoro-phenyl]-amide, 5-Fluoro-pyridine-2-carboxylic acid [3-((S)-3-amino-2,2,5-trimethyl-2,5,6,7-tetrahydro-[1,4]oxazepin-5-yl)-4-fluoro-phenyl]-amide, 5-Fluoro-pyridine-2-carboxylic acid [3-((S)-3-amino-5-ethyl-2,5,6,7-tetrahydro-[1,4]oxazepin-5-yl)-4-fluoro-phenyl]-amide, N-(3-((5R,6R)-3-amino-6-fluoro-5-methyl-2,5,6,7-tetrahydro-1,4-oxazepin-5-yl)-4-fluorophenyl)-5-chloropicolinamide, N-(3-((5R,6R)-3-amino-6-fluoro-5-methyl-2,5,6,7-tetrahydro-1,4-oxazepin-5-yl)-4-fluorophenyl)-5-fluoropicolinamide, N-(3-((5R,6R)-3-amino-6-fluoro-5-methyl-2,5,6,7-tetrahydro-1,4-oxazepin-5-yl)-4-fluorophenyl)-5-cyanopicolinamide and Pyridine-2-carboxylic acid [3-((S)-3-amino-5-methyl-2,5,6,7-tetrahydro-[1,4]oxazepin-5-yl)-4-fluoro-phenyl]-amide, or pharmaceutically acceptable salts thereof.

The pharmaceutically acceptable salts of the compounds of formula I also individually constitute compounds of the present invention.

In a further embodiment, the invention relates to a compound of formula I with HCl, formic acid and trifluoroacetic acid ($CF_3COOH$), i.e. the chloride salts, the formate salts and trifluoroacetate salts.

In a further embodiment, the invention relates to a compound of formula I which is (R)-N-(3-(3-amino-6,6-difluoro-5-methyl-2,5,6,7-tetrahydro-1,4-oxazepin-5-yl)-4-fluorophenyl)-3,5-dichloropicolinamide formate.

In a further embodiment, the invention relates to a compound of formula I selected from the group consisting of
5-chloro-pyridine-2-carboxylic acid [3-((S)-3-amino-5-methyl-2,5,6,7-tetrahydro-[1,4]oxazepin-5-yl)-4-fluoro-phenyl]-amide, salt with formic acid,
3-fluoro-pyridine-2-carboxylic acid [3-((S)-3-amino-5-methyl-2,5,6,7-tetrahydro-[1,4]oxazepin-5-yl)-4-fluoro-phenyl]-amide, salt with formic acid,
(R)-N-(3-(3-amino-6,6-difluoro-5-methyl-2,5,6,7-tetrahydro-1,4-oxazepin-5-yl)-4-fluorophenyl)-3-fluoropicolinamide, salt with formic acid,
(R)-N-(3-(3-amino-6,6-difluoro-5-methyl-2,5,6,7-tetrahydro-1,4-oxazepin-5-yl)-4-fluorophenyl)-5-fluoropicolinamide, salt with formic acid,
(R)-N-(3-(3-amino-6,6-difluoro-5-methyl-2,5,6,7-tetrahydro-1,4-oxazepin-5-yl)-4-fluorophenyl)-5-cyanopicolinamide, salt with formic acid, (R)-N-(3-(3-amino-6,6-difluoro-5-methyl-2,5,6,7-tetrahydro-1,4-oxazepin-5-yl)-4-fluorophenyl)-5-chloro-3-methylpicolinamide, salt with formic acid,
(R)-N-(3-(3-amino-6,6-difluoro-5-methyl-2,5,6,7-tetrahydro-1,4-oxazepin-5-yl)-4-fluorophenyl)-3,5-difluoropicolinamide, salt with formic acid,
(R)-N-(3-(3-amino-6,6-difluoro-5-methyl-2,5,6,7-tetrahydro-1,4-oxazepin-5-yl)-4-fluorophenyl)-1-(trifluoromethyl)cyclopropanecarboxamide, salt with formic acid,
N-(3-((R)-3-amino-6,6-difluoro-5-methyl-2,5,6,7-tetrahydro-1,4-oxazepin-5-yl)-4-fluorophenyl)-2,2-difluorocyclopropanecarboxamide, salt with formic acid,
(R)-N-(3-(3-amino-6,6-difluoro-5-methyl-2,5,6,7-tetrahydro-1,4-oxazepin-5-yl)-4-fluorophenyl)picolinamide, salt with formic acid,
(R)-N-(3-(3-amino-6,6-difluoro-5-methyl-2,5,6,7-tetrahydro-1,4-oxazepin-5-yl)-4-fluorophenyl)-3-chloropicolinamide, salt with formic acid,
(R)-N-(3-(3-amino-6,6-difluoro-5-methyl-2,5,6,7-tetrahydro-1,4-oxazepin-5-yl)-4-fluorophenyl)-3-(trifluoromethyl)picolinamide, salt with formic acid,
(R)-N-(3-(3-amino-6,6-difluoro-5-methyl-2,5,6,7-tetrahydro-1,4-oxazepin-5-yl)-4-fluorophenyl)-5-chloropyrazine-2-carboxamide, salt with formic acid,
(R)-N-(3-(3-amino-6,6-difluoro-5-methyl-2,5,6,7-tetrahydro-1,4-oxazepin-5-yl)-4-fluorophenyl)-3,5-dichloropicolinamide, salt with formic acid,
(R)-N-(3-(3-amino-6,6-difluoro-5-methyl-2,5,6,7-tetrahydro-1,4-oxazepin-5-yl)-4-fluorophenyl)-3-chloro-5-fluoropicolinamide, salt with formic acid,
(R)-N-(3-(3-amino-6,6-difluoro-5-methyl-2,5,6,7-tetrahydro-1,4-oxazepin-5-yl)-4-fluorophenyl)-4-chloro-1-methyl-1H-pyrazole-3-carboxamide, salt with formic acid,
(R)-N-(3-(3-amino-6,6-difluoro-5-methyl-2,5,6,7-tetrahydro-1,4-oxazepin-5-yl)-4-fluorophenyl)-2-methyloxazole-4-carboxamide, salt with formic acid,
(R)-N-(3-(3-amino-6,6-difluoro-5-methyl-2,5,6,7-tetrahydro-1,4-oxazepin-5-yl)-4-fluorophenyl)-1-methyl-1H-pyrazole-3-carboxamide, salt with formic acid,
(R)-N-(3-(3-amino-6,6-difluoro-5-methyl-2,5,6,7-tetrahydro-1,4-oxazepin-5-yl)-4-fluorophenyl)-1-(difluoromethyl)-1H-pyrazole-3-carboxamide, salt with formic acid,
(R)-N-(3-(3-amino-6,6-difluoro-5-methyl-2,5,6,7-tetrahydro-1,4-oxazepin-5-yl)-4-fluorophenyl)-5-(difluoromethoxy)picolinamide, salt with formic acid,
(R)-N-(3-(3-amino-6,6-difluoro-5-methyl-2,5,6,7-tetrahydro-1,4-oxazepin-5-yl)-4-fluorophenyl)-5-(2,2,2-trifluoroethoxy)picolinamide, salt with formic acid,
3-chloro-5-trifluoromethyl-pyridine-2-carboxylic acid [3-((R)-3-amino-5-oxa-2-aza-bicyclo[5.1.0]oct-2-en-1-yl)-phenyl]-amide; salt with trifluoroacetic acid,
(R)-N-(3-(3-amino-6,6-difluoro-5-methyl-2,5,6,7-tetrahydro-1,4-oxazepin-5-yl)-4-fluorophenyl)-5-(2,2,3,3-tetrafluoropropoxy)picolinamide, salt with formic acid,
N-(3-((R)-3-amino-6,6-difluoro-5-methyl-2,5,6,7-tetrahydro-1,4-oxazepin-5-yl)-4-fluorophenyl)-2-methoxypropanamide, salt with formic acid,
(R)-N-(3-(3-amino-6,6-difluoro-5-methyl-2,5,6,7-tetrahydro-1,4-oxazepin-5-yl)-4-fluorophenyl)-3-chloro-5-cyanopicolinamide; salt with formic acid,
(R)-N-(3-(3-amino-6,6-difluoro-5-methyl-2,5,6,7-tetrahydro-1,4-oxazepin-5-yl)-4-fluorophenyl)-5-(ethoxymethyl)picolinamide, salt with formic acid,
(R)-ethyl 6-(3-(3-amino-6,6-difluoro-5-methyl-2,5,6,7-tetrahydro-1,4-oxazepin-5-yl)-4-fluorophenylcarbamoyl)nicotinate, salt with formic acid, and
(R)-N-(3-(3-amino-6,6-difluoro-5-methyl-2,5,6,7-tetrahydro-1,4-oxazepin-5-yl)-4-fluorophenyl)-5-(2,2-difluoroethoxy)picolinamide, salt with formic acid.

The skilled person in the art will recognize that the compounds of formula I can exist in tautomeric forms, e.g. in the following tautomeric form:

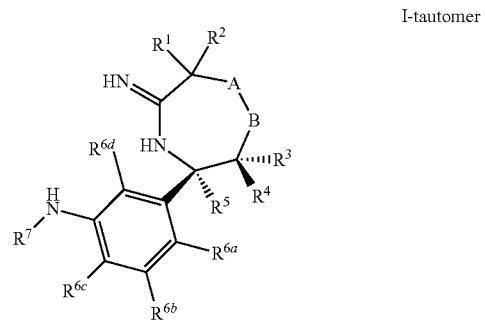

I-tautomer

All tautomeric forms are encompassed in the present invention.

It will be appreciated, that the compounds of general formula I in this invention may be derivatised at functional groups to provide derivatives which are capable of conversion back to the parent compound in vivo. Physiologically acceptable and metabolically labile derivatives, which are capable of producing the parent compounds of general formula I in vivo are also within the scope of this invention.

A further aspect of the present invention is the process for the manufacture of compounds of formula I as defined above, which process comprises a) reacting an amine of the formula II

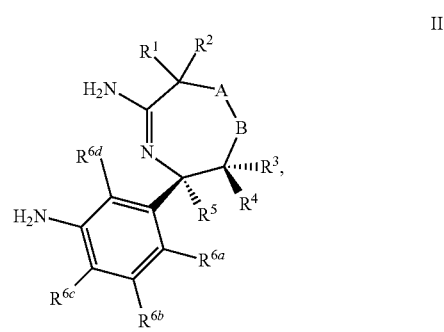

II wherein A, B, $R^1$ to $R^{6d}$ are as defined herein before, with a carboxylic acid of the formula III

III wherein $R^{10}$ is as defined herein before, in the presence of a coupling reagent under basic conditions or with the help of a triazine derivative to obtain a compound of the formula I

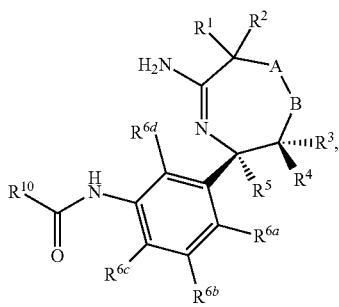

wherein A, B, $R^1$ to $R^{6d}$ are as defined herein before, or, alternatively,
b) reacting an amide of the formula IV

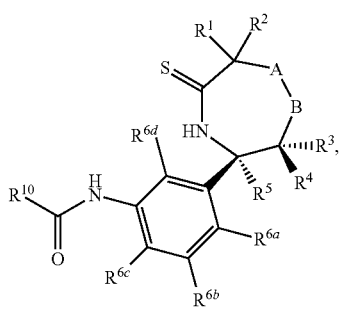

wherein A, B, $R^1$ to $R^{6d}$ and $R^{10}$ are as defined herein before, with ammonia in or without the presence of a mild oxidant in a protic solvent to obtain a compound of the formula I

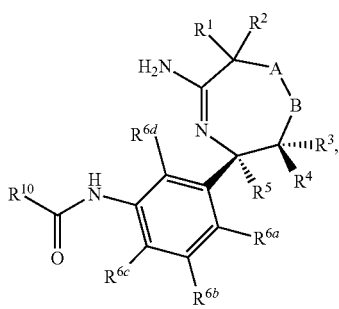

wherein A, B, $R^1$ to $R^{6d}$ are as defined herein before, or, alternatively,
c) reacting a lactam of the formula V

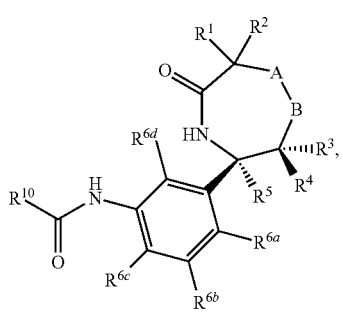

wherein A, B, $R^1$ to $R^{6d}$ and $R^{10}$ are as defined herein before, with an alkyl oxonium salt followed by treatment with an ammonium salt in a polar solvent to obtain a compound of the formula I

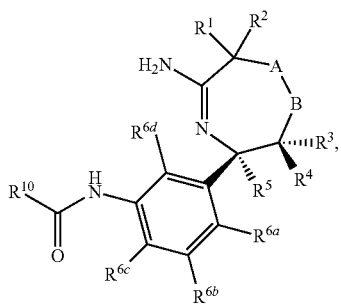

wherein A, B, and $R^1$ to $R^{6d}$ are as defined herein before, or, alternatively,
d) reacting an amine of the formula II

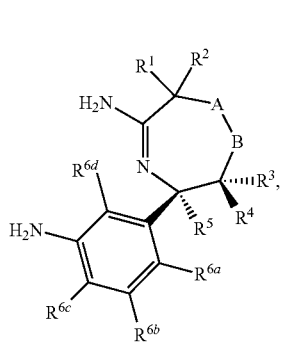

wherein A, B, and $R^1$ to $R^{6d}$ are as defined herein before, with a carbonyl compound of the formula VI

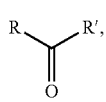

wherein R and R' are hydrogen or $C_{1-7}$-alkyl or R and R' together with the carbon atom of the carbonyl function form a $C_{3-7}$-cycloalkyl ring, in the presence of acetic acid and sodium triacetoxyborohydride to obtain a compound of the formula Ib

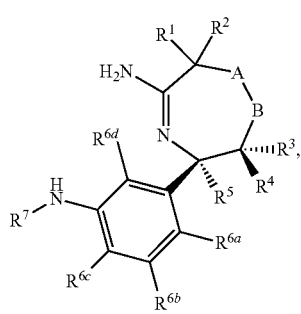

wherein A, B, $R^1$ to $R^{6d}$ and $R^7$ are as defined herein before.

The invention further relates to compounds of formula I as defined above obtainable according to a process as defined above.

A further embodiment of the invention relates to a compound of formula I as defined herein and a pharmaceutically acceptable carrier and/or adjuvant.

A further embodiment of the invention relates to a compound of formula I as defined herein for use as medicaments.

A further embodiment of the invention relates to a compound of formula I as defined herein for use in the therapeutic and/or prophylactic treatment of Alzheimer's disease and/or type 2 diabetes.

A further embodiment of the invention relates to a compound of formula I as defined herein for use in the therapeutic and/or prophylactic treatment of Alzheimer's disease.

A further embodiment of the invention relates to a compound of formula I as defined herein for use in the therapeutic and/or prophylactic treatment of type 2 diabetes.

A further embodiment of the invention relates to a compound of formula I as defined herein for the use as therapeutically active substance for the therapeutic and/or prophylactic treatment of amyotrophic lateral sclerosis (ALS), arterial thrombosis, autoimmune/inflammatory diseases, cancer such as breast cancer, cardiovascular diseases such as myocardial infarction and stroke, dermatomyositis, Down's Syndrome, gastrointestinal diseases, Glioblastoma multiforme, Graves Disease, Huntington's Disease, inclusion body myositis (IBM), inflammatory reactions, Kaposi Sarcoma, Kostmann Disease, lupus erythematosus, macrophagic myofasciitis, juvenile idiopathic arthritis, granulomatous arthritis, malignant melanoma, multiple mieloma, rheumatoid arthritis, Sjogren syndrome, SpinoCerebellar Ataxia 1, SpinoCerebellar Ataxia 7, Whipple's Disease or Wilson's Disease.

A further embodiment of the invention relates to a compound of formula I as defined herein for the preparation of medicaments for the therapeutic and/or prophylactic treatment of Alzheimer's disease and/or type 2 diabetes.

A further embodiment of the invention relates to a compound of formula I as defined herein for the preparation of medicaments for the therapeutic and/or prophylactic treatment of Alzheimer's disease.

A further embodiment of the invention relates to a compound of formula I as defined herein for the preparation of medicaments for the therapeutic and/or prophylactic treatment of type 2 diabetes.

A further embodiment of the invention relates to a method for the therapeutic and/or prophylactic treatment of diseases which can be ameliorated with the inhibition of BACE1 and/or BACE 2 activity, particularly for the treatment of Alzheimer's disease and type 2 diabetes, which method comprises administering a therapeutically active amount of a compound of formula I as described herein to a human being or animal.

A further embodiment of the invention relates to a compound of formula I as defined herein for use in the manufacture of a medicament for use in the therapeutic and/or prophylactic treatment of Alzheimer's disease and/or type 2 diabetes.

The compounds of formula I may contain one or more asymmetric centers and can therefore occur as racemates, racemic mixtures, single enantiomers, diastereomeric mixtures and individual diastereomers. Additional asymmetric centers may be present depending upon the nature of the various substituents on the molecule. Each such asymmetric centre will independently produce two optical isomers and it is intended that all of the possible optical isomers and diastereomers in mixtures and as pure or partially purified compounds are included within this invention. The present invention is meant to encompass all such isomeric forms of these compounds. The independent syntheses of these diastereomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric centre of known absolute configuration. If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography.

In more detail, compounds of formula I according to the present invention can be prepared by the methods and procedures given below. Some typical procedures for the preparation of compounds of formula I are illustrated in Schemes A ($R^{12}$=H, Br or $NO_2$), A', B & C:

Sulfinyl imines of general formula A2 can be prepared in analogy to T. P. Tang & J. A. Ellman, J. Org. Chem. 1999, 64, 12, by condensation of an aryl ketone and a sulfinamide, e.g. an alkyl sulfinamide, most preferably (R)-(+)-tert-butylsulfinamide in the presence of a Lewis acid such as e.g. a titanium (IV)alkoxyde, more preferably titanium(IV)ethoxide in a solvent such as an ether, e.g. diethyl ether or more preferably THF.

The conversion of the sulfinyl imine A2 to the sulfinamide ester A3 proceeds stereoselectively by the chiral directing group as described by Tang & Ellman. The sulfinyl imine A2 can be reacted with a titanium enolate generated from e.g. an alkyl acetate, preferably ethyl acetate, LDA and chlorotriisopropoxytitanium at low temperature, preferably at −78° C. in a solvent such as an ether, e.g. diethyl ether or more preferably THF. Alternatively sulfinamide ester A3 can be produced from sulfinyl imine A2 by Reformatsky reaction of a bromoacetic ester derivative and zinc dust, optionally in the presence of copper(I) chloride, in a solvent such as an ether, e.g. diethyl ether or more preferably THF, at temperatures from 0 to 70° C., preferably at 23° C.

Sulfinamide ester A3 can be reduced to the alcohol A4 by the reduction of the ethylester with an alkali hydride, preferably lithium borohydride or lithium aluminium hydride in a solvent such as an ether, e.g. diethyl ether or more preferably THF.

Alkylation of the alcohol A4 to the nitrile A5 can be accomplished with a suitable mild base preferably silver(I) oxide in a solvent such as THF or $CH_2Cl_2$, more preferably $CH_2Cl_2$ in the presence of an alkylating catalyst such as tertra butyl ammonium iodide.

Hydrolysis of the chiral directing group in the nitrile A5 to give the amino nitrile A6 can be accomplished with a mineral acid, e.g. sulfuric acid or preferably hydrochloric acid in a solvent such as an ether, e.g. diethyl ether or more preferably 1,4-dioxane.

Aminooxazepine A7 can be prepared by the reaction of amino nitrile A6 and trimethyl aluminium in a solvent such as an xylene, preferably toluene.

The protection of the in amino oxazine A7 to give A8 can be accomplished with a triphenylmethyl protecting group, prefereably 4,4'-dimethoxytrityl and a base, e.g an alkyl amine, preferably triethyl amine in an inert solvent such as dichloromethane.

Scheme A
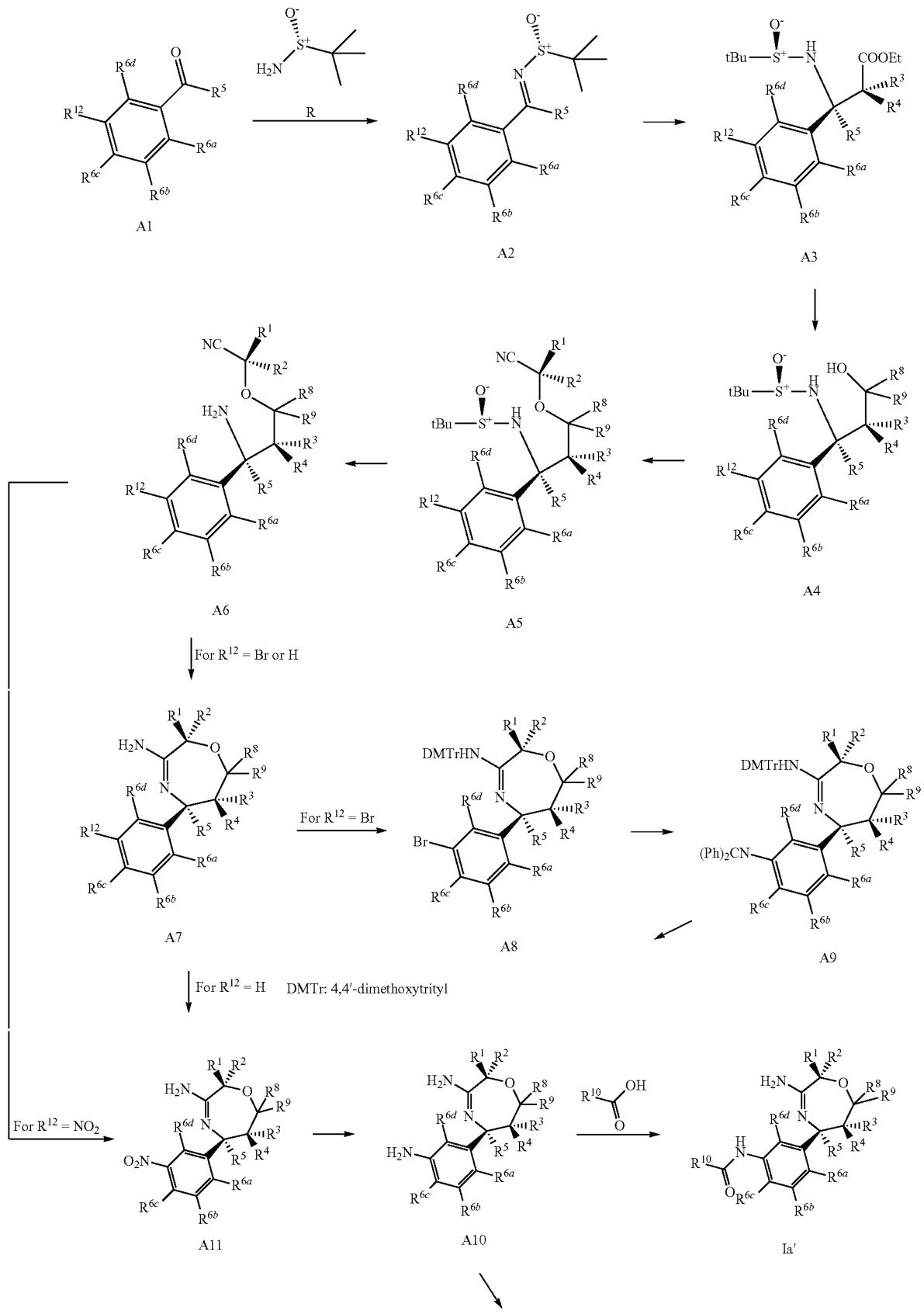

-continued

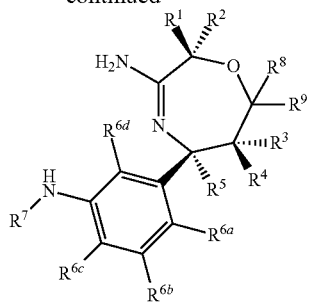

Ib'

The conversion of the bromophenyl compound A8 to the diphenylmethyl imine A9 can be effected with an imine, e.g benzophenone imine and a base, e.g an metal alkoxyde or more preferably sodium t-butoxide and a palladium complex, e.g. 2-di-t-butylphosphino-2',4',6'-triisopropylbiphenyl and tris(dibenzylideneacetone)dipalladium chloroform adduct in a solvent such as benzene derivative, e.g. toluene.

Global deprotection of the imine A9 to the aniline A10 can be accomplished in a two step procedure involving a strong carbonic acid, e.g. trifuoroacetic acid in a halogenated solvent, e.g dichloromethane followed by addition of a mineral acid, e.g. hydrochloric acid in a water soluble solvent, e.g. dioxane.

Introduction of the nitro group in A7 ($R^{12}$=H) to give A11 was best performed according to the standard procedure involving sulfuric acid and nitric acid at low temperature, preferably at 0° C.

Aminooxazepine A11 can be prepared by the reaction of amino nitrile A6 (for $R^{12}$=$NO_2$) and trimethyl aluminium in a solvent such as an xylene, preferably toluene.

The reduction of the nitro group in aminooxazepine A11 to the aniline A10 can be accomplished by hydrogenation using a catalysts such as Pd/C in protic solvents, such as alcohols, perferrabyl ethanol or methanol or by metal reduction such as Iron or Tin, more preferably Tin chloride in alcohol, more preferably aqueous ethanol at elevated temperature, more preferably 80° C.

Amide coupling of the aniline A10 and a carboxylic acid to give the amide 1a' can be effected with a carbodiimide, e.g. DCC or EDCI in a solvent such as dichloromethane. Target amines 1b' can be prepared via reductive amination of aniline A10 performed with a borohydride reducing agent, e.g. sodium borohydride, preferable sodium triacetoxyborohydride and an weak acid, e.g. acetic acid in a solvent such as tetrahydrofuran or dichloromethane.

Sulfinamide ester A3 can be transformed into alcohol A4 by the reaction of the ethylester with an excess of a Grignard or an organolithium reagent, e.g. methyl- or ethylmagnesium halide, methyllithium etc., in a solvent such as an ether, e.g. diethyl ether or more preferably THF, at temperatures between −78 and 70° C., preferably at 0 to 23° C.

Hydrolysis of the chiral directing group in the alcohol A4 to give the amino alcohol A'2 can be accomplished with a mineral acid, e.g. sulfuric acid or preferably hydrochloric acid in a solvent such as an ether, e.g. diethyl ether or THF, more preferably 1,4-dioxane, at temperatures from 0 to 23° C.

Scheme A'

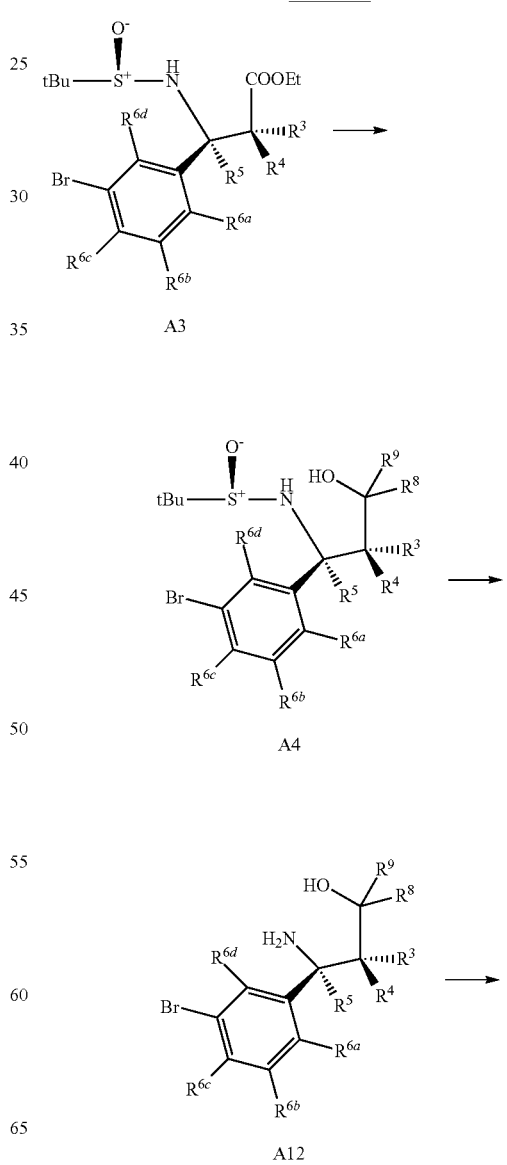

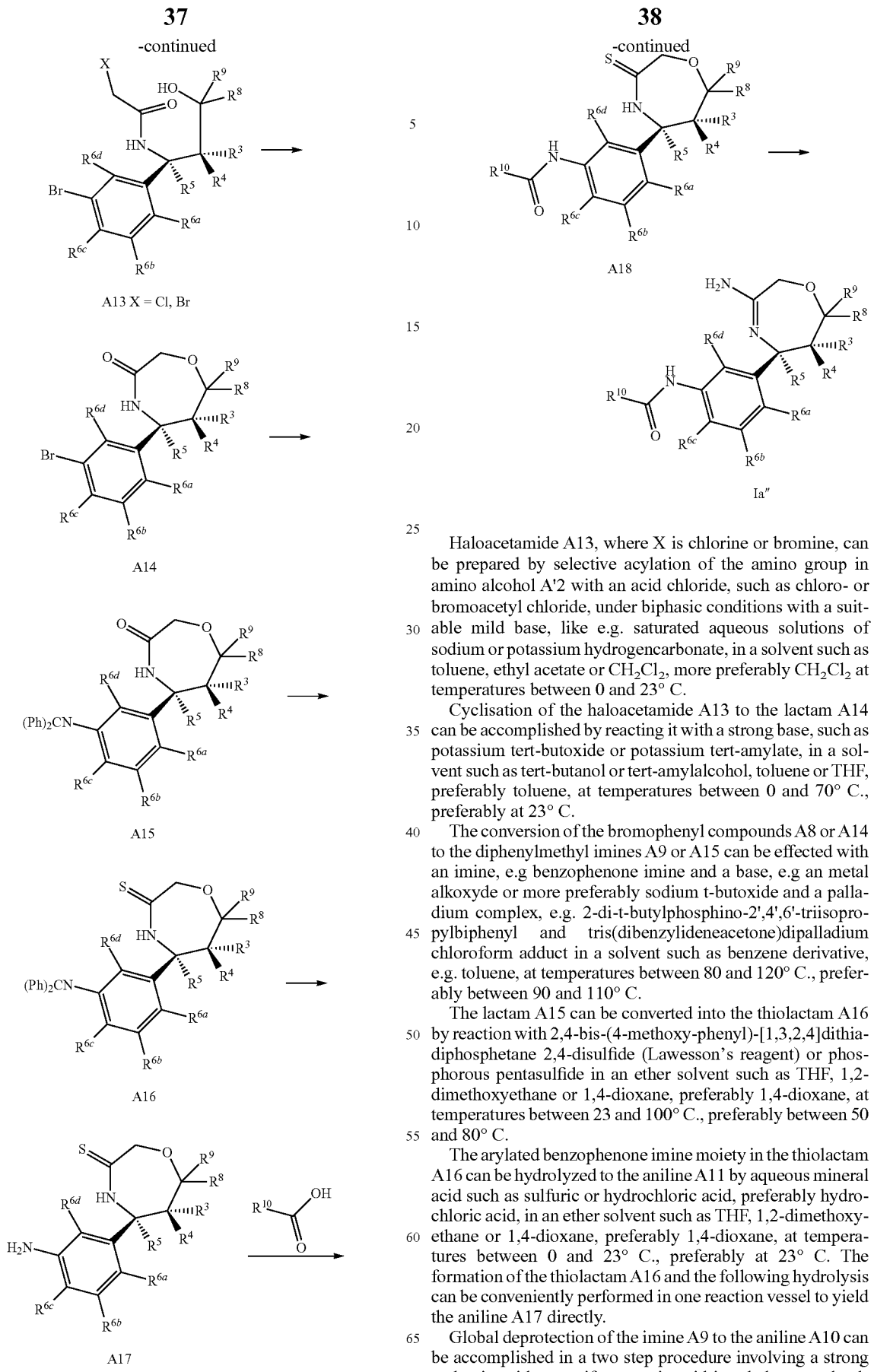

Haloacetamide A13, where X is chlorine or bromine, can be prepared by selective acylation of the amino group in amino alcohol A'2 with an acid chloride, such as chloro- or bromoacetyl chloride, under biphasic conditions with a suitable mild base, like e.g. saturated aqueous solutions of sodium or potassium hydrogencarbonate, in a solvent such as toluene, ethyl acetate or $CH_2Cl_2$, more preferably $CH_2Cl_2$ at temperatures between 0 and 23° C.

Cyclisation of the haloacetamide A13 to the lactam A14 can be accomplished by reacting it with a strong base, such as potassium tert-butoxide or potassium tert-amylate, in a solvent such as tert-butanol or tert-amylalcohol, toluene or THF, preferably toluene, at temperatures between 0 and 70° C., preferably at 23° C.

The conversion of the bromophenyl compounds A8 or A14 to the diphenylmethyl imines A9 or A15 can be effected with an imine, e.g benzophenone imine and a base, e.g an metal alkoxyde or more preferably sodium t-butoxide and a palladium complex, e.g. 2-di-t-butylphosphino-2',4',6'-triisopropylbiphenyl and tris(dibenzylideneacetone)dipalladium chloroform adduct in a solvent such as benzene derivative, e.g. toluene, at temperatures between 80 and 120° C., preferably between 90 and 110° C.

The lactam A15 can be converted into the thiolactam A16 by reaction with 2,4-bis-(4-methoxy-phenyl)-[1,3,2,4]dithiadiphosphetane 2,4-disulfide (Lawesson's reagent) or phosphorous pentasulfide in an ether solvent such as THF, 1,2-dimethoxyethane or 1,4-dioxane, preferably 1,4-dioxane, at temperatures between 23 and 100° C., preferably between 50 and 80° C.

The arylated benzophenone imine moiety in the thiolactam A16 can be hydrolyzed to the aniline A11 by aqueous mineral acid such as sulfuric or hydrochloric acid, preferably hydrochloric acid, in an ether solvent such as THF, 1,2-dimethoxyethane or 1,4-dioxane, preferably 1,4-dioxane, at temperatures between 0 and 23° C., preferably at 23° C. The formation of the thiolactam A16 and the following hydrolysis can be conveniently performed in one reaction vessel to yield the aniline A17 directly.

Global deprotection of the imine A9 to the aniline A10 can be accomplished in a two step procedure involving a strong carbonic acid, e.g. trifuoroacetic acid in a halogenated solvent, e.g dichloromethane followed by addition of a mineral acid, e.g. hydrochloric acid in a water soluble solvent, e.g. dioxane.

Introduction of the nitro group in A7 was best performed according to the standard procedure involving sulfuric acid and nitric acid at low temperature, preferably 0° C.

The nitro group in A11 can be reduced to the aniline A10 using standard hydrogenation conditions, i.e. palladium on carbon in the presence of hydrogen and a solvent, e.g. an alcohol, preferably ethanol.

The coupling of the anilines A10 and the acid was best effected with a triazine derivative, 4-(4,6-dimethoxy-1,3,5-triazin-2yl)-4-methyl-morpholiniumchloride in an alcohol preferably methanol to give the amides Ia'.

The coupling of the anilines A11 and the acid was best achieved by appropriate coupling agents like carbodiimides or uronium salts, such as for example N,N'-carbonyldiimidazole (CDI), N,N'-dicyclohexylcarbodiimide (DCC), N-(3-dimethylaminopropyl)-N'-ethyl-carbodiimide-hydrochloride (EDCI), O-(benzotriazol-1-yl)-N,N,N,N-tetramethyluronium tetrafluoroborate (TBTU) and 1-[bis(dimethylamino)methylene]-1H-1,2,3-triazolo[4,5-b]pyridinium-3-oxide hexafluorophosphate (HATU) under basic conditions, i.e. in the presence of a base, preferably an alkylamine such as diisopropylethylamine (DIEA) or triethylamine (TEA), or a tertiary amine such as N-methylmorpholine or 4-(dimethylamino)-pyridine. The reaction is carried out in a suitable solvent such as for example N,N-dimethylformamide (DMF), dimethylacetamide (DMAc) or dichloromethane (DCM), at temperatures between 0° C. and ambient temperature, to give the amides A18.

Alternatively, the aminooxazepine Ia" can be prepared from the thiolactam A18 by reaction with an solution of ammonia in a protic solvent such as methanol, ethanol or water, preferably methanol, with or without presence of a mild oxidant such as tert-butylhydroperoxide at temperatures between 0 and 60° C., preferably at 23° C. in the presence of an oxidant or at 50 to 60° C. in the absence of an oxidant.

The reductive amination of the aniline A10 and the ketone to give the alkyl aniline Ib' was performed with a borohydride reducing agent, e.g. sodium borohydride, preferable sodium triacetoxyborohydride and an weak acid, e.g. acetic acid in a solvent such as tetrahydrofuran or dichloromethane.

Compounds of general formula A19 can be prepared by selective O-allylation by reacting the alcohol of the general formula A4 with allyl tent-butyl carbonate [CAS no. 70122-89-3] in the presence of catalytic amounts of a palladium(II) salt, like e.g. palladium(II) acetate, and a phosphine ligand, like e.g. triphenylphosphine, or with a palladium(0) catalyst, like e.g. tetrakistriphenylphosphinepalladium(0), in a solvent such as e.g. tetrahydrofuran or dioxane at temperatures between 23 and 100° C., preferably at 50 to 80° C. as described by Haight, A. R.; Stoner, E. J.; Peterson, M. J.; Grover, V. K.; in *J. Org. Chem.* 2003, 68 (21), 8092 (DOI: 10.1021/jo0301907).

The acids of general formula A20 can be prepared by oxidation of the O-allyl ethers of general formula A19 by reacting it with a periodate salt, such as sodium or potassium periodate, in the presence of a catalytic amount of a ruthenium salt, such as e.g. ruthenium(III) chloride, in a solvent mixture consisting of ethyl acetate or tetrachloromethane, acetonitrile and water at temperatures between 0 and 40° C., preferably 20 to 30° C. These reaction conditions will cause concomitant oxidation of the tert-butylsulfinic acid amide into the corresponding tert-butylsulfonic acid amide.

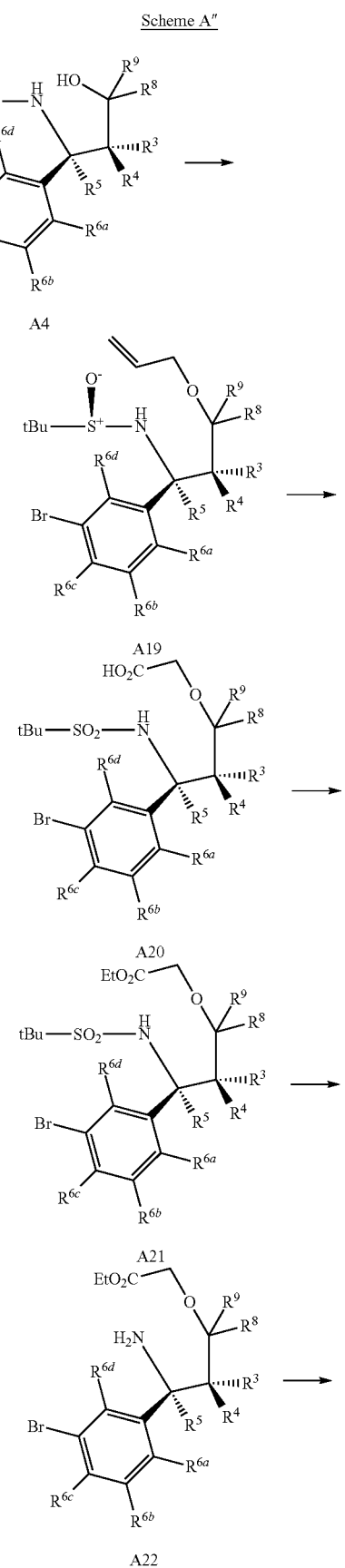

Scheme A"

-continued

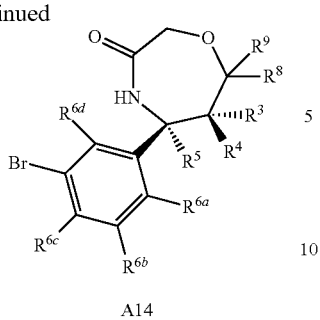

A14

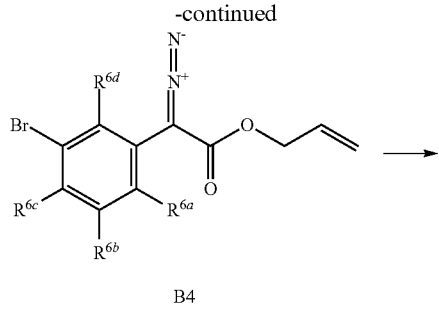

B4

The acids of general formula A20 can be converted into the ethyl esters of general formual A21 by treatment with thionyl chloride in ethanol at temperatures between 23 and 80° C. The amino esters of general formula A22 can be prepared by cleavage of the tert-butylsulfonic acid amide in compounds of general formula A21 by treatment with a strong acid, preferably trifluoromethanesulfonic acid, in a chlorinated solvent, such as e.g. dichloromethane, at temperatures between 0 and 30° C., preferably at 23° C. This method has been described by Sun P., Weinreb S. M., Shang M. in *J. Org. Chem.* 1997, 62(24), 8604.

Cyclization of the amino esters of general formula A22 to the lactams of general formula A14 can be achieved by the reaction with trimethyl aluminium in a solvent such as an xylene, preferably toluene, at temperatures between 0 and 100° C., preferably 23° C.

Scheme B

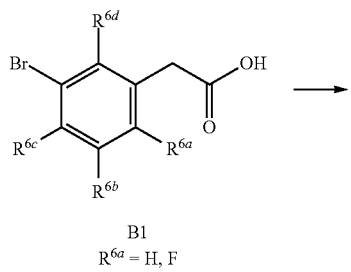

B1
$R^{6a} = H, F$

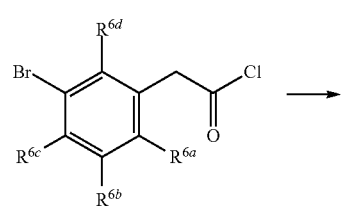

B2

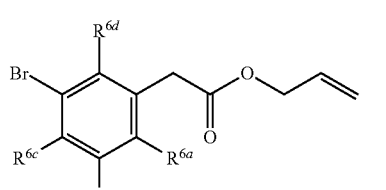

B3

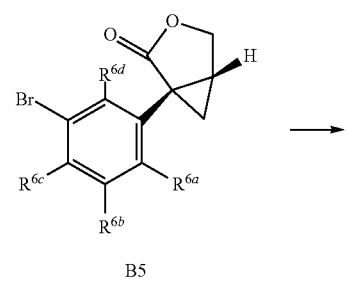

B5

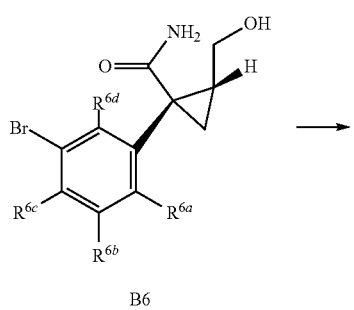

B6

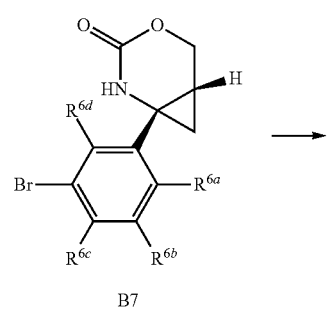

B7

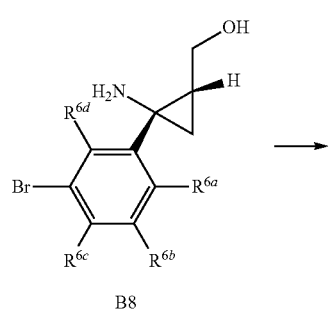

B8

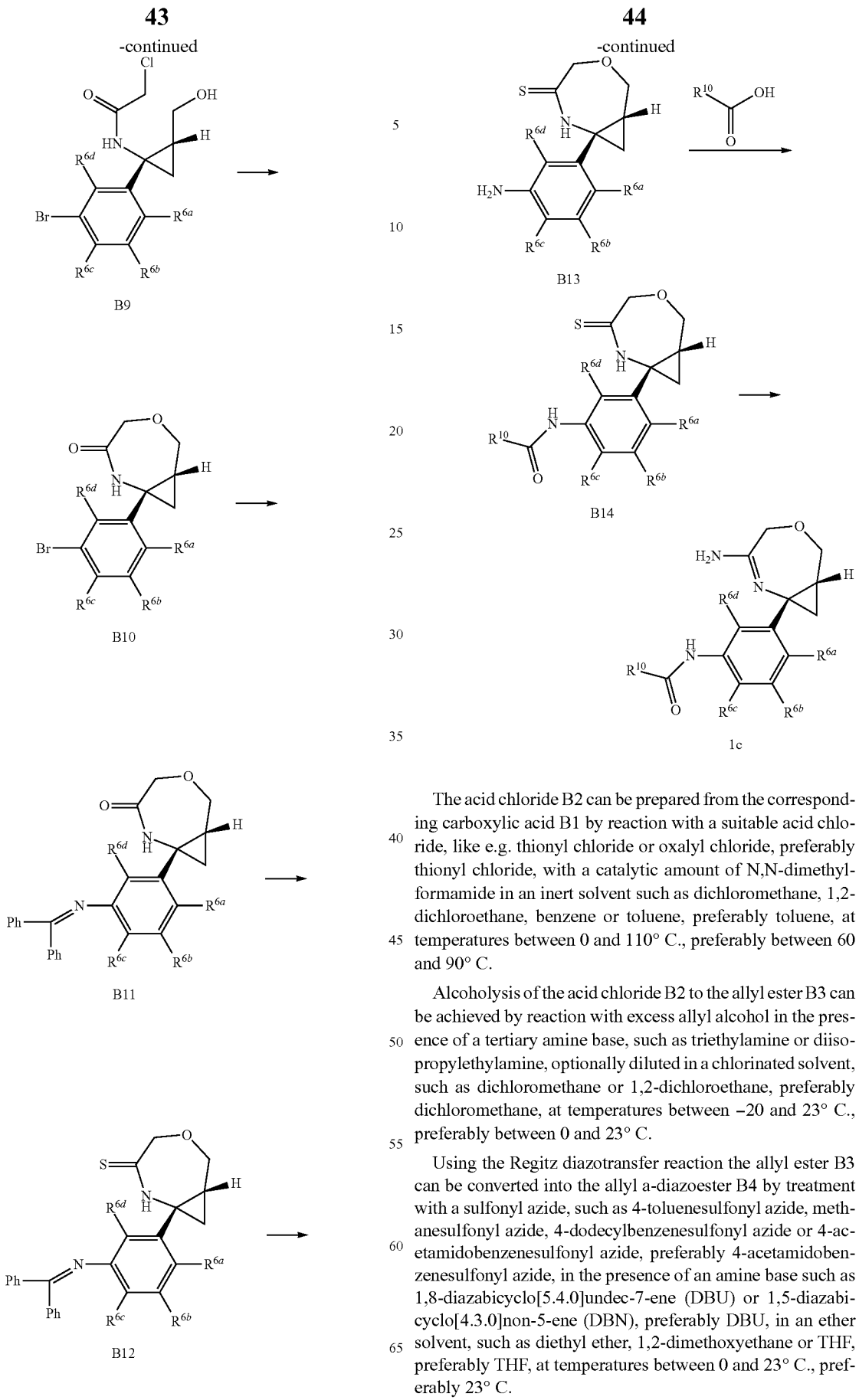

The acid chloride B2 can be prepared from the corresponding carboxylic acid B1 by reaction with a suitable acid chloride, like e.g. thionyl chloride or oxalyl chloride, preferably thionyl chloride, with a catalytic amount of N,N-dimethylformamide in an inert solvent such as dichloromethane, 1,2-dichloroethane, benzene or toluene, preferably toluene, at temperatures between 0 and 110° C., preferably between 60 and 90° C.

Alcoholysis of the acid chloride B2 to the allyl ester B3 can be achieved by reaction with excess allyl alcohol in the presence of a tertiary amine base, such as triethylamine or diisopropylethylamine, optionally diluted in a chlorinated solvent, such as dichloromethane or 1,2-dichloroethane, preferably dichloromethane, at temperatures between −20 and 23° C., preferably between 0 and 23° C.

Using the Regitz diazotransfer reaction the allyl ester B3 can be converted into the allyl α-diazoester B4 by treatment with a sulfonyl azide, such as 4-toluenesulfonyl azide, methanesulfonyl azide, 4-dodecylbenzenesulfonyl azide or 4-acetamidobenzenesulfonyl azide, preferably 4-acetamidobenzenesulfonyl azide, in the presence of an amine base such as 1,8-diazabicyclo[5.4.0]undec-7-ene (DBU) or 1,5-diazabicyclo[4.3.0]non-5-ene (DBN), preferably DBU, in an ether solvent, such as diethyl ether, 1,2-dimethoxyethane or THF, preferably THF, at temperatures between 0 and 23° C., preferably 23° C.

The allyl α-diazoester B4 can be cyclized to the lactone B5 under extrusion of dinitrogen by treatment with a catalytic amount of a transition metal complex, such as copper(I) or copper(II) complexes, like e.g. ((4S,4'S)-4,4',5,5'-tetrahydro-2,2'-methylene-4,4'-dibenzyl-bisoxazole)copper(I) trifluoromethanesulfonate, copper(II)(acetylacetonate)$_2$ or bis(N-tert-butylsalicylaldiminato)copper(II), cobalt(II) complexes, like e.g. (1,3-bis((6aR,7aS)-7,7-dimethyl-6,6a,7,7a-tetrahydro-5H-cyclopropa(h)quinolin-2-imino)-4,5,6,7-tetraphenylisoindol-1-yl)cobalt(II) acetate, ruthenium(I) or ruthenium(II) complexes, like e.g. Ru((1R,2R)-N,N'-bis(2-bromosalicylidene)-1,2-cyclohexanediamine)(PPh$_3$)$_2$, rhodium(II) complexes, like e.g. rhodium (II) acetate dimer, rhodium (II) octanoate dimer, dirhodium(II) tetrakis((R)-N-((4-dodecyl)phenylsulfonyl)prolinate), dirhodium(II) tetrakis(4'-fluorobenzyl 2-azetidinone-4(S)-carboxylate), dirhodium(II) tetrakis(methyl azetidin-2-one-4(S)-carboxylate), preferably rhodium(II) complexes, more preferably rhodium(II) carboxylate dimers, in an inert solvent such as dichloromethane, 1,2-dichloroethane, benzene or toluene, preferably dichloromethane, at temperatures between 0 and 110° C., preferably between 23 and 40° C.

Examples for a similar sequence as described here from acid B1 to lactone B5 and the potential of using a chiral ligand in the rhodium(II) complexes for the generation of an enantiomerically enriched or pure compound has been described several times by Doyle, M. P. et al. in *Org. Lett.* 2000, 2(8), 1145-1147, *Adv. Synth. Catal.* 2001, 343(1), 112-117 and in *Adv. Synth. Catal.* 2001, 343(3), 299-302.

Ring opening of the lactone B5 to the amide B6 can be accomplished by reaction with ammonia in an alcoholic solvent such as methanol or ethanol, preferably methanol, in a sealed vessel at temperatures between 23 and 100° C., preferably at 50 to 60° C.

The Hoffmann rearrangement of the amide B6 to the cyclic carbamate B7 can be achieved by treatment with a hypochlorite or hypobromite solution, preferably hypobromite, in a solvent mixture consisting of water, an alcohol, such as methanol or ethanol, preferably methanol, and an ether, such as diethyl ether, 1,2-dimethoxyethane, 1,4-dioxane or THF, preferably THF, at temperatures between −20 and 23° C., preferably at 23° C. During this reaction the intermediate isocyanate either cyclizes with the hydroxy group to the cyclic carbamate B7 or the corresponding ring openend carbamate (not shown) with the alcohol used as solvent incorporated might be additionally isolated.

The product of the Hoffmann rearrangement B7 can be saponified to the amino alcohol B8 by reaction with an aqueous hydroxide solution, like e.g. lithium hydroxide, sodium hydroxide or potassium hydroxide, preferably lithium hydroxide, in presence of an alcohol such as methanol, ethanol, n-propanol or isopropanol, preferably ethanol, at temperatures between 23 and 120° C., preferably between 80 and 100° C.

Haloacetamide B9, where X is chlorine or bromine, can be prepared by selective acylation of the amino group in amino alcohol B8 with an acid chloride, such as chloro- or bromoacetyl chloride, under biphasic conditions with a suitable mild base, like e.g. saturated aqueous solutions of sodium or potassium hydrogencarbonate, in a solvent such as toluene, ethyl acetate or CH$_2$Cl$_2$, more preferably CH$_2$Cl$_2$ at temperatures between 0 and 23° C.

Cyclisation of the haloacetamide B9 to the lactam B10 can be accomplished by reacting it with a strong base, such as potassium tert-butoxide or potassium tert-amylate, in a solvent such as tert-butanol or tert-amylalcohol, toluene or THF, preferably tert-butanol, at temperatures between 0 and 70° C., preferably at 23° C.

The conversion of the bromophenyl compound B10 to the diphenylmethyl imines B11 can be effected with an imine, e.g benzophenone imine and a base, e.g an metal alkoxyde or more preferably sodium t-butoxide and a palladium complex, e.g. 2-di-t-butylphosphino-2',4',6'-triisopropylbiphenyl and tris(dibenzylideneacetone)dipalladium chloroform adduct in a solvent such as benzene derivative, e.g. toluene, at temperatures between 80 and 120° C., preferably between 90 and 110° C.

The lactam B11 can be converted into the thiolactam B12 by reaction with 2,4-bis-(4-methoxy-phenyl)-[1,3,2,4]dithiadiphosphetane 2,4-disulfide (Lawesson's reagent) or phosphorous pentasulfide in an ether solvent such as THF, 1,2-dimethoxyethane or 1,4-dioxane, preferably 1,4-dioxane, at temperatures between 23 and 100° C., preferably between 50 and 80° C.

The arylated benzophenone imine moiety in the thiolactam B12 can be hydrolyzed to the aniline B13 by aqueous mineral acid such as sulfuric or hydrochloric acid, preferably hydrochloric acid, in an ether solvent such as THF, 1,2-dimethoxyethane or 1,4-dioxane, preferably 1,4-dioxane, at temperatures between 0 and 23° C., preferably at 23° C. The formation of the thiolactam B12 and the following hydrolysis can be conveniently performed in one reaction vessel to yield the aniline B13 directly.

The coupling of the anilines B13 and the acid was achieved by appropriate coupling agents like carbodiimides or uronium salts, such as for example N,N'-carbonyldiimidazole (CDI), N,N'-dicyclohexylcarbodiimide (DCC), N-(3-dimethylaminopropyl)-N'-ethyl-carbodiimide-hydrochloride (EDCI), O-(benzotriazol-1-yl)-N,N,N,N-tetramethyluronium tetrafluoroborate (TBTU) and 1-[bis(dimethylamino)methylene]-1H-1,2,3-triazolo[4,5-b]pyridinium-3-oxide hexafluorophosphate (HATU) under basic conditions, i.e. in the presence of a base, preferably an alkylamine such as diisopropylethylamine (DIEA) or triethylamine (TEA), or a tertiary amine such as N-methylmorpholine or 4-(dimethylamino)-pyridine. The reaction is carried out in a suitable solvent such as for example N,N-dimethylformamide (DMF), dimethylacetamide (DMAc) or dichloromethane (DCM), at temperatures between 0° C. and ambient temperature, to give the amides B14.

The aminooxazepine Ic can be prepared from the thiolactam B14 by reaction with an solution of ammonia in a protic solvent such as methanol, ethanol or water, preferably methanol, with or without presence of a mild oxidant such as tert-butylhydroperoxide at temperatures between 0 and 60° C., preferably at 23° C. in the presence of an oxidant or at 50 to 60° C. in absence of an oxidant.

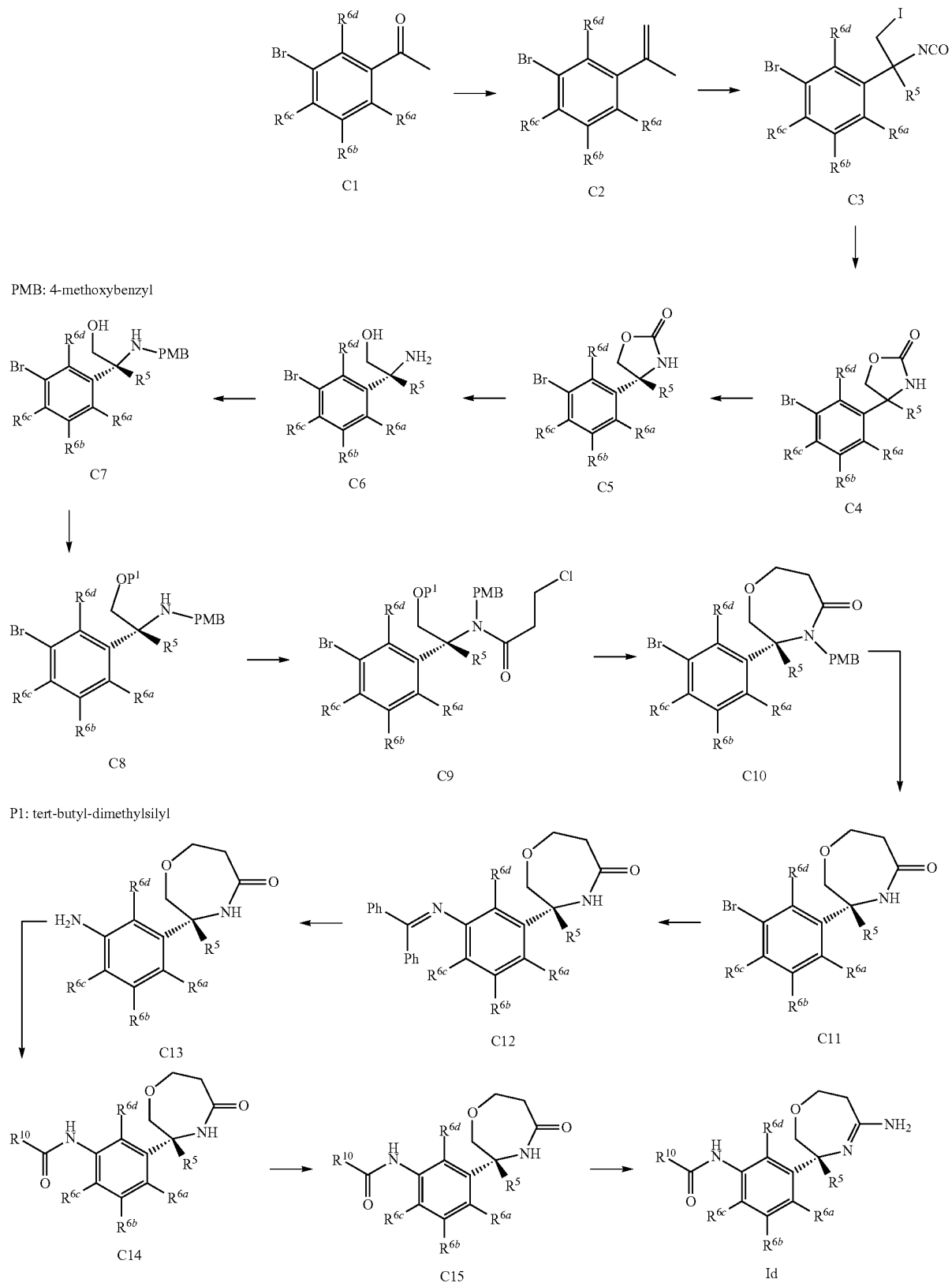

Compounds of formula Id can be obtained as follows: According to scheme C, the formation of a methyltriphenylphosphonium ylide produced by strong base such as butyllithium in solvents such as tetrahydrofuran or toluene at temperatures between −78° C. and 0° C. followed by addition of the ketone of formula C1 yields the desired alkene of formula C2.

The alkene of formula C2 can then be reacted with a mixture of silver cyanate and iodine in solvents such as diethyl ether or mixtures of ethyl acetate and acetonitrile. The resultant iodoisocyanate of formula C3 can then be heated with alcohols like tert-butanol and a base like triethylamine or Huenig's base, optionally in presence of silver tetrafluoroborate, to yield the oxazolidinone of formula C4.

Due to their solubility, oxazolidinones of formula C4 represent a preferred intermediate for the separation of enantiomers on chiral phase to yield the enatiomer of formula C5 and its optical antipode.

Hydrolysis of the resultant oxazolidinone of formula C5 with aqueous base like lithium hydroxide yields the aminoalcohol of formula C6.

Selective N-protection of the aminoalcohol of formula C6 can be effected by reductive amination with benzaldehydes, preferably with 4-methoxybenzaldehyde, in presence of reducing agents like sodium borohydride or sodium cyano borohydride, preferably sodium triacetoxyborohydride to give the amine of formula C7.

Advantageously, the O-protection of compound C7 can be effected by a silyl group, eg. tert-butyldimethylsilyl, cleavable by fluoride which at the same time can later on act as a base in the cyclisation step of compounds of formula C9 to yield compounds of formula C10.

Beforehand, the N-acylation of the diprotected aminoalcohol of formula C8 can be effected by condensation with halogenated propionic acid derivatives, preferably with 3-chloropropanoyl chloride using Schotten-Baumann conditions with e.g. chloroform as the organic solvent and sodium hydrogen carbonate as the aqueous base to form the biphasic system to yield the amide of formula C9.

Cleavage of the N-protecting group of compound C10 can be accomplished preferably by strong acid, e.g. trifluoromethanesulfonic acid, in presence of anisole and with trifluoroacetic acid as the solvent to yield the lactam of formula C11.

For the further transformation to the aniline derivative of formula C13, Pd(0)-catalyzed amination reactions of aryl halides can be applied wherein as ammonia equivalents lithium bis(trimethylsilyl)amide, triphenylsilylamine, or benzophenone imine are used as described in the art (Organic Letters, 2001, 3(21), 3417-3419 or Bioorganic & Medicinal Chemistry Letters 14(2004), 6011-6016). In scheme C, the reaction leading to the benzophenone imine derivative of formula C12 is exemplified as well as its cleavage under acidic conditions to yield the aniline derivative of formula C13.

The synthesis of the amide of formula C14 can be performed by standard procedures, such as e.g. by reaction with activated acyl derivatives, e.g. acyl halides or anhydrides, or by condensation reactions of the acid using as condensation reagent carbodiimides, e.g. 1-(3-dimethylaminopropyl)-3-ethylcarbodiimide, or benzotriazol derivatives, e.g. O-(benzotriazol-1-yl)-N,N,N',N'-tetramethyluronium-hexafluoro-phosphate (HBTU) and the like known to those skilled in the art.

The iminoether of formula C15 can be obtained by treatment of the lactam of formula C14 with alkyl oxonium salts, e.g. trimethyloxonium tetrafluoroborate or triethyloxonium tetrafluoroborate.

Treatment of the iminoether of formula C15 with ammonium salts such as ammonium chloride in polar solvents like alcohols, e.g. methanol, yields the final compound of formula Id.

In a further aspect, the present invention relates to a compound of formula I, as defined herein before, for use as therapeutically active substance or medicament.

The present invention relates to a compound of formula I for use as inhibitor of BACE1 and/or BACE2 activity. Thus, in one aspect, the invention relates to compounds of formula I, as defined in any of the paragraphs before, for the use in inhibition of BACE1 activity. In a further aspect, the invention is concerned with compounds of formula I, as defined in any of the paragraphs before, for the use in inhibition of BACE2 activity. In another aspect, the invention refers to compounds of formula I, as defined in any of the paragraphs before, for the use in inhibition of BACE1 and BACE2 activity. In yet another aspect, the invention relates to compounds of formula I, as defined in any of the paragraphs before, for the use in inhibition of BACE1 or BACE2 activity.

As described herein before, the compounds of formula I of the present invention can be used for the therapeutic and/or prophylactic treatment of diseases which can be ameliorated with the inhibition of BACE1 and/or BACE2 activity. As defined below, such diseases include diseases and disorders characterized by elevated β-amyloid levels and/or β-amyloid oligomers and/or β-amyloid plaques and further deposits, particularly Alzheimer's disease, and diabetes, particularly type 2 diabetes, and other metabolic disorders. The use for the therapeutic and/or prophylactic treatment of Alzheimer's disease and/or type 2 diabetes is of particular interest.

In one aspect, the compounds of formula I of the present invention can be used for the therapeutic and/or prophylactic treatment of diseases which can be ameliorated with the inhibition of BACE1 activity. 'Diseases which can be ameliorated with the inhibition of BACE1 activity' are diseases and disorders characterized by elevated β-amyloid levels and/or β-amyloid oligomers and/or β-amyloid plaques and further deposits, particularly Alzheimer's disease.

In particular, the present invention relates to a compound of formula I, as defined in any of the paragraphs before, for the use as therapeutically active substance for the therapeutic and/or prophylactic treatment of Alzheimer's disease.

In another aspect of the invention, the compounds of formula I of the present invention can be used for the therapeutic and/or prophylactic treatment of diseases which can be ameliorated with the inhibition of BACE2 activity.

As described herein before, the compounds of formula I of the invention will be useful in preserving and restoring beta-cell function and stimulating insulin secretion in diabetic patients and in non-diabetic patients who have impaired glucose tolerance or who are in a pre-diabetic condition. They may be useful in treating type 1 diabetes or in delaying or preventing a patient with type 2 diabetes from needing insulin therapy. The compounds of formula I are further useful to ameliorate hyperinsulinemia, which often occurs in diabetic or pre-diabetic patients and in reducing the risks associated with metabolic syndrome, they may also be useful in treating vascular diseases such as hypertension.

Thus, the expression 'diseases which can be ameliorated with the inhibition of BACE2 activity' means diseases such as metabolic and cardiovascular diseases, in particular diabetes, more particularly type 2 diabetes, gestational diabetes, impaired fasting glucose, impaired glucose tolerance, insulin resistance, pre-diabetes, metabolic syndrome, diabetes type 1, complications of diabetes including diabetic nephropathy, diabetic retinopathy and diabetic neuropathy, chronic kidney disease, dyslipidemia, atherosclerosis, myocardial infarction, hypertension and further metabolic and cardiovascular disorders.

In particular, the expression 'diseases which can be ameliorated with the inhibition of BACE2 activity' relates to diabetes, particularly type 2 diabetes, impaired glucose tolerance, pre-diabetes, metabolic syndrome and hypertension. More particularly, the expression 'diseases which are associated with the inhibition of BACE2 activity' relates to diabetes, particularly type 2 diabetes.

In particular, the present invention relates to a compound of formula I, as defined in any of the paragraphs before, for the use as therapeutically active substance for the therapeutic and/or prophylactic treatment of type 2 diabetes.

The invention also relates to pharmaceutical compositions comprising a compound of formula I as defined above as an active ingredient and a pharmaceutically acceptable carrier and/or a pharmaceutically acceptable auxiliary substance. More specifically, the invention relates to pharmaceutical compositions comprising a compound of formula I useful for the therapeutic and/or prophylactic treatment of diseases which can be ameliorated with the inhibition of BACE1 and/or BACE2 activity.

The invention further relates to the use of a compound of formula I as defined herein before for the manufacture of a medicament for the therapeutic and/or prophylactic treatment of diseases which can be ameliorated with the inhibition of BACE1 and/or BACE2 activity, in particular for the therapeutic and/or prophylactic treatment of diseases and disorders characterized by elevated β-amyloid levels and/or β-amyloid oligomers and/or β-amyloid plaques and further deposits, particularly Alzheimer's disease, and diabetes, particularly type 2 diabetes, and other metabolic disorders.

In one aspect, the invention is concerned with the use of a compound of formula I for the manufacture of a medicament for the therapeutic and/or prophylactic treatment of diseases which can be ameliorated with the inhibition of BACE1 activity. In particular, the invention relates to use of a compound of formula I for the manufacture of a medicament for the therapeutic and/or prophylactic treatment of diseases and disorders characterized by elevated β-amyloid levels and/or β-amyloid oligomers and/or β-amyloid plaques and further deposits, particularly Alzheimer's disease.

In another aspect, the invention is concerned with the use of a compound of formula I for the manufacture of a medicament for the therapeutic and/or prophylactic treatment of diseases which can be ameliorated with the inhibition of BACE2 activity. In particular, the invention relates to use of a compound of formula I for the manufacture of a medicament for the therapeutic and/or prophylactic treatment of diabetes, particularly type 2 diabetes.

In another aspect, the invention relates to a method for the therapeutic and/or prophylactic treatment of diseases which can be ameliorated with the inhibition of BACE1 and/or BACE2 activity, which method comprises administering a therapeutically active amount of a compound of formula I to a human being or animal. In particular, such method relates to the therapeutic and/or prophylactic treatment of diseases and disorders characterized by elevated β-amyloid levels and/or β-amyloid oligomers and/or β-amyloid plaques and further deposits, particularly Alzheimer's disease, and diabetes, particularly type 2 diabetes, and other metabolic disorders.

The invention further relates to the use of compounds of formula I as defined above for the therapeutic and/or prophylactic treatment of diseases which can be ameliorated with the inhibition of BACE1 and/or BACE2 activity.

Pharmacological Tests

The compounds of formula I and their pharmaceutically acceptable salts possess valuable pharmacological properties. It has been found that the compounds of the present invention are associated with inhibition of BACE1 and/or BACE2 activity. The compounds were investigated in accordance with the tests given hereinafter.

Cellular Aβ-Lowering Assay:

Human HEK293 cells which are stably transfected with a vector expressing a cDNA of the human APP wt gene (APP695) were used to assess the potency of the compounds in a cellular assay. The cells were seeded in 96-well microtiter plates in cell culture medium (Iscove, plus 10% (v/v) fetal bovine serum, glutamine, penicillin/streptomycin) to about 80% confluence and the compounds were added at a 10× concentration in $\frac{1}{10}$ volume of medium without FCS containing 8% DMSO (final concentration of DMSO was kept at 0.8% v/v). After 18-20 hrs incubation at 37° C. and 5% $CO_2$ in a humidified incubator the culture supernatant was harvested for the determination of Aβ40 concentrations. 96well ELISA plates (e.g., Nunc MaxiSorb) were coated with monoclonal antibody which specifically recognize the C-terminal end of Aβ40 (Brockhaus et al., NeuroReport 9, 1481-1486; 1998). After blocking of non-specific binding sites with e.g. 1% BSA and washing, the culture supernatants were added in suitable dilutions together with a horseradish peroxidase-coupled Aβ detection antibody (e.g., antibody 4G8, Senetek, Maryland Heights, Mo.) and incubated for 5 to 7 hrs. Subsequently the wells of the microtiter plate were washed extensively with Tris-buffered saline containing 0.05% Tween 20 and the assay was developed with tetramethylbenzidine/ $H_2O_2$ in citric acid buffer. After stopping the reaction with one volume 1 N $H_2SO_4$ the reaction was measured in an ELISA reader at 450 nm wavelength. The concentrations of Aβ in the culture supernatants were calculated from a standard curve obtained with known amounts of pure Aβ peptide.

Assay for BACE Inhibition by Measuring Cellular TMEM27 Cleavage:

The assay uses the principle of inhibition of human TMEM27 cleavage by endogenous cellular BACE2 in the Ins1e rat cell line and shedding from the cell surface into the culture medium, followed by detection in an ELISA assay. Inhibition of BACE2 prevents the cleavage and shedding in a dose-dependent manner.

The stable cell line "INS-TMEM27" represents an INS1e-derived cell line with inducible expression (using the TetOn system) of full-length hTMEM27 in a doxycycline-dependent manner. The cells are cultured throughout the experiment in RPMI1640+ Glutamax (Invitrogen) Penicillin/Streptomycin, 10% Fetal bovine serum, 100 mM pyruvate, 5 mM beta-mercatptoethanol, 100 micrograms/ml G418 and 100 microgram/ml hygromycin and are grown inadherent culture at 37° C. in a standard $CO_2$ cell culture incubator.

INS-TMEM27 cells are seeded in 96-well plates. After 2 days in culture, BACE2 inhibitor is added in a range of concentrations as required by the assay and after a further two hours, doxycycline is added to a final concentration of 500 ng/ml. The cells are incubated for a further 46 hours and the supernatant harvested for detection of shed TMEM27.

An ELISA assay (using a pair of mouse anti-human-TMEM27 antibodies, raised against the extracellular domain of TMEM27) is used for detection of TMEM27 in the culture medium. An $EC_{50}$ for BACE2 inhibition is calculated using the ELISA readout for each inhibitor concentration with standard curve-fitting software such as XLFit for the Excel spreadsheet program.

Immunofluorescence Resonance Energy Transfer (FRET) Assay for BACE2 Inhibition:

BACE2 enzyme ectodomain (derived from plasmid "pET17b-T7-hu proBACE2") was prepared as described in Ostermann et al., "Crystal Structure of Human BACE2 in Complex with a Hydroxyethylamine Transition-state Inhibitor", Journal of Molecular Biology 2006, 355, 249-261. The pro-enzyme was stored at 4° C. at a concentration of 70 μg/ml.

The FRET assay was performed essentially as described in Grüninger-Leitch et al., Journal of Biological Chemistry (2002) 277(7) 4687-93 ("Substrate and inhibitor profile of BACE (beta-secretase) and comparison with other mammalian aspartic proteases"). In summary, a peptide is designed that is cleaved by the protease. The peptide is labelled with dabcyl at the N terminus and Lucifer Yellow at the C-terminus, such that for an intact peptide the Lucifer Yellow fluorescence is quenched by the dabcyl. When the peptide is cut by BACE2, the quenching is removed and a fluorescent signal is generated.

The assay was performed as described in Grueninger et al. 2002 at pH 4.5 using a substrate concentration of 5 μM. A FRET peptide based on the TMEM27 sequence was devised. dabcyl—QTLEFLKIPS—LucY. BACE2 had a high activity against this sequence, which is unrelated to the known APP-based substrates. Conversely, BACE1 had insignificant activity against this peptide.

The assay readout is the initial rate of change of fluorescence intensity giving a relative measure of BACE2 activity. Small values correspond to high inhibition and larger values to low inhibition. To determine $IC_{50}$ values (i.e. the concentration inhibiting the enzyme activity by 50%) of the compound for BACE2, typically, 12 assays were made with a range of concentrations chosen empirically to give low, high and intermediate inhibition of the protease. $IC_{50}$ values were determined using these assay values generated for a range of inhibitor concentrations and the curve fitting software XLfit (IDBS) using the Sigmoidal Dose-Response Model.

The preferred compounds according to formula I have an inhibitory activity in the above assay ($IC_{50}$) preferably of 5 nM to 50 μM, more preferably of 5 nM to 1 μM.

For example, the following compounds showed the following $IC_{50}$ values in the assay described above:

| Example | Cellular assay TMEM27 $IC_{50}$ [μM] | Cellular assay Abeta40 $IC_{50}$ [μM] |
| --- | --- | --- |
| 1 | 11.06 | 0.073 |
| 2 | >10.00 | 2.197 |
| 3 | 0.245 | 0.034 |
| 4 | 8.9 | 0.63 |
| 5 | 0.000885 | 0.0009 |
| 6 | 0.0036 | 0.036 |
| 7 | 0.00145 | 0.016 |
| 8 | 0.0018 | 0.0025 |
| 9 | 0.01 | 0.0016 |
| 10 | 0.0016 | 0.0011 |
| 11 | 0.002 | 0.0021 |
| 12 | 0.12 | 0.009 |
| 13 | 0.044 | 0.25 |
| 14 | 0.0695 | 0.093 |
| 15 | 0.038 | 0.88 |
| 16 | 0.0135 | 0.014 |
| 17 | 0.4 | 0.92 |
| 18 | 0.12 | 0.022 |
| 19 | 0.056 | 0.44 |
| 20 | 0.038 | 0.22 |
| 21 | 0.0087 | 0.0032 |
| 22 | 0.055 | 0.98 |
| 23 | 0.14 | 1.64 |
| 24 | 0.028 | 5.87 |
| 25 | 0.051 | 0.007 |
| 26 | 0.0053 | 0.0013 |
| 27 | 0.058 | 0.044 |
| 28 | 0.13 | 0.34 |
| 29 | 0.0033 | 0.0053 |
| 30 | 0.043 | 0.0021 |
| 31 | 0.0026 | 0.001 |
| 32 | 0.0044 | 0.0045 |
| 33 | 0.24 | 0.09 |
| 34 | 0.38 | 0.076 |
| 35 | 0.029 | 0.014 |
| 36 | 0.0084 | 0.038 |
| 37 | 0.025 | 0.054 |
| 38 | 0.17 | 0.055 |
| 39 | 0.003 | 0.0026 |
| 40 | 0.0062 | 0.0059 |
| 41 | 0.003 | 0.0072 |
| 42 | 0.0024 | 0.0074 |
| 43 | 0.0047 | 0.023 |
| 44 | 0.0012 | 0.0024 |
| 45 | 0.011 | 0.011 |
| 46 | 0.0065 | 0.0017 |
| 47 | 0.046 | 0.058 |
| 48 | 0.088 | 0.001 |
| 49 | 1.11 | 0.022 |
| 50 | 0.071 | 0.16 |
| 51 | 8.59 | 0.1 |
| 52 | 0.12 | 0.049 |
| 53 | 0.041 | 0.01 |
| 54 | 0.57 | 0.029 |
| 55 | 0.19 | 0.14 |
| 56 | 0.0156 | 0.0015 |
| 57 | 0.28 | 0.014 |
| 58 | 0.139 | 0.12 |
| 59 | 0.17 | 0.16 |
| 60 | 4.16 | 0.026 |
| 61 | 0.001 | 0.0002 |
| 62 | 0.001 | 0.0018 |
| 63 | 0.091 | 0.0003 |
| 64 | 0.400 | 0.36 |
| 65 | 0.056 | 0.048 |
| 66 | 0.05444 | 0.0153 |
| 67 | 67.4 | 0.2881 |
| 68 | 5.24908 | 3.85 |
| 69 | 142.1 | 5.07 |
| 70 | 0.17162 | 0.0052 |
| 71 | 12.4 | 1.5 |
| 72 | 2.43721 | 0.59 |
| 73 | 6.51529 | 0.3 |
| 74 | 3.38 | 0.01 |
| 75 | 0.08976 | 0.41 |
| 76 | 0.56831 | 0.004 |
| 77 | 0.17856 | 0.75 |
| 78 | 0.0743 | 0.06 |
| 79 | 0.06708 | 0.07 |
| 80 | 0.05591 | 0.023 |
| 81 | 420.6 | 5.68 |
| 82 | 0.03617 | 0.04 |
| 83 | 0.01969 | 0.015 |
| 84 | 0.06022 | 0.13 |
| 85 | 0.02925 | 0.28 |
| 86 | 0.49082 | 0.37 |
| 87 | 0.13403 | 1.12 |
| 88 | 0.35381 | 0.005 |
| 89 | 5.76 | 29.3 |
| 90 | 0.0853 | 0.005 |
| 91 | 0.4534 | 1.23 |
| 92 | 0.73094 | 2.8 |
| 93 | 155 | 0.51 |
| 94 | 0.02427 | 0.01 |

-continued

| Example | Cellular assay TMEM27 IC$_{50}$ [µM] | Cellular assay Abeta40 IC$_{50}$ [µM] |
|---|---|---|
| 95 | 0.06631 | 0.022 |
| 96 | 0.2953 | 0.057 |
| 97 | 0.44372 | 0.22 |
| 98 | 0.13113 | 0.039 |
| 99 | 0.11839 | 0.13 |
| 100 | 0.51609 | 2.8 |
| 101 | 1.11367 | 0.012 |
| 102 | 2.20412 | 0.033 |
| 103 | 0.307 | 0.0029 |
| 104 | 0.09559 | 0.16 |
| 105 | 0.37798 | 0.013 |
| 106 | 2.16749 | 0.63 |
| 107 | 0.88577 | 0.79 |
| 108 | 0.04955 | 0.0057 |
| 109 | 0.14301 | 0.0019 |
| 110 | 0.00903 | 0.0008 |
| 111 | 0.03051 | 0.0007 |
| 112 | 0.129 | 0.069 |
| 113 | 0.12282 | 0.0358 |
| 114 | 0.00968 | 0.0049 |
| 115 | 0.006 | 0.0038 |
| 116 | 0.189 | 0.02 |
| 117 | 30.04 | 0.034 |
| 118 | 14.84 | 0.34 |
| 119 | 0.00903 | 0.0008 |

Pharmaceutical Compositions

The compounds of formula I and the pharmaceutically acceptable salts can be used as therapeutically active substances, e.g. in the form of pharmaceutical preparations. The pharmaceutical preparations can be administered orally, e.g. in the form of tablets, coated tablets, dragés, hard and soft gelatin capsules, solutions, emulsions or suspensions. The administration can, however, also be effected rectally, e.g. in the form of suppositories, or parenterally, e.g. in the form of injection solutions.

The compounds of formula I and the pharmaceutically acceptable salts thereof can be processed with pharmaceutically inert, inorganic or organic carriers for the production of pharmaceutical preparations. Lactose, corn starch or derivatives thereof, talc, stearic acids or its salts and the like can be used, for example, as such carriers for tablets, coated tablets, dragées and hard gelatin capsules. Suitable carriers for soft gelatin capsules are, for example, vegetable oils, waxes, fats, semi-solid and liquid polyols and the like. Depending on the nature of the active substance no carriers are however usually required in the case of soft gelatin capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical preparations can, moreover, contain pharmaceutically acceptable auxiliary substances such as preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

Medicaments containing a compound of formula I or a pharmaceutically acceptable salt thereof and a therapeutically inert carrier are also an object of the present invention, as is a process for their production, which comprises bringing one or more compounds of formula I and/or pharmaceutically acceptable salts thereof and, if desired, one or more other therapeutically valuable substances into a galenical administration form together with one or more therapeutically inert carriers.

The dosage can vary within wide limits and will, of course, have to be adjusted to the individual requirements in each particular case. In the case of oral administration the dosage for adults can vary from about 0.01 mg to about 1000 mg per day, especially from about 1 to 500 mg per day, of a compound of formula I or of the corresponding amount of a pharmaceutically acceptable salt thereof. Depending on severity of the disease and the precise pharmacokinetic profile of the compound, the daily dosage may be administered as single dose or in divided doses and, in addition, the upper limit can also be exceeded when this is found to be indicated.

The following examples illustrate the present invention without limiting it, but serve merely as representative thereof Examples of compositions according to the invention are:

EXAMPLE A

Tablets of the following composition are manufactured in the usual manner:

TABLE 1 possible tablet composition

| ingredient | mg/tablet | | | |
|---|---|---|---|---|
| | 5 | 25 | 100 | 500 |
| Compound of formula I | 5 | 25 | 100 | 500 |
| Lactose Anhydrous DTG | 125 | 105 | 30 | 150 |
| Sta-Rx 1500 | 6 | 6 | 6 | 60 |
| Microcrystalline Cellulose | 30 | 30 | 30 | 450 |
| Magnesium Stearate | 1 | 1 | 1 | 1 |
| Total | 167 | 167 | 167 | 831 |

Manufacturing Procedure:
1. Mix ingredients 1, 2, 3 and 4 and granulate with purified water.
2. Dry the granules at 50° C.
3. Pass the granules through suitable milling equipment.
4. Add ingredient 5 and mix for three minutes; compress on a suitable press.

EXAMPLE B-1

Capsules of the following composition are manufactured:

TABLE 2 possible capsule ingredient composition

| ingredient | mg/capsule | | | |
|---|---|---|---|---|
| | 5 | 25 | 100 | 500 |
| Compound of formula I | 5 | 25 | 100 | 500 |
| Hydrous Lactose | 159 | 123 | 148 | — |
| Corn Starch | 25 | 35 | 40 | 70 |
| Talk | 10 | 15 | 10 | 25 |
| Magnesium Stearate | 1 | 2 | 2 | 5 |
| Total | 200 | 200 | 300 | 600 |

Manufacturing Procedure:
1. Mix ingredients 1, 2 and 3 in a suitable mixer for 30 minutes.
2. Add ingredients 4 and 5 and mix for 3 minutes.
3. Fill into a suitable capsule.

The compound of formula I, lactose and corn starch are firstly mixed in a mixer and then in a comminuting machine. The mixture is returned to the mixer, the talc is added thereto and mixed thoroughly. The mixture is filled by machine into suitable capsules, e.g. hard gelatin capsules.

EXAMPLE B-2

Soft Gelatin Capsules of the following composition are manufactured:

TABLE 3 possible soft gelatin capsule ingredient composition

| ingredient | mg/capsule |
|---|---|
| Compound of formula I | 5 |
| Yellow wax | 8 |
| Hydrogenated Soya bean oil | 8 |
| Partially hydrogenated plant oils | 34 |
| Soya bean oil | 110 |
| Total | 165 |

TABLE 4 possible soft gelatin capsule composition

| ingredient | mg/capsule |
|---|---|
| Gelatin | 75 |
| Glycerol 85% | 32 |
| Karion 83 | 8 (dry matter) |
| Titan dioxide | 0.4 |
| Iron oxide yellow | 1.1 |
| Total | 116.5 |

Manufacturing Procedure

The compound of formula I is dissolved in a warm melting of the other ingredients and the mixture is filled into soft gelatin capsules of appropriate size. The filled soft gelatin capsules are treated according to the usual procedures.

EXAMPLE C

Suppositories of the following composition are manufactured:

TABLE 5 possible suppository composition

| ingredient | mg/supp. |
|---|---|
| Compound of formula I | 15 |
| Suppository mass | 1285 |
| Total | 1300 |

Manufacturing Procedure

The suppository mass is melted in a glass or steel vessel, mixed thoroughly and cooled to 45° C. Thereupon, the finely powdered compound of formula I is added thereto and stirred until it has dispersed completely. The mixture is poured into suppository moulds of suitable size, left to cool, the suppositories are then removed from the moulds and packed individually in wax paper or metal foil.

EXAMPLE D

Injection solutions of the following composition are manufactured:

TABLE 6 possible injection solution composition

| ingredient | mg/injection solution. |
|---|---|
| Compound of formula I | 3 |
| Polyethylene Glycol 400 | 150 |
| acetic acid | q.s. ad pH 5.0 |
| water for injection solutions | ad 1.0 ml |

Manufacturing Procedure

The compound of formula I is dissolved in a mixture of Polyethylene Glycol 400 and water for injection (part). The pH is adjusted to 5.0 by acetic acid. The volume is adjusted to 1.0 ml by addition of the residual amount of water. The solution is filtered, filled into vials using an appropriate overage and sterilized.

EXAMPLE E

Sachets of the following composition are manufactured:

TABLE 7 possible sachet composition

| ingredient | mg/sachet |
|---|---|
| Compound of formula I | 50 |
| Lactose, fine powder | 1015 |
| Microcrystalline cellulose (AVICEL PH 102) | 1400 |
| Sodium carboxymethyl cellulose | 14 |
| Polyvinylpyrrolidone K 30 | 10 |
| Magnesium stearate | 10 |
| Flavoring additives | 1 |
| Total | 2500 |

Manufacturing Procedure

The compound of formula I is mixed with lactose, microcrystalline cellulose and sodium carboxymethyl cellulose and granulated with a mixture of polyvinylpyrrolidone in water. The granulate is mixed with magnesium stearate and the flavoring additives and filled into sachets.

EXAMPLES

General:

MS: Mass spectra (MS) were measured either with ion spray positive or negative (ISP or ISN) method on a Perkin-Elmer SCIEX API 300 or with electron impact method (EI, 70 eV) on a Finnigan MAT SSQ 7000 spectrometer.

Abbreviations:

DCC=N,N'-diisopropyl-carbodiimide, DCE=1,2-dichloroethane, DCM=dichloromethane, DIEA=diisopropylethylamine, DMAc=dimethylacetamide, DMAP=4-dimethylaminopyridine, DMF=N,N-dimethylformamide, DMSO=dimethyl sulfoxide, EDCI=N-(3-dimethylaminopropyl)-N'-ethyl-carbodiimide hydrochloride, HATU=1-[bis(dimethylamino)methylene]-1H-1,2,3-triazolo[4,5-b]pyridinium-3-oxide hexafluorophosphate, HCl=hydrogen chloride, HPLC=high performance liquid chromatography, LDA=lithium diisopropylamide, MS=mass spectrum, NMR=nuclear magnetic resonance, TEA=triethylamine, TBME=tert-butyl methyl ether, and THF=tetrahydrofuran.

The following examples 1-65 are provided for illustration of the invention. They should not be considered as limiting the scope of the invention, but merely as being representative thereof Synthesis of the intermediate
1-(2-fluoro-5-nitro-phenyl)-propan-1-one A1A

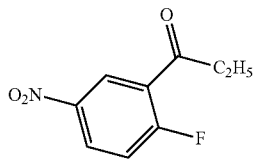 [SMILES: CCC(=O)c1cc([N+](=O)[O-])ccc1F]

To a solution of the 1-(2-fluoro-phenyl)-propan-1-one (99 mmol) in concentrated sulfuric acid (80 ml) cooled down to −30° C. was added slowly fuming nitric acid (8 ml) over 20 min and the solution was stirred at −30° C. for 15 min. The mixture was slowly poured into a stirred mixture of 200 ml of water and 400 g ice. The aqueous phase was extracted with ethyl acetate, the organic layer was extracted again with water and aqueous $NaHCO_3$ 1M. The organic layer was dried over $Na_2SO_4$, evaporated and the residue was purified by chromatography on silica using a mixture of heptane and ethylacetate as eluent to afford the pure nitro intermediate J. MS (ISP): m/z=198.1 [M+H]+.

Synthesis of the Intermediate Sulfinyl Imines A2

General Procedure

To a solution of the (R)-(+)-tert-butylsulfinamide (66 mmol) in THF (350 ml) was added subsequently the ketone A1 (72.6 mmol) and titanium(IV)ethoxide (132 mmol) and the solution was stirred at reflux temperature for 5 h. The mixture was cooled to 22° C., treated with brine (400 ml), the suspension was stirred for 10 min and filtered over dicalite. The layers were separated, the aqueous layer was extracted with ethyl acetate, the combined organic layers were washed with water, dried and concentrated in vacuo. The residue was purified by chromatography on silica using cylohexane/ethyl acetate to give the pure sulfinyl imine A2.

Intermediate A2A

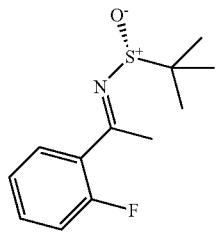 [SMILES: C/C(=N\[S@+]([O-])C(C)(C)C)c1ccccc1F]

Starting from 1-(2-fluorophenyl)-ethanone, the product (R)-2-methyl-propane-2-sulfinic acid [1-(2-fluorophenyl)-(E)-ethylidene]-amide was obtained as pale brown oil. MS (ISP): m/z=242.3 [M+H]−.

Intermediate A2B

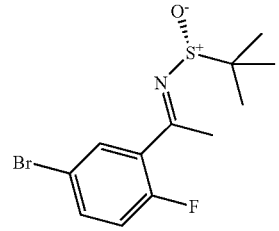 [SMILES: C/C(=N\[S@+]([O-])C(C)(C)C)c1cc(Br)ccc1F]

Starting from commercially available 1-(2-fluoro-5-bromo-phenyl)-ethanone [CAS No. 477-89-3], the product (R)-2-methyl-propane-2-sulfinic acid [1-(2-fluoro-5-bromo-phenyl)-(E)-ethylidene]-amide was obtained as a pale red oil. MS (ISP): m/z=320.3 [M+H]+.

Intermediate A2C

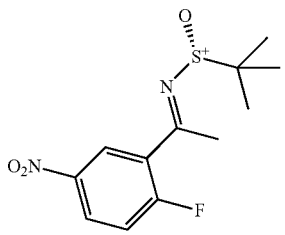 [SMILES: C/C(=N\[S@+](O)C(C)(C)C)c1cc([N+](=O)[O-])ccc1F]

Starting from 2'-fluoro-5'-nitroacetophenone, the product (R)-2-methyl-propane-2-sulfinic acid [1-(2-fluoro-5-nitro-phenyl)-(E)-ethylidene]-amide was obtained as a pale red oil. MS (ISP): m/z=287.2 [M+H]+.

Intermediate A2D

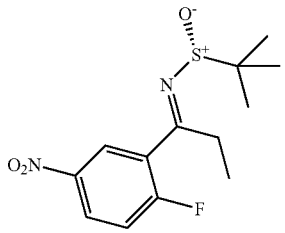 [SMILES: CC/C(=N\[S@+]([O-])C(C)(C)C)c1cc([N+](=O)[O-])ccc1F]

Starting from 1-(2-fluoro-5-nitro-phenyl)-propan-1-one, the product (R)-2-methyl-propane-2-sulfinic acid [1-(2-fluoro-5-nitro-phenyl)-prop-(E)-ylidene]-amide was obtained as pale red oil. MS (ISP): m/z=301.3 [M+H]+.

Intermediate A2E

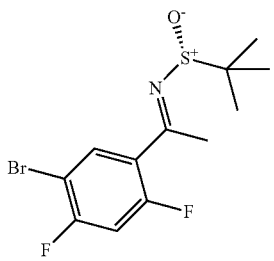 [SMILES: C/C(=N\[S@+]([O-])C(C)(C)C)c1cc(Br)c(F)cc1F]

Starting from commercially available 1-(5-bromo-2,4-difluorophenyl)-ethanone [CAS No. 864773-64-8] the product 2-methyl-propane-2-sulfinic acid [1-(5-bromo-2,4-difluorophenyl)-eth-(E)-ylidene]-amide was obtained as a pale red oil. MS (ISP): m/z=338.1 [M+H]⁺ and 340.1 [M+2+H]⁺.

Intermediate A2F

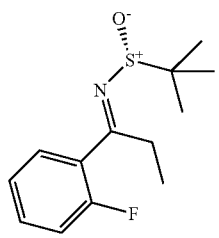 [SMILES: CC/C(=N\[S@+]([O-])C(C)(C)C)c1ccccc1F]

Starting from 1-(2-fluoro-phenyl)-propan-1-one, the product 2-methyl-propane-2-sulfinic acid [1-(2-fluoro-phenyl)-prop-(E)-ylidene]-amide was obtained as pale yellow oil. MS: m/z=256.2 [M+H]⁻.

Synthesis of the Intermediate Sulfinamide Esters A3

General Procedure (via Reformatsky Reaction)

In a dry apparatus a suspension of freshly activated zinc powder (1.63 g, 24.9 mmol) in dry THF (70 ml) was heated under inert atmosphere to reflux. A solution of the sulfinyl imine A2 (24.9 mmol) and the bromo-acetate (24.9 mmol) in dry THF (15 ml) was added dropwise over a period of 15 min and the suspension was heated to reflux for 5 h. The cooled mixture was partitioned between aqueous saturated NH₄Cl and ethyl acetate, the organic layer was dried and evaporated. The crude material was purified by flash chromatography using heptane/ethyl acetate to give the sulfinamide ester A3.

Intermediates A3A and A3B

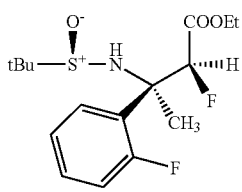

A3A

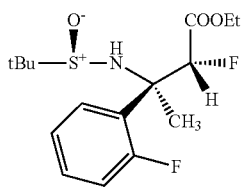

A3B

Starting from (R)-2-methyl-propane-2-sulfinic acid [1-(2-fluorophenyl)-(E)-ethylidene]-amide and ethyl 2-bromo-2-fluoroacetate, the faster eluting minor isomer (2S,3R)-ethyl 3-((R)-1,1-dimethylethylsulfinamido)-2-fluoro-3-(2-fluorophenyl)butanoate (intermediate A3A) was obtained as a dark brown oil. MS (ISP): m/z=348.2 [M+H]⁺.

The second fraction contained the slower eluting major isomer (2R,3R)-ethyl 3-((R)-1,1-dimethylethylsulfinamido)-2-fluoro-3-(2-fluorophenyl)butanoate (intermediate A3B) as a brown oil. MS (ISP): m/z=348.2 [M+H]⁻.

Intermediate A3C

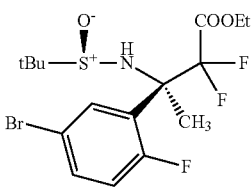 [SMILES: CCOC(=O)C(F)(F)[C@](C)(N[S@@+]([O-])C(C)(C)C)c1cc(Br)ccc1F]

Starting from (R)-2-methyl-propane-2-sulfinic acid [1-(2-fluoro-5-bromo-phenyl)-(E)-ethylidene]-amide and ethyl 2-bromo-2,2-difluoroacetate, the product (3R)-ethyl 3-((R)-1,1-dimethylethylsulfinamido)-2,2-difluoro-3-(2-fluoro-5-bromo-phenyl)butanoate was obtained as an orange oil. MS (ISP): m/z=446.1 [M+H]⁺.

Intermediate A3D

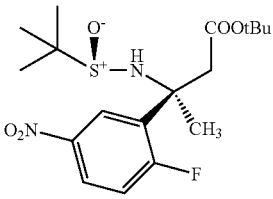

Starting from (R)-2-methyl-propane-2-sulfinic acid [1-(2-fluoro-5-nitro-phenyl)-eth-(E)-ylidene]-amide, the product (S)-3-(2-fluoro-5-nitro-phenyl)-(R)-3-(2-methyl-propane-2-sulfinylamino)-butyric acid tert-butyl ester was obtained as an orange oil. MS (ISP): m/z=403.0 [M+H]⁺.

Intermediate A3E

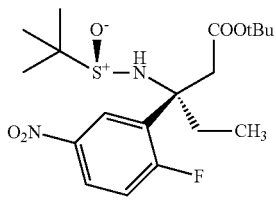

Starting from (R)-2-methyl-propane-2-sulfinic acid [1-(2-fluoro-5-nitro-phenyl)-prop-(E)-ylidene]-amide, the product (S)-3-(2-fluoro-5-nitro-phenyl)-(R)-3-(2-methyl-propane-2-sulfinylamino)-pentanoic acid tert-butyl ester was obtained as an orange oil. MS (ISP): m/z=417.5 [M+H]⁻.

Intermediate A3F (S)-3-(5-bromo-2-fluoro-phenyl)-3-((R)-2-methyl-propane-2-sulfinylamino)-butyric acid ethyl ester

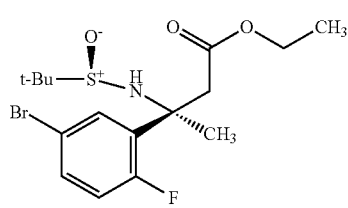 [SMILES: CCOC(=O)C[C@](C)(N[S@+]([O-])C(C)(C)C)c1cc(Br)ccc1F]

A dried four-necked 750 ml round-bottom flask equipped with mechanical stirrer, reflux condenser, internal thermometer and septum was charged with activated zinc powder (30.6 g, 468 mmol) and copper(I) chloride (4.64 g, 47 mmol), the two solids were mixed under a slow stream of nitrogen while the flask was dried with a heat gun. After cooling to 23° C., dry THF (90 ml) was added to produce a dark slurry, heated to reflux and stirred vigorously for 30 min. The heating bath was removed and a solution of ethyl bromoacetate (12.95 ml, 117 mmol) in dry THF (50 ml) was added at such rate that reflux was reinitiated and a controllable reflux was maintained. Once addition was complete, the mixture was stirred for 30 min at 50° C. Cooled to 5° C., a solution of (R)-2-methyl-propane-2-sulfinic acid [1-(2-fluoro-5-bromo-phenyl)-(E)-ethylidene]-amide (intermediate A2B) (15.0 g, 47 mmol) in dry THF (60 ml) was added dropwise and the mixture was stirred at 0° C. for 1 h. The reaction mixture was filtered through dicalit, washed with TBME, the filtrate was washed with 5% citric acid, sat. NaHCO₃-sol. and brine, dried over Na₂SO₄. Removal of the solvent in vacuum left the crude title compound as an orange oil (20.3 g, 106%), which was used in the next step without further purification. MS (ISP): m/z=408.0 [(M+H)⁺] and 410.1 [(M+2+H)⁺].

Intermediate A3G

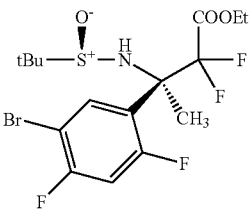 [SMILES: CCOC(=O)C(F)(F)[C@](C)(N[S@@+]([O-])C(C)(C)C)c1cc(Br)c(F)cc1F]

Starting from 2-methyl-propane-2-sulfinic acid [1-(5-bromo-2,4-difluoro-phenyl)-eth-(E)-ylidene]-amide (intermediate A2E) and ethyl 2-bromo-2,2-difluoroacetate, the product (R)-3-(5-bromo-2,4-difluoro-phenyl)-2,2-difluoro-3-((R)-2-methyl-propane-2-sulfinylamino)-butyric acid ethyl ester was obtained as an orange oil. MS (ISP): m/z=462.1 [M+H]⁺ and 464.1 [M+2+H]⁻.

Intermediates A3H

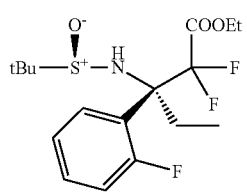 [SMILES: CCOC(=O)C(F)(F)[C@](CC)(N[S@@+]([O-])C(C)(C)C)c1ccccc1F]

Starting from 2-methyl-propane-2-sulfinic acid [1-(2-fluoro-phenyl)-prop-(E)-ylidene]-amide, the product (R)-2,2-difluoro-3-(2-fluoro-phenyl)-3-((R)-2-methyl-propane-2-sulfinylamino)-pentanoic acid ethyl ester was obtained as a colorless oil. MS: m/z=380.2 [M+H]⁺.

General Procedure (via Titanium Enolate Reaction)

To a solution of diisopropylamide (21.9 ml) in THF (250 ml) was added at −78° C. n-butyllithium (1.6 M solution in hexane, 97.2 ml) and stirring was continued at −78° C. for 30 min. The solution was treated with methyl acetate (12.4 ml) and after 30 min a solution of chlorotriisopropoxytitanium (43.0 g) in THF (50 ml) was added and stirring was continued at −78° C. for 30 min. The mixture was treated with a solution of the sulfinyl imine A2 (47.1 mmol) in THF (25 ml) and stirring was continued at −78° C. for 3 h. The mixture was quenched with saturated aqueous NH₄Cl solution (300 ml) and the mixture was filtered over dicalite. The layers were separated, the aqueous layer was extracted with ethyl acetate, the combined organic layers were washed with water, dried and evaporated. The residue was purified by chromatography on silica using cylohexane/ethyl acetate (1:2) to give the pure sulfinamide ester A3.

Synthesis of the Intermediate Sulfinamide Alcohols
A4

General Procedure

A solution of the sulfinamide ester A3 (12.7 mmol) in dry THF (50 ml) was treated at 0° C. with lithium borohydride (25.3 mmol) and stirring was continued at 0° C. for 4 h. The reaction mixture was quenched by addition of acetic acid (2 ml) and water (50 ml), extracted with ethyl acetate and the organic layer was dried and evaporated. The residue was purified by chromatography on silica using a mixture of n-heptane and ethyl acetate to give the pure intermediate sulfinamide alcohol A4.

Intermediate A4A

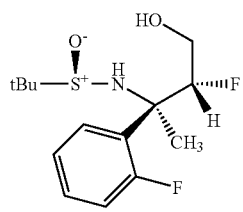 [SMILES: CC(C)(C)[S@+]([O-])N[C@](C)(c1ccccc1F)[C@@H](F)CO]

Starting from (2R,3R)-ethyl 3-((R)-1,1-dimethylethylsulfinamido)-2-fluoro-3-(2-fluorophenyl)butanoate, the product (R)-2-methyl-propane-2-sulfinic acid [(1R,2R)-2-fluoro-1-(2-fluoro-phenyl)-3-hydroxy-1-methyl-propyl]-amide was obtained as pale red crystals. MS (ISP): m/z=306.1 [M+H]⁻.

Intermediate A4B

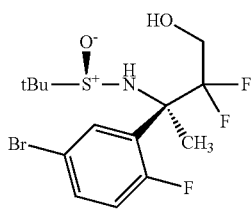

Starting from (3R)-ethyl 3-((R)-1,1-dimethylethylsulfinamido)-2,2-difluoro-3-(2-fluoro-5-bromo-phenyl)butanoate, the product (S)-N-((R)-2-(5-bromo-2-fluorophenyl)-3,3-difluoro-4-hydroxybutan-2-yl)-2-methylpropane-2-sulfinamide was obtained as a colorless solid. MS (ISP): m/z=402.2 [M+H]⁺.

Intermediate A4C

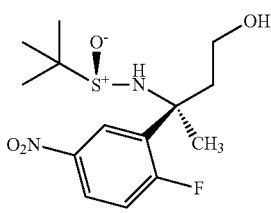 [SMILES: CC(C)(C)[S@+]([O-])N[C@@](C)(CCO)c1cc([N+](=O)[O-])ccc1F]

Starting from (S)-3-(2-fluoro-5-nitro-phenyl)-(R)-3-(2-methyl-propane-2-sulfinylamino)-butyric acid tert-butyl ester, the product (R)-2-methyl-propane-2-sulfinic acid [(S)-1-(2-fluoro-5-nitro-phenyl)-3-hydroxy-1-methyl-propyl]-amide was obtained as an orange oil. MS (ISP): m/z=333.0 [M+H]⁺.

Intermediate A4D

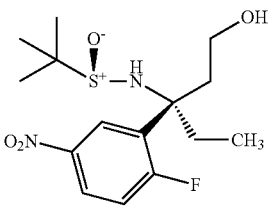 [SMILES: CC[C@@](CCO)(N[S@@+]([O-])C(C)(C)C)c1cc([N+](=O)[O-])ccc1F]

Starting from (S)-3-(2-fluoro-5-nitro-phenyl)-(R)-3-(2-methyl-propane-2-sulfinylamino)-pentanoic acid tert-butyl ester, the product (R)-2-methyl-propane-2-sulfinic acid [(S)-1-ethyl-1-(2-fluoro-5-nitro-phenyl)-3-hydroxy-propyl]-amide was obtained as an orange oil. MS (ISP): m/z=347.0 [M+H]⁻.

Intermediate A4E (R)-2-Methyl-propane-2-sulfinic acid [(S)-1-(5-bromo-2-fluoro-phenyl)-3-hydroxy-1,3-dimethyl-butyl]-amide

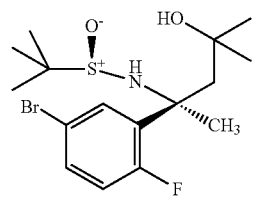 [SMILES: CC(C)(O)C[C@](C)(N[S@+]([O-])C(C)(C)C)c1cc(Br)ccc1F]

To a solution of (S)-3-(5-bromo-2-fluoro-phenyl)-3-((R)-2-methyl-propane-2-sulfinylamino)-butyric acid ethyl ester (intermediate A3F) (10.0 g, 24 mmol) in anhydrous THF (300 ml) at −70° C. was dropwise added a methyl magnesium bromide solution (3.2 M in THF; 61.2 ml, 196 mmol) within 30 min. The yellow solution was stirred for 1 h at −70° C. and then for 16 h at 23° C. The yellow solution was quenched with 200 ml ice cold sat. NH₄Cl solution and extracted with ethyl acetate. The organic layer was washed with water and brine, dried over Na₂SO₄, filtered and evaporated to give the title compound as a yellow oil (10.8 g, 95%; ca. 85% purity), which was used in the next step without further purification. MS (ISP): m/z=394.1 [(M+H)⁺] and 396.1 [(M+2+H)⁺].

Intermediate A4F (R)-N-((R)-2-(5-bromo-2-fluorophenyl)-3,3-difluoro-4-hydroxy-4-methylpentan-2-yl)-2-methylpropane-2-sulfinamide

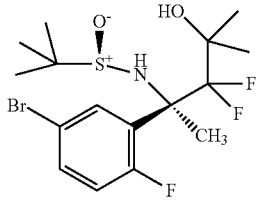 [SMILES: CC(C)(C)[S@@+]([O-])N[C@](C)(c1cc(Br)ccc1F)C(F)(F)C(C)(C)O]

To a solution of (R)-ethyl 3-(5-bromo-2-fluorophenyl)-3-((R)-1,1-dimethylethylsulfinamido)-2,2-difluorobutanoate (intermediate A3C) (10.5 g, 23.6 mmol) in anhydrous THF (150 ml) at −78° C. was dropwise added a methylmagnesium bromide solution (3.2 M in 2-methyl-THF; 59.1 ml, 189 mmol), the cooling bath was removed and the mixture was stirred at 23° C. for 18 h. Poured cautiously into sat. NH4Cl-sol., extracted with ethyl acetate, washed organic layer with brine and dried over Na2SO4. Removal of the solvent in vacuum left the (R)-N-((R)-2-(5-bromo-2-fluorophenyl)-3,3-difluoro-4-hydroxy-4-methylpentan-2-yl)-2-methylpropane-2-sulfinamide (10.565 g, 23.6 mmol, 99.7% yield) as a yellow gum, which was used in the next step without further purification. MS (ISP): m/z=430.1 [(M+H)+] and 432.1 [(M+2+H)+].

Intermediate A4G (R)-N-((R)-2-(5-bromo-2,4-difluorophenyl)-3,3-difluoro-4-hydroxy-4-methylpentan-2-yl)-2-methyl-propane-2-sulfinamide

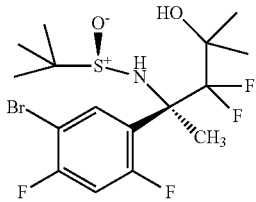 [SMILES: CC(C)(C)[S@@+]([O-])N[C@](C)(c1cc(Br)c(F)cc1F)C(F)(F)C(C)(C)O]

To a solution of (R)-ethyl 3-(5-bromo-2,4-difluorophenyl)-3-((R)-1,1-dimethylethylsulfinamido)-2,2-difluorobutanoate (intermediate A3G) (23.1 g, 50.0 mmol) in anhydrous THF (700 ml) at −78° C. was dropwise added a methylmagnesium bromide solution (3.2 M in 2-methyl-THF; 125 ml, 400 mmol), the cooling bath was removed and the mixture was stirred at 23° C. for 18 h. Poured cautiously into sat. NH4Cl-sol., extracted with ethyl acetate, washed organic layer with brine and dried over Na2SO4. Removal of the solvent in vacuum left the (R)-N-((R)-2-(5-bromo-2,4-difluorophenyl)-3,3-difluoro-4-hydroxy-4-methylpentan-2-yl)-2-methylpropane-2-sulfinamide (21.4 g, 47.7 mmol, 95.5% yield) as a light yellow solid, which was used in the next step without further purification. MS (ISP): m/z=448.1 [(M+H)+] and 450.1 [(M+2+H)+].

Intermediates A4H

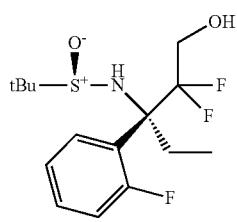 [SMILES: CC[C@@](N[S@@+]([O-])C(C)(C)C)(c1ccccc1F)C(F)(F)CO]

Starting from (R)-2,2-difluoro-3-(2-fluoro-phenyl)-3-((R)-2-methyl-propane-2-sulfinylamino)-butyric acid ethyl ester, the product 2-methyl-propane-2-sulfinic acid [(R)-1-ethyl-2,2-difluoro-1-(2-fluoro-phenyl)-3-hydroxy-propyl]-amide was obtained as a white solid. MS: m/z=338.1 [M+H]+.

Intermediate A4G (R)-2-Methyl-propane-2-sulfinic acid [(1S,3S)-1-(2-fluoro-5-nitro-phenyl)-3-hydroxy-1-methyl-3-phenyl-propyl]-amide

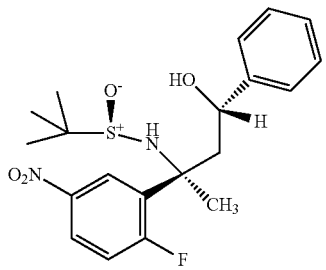 [SMILES: CC(C)(C)[S@@+]([O-])N[C@@](C)(C[C@H](O)c1ccccc1)c1cc([N+](=O)[O-])ccc1F]

To a solution of (R)-2-methyl-propane-2-sulfinic acid [(S)-1-(2-fluoro-5-nitro-phenyl)-3-hydroxy-1-methyl-propyl]-amide (intermediate A4C) (1.1 g, 3.3 mmol) in anhydrous CH2Cl2 (35 ml) at 23° C. was added Dess-Martin Periodinan (1.825 g, 4.3 mmol) and the mixture was stirred at 23° C. for 3 h. Reaction mixture was poured into 20 mL of a 1M aqueous NaHCO3 solution containing 2 g of sodium thiosulfate, pentahydrate and the mixture was stirred at 23° C. for 15 min. The two phases were separated, the collected organic phase was dried over Na2SO4 and removal of the solvent in vacuum left a residue. Purification of the residue was performed by chromatography on silica using a mixture of Heptane and a solution of 3% Triethylamine in Ethylacetate which yielded the (R)-2-Methyl-propane-2-sulfinic acid [(S)-1-(2-fluoro-5-nitro-phenyl)-1-methyl-3-oxo-propyl]-amide (970 mg, 47.7 mmol, 88% yield) as a off-white solid. MS (ISP): m/z=331.1 [(M+H)+].

To a solution of the chlorotitaniumtriisopropoxide (6.57 g, 25.2 mmol) in 80 mL dry THF at 0° C. was slowly added phenyllithium (2.0M solution in dibutylether, 12.6 mL, 25.2 mmol) and the mixture was stirred at 0° C. for 30 min, followed by a slow addition of a solution of (R)-2-Methyl-propane-2-sulfinic acid [(S)-1-(2-fluoro-5-nitro-phenyl)-1-methyl-3-oxo-propyl]-amide (4.2 g, 12.6 mmol) in 30 mL dry THF. The resulting reaction mixture was let to warm up to 23° C. and stirred at 23° C. for 2 h. The reaction medium was slowly poured into a stirred mixture of a saturated NaCl aqueous solution and ethylacetate, which was stirred for 15 min until precipitation occured. The suspension was filtered over celite, the filtrate was poured in a reparatory and extracted with water. The collected organic phase was dried over Na2SO4 and removal of solvent in vaccum yielded a crude yellow oil. The crude was purified by chromatography on silica using a mixture of heptane and ethylacetate which gave the desired diastereoisomer (R)-2-Methyl-propane-2-sulfinic acid [(1S,3S)-1-(2-fluoro-5-nitro-phenyl)-3-hydroxy-1-methyl-3-phenyl-propyl]-amide (1 g, 2.43 mmol, yield: 19.3%). MS (ISP): m/z=409.3 [(M+H)+] and a second diastereoisomer (R)-2-Methyl-propane-2-sulfinic acid [(1S,3R)-1-(2-fluoro-5-nitro-phenyl)-3-hydroxy-1-methyl-3-phenyl-propyl]-amide (2.6 g, 6.32 mmol, yield: 50.2%). MS (ISP):m/z=409.0 [(M+H)−].

Synthesis of the Intermediate Sulfinamide Nitrile A5
(R$^1$=R$^2$=H)

General Procedure

To a solution of the sulfinamide alcohol A4 (4.1 mmol) in dichloromethane (23 ml) was subsequently added at 22° C. 2-bromoacetonitrile (6.2 mmol), silver(I) oxide (1.9 g) and tetrabutylammonium iodide (0.30 g) and stirring was continued for 2 h. The suspension was filtered, the filtrate was washed with aqueous saturated NaHCO$_3$ solution, the organic layer was dried and evaporated to give the crude sulfinamide nitrile A5 which was used without further purification.

Intermediate A5A

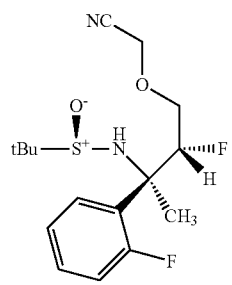 [SMILES: CC(C)(C)[S@+]([O-])N[C@](C)(c1ccccc1F)[C@@H](F)COCC#N]

Starting from (R)-2-methyl-propane-2-sulfinic acid [(1R, 2R)-2-fluoro-1-(2-fluoro-phenyl)-3-hydroxy-1-methyl-propyl]-amide, the product (R)-N-((2R,3R)-4-(cyanomethoxy)-3-fluoro-2-(2-fluorophenyl)butan-2-yl)-2-methylpropane-2-sulfinamide was obtained as a pale yellow oil. MS (ISP): m/z=345.2 [M+H]$^+$.

Intermediate A5B

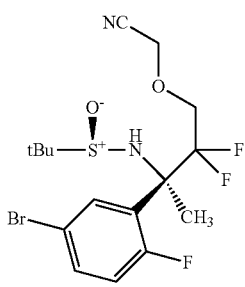 [SMILES: CC(C)(C)[S@+]([O-])N[C@](C)(c1cc(Br)ccc1F)C(F)(F)COCC#N]

Starting from (S)-N-((R)-2-(5-bromo-2-fluorophenyl)-3,3-difluoro-4-hydroxybutan-2-yl)-2-methylpropane-2-sulfinamide, the product (S)-N-((R)-2-(5-bromo-2-fluorophenyl)-4-(cyanomethoxy)-3,3-difluorobutan-2-yl)-2-methylpropane-2-sulfinamide was obtained as a colorless oil. MS (ISP): m/z=441.1 [M+H]$^-$.

Intermediate A5C

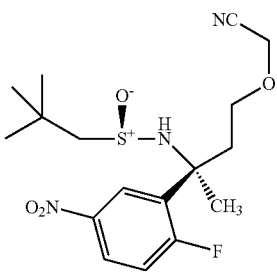 [SMILES: CC(C)(C)C[S@+]([O-])N[C@@](C)(CCOCC#N)c1cc([N+](=O)[O-])ccc1F]

Starting from (R)-2-methyl-propane-2-sulfinic acid [(S)-1-(2-fluoro-5-nitro-phenyl)-3-hydroxy-1-methyl-propyl]-amide, the product (R)-2-methyl-propane-2-sulfinic acid [(S)-3-cyanomethoxy-1-(2-fluoro-5-nitro-phenyl)-1-methyl-propyl]-amide was obtained as an orange oil. MS (ISP): m/z=372.0 [M+H]$^+$.

Intermediate A5D

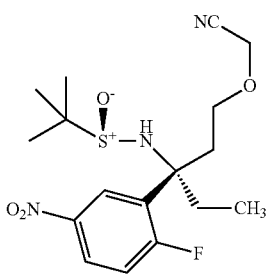 [SMILES: CC[C@@](CCOCC#N)(N[S@@+]([O-])C(C)(C)C)c1cc([N+](=O)[O-])ccc1F]

Starting from (R)-2-methyl-propane-2-sulfinic acid [(S)-1-ethyl-1-(2-fluoro-5-nitro-phenyl)-3-hydroxy-propyl]-amide, the product (R)-2-methyl-propane-2-sulfinic acid [(S)-3-cyanomethoxy-1-ethyl-1-(2-fluoro-5-nitro-phenyl)-propyl]-amide was obtained as an orange oil. MS (ISP): m/z=386.1 [M+H]$^-$.

Synthesis of the Intermediate Sulfinamide Nitrile A5
(R$^1$=R$^2$=Me)

To a solution of acetone cyanohydrin (307 mg, 3.6 mmol) in 10 ml DCE was added to a solution of SnCl$_4$ 1.0 M in DCM (3.91 ml, 3.9 mmol) at RT, then addition of the alcohol (1 g, 3 mmol). The reaction mixture was stirred at RT for 10 min, then stirred at 60° C. for two days, control by TLC (EE pure). Reaction mixture cooled down to RT and poured into a mixture of DCM and aq. Na$_2$CO$_3$, solution stirred for 20 min. A white precipitate formed and was filtered over Celite, separation of the two phases in the filtrate, organic phase dried over Na$_2$SO$_4$, filtered and evaporated down to dryness. The residue was purified by chromatography on silica with a mixture of heptane and ethyl acetate to give a yellow oil.

Intermediate A5E

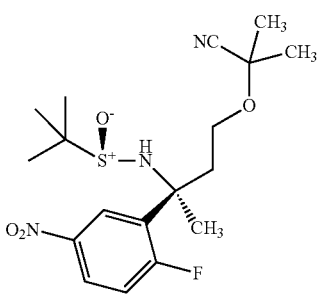 [SMILES: CC(C)(C#N)OCC[C@](C)(N[S@@+]([O-])C(C)(C)C)c1cc([N+](=O)[O-])ccc1F]

Starting from (R)-2-methyl-propane-2-sulfinic acid [(S)-1-(2-fluoro-5-nitro-phenyl)-3-hydroxy-1-methyl-propyl]-amide, the product (R)-2-methyl-propane-2-sulfinic acid [(S)-3-(cyano-dimethyl-methoxy)-1-(2-fluoro-5-nitro-phenyl)-1-methyl-propyl]-amide was obtained as an orange oil. MS (ISP): m/z=400.1 [M+H]$^+$.

Intermediates A5F

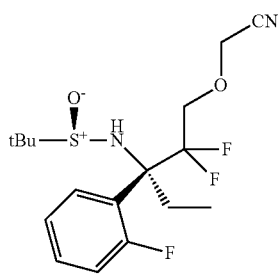 [SMILES: CC[C@@](N[S@@+]([O-])C(C)(C)C)(c1ccccc1F)C(F)(F)COCC#N]

Starting from 2-methyl-propane-2-sulfinic acid [(R)-1-ethyl-2,2-difluoro-1-(2-fluoro-phenyl)-3-hydroxy-propyl]-amide, the product 2-methyl-propane-2-sulfinic acid [(R)-3-cyanomethoxy-1-ethyl-2,2-difluoro-1-(2-fluoro-phenyl)-propyl]-amide was obtained as an oil. MS: m/z=377.3 [M+H]$^+$.

Intermediate A5G

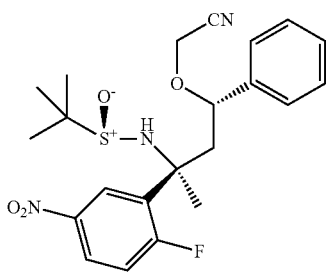 [SMILES: CC(C)(C)[S@+]([O-])N[C@@](C)(C[C@H](OCC#N)c1ccccc1)c1cc([N+](=O)[O-])ccc1F]

Starting from (R)-2-Methyl-propane-2-sulfinic acid [(1S,3S)-1-(2-fluoro-5-nitro-phenyl)-3-hydroxy-1-methyl-3-phenyl-propyl]-amide, the product (R)-2-Methyl-propane-2-sulfinic acid [(1S,3S)-3-cyanomethoxy-1-(2-fluoro-5-nitro-phenyl)-1-methyl-3-phenyl-propyl]-amide was obtained as an orange oil. MS (ISP): m/z=448.0 [M+H]$^+$.

Synthesis of the Intermediate Amino Nitrile A6

General Procedure

A solution of the sulfinamide nitrile A5 (4.25 mmol) in 1,4-dioxane (20 ml) was treated with a solution of HCl in 1,4-dioxane (4 M, 5.3 ml) and stirring was continued at 22° C. for 1 h. The mixture was diluted with ethyl acetate, washed with saturated aqueous Na$_2$CO$_3$ solution, the organic layer was dried and evaporated. The crude material was purified on silica using n-heptane/ethyl acetate to give the pure amino nitrile A6.

Intermediate A6A

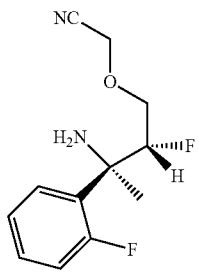 [SMILES: C[C@@](N)(c1ccccc1F)[C@@H](F)COCC#N]

Starting from (R)-N-((2R,3R)-4-(cyanomethoxy)-3-fluoro-2-(2-fluorophenyl)butan-2-yl)-2-methylpropane-2-sulfinamide, the product 2-((2R,3R)-3-amino-2-fluoro-3-(2-fluorophenyl)butoxy)acetonitrile was obtained as a pale yellow oil. MS (ISP): m/z=241.1 [M+H]$^+$.

Intermediate A6B

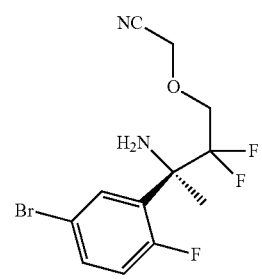 [SMILES: C[C@@](N)(c1cc(Br)ccc1F)C(F)(F)COCC#N]

Starting from (S)-N-((R)-2-(5-bromo-2-fluorophenyl)-4-(cyanomethoxy)-3,3-difluorobutan-2-yl)-2-methylpropane-2-sulfinamide, the product (R)-2-(3-amino-3-(5-bromo-2-fluorophenyl)-2,2-difluorobutoxy)acetonitrile was obtained as a colorless oil. MS (ISP): m/z=337.2 [M+H]$^-$.

Intermediate A6C

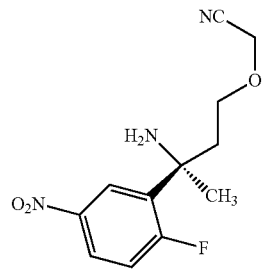 [SMILES: C[C@](N)(CCOCC#N)c1cc([N+](=O)[O-])ccc1F]

Starting from (R)-2-methyl-propane-2-sulfinic acid [(S)-3-cyanomethoxy-1-(2-fluoro-5-nitro-phenyl)-1-methyl-propyl]-amide, the product [(S)-3-amino-3-(2-fluoro-5-nitro-phenyl)-butoxy]-acetonitrile was obtained as an orange oil. MS (ISP): m/z=268.0 [M+H]$^+$.

Intermediate A6D

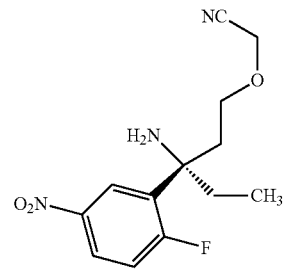 [SMILES: CC[C@](N)(CCOCC#N)c1cc([N+](=O)[O-])ccc1F]

Starting from (R)-2-methyl-propane-2-sulfinic acid [(S)-3-cyanomethoxy-1-ethyl-1-(2-fluoro-5-nitro-phenyl)-propyl]-amide, the product [(S)-3-amino-3-(2-fluoro-5-nitrophenyl)-pentyloxy]-acetonitrile was obtained as an orange oil. MS (ISP): m/z=282.4 [M+H]⁺.

Intermediate A6E

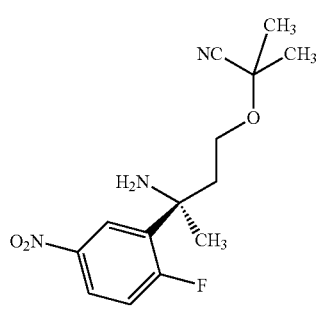 [SMILES: CC(C)(C#N)OCC[C@](C)(N)c1cc([N+](=O)[O-])ccc1F]

Starting from (R)-2-methyl-propane-2-sulfinic acid [(S)-3-(cyano-dimethyl-methoxy)-1-(2-fluoro-5-nitro-phenyl)-1-methyl-propyl]-amide, the product 2-[(S)-3-amino-3-(2-fluoro-5-nitro-phenyl)-butoxy]-2-methyl-propionitrile was obtained as an orange oil. MS (ISP): m/z=296.3 [M+H]⁻.

Intermediates A6F

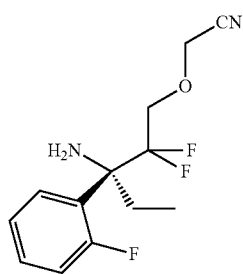 [SMILES: CC[C@@](N)(c1ccccc1F)C(F)(F)COCC#N]

Starting from 2-methyl-propane-2-sulfinic acid [(R)-3-cyanomethoxy-1-ethyl-2,2-difluoro-1-(2-fluoro-phenyl)-propyl]-amide, the product [(R)-3-amino-2,2-difluoro-3-(2-fluoro-phenyl)-pentyloxy]-acetonitrile was obtained as a pale yellow oil. MS: m/z=273.1 [M+H]⁺.

Intermediate A6G

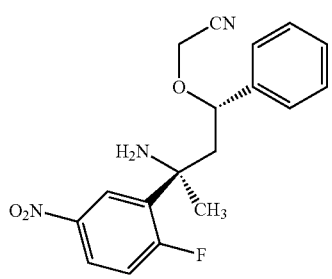 [SMILES: C[C@](N)(C[C@H](OCC#N)c1ccccc1)c1cc([N+](=O)[O-])ccc1F]

Starting from (R)-2-Methyl-propane-2-sulfinic acid [(1S,3S)-3-cyanomethoxy-1-(2-fluoro-5-nitro-phenyl)-1-methyl-3-phenyl-propyl]-amide, the product [(1S,3S)-3-Amino-3-(2-fluoro-5-nitro-phenyl)-1-phenyl-butoxy]-acetonitrile was obtained as an orange oil. MS (ISP): m/z=344.1 [M+H]⁺.

Synthesis of the Intermediate 1,4-oxazepine A7

General Procedure

To a solution of the amino nitrile A6 (2.20 mmol) in toluene (38 ml) was added at 22° C. a solution of AlMe₃ in toluene (2 M, 1.2 ml) and the mixture was heated to 80° C. for 1 h. The mixture was cooled to 0° C., diluted with saturated aqueous Na₂CO₃ and the aqueous layer was extracted with ethyl acetate. The combined organic layers were dried, evaporated and the residue purified by chromatography on NH₂-silica using n-heptane/ethyl acetate to give the pure 1,4-oxazepine A7.

Intermediate A7A

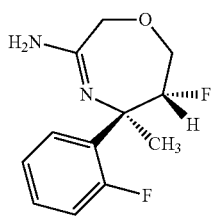 [SMILES: C[C@]1(c2ccccc2F)N=C(N)COC[C@@H]1F]

Starting from 2-((2R,3R)-3-amino-2-fluoro-3-(2-fluorophenyl)butoxy)acetonitrile, the product (5R,6R)-6-fluoro-5-(2-fluorophenyl)-5-methyl-2,5,6,7-tetrahydro-1,4-oxazepin-3-amine was obtained as a pale yellow solid. MS (ISP): m/z=241.2 [M+H]⁺.

Intermediate A7B

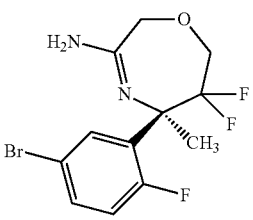 [SMILES: C[C@]1(c2cc(Br)ccc2F)N=C(N)COCC1(F)F]

Starting from (R)-2-(3-amino-3-(5-bromo-2-fluorophenyl)-2,2-difluorobutoxy)acetonitrile, the product (R)-5-(5-bromo-2-fluorophenyl)-6,6-difluoro-5-methyl-2,5,6,7-tetrahydro-1,4-oxazepin-3-amine was obtained as a colorless oil. MS (ISP): m/z=337.2 [M+H]⁺.

Intermediates A7C

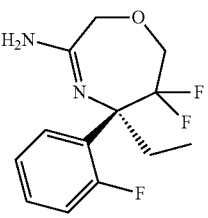 [SMILES: CC[C@]1(c2ccccc2F)N=C(N)COCC1(F)F]

Starting from [(R)-3-amino-2,2-difluoro-3-(2-fluoro-phenyl)-pentyloxy]-acetonitrile, the product (R)-5-ethyl-6,6-difluoro-5-(2-fluoro-phenyl)-2,5,6,7-tetrahydro-[1,4]oxazepin-3-ylamine was obtained as a brown oil. MS: m/z=273.1 [M+H]⁺.

Synthesis of the Intermediate DMT-1,4-oxazepine A8A

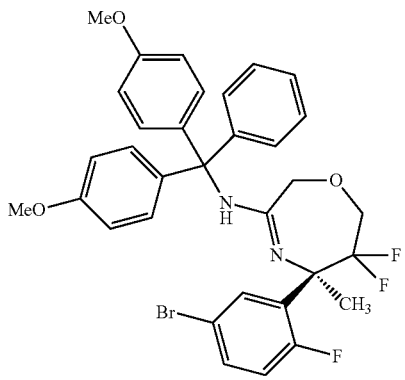 [SMILES: COc1ccc(C(NC2=N[C@](C)(c3cc(Br)ccc3F)C(F)(F)COC2)(c2ccccc2)c2ccc(OC)cc2)cc1]

To a solution of (R)-5-(5-bromo-2-fluorophenyl)-6,6-difluoro-5-methyl-2,5,6,7-tetrahydro-1,4-oxazepin-3-amine (9.0 mmol) in dichloromethane (150 ml) was subsequently added at 0° C. NEt₃ (18.0 mmol) and 4,4'-dimethoxytriphenylmethyl chloride (9.9 mmol) and stirring was continued at 22° C. for 2 h. The mixture was washed with saturated aqueous NH₄Cl, the organic layer was dried, evaporated and the residue was purified by chromatography on silica using cyclohexane/ethyl acetate to give pure (R)-N-(bis(4-methoxyphenyl)(phenyl)methyl)-5-(5-bromo-2-fluorophenyl)-6,6-difluoro-5-methyl-2,5,6,7-tetrahydro-1,4-oxazepin-3-amine (A8A) as a colorless foam. MS (ISP): m/z=639.3 [M+H]⁺.

Synthesis of the Intermediate Imine A9A

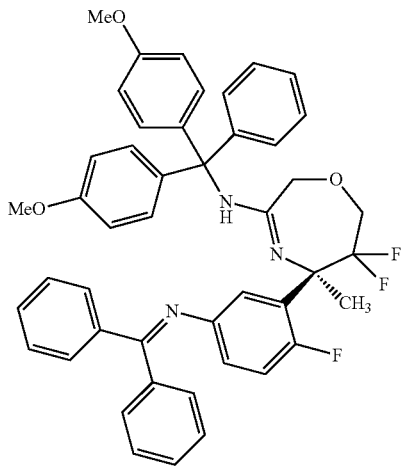 [SMILES: COc1ccc(C(NC2=N[C@](C)(c3cc(N=C(c4ccccc4)c4ccccc4)ccc3F)C(F)(F)COC2)(c2ccccc2)c2ccc(OC)cc2)cc1]

To a solution of (R)-N-(bis(4-methoxyphenyl)(phenyl)methyl)-5-(5-bromo-2-fluorophenyl)-6,6-difluoro-5-methyl-2,5,6,7-tetrahydro-1,4-oxazepin-3-amine (1.2 mmol) in toluene (15 ml) was added subsequently at 22° C. and under a argon atmosphere benzophenone imine (2.4 mmol), sodium t-butoxide (3.6 mmol) and 2-di-t-butylphosphino-2',4',6'-triisopropylbiphenyl (0.12 mmol). To the mixture was added tris(dibenzylideneacetone) dipalladium chloroform adduct (0.036 mmol), the tube was sealed and heated to 105° C. for 3 h. The mixture was cooled to 22° C., partitioned between saturated aqueous NaHCO₃ and ethyl acetate, the organic layer was dried and evaporated to give the crude (R)-N-(bis(4-methoxyphenyl)(phenyl)methyl)-5-(5-(diphenylmethyleneamino)-2-fluorophenyl)-6,6-difluoro-5-methyl-2,5,6,7-tetrahydro-1,4-oxazepin-3-amine (A9A) as a yellow oil. MS (ISP): m/z=738.5 [M−H]⁻.

Synthesis of the Intermediate Aniline A10A from the Imine A9A

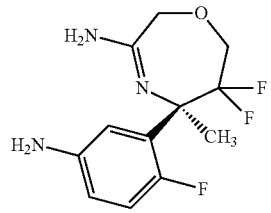 [SMILES: C[C@]1(c2cc(N)ccc2F)N=C(N)COCC1(F)F]

To a solution of crude (R)-N-(bis(4-methoxyphenyl)(phenyl)methyl)-5-(5-(diphenylmethyleneamino)-2-fluorophenyl)-6,6-difluoro-5-methyl-2,5,6,7-tetrahydro-1,4-oxazepin-3-amine (1.2 mmol) in dichloromethane (20 ml) was added at 22° C. trifuoroacetic acid (2.6 ml) and stirring was continued for 1 h. The mixture was diluted with 1,4-dioxane (40 ml) and aqueous hydrochloric acid (1 M, 33 ml) and vigorous stirring of the emulsion at 22° C. was continued for 16 h. The mixture was evaporated and the residue partitioned between saturated aqueous NaCl and ethyl acetate, the aqueous layer was separated, the pH was adjusted to 14 using saturated aqueous Na₂CO₃ solution and extracted with ethyl acetate. The organic layer was dried, evaporated and the residue purified by chromatography on silica-NH₂ using dichloromethane to give (R)-5-(5-amino-2-fluorophenyl)-6,6-difluoro-5-methyl-2,5,6,7-tetrahydro-1,4-oxazepin-3-amine as a colorless oil. MS (ISP): m/z=274.3 [M+H]⁺.

General Procedure for Synthesis of Nitrobenzenes A11 Directly from Nitriles A6

To a solution of the amino nitrile A6 (2.20 mmol) in toluene (38 ml) was added at 22° C. a solution of AlMe₃ in toluene (2 M, 1.2 ml) and the mixture was heated to 80° C. for 1 h. The mixture was cooled to 0° C., diluted with saturated aqueous Na₂CO₃ and the aqueous layer was extracted with ethyl acetate. The combined organic layers were dried, evaporated and the residue purified by chromatography on NH₂-silica using n-heptane/ethyl acetate to give the pure 1,4-oxazepine A11.

Intermediate Nitrobenzene A11A

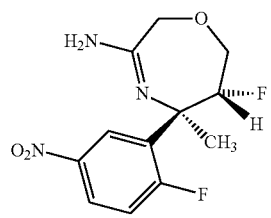

To a solution of (5R,6R)-6-fluoro-5-(2-fluorophenyl)-5-methyl-2,5,6,7-tetrahydro-1,4-oxazepin-3-amine (1.2 mmol) in sulfuric acid (5.0 ml) was added at 0° C. red fuming nitric acid (1.9 mmol) over a period of 20 min and stirring was continued for 30 min. The solution was dropped slowly into ice/water (60 ml), the pH was adjusted to 9 by addition of aqueous 4 N NaOH and extracted with ethyl acetate. The organic layer was dried, evaporated and the residue purified by chromatography on silca-NH$_2$ using n-heptane/ethyl acetate to give (5R,6R)-6-fluoro-5-(2-fluoro-5-nitro-phenyl)-5-methyl-2,5,6,7-tetrahydro-[1,4]oxazepin-3-ylamine as a pale yellow solid. MS (ISP): m/z=286.2 [M+H]$^+$.

Intermediate A11B

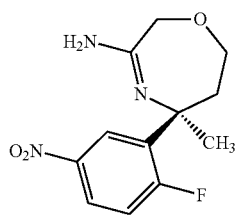 [SMILES: C[C@@]1(c2cc([N+](=O)[O-])ccc2F)CCOCC(N)=N1]

Starting from [(S)-3-amino-3-(2-fluoro-5-nitro-phenyl)-butoxy]-acetonitrile, the product (S)-5-(2-fluoro-5-nitro-phenyl)-5-methyl-2,5,6,7-tetrahydro-[1,4]oxazepin-3-ylamine was obtained as an orange oil. MS (ISP): m/z=268.3 [M+H]$^+$.

Intermediate A11C

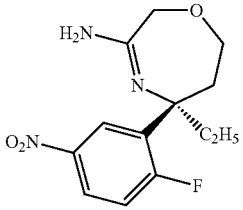 [SMILES: CC[C@@]1(c2cc([N+](=O)[O-])ccc2F)CCOCC(N)=N1]

Starting from [(S)-3-amino-3-(2-fluoro-5-nitro-phenyl)-pentyloxy]-acetonitrile, the product (S)-5-ethyl-5-(2-fluoro-5-nitro-phenyl)-2,5,6,7-tetrahydro-[1,4]oxazepin-3-ylamine was obtained as an orange oil. MS (ISP): m/z=282.3 [M+H]$^+$.

Intermediate A11D

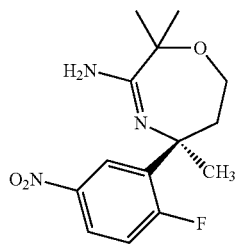 [SMILES: CC1(C)OCC[C@@](C)(c2cc([N+](=O)[O-])ccc2F)N=C1N]

Starting from 2-[(S)-3-amino-3-(2-fluoro-5-nitro-phenyl)-butoxy]-2-methyl-propionitrile, the product (S)-5-(2-fluoro-5-nitro-phenyl)-2,2,5-trimethyl-2,5,6,7-tetrahydro-[1,4]oxazepin-3-ylamine was obtained as an orange oil. MS (ISP): m/z=296.3 [M+H]$^+$.

Intermediate A11E

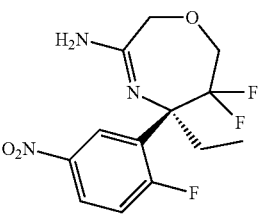 [SMILES: CC[C@]1(c2cc([N+](=O)[O-])ccc2F)N=C(N)COCC1(F)F]

To a solution of (R)-5-ethyl-6,6-difluoro-5-(2-fluoro-phenyl)-2,5,6,7-tetrahydro-[1,4]oxazepin-3-ylamine (1.2 mmol) in sulfuric acid (5.0 ml) was added at 0° C. red fuming nitric acid (1.9 mmol) over a period of 20 min and stirring was continued for 30 min. The solution was dropped slowly into ice/water (60 ml), the pH was adjusted to 9 by addition of aqueous 4 N NaOH and extracted with ethyl acetate. The organic layer was dried, evaporated and the residue purified by chromatography on silca-NH$_2$ using n-heptane/ethyl acetate to give (R)-5-ethyl-6,6-difluoro-5-(2-fluoro-5-nitro-phenyl)-2,5,6,7-tetrahydro-[1,4]oxazepin-3-ylamine as a pale yellow solid. MS: m/z=318.1 [M+H]$^+$.

Intermediate A11F

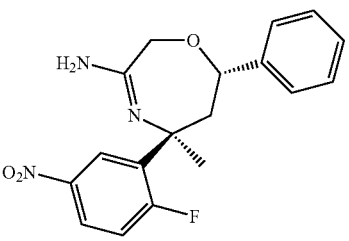 [SMILES: C[C@@]1(c2cc([N+](=O)[O-])ccc2F)C[C@@H](c2ccccc2)OCC(N)=N1]

Starting from [(1S,3S)-3-Amino-3-(2-fluoro-5-nitro-phenyl)-1-phenyl-butoxy]-acetonitrile, the product (5S,7S)-5-(2-Fluoro-5-nitro-phenyl)-5-methyl-7-phenyl-2,5,6,7-tetrahydro-[1,4]oxazepin-3-ylamine was obtained as an orange oil. MS (ISP): m/z=344.1 [M+H]$^+$.

Synthesis of the Intermediate Aniline A10B via Reduction of the Nitrobenzene A11A

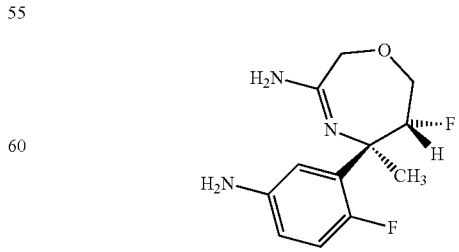

A suspension of (5R,6R)-6-fluoro-5-(2-fluoro-5-nitro-phenyl)-5-methyl-2,5,6,7-tetrahydro-[1,4]oxazepin-3- ylamine (1.0 mmol) in ethanol (9 ml) and Pd/C (10%, 100 mg) was hydrogenated at 22° C. and atmospheric pressure for 2 h. The suspension was filtered and the residue evaporated to give (5R,6R)-5-(5-amino-2-fluoro-phenyl)-6-fluoro-5-methyl-2,5,6,7-tetrahydro-[1,4]oxazepin-3-ylamine as a yellow solid. MS (ISP): m/z=256.3 [M+H]$^+$.

General Procedure for Syntheses of Intermediate Anilines A10 via Alternative Reduction Method of Intermediate Nitrobenzenes A11

To a solution of nitrobenzene (140 mg, 0.47 mmol) in 4.0 ml EtOH was added SnCl$_2$.2H$_2$O (321 mg, 1.42 mmol) (precipitate formed instantly which dissolved upon heating). Reaction stirred at 80° C. for 1.5 h and controlled by TLC Si—NH$_2$ (CH$_2$Cl$_2$/MeOH/NH$_4$OH 80:18:2) which showed complete conversion. Reaction mixture poured into an aqueous solution NaOH 1N, addition of ethyl acetate and the mixture was stirred for 10 min. Precipitate was filtred over Celite, the two phases in the filtrate were separated. The organic phase was dried over Na$_2$SO$_4$, filtered and evaporated down to dryness. The residue was purified by chromatography on an amine-modified silica with a mixture of CH$_2$Cl$_2$ and MeOH to give the pure aniline.

Intermediate A10C

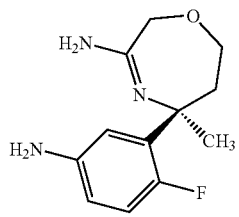 [SMILES: C[C@@]1(c2cc(N)ccc2F)CCOCC(N)=N1]

Starting from (S)-5-(2-fluoro-5-nitro-phenyl)-5-methyl-2,5,6,7-tetrahydro-[1,4]oxazepin-3-ylamine, the product (S)-5-(5-amino-2-fluoro-phenyl)-5-methyl-2,5,6,7-tetrahydro-[1,4]oxazepin-3-ylamine was obtained as an orange oil. MS (ISP): m/z=237.9 [M+H]$^+$.

Intermediate A10D

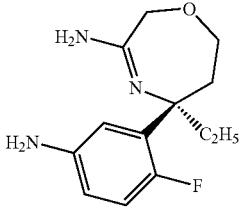 [SMILES: CC[C@@]1(c2cc(N)ccc2F)CCOCC(N)=N1]

Starting from (S)-5-ethyl-5-(2-fluoro-5-nitro-phenyl)-2,5,6,7-tetrahydro-[1,4]oxazepin-3-ylamine, the product (S)-5-(5-amino-2-fluoro-phenyl)-5-ethyl-2,5,6,7-tetrahydro-[1,4]oxazepin-3-ylamine was obtained as an orange oil. MS (ISP): m/z=252.3 [M+H]$^+$.

Intermediate A10E

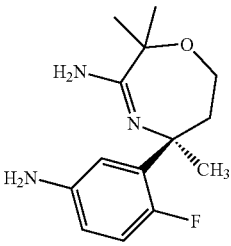 [SMILES: CC1(C)OCC[C@@](C)(c2cc(N)ccc2F)N=C1N]

Starting from (S)-5-(2-fluoro-5-nitro-phenyl)-2,2,5-trimethyl-2,5,6,7-tetrahydro-[1,4]oxazepin-3-ylamine, the product (S)-5-(5-amino-2-fluoro-phenyl)-2,2,5-trimethyl-2,5,6,7-tetrahydro-[1,4]oxazepin-3-ylamine was obtained as an orange oil. MS (ISP): m/z=266.1 [M+H]$^+$.

Intermediate A10F

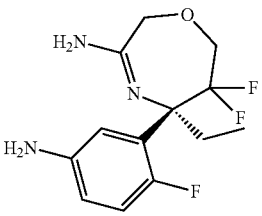 [SMILES: CC[C@]1(c2cc(N)ccc2F)N=C(N)COCC1(F)F]

Starting from (R)-5-ethyl-6,6-difluoro-5-(2-fluoro-5-nitro-phenyl)-2,5,6,7-tetrahydro-[1,4]oxazepin-3-ylamine and using the hydrogenation procedure, the product (R)-5-(5-amino-2-fluoro-phenyl)-5-ethyl-6,6-difluoro-2,5,6,7-tetrahydro-[1,4]oxazepin-3-ylamine as a pale yellow solid. MS: m/z=288.1 [M+H]$^+$.

Intermediate A10G

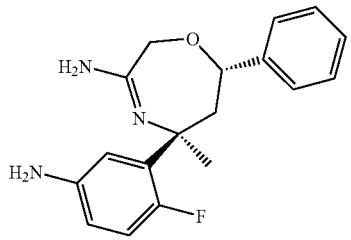 [SMILES: C[C@@]1(c2cc(N)ccc2F)C[C@@H](c2ccccc2)OCC(N)=N1]

Starting from (5S,7S)-5-(2-Fluoro-5-nitro-phenyl)-5-methyl-7-phenyl-2,5,6,7-tetrahydro-[1,4]oxazepin-3-ylamine, the product (5S,7S)-5-(5-Amino-2-fluoro-phenyl)-5-methyl-7-phenyl-2,5,6,7-tetrahydro-[1,4]oxazepin-3-ylamine was obtained as an orange oil. MS (ISP): m/z=314.2 [M+H]$^-$.

Synthesis of the Amides Ia from the Anilines A10

General Procedure:

To a solution of the acid (0.16 mmol) in MeOH (1 ml) was added at 22° C. 4-(4,6-dimethoxy-1,3,5-triazin-2yl)-4-methyl-morpholiniumchloride (0.19 mmol) and stirring was continued at 0° C. for 30 min. To the mixture was added a solution of the aniline A10 (0.15 mmol) in MeOH (2 ml) and stirring was continued at 0° C. for 2 h. The mixture was diluted with saturated aqueous $Na_2CO_3$, the MeOH was evaporated and the aqueous solution was extracted with ethyl acetate. The organic layer was dried, evaporated and the residue was purified on preparative HPLC RP18 column using a gradient of water/HCOOH (99.9:0.1)→MeOH to give the formiate salt or a gradient of water/$NEt_3$ (99.9:0.1)→$CH_3CN$ to give the free base of the amide Ia.

Synthesis of the Amines Ib from the Anilines A10 by Reductive Amination

General Procedure:

To a solution of the aniline A10 (0.1 mmol) in dichloromethane (0.7 ml) was subsequently added at 22° C. the carbonyl compound (0.11 mmol), acetic acid (0.2 mmol) and sodium triacetoxyborohydride (0.14 mmol) and stirring of the mixture was continued for 18 h. The mixture was dilued with water (1 ml), the organic layer was washed with saturated aqueous $NaHCO_3$, dried and evaporated. The residue was purified by chromatography on a silica-$NH_2$ column using dichloromethane to give the amines Ib.

Intermediate A12A (S)-4-Amino-4-(5-bromo-2-fluoro-phenyl)-2-methyl-pentan-2-ol

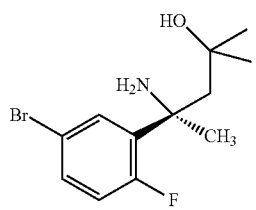 [SMILES: CC(C)(O)C[C@](C)(N)c1cc(Br)ccc1F]

The compound was prepared in an analogous manner as described for intermediate A6 from (R)-2-methyl-propane-2-sulfinic acid [(S)-1-(5-bromo-2-fluoro-phenyl)-3-hydroxy-1,3-dimethyl-butyl]-amide (intermediate A'1A) (10.8 g; 27 mmol; 85% purity). After silica gel column chromatography the compound was obtained as a light brown solid (2.22 g, 33%). MS (ISP): m/z=290.0 [(M+H)$^+$] and 292.0 [(M+2+H)$^+$].

Intermediate A13A

N-[(S)-1-(5-Bromo-2-fluoro-phenyl)-3-hydroxy-1,3-dimethyl-butyl]-2-chloro-acetamide

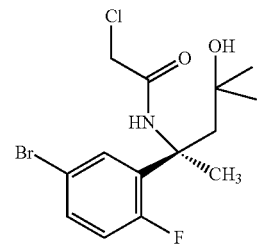 [SMILES: CC(C)(O)C[C@](C)(NC(=O)CCl)c1cc(Br)ccc1F]

The compound was prepared in an analogous manner as described below for intermediate B9A from (S)-4-amino-4-(5-bromo-2-fluoro-phenyl)-2-methyl-pentan-2-ol (intermediate A12A) (2.22 g; 7.7 mmol). The crude product was obtained as a colourless oil (3.11 g, 111%), which was used in the next step without further purification. MS (ISP): m/z=366.0 [(M+H)$^+$], 368.0 [(M+2+H)$^+$] and 370.0 [(M+4+H)$^+$].

Intermediate A14A (S)-5-(5-Bromo-2-fluoro-phenyl)-5,7,7-trimethyl-[1,4]oxazepan-3-one

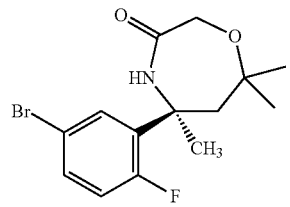 [SMILES: CC1(C)C[C@@](C)(c2cc(Br)ccc2F)NC(=O)CO1]

To a solution of N-[(S)-1-(5-bromo-2-fluoro-phenyl)-3-hydroxy-1,3-dimethyl-butyl]-2-chloro-acetamide (intermediate A13A) (3.11 g, 8.5 mmol) in toluene (150 ml) at 23° C. was added dropwise a solution of potassium amylate (1.7 M in toluene; 25.0 ml, 42 mmol) within 10 min (slightly exotermic). The light brown solution was stirred at 23° C. for 2 h. Diluted with water, 1N HCl and brine and extracted twice with ethyl acetate. The organic layers were washed with sat. $NaHCO_3$ solution and brine, dried over $Na_2SO_4$, filtered and evaporated to give a light brown oil, which was purified by silica gel column chromatography with n-heptane/ethyl acetate to give the title compound as an off-white solid (1.05 g, 37%). MS (ISP): m/z=330.0 [(M+H)$^+$] and 332.0 [(M+2+H)$^+$].

Intermediate A14B (R)-5-(5-bromo-2-fluorophenyl)-6,6-difluoro-5,7,7-trimethyl-[1,4]oxazepan-3-one

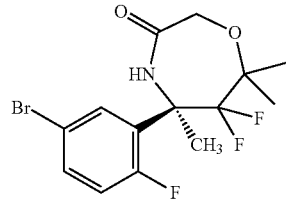 [SMILES: CC1(C)OCC(=O)N[C@](C)(c2cc(Br)ccc2F)C1(F)F]

MS (ISN): m/z=530.2 [(M−H)⁻] and 532.0 [(M+2−H)⁻].

To a solution of (R)-ethyl 2-(4-amino-4-(5-bromo-2-fluorophenyl)-3,3-difluoro-2-methylpentan-2-yloxy)acetate (intermediate A22A) (6.85 g, 16.6 mmol) in toluene (205 ml) at 23° C. was dropwise added trimethylaluminum (2 M in toluene, 10.8 ml, 21.6 mmol) and the light yellow solution was stirred at 23° C. for 2 h. Poured into sat. NaHCO$_3$-sol., extracted with ethyl acetate, washed organic layer with brine, dried over Na$_2$SO$_4$, filtered off and evaporated totally, dried in high vacuum to give the (R)-5-(5-bromo-2-fluorophenyl)-6,6-difluoro-5,7,7-trimethyl-1,4-oxazepan-3-one (5.95 g, 16.2 mmol, 97.8% yield) as a light yellow solid, which was used without further purification. MS (ISP): m/z=366.2 [(M+H)⁺] and 368.1 [(M+2+H)⁺].

Intermediate A14C (R)-5-(5-bromo-2,4-difluorophenyl)-6,6-difluoro-5,7,7-trimethyl-[1,4]oxazepan-3-one

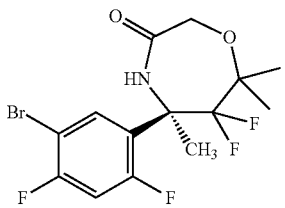 [SMILES: CC1(C)OCC(=O)N[C@](C)(c2cc(Br)c(F)cc2F)C1(F)F]

Prepared in an analogous manner as described for intermediate A22A from (R)-ethyl 2-(4-amino-4-(5-bromo-2,4-difluorophenyl)-3,3-difluoro-2-methylpentan-2-yloxy)acetate (intermediate A22B) (16.1 g; 37.4 mmol). After silica gel column chromatography with heptane and ethyl acetate the (R)-5-(5-bromo-2,4-difluorophenyl)-6,6-difluoro-5,7,7-trimethyl-[1,4]oxazepan-3-one (9.0 g, 23.4 mmol, 63% yield) was obtained as an off-white solid. MS (ISP): m/z=384.2 [(M+H)⁺] and 386.1 [(M+2+H)⁺].

Intermediate A15A (S)-5-[5-(Benzhydrylidene-amino)-2-fluoro-phenyl]-5,7,7-trimethyl-[1,4]oxazepan-3-one

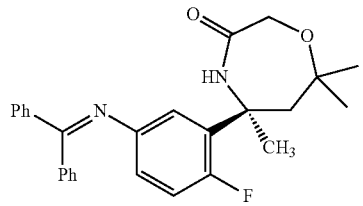 [SMILES: CC1(C)C[C@@](C)(c2cc(N=C(c3ccccc3)c3ccccc3)ccc2F)NC(=O)CO1]

The compound was prepared in an analogous manner as described for intermediate B11A below from (S)-5-(5-bromo-2-fluoro-phenyl)-5,7,7-trimethyl-[1,4]oxazepan-3-one (intermediate A14A) (1.0 g, 3.0 mmol). The compound was obtained as light yellow foam (1.15 g, 88%). MS (ISP): m/z=431.3 [(M+H)⁺].

Intermediate A15B (R)-5-(5-(diphenylmethyleneamino)-2-fluorophenyl)-6,6-difluoro-5,7,7-trimethyl-[1,4]oxazepan-3-one

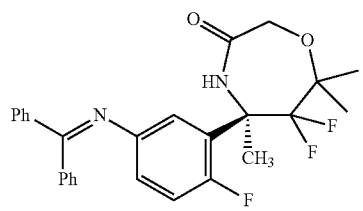 [SMILES: CC1(C)OCC(=O)N[C@](C)(c2cc(N=C(c3ccccc3)c3ccccc3)ccc2F)C1(F)F]

The compound was prepared in an analogous manner as described for intermediate B11A below from (R)-5-(5-bromo-2-fluorophenyl)-6,6-difluoro-5,7,7-trimethyl-[1,4]oxazepan-3-one (intermediate A14B) (1.03 g, 2.81 mmol). The compound was obtained as yellow solid (1.05 g, 2.25 mmol, 80%). MS (ISP): m/z=467.3 [(M+H)⁺].

Intermediate A15C (R)-5-(5-(diphenylmethyleneamino)-2,4-difluorophenyl)-6,6-difluoro-5,7,7-trimethyl-[1,4[oxazepan-3-one

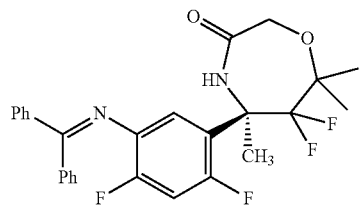 [SMILES: CC1(C)OCC(=O)N[C@](C)(c2cc(N=C(c3ccccc3)c3ccccc3)c(F)cc2F)C1(F)F]

The compound was prepared in an analogous manner as described for intermediate B11A below from (R)-5-(5-bromo-2,4-difluorophenyl)-6,6-difluoro-5,7,7-trimethyl-[1,4]oxazepan-3-one (intermediate A14C) (1.5 g, 3.9 mmol). The compound was obtained as a light yellow foam (0.75 g, 1.55 mmol, 40%). MS (ISP): m/z=485.3 [(M+H)⁺].

Intermediate A17B (R)-5-(5-amino-2-fluorophenyl)-6,6-difluoro-5,7,7-trimethyl-[1,4]oxazepane-3-thione

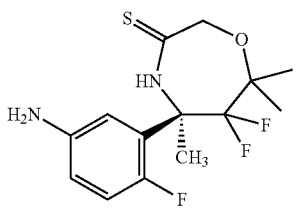 [SMILES: CC1(C)OCC(=S)N[C@](C)(c2cc(N)ccc2F)C1(F)F]

The compound was prepared in an analogous manner as described for intermediate B12A below from (R)-5-(5-(diphenylmethyleneamino)-2-fluorophenyl)-6,6-difluoro-5, 7,7-trimethyl-[1,4]oxazepan-3-one (intermediate A15B) (3.13 g, 6.71 mmol). The compound was obtained as a yellow foam (1.0 g, 3.14 mmol, 47%). MS (ISP): m/z=319.2 [(M+H)+].

Intermediate A17C (R)-5-(5-amino-2,4-difluorophenyl)-6,6-difluoro-5,7,7-trimethyl-[1,4]oxazepane-3-thione

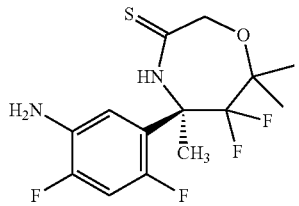 [SMILES: CC1(C)OCC(=S)N[C@](C)(c2cc(N)c(F)cc2F)C1(F)F]

The compound was prepared in an analogous manner as described for intermediate B12A below from (R)-5-(5-(diphenylmethyleneamino)-2,4-difluorophenyl)-6,6-difluoro-5,7,7-trimethyl-[1,4[oxazepan-3-one (intermediate A15C) (0.75 g, 1.55 mmol). The compound was obtained as a light yellow foam (0.29 g, 0.86 mmol, 56%). MS (ISP): m/z=337.2 [(M+H)+].

Intermediate A17A (S)-5-(5-Amino-2-fluoro-phenyl)-5,7,7-trimethyl-[1,4]oxazepane-3-thione

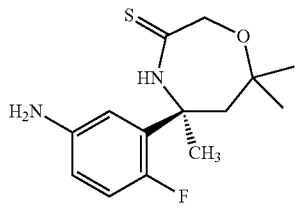 [SMILES: CC1(C)C[C@@](C)(c2cc(N)ccc2F)NC(=S)CO1]

The title compound was prepared in an analogous manner as described for intermediate B12A below from (S)-5-[5-(benzhydrylidene-amino)-2-fluoro-phenyl]-5,7,7-trimethyl-[1,4]oxazepan-3-one (intermediate A15A) (1.15 g, 2.7 mmol) to obtain a crude solution of the (S)-5-[5-(benzhydrylidene-amino)-2-fluoro-phenyl]-5,7,7-trimethyl-[1,4]oxazepane-3-thione (intermediate A16A), which was directly converted to the title compound in an analogous manner as described for intermediate B13A. The compound was obtained as light brown foam (575 mg, 76%). MS (ISP): m/z=283.1 [(M+H)+].

Intermediate A18A

5-Chloro-pyridine-2-carboxylic acid [4-fluoro-3-((S)-5,7,7-trimethyl-3-thioxo-[1,4]oxazepan-5-yl)-phenyl]-amide

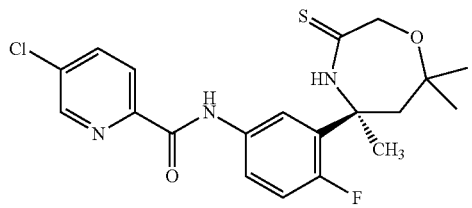 [SMILES: CC1(C)C[C@@](C)(c2cc(NC(=O)c3ccc(Cl)cn3)ccc2F)NC(=S)CO1]

The compound was prepared in an analogous manner as described for intermediate B14A from (S)-5-(5-amino-2-fluoro-phenyl)-5,7,7-trimethyl-[1,4]oxazepane-3-thione (intermediate A17A) (132 mg, 0.47 mmol) and commercially available 5-chloro-pyridine-2-carboxylic acid [CAS No. 86873-60-1] (92 mg, 0.58 mmol). The compound was obtained as white foam (177 mg, 72%). MS (ISP): m/z=422.1 [(M+H)+] and 424.1 [(M+2+H)+].

Intermediate A18B

5-Difluoromethoxy-pyridine-2-carboxylic acid [4-fluoro-3-((S)-5,7,7-trimethyl-3-thioxo-[1,4]oxazepan-5-yl)-phenyl]-amide

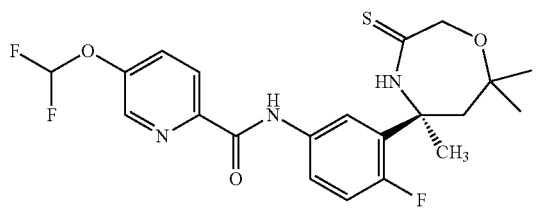 [SMILES: CC1(C)C[C@@](C)(c2cc(NC(=O)c3ccc(OC(F)F)cn3)ccc2F)NC(=S)CO1]

The compound was prepared in an analogous manner as described for intermediate B14A from (S)-5-(5-amino-2-fluoro-phenyl)-5,7,7-trimethyl-[1,4]oxazepane-3-thione (intermediate A17A) (75 mg, 0.26 mmol) and 5-difluoromethoxy-pyridine-2-carboxylic acid [CAS No. 1174323-34-2, described in example 48] (50 mg, 0.26 mmol). The compound was obtained as white foam (99 mg, 82%). MS (ISP): m/z=454.1 [(M+H)+].

Intermediate A18C 5-(2,2,2-Trifluoro-ethoxy)-pyridine-2-carboxylic acid [4-fluoro-3-((S)-5,7,7-trimethyl-3-thioxo-[1,4]oxazepan-5-yl)-phenyl]-amide

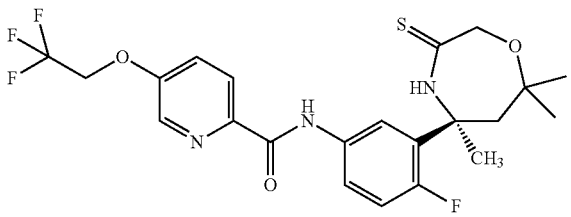 [SMILES: CC1(C)C[C@@](C)(c2cc(NC(=O)c3ccc(OCC(F)(F)F)cn3)ccc2F)NC(=S)CO1]

The title compound was prepared in an analogous manner as described for intermediate B14A from (S)-5-(5-amino-2-fluoro-phenyl)-5,7,7-trimethyl-[1,4]oxazepane-3-thione (intermediate A'7A) (108 mg, 0.38 mmol) and 5-(2,2,2-trifluoro-ethoxy)-pyridine-2-carboxylic acid [CAS No. 881409-53-6; described in intermediate 49] (94 mg, 0.43 mmol). The compound was obtained as a light yellow foam (156 mg, 76%). MS (ISP): m/z=486.3 [(M+H)+].

Intermediate A18D 2,2-Difluoro-cyclopropanecarboxylic acid [4-fluoro-3-((S)-5,7,7-trimethyl-3-thioxo-[1,4]oxazepan-5-yl)-phenyl]-amide

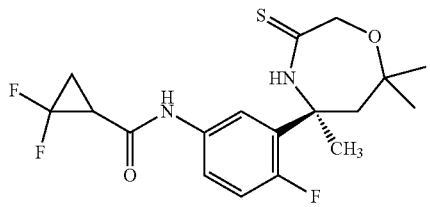 [SMILES: CC1(C)C[C@@](C)(c2cc(NC(=O)C3CC3(F)F)ccc2F)NC(=S)CO1]

The compound was prepared in an analogous manner as described for intermediate B14A from (S)-5-(5-amino-2-fluoro-phenyl)-5,7,7-trimethyl-[1,4]oxazepane-3-thione (intermediate A17A) (151 mg, 0.54 mmol) and commercially available 2,2-difluoro-cyclopropanecarboxylic acid [CAS No. 107873-03-0] (82 mg, 0.67 mmol). The compound was obtained as light yellow foam (158 mg, 61%). MS (ISP): m/z=387.1 [(M+H)⁺].

Intermediate A18E

1-Trifluoromethyl-cyclopropanecarboxylic acid [4-fluoro-3-((S)-5,7,7-trimethyl-3-thioxo-[1,4]oxazepan-5-yl)-phenyl]-amide

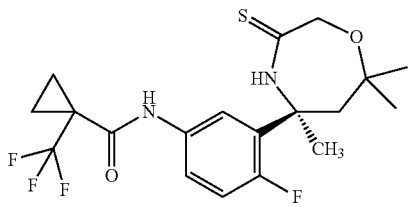 [SMILES: CC1(C)C[C@@](C)(c2cc(NC(=O)C3(C(F)(F)F)CC3)ccc2F)NC(=S)CO1]

The compound was prepared in an analogous manner as described for intermediate B14A from (S)-5-(5-amino-2-fluoro-phenyl)-5,7,7-trimethyl-[1,4]oxazepane-3-thione (intermediate A17A) (110 mg, 0.39 mmol) and commercially available 1-trifluoromethyl-cyclopropanecarboxylic acid [CAS No. 277756-46-4] (67 mg, 0.44 mmol). The compound was obtained as light yellow foam (167 mg, 92%). MS (ISP): m/z=419.2 [(M+H)⁺].

Intermediate A18F

3-Chloro-5-trifluoromethyl-pyridine-2-carboxylic acid [4-fluoro-3-((S)-5,7,7-trimethyl-3-thioxo-[1,4]oxazepan-5-yl)-phenyl]-amide

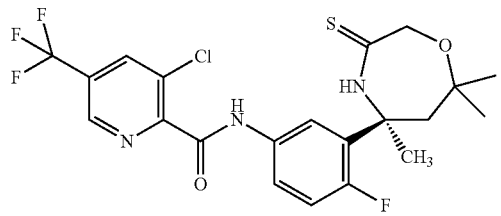 [SMILES: CC1(C)C[C@@](C)(c2cc(NC(=O)c3ncc(C(F)(F)F)cc3Cl)ccc2F)NC(=S)CO1]

The compound was prepared in an analogous manner as described for intermediate B14A from (S)-5-(5-amino-2-fluoro-phenyl)-5,7,7-trimethyl-[1,4]oxazepane-3-thione (intermediate A17A) (106 mg, 0.38 mmol) and commercially available 3-chloro-5-(trifluoromethyl)pyridine-2-carboxylic acid [CAS No. 80194-68-9] (100 mg, 0.44 mmol). The compound was obtained as light yellow foam (133 mg, 61%). MS (ISP): m/z=490.2 [(M+H)⁺] and 492.3 [(M+2+H)⁺].

Intermediate A18G 3,3,3-Trifluoro-N-[4-fluoro-3-((S)-5,7,7-trimethyl-3-thioxo-[1,4]oxazepan-5-yl)-phenyl]-propionamide

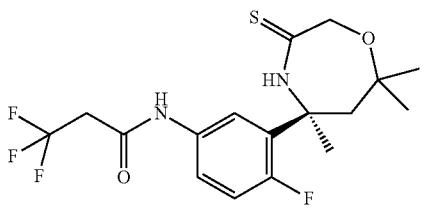 [SMILES: CC1(C)C[C@@](C)(c2cc(NC(=O)CC(F)(F)F)ccc2F)NC(=S)CO1]

The compound was prepared in an analogous manner as described for intermediate B14A from (S)-5-(5-amino-2-fluoro-phenyl)-5,7,7-trimethyl-[1,4]oxazepane-3-thione (intermediate A'7A) (94 mg, 0.33 mmol) and commercially available 3,3,3-trifluoropropionic acid [CAS-no 2516-99-6] (50 mg, 0.39 mmol). The compound was obtained as light yellow foam (71 mg, 46%). MS (ISP): m/z=393.1 [(M+H)⁺].

Intermediate A18H (R)-5-chloro-N-(3-(6,6-difluoro-5,7,7-trimethyl-3-thioxo-[1,4]oxazepan-5-yl)-4-fluorophenyl)picolinamide

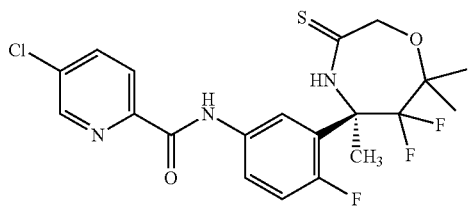 [SMILES: CC1(C)OCC(=S)N[C@](C)(c2cc(NC(=O)c3ccc(Cl)cn3)ccc2F)C1(F)F]

The compound was prepared in an analogous manner as described for intermediate B14A from (R)-5-(5-amino-2-fluorophenyl)-6,6-difluoro-5,7,7-trimethyl-[1,4]oxazepane-3-thione (intermediate A17B) (150 mg, 0.47 mmol) and commercially available 5-chloro-pyridine-2-carboxylic acid [CAS No. 86873-60-1] (111 mg, 0.71 mmol). The compound was obtained as a yellow foam (330 mg, 99%, 65% purity). MS (ISP): m/z=460.4 [(M+H)⁺] and 462.1 [(M+2+H)⁺].

Intermediate A18I (R)-5-cyano-N-(3-(6,6-difluoro-5,7,7-trimethyl-3-thioxo-[1,4]oxazepan-5-yl)-4-fluorophenyl)picolinamide

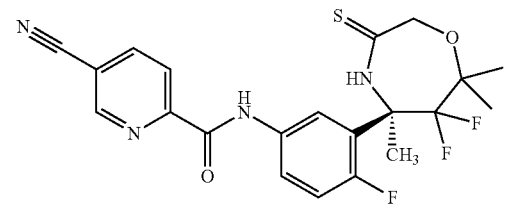 [SMILES: CC1(C)OCC(=S)N[C@](C)(c2cc(NC(=O)c3ccc(C#N)cn3)ccc2F)C1(F)F]

The compound was prepared in an analogous manner as described for intermediate B14A from (R)-5-(5-amino-2-fluorophenyl)-6,6-difluoro-5,7,7-trimethyl-[1,4]oxazepane- 3-thione (intermediate A17B) (150 mg, 0.47 mmol) and commercially available 5-cyano-pyridine-2-carboxylic acid [CAS No. 53234-55-2] (105 mg, 0.71 mmol). The compound was obtained as a light brown oil (280 mg, 99%, 75% purity). MS (ISP): m/z=449.2 [(M+H)$^+$].

Intermediate A18J (R)-5-chloro-N-(5-(6,6-difluoro-5,7,7-trimethyl-3-thioxo-[1,4]oxazepan-5-yl)-2,4-difluorophenyl)picolinamide

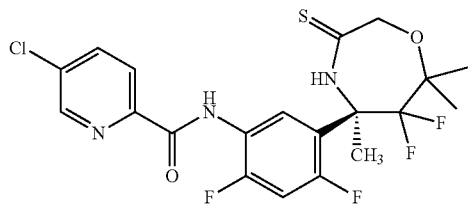 [SMILES: CC1(C)OCC(=S)N[C@](C)(c2cc(NC(=O)c3ccc(Cl)cn3)c(F)cc2F)C1(F)F]

The compound was prepared in an analogous manner as described for intermediate B14A from (R)-5-(5-amino-2,4-difluorophenyl)-6,6-difluoro-5,7,7-trimethyl-[1,4]oxazepane-3-thione (intermediate A17C) (70 mg, 0.208 mmol) and commercially available 5-chloro-pyridine-2-carboxylic acid [CAS No. 86873-60-1] (49 mg, 0.312 mmol). The compound was obtained as a white solid (90 mg, 91%). MS (ISP): m/z=476.1 [(M+H)$^+$] and 478.1 [(M+2+H)$^+$].

Intermediate A18K (R)-5-cyano-N-(5-(6,6-difluoro-5,7,7-trimethyl-3-thioxo-[1,4]oxazepan-5-yl)-2,4-difluorophenyl)picolinamide

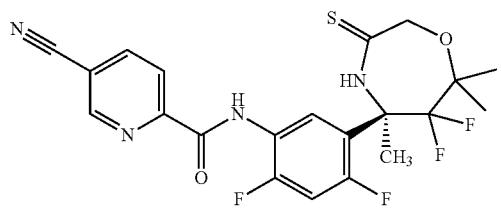 [SMILES: CC1(C)OCC(=S)N[C@](C)(c2cc(NC(=O)c3ccc(C#N)cn3)c(F)cc2F)C1(F)F]

The compound was prepared in an analogous manner as described for intermediate B14A from (R)-5-(5-amino-2,4-difluorophenyl)-6,6-difluoro-5,7,7-trimethyl-[1,4]oxazepane-3-thione (intermediate A17C) (70 mg, 0.208 mmol) and commercially available 5-cyano-pyridine-2-carboxylic acid [CAS No. 53234-55-2] (46 mg, 0.312 mmol). The compound was obtained as a light yellow foam (80 mg, 82%). MS (ISP): m/z=467.1 [(M+H)$^+$].

Synthesis of the O-Allyl Compounds A19 from the Alcohols A4

General Procedure:

To a solution of the alcohol A4 (29.25 mmol) in dry tetrahydrofuran (290 mL) at 23° C. was added commercially available allyl tent-butyl carbonate (5.56 g, 35.1 mmol), argon was bubbled through the solution and tetrakistriphenylphosphinepalladium(0) (1.02 g, 878 µmol) was added and the mixture was stirred at 70° C. for 8 hours. Cooled to 23° C., extracted with ethyl acetate and water, dried the organic layer over Na$_2$SO$_4$, filtered and evaporated totally. The residue was chromatographed on silica gel with ethyl acetate 0%-80% in heptane to give the O-allylated compounds A19.

Intermediate A19A (R)-N-((R)-4-(allyloxy)-2-(5-bromo-2-fluorophenyl)-3,3-difluoro-4-methylpentan-2-yl)-2-methylpropane-2-sulfinamide

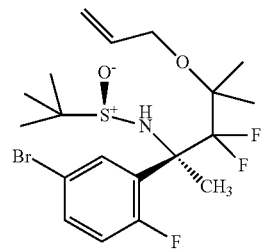 [SMILES: C=CCOC(C)(C)C(F)(F)[C@](C)(N[S@+]([O-])C(C)(C)C)c1cc(Br)ccc1F]

The compound was prepared from (R)-N-((R)-2-(5-bromo-2-fluorophenyl)-3,3-difluoro-4-hydroxy-4-methylpentan-2-yl)-2-methylpropane-2-sulfinamide (intermediate A4F) (12.58 g; 29.25 mmol). The (R)-N-((R)-4-(allyloxy)-2-(5-bromo-2-fluorophenyl)-3,3-difluoro-4-methylpentan-2-yl)-2-methylpropane-2-sulfinamide (9.5 g, 20.2 mmol, 69% yield) was obtained as a light yellow solid. MS (ISP): m/z=470.0 [(M+H)$^+$] and 472.0 [(M+2+H)$^+$].

Intermediate A19B (R)-N-((R)-4-(allyloxy)-2-(5-bromo-2,4-difluorophenyl)-3,3-difluoro-4-methylpentan-2-yl)-2-methylpropane-2-sulfinamide

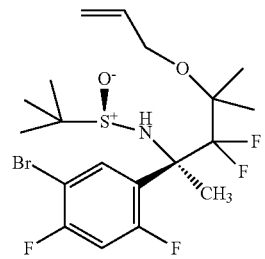 [SMILES: C=CCOC(C)(C)C(F)(F)[C@](C)(N[S@+]([O-])C(C)(C)C)c1cc(Br)c(F)cc1F]

The compound was prepared from (R)-N-((R)-2-(5-bromo-2,4-difluorophenyl)-3,3-difluoro-4-hydroxy-4-methylpentan-2-yl)-2-methylpropane-2-sulfinamide (intermediate A4G) (21.4 g; 47.7 mmol). The (R)-N-((R)-4-(allyloxy)-2-(5-bromo-2,4-difluorophenyl)-3,3-difluoro-4-methylpentan-2-yl)-2-methylpropane-2-sulfinamide (16.15 g, 33.1 mmol, 69% yield) was obtained as a light brown oil. MS (ISP): m/z=488.1 [(M+H)$^+$] and 490.0 [(M+2+H)$^+$].

Synthesis of the Acids A20 from the Allyl Ethers A19

General Procedure:

To a solution of the allyl ether A19 (20.2 mmol) in ethyl acetate (95 mL), acetonitrile (95 mL) and water (142 mL) at 23° C. was added sodium periodate (28.1 g, 131 mmol) followed by ruthenium(III) chloride hydrate (91 mg, 0.4 mmol) and the mixture was stirred at 23° C. for 3 hours. Diluted with ethyl acetate and extracted with 1 N HCl+ diluted NaHSO$_3$-sol., dried the organic layer over Na$_2$SO$_4$, filtered off, evaporated totally and dried in high vacuum to give the crude product (acid A20), which was used without further purification.

Intermediate A20A (R)-2-(4-(5-bromo-2-fluorophenyl)-4-(1,1-dimethyl-ethylsulfonamido)-3,3-difluoro-2-methylpentan-2-yloxy)acetic acid

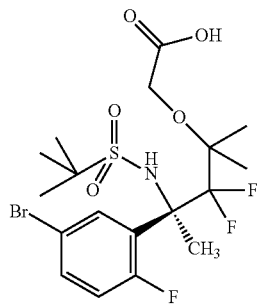 [SMILES: CC(C)(OCC(=O)O)C(F)(F)[C@](C)(NS(=O)(=O)C(C)(C)C)c1cc(Br)ccc1F]

The compound was prepared from (R)-N-((R)-4-(allyloxy)-2-(5-bromo-2-fluorophenyl)-3,3-difluoro-4-methylpentan-2-yl)-2-methylpropane-2-sulfinamide (intermediate A 19A) (9.5 g; 20.2 mmol). The (R)-2-(4-(5-bromo-2-fluorophenyl)-4-(1,1-dimethylethylsulfonamido)-3,3-difluoro-2-methylpentan-2-yloxy)acetic acid (10.2 g, 20.2 mmol, 100% yield) was obtained as a light yellow foam. MS (ISN): m/z=502.0 [(M−H)⁻] and 503.9 [(M+2−H)⁻].

Intermediate A20B (R)-2-(4-(5-bromo-2,4-difluorophenyl)-4-(1,1-dimethylethylsulfonamido)-3,3-difluoro-2-methylpentan-2-yloxy)acetic acid

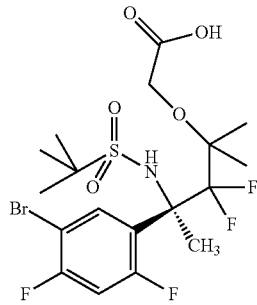 [SMILES: CC(C)(OCC(=O)O)C(F)(F)[C@](C)(NS(=O)(=O)C(C)(C)C)c1cc(Br)c(F)cc1F]

The compound was prepared from (R)-N-((R)-4-(allyloxy)-2-(5-bromo-2,4-difluorophenyl)-3,3-difluoro-4-methylpentan-2-yl)-2-methylpropane-2-sulfinamide (intermediate A19B) (16.14 g; 33 mmol). The (R)-2-(4-(5-bromo-2,4-difluorophenyl)-4-(1,1-dimethylethylsulfonamido)-3,3-difluoro-2-methylpentan-2-yloxy)acetic acid (17.3 g, 33.1 mmol, 100% yield) was obtained as a light grey solid. MS (ISN): m/z=520.0 [(M−H)⁻] and 521.9 [(M+2−H)⁻].

Synthesis of the Ethyl Esters A21 from the Acids A20

General Procedure:
To a solution of the acid A20 (18.2 mmol) in ethanol (200 mL) at 23° C. was dropwise added thionyl chloride (5.3 mL, 72.8 mmol) and the mixture was stirred at reflux for 18 hours. Cooled to 23° C., diluted with ethyl acetate and extracted with sat NaHCO₃-sol. and brine, dried over Na₂SO₄, filtered off and evaporated totally to give the crude ethyl esters A21, which were used without further purification.

Intermediate A21A (R)-ethyl 2-(4-(5-bromo-2-fluorophenyl)-4-(1,1-dimethylethylsulfonamido)-3,3-difluoro-2-methylpentan-2-yloxy)acetate

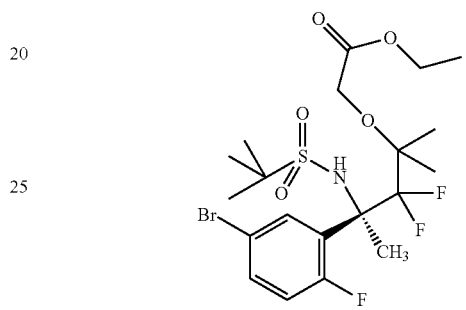

The compound was prepared from (R)-2-(4-(5-bromo-2-fluorophenyl)-4-(1,1-dimethylethylsulfonamido)-3,3-difluoro-2-methylpentan-2-yloxy)acetic acid (intermediate A20A) (10.2 g; 18.2 mmol). The (R)-ethyl 2-(4-(5-bromo-2-fluorophenyl)-4-(1,1-dimethylethylsulfonamido)-3,3-difluoro-2-methylpentan-2-yloxy)acetate (10 g, 103% yield) was obtained as a light brown solid. MS (ISN): m/z=530.2 [(M−H)⁻] and 532.0 [(M+2−H)⁻].

Intermediate A21B (R)-ethyl 2-(4-(5-bromo-2,4-difluorophenyl)-4-(1,1-dimethylethylsulfonamido)-3,3-difluoro-2-methylpentan-2-yloxy)acetate

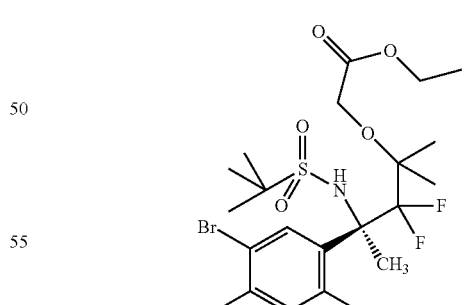

The compound was prepared from (R)-2-(4-(5-bromo-2,4-difluorophenyl) -4-(1,1-dimethylethylsulfonamido)-3,3-difluoro-2-methylpentan-2-yloxy)acetic acid (intermediate A20B) (17.1 g; 33 mmol). The (R)-ethyl 2-(4-(5-bromo-2,4-difluorophenyl)-4-(1,1-dimethylethylsulfonamido)-3,3-difluoro-2-methylpentan-2-yloxy)acetate (20.55 g, 37.3 mmol, 113% yield) was obtained as a light brown oil. MS (ISP): m/z=550.2 [(M+H)⁺] and 552.3 [(M+2+H)⁺].

Synthesis of the Amino Esters A22 from the Sulfonamides A21

General Procedure:

To a solution of the sulfonamide A21 (18.8 mmol) in dichloromethane (190 mL) at 0° C. was dropwise added a 0.25 M solution of trifluoromethanesulfonic acid (225 mL, 56.3 mmol) and the mixture was stirred at 23° C. for 30 min. Poured into sat NaHCO$_3$-sol., extracted with dichloromethane, dried the organic layer over Na$_2$SO$_4$, filtered off and evaporated totally to give the crude amino esters A22, which were used without further purification or alternatively purified by silica gel column chromatography with heptane and ethyl acetate.

Dropwise addition of TRIFLUOROMETHANESULFONIC ACID in CH2Cl2 0.25 M (225 ml, 56.3 mmol, Eq: 3) to a solution of (R)-ethyl 2-(4-(5-bromo-2-fluorophenyl)-4-(1,1-dimethylethylsulfonamido)-3,3-difluoro-2-methylpentan-2-yloxy)acetate (RO5545483-000-005) (10 g, 18.8 mmol, Eq: 1.00) in Dichloromethane (188 ml) at 0° C. this reaction mixture was stirred at room temperature for 30 minutes Extracted with sat NaHCO3, CH2Cl2, dried over Na2SO4, filtered off, evaporated, dried in HV to give a brown oil (8.8 g; 114%) The residue was chromatographed, 50 g SiO2 (Flashmaster) with EtOAc 0%-50% in heptane to give (R)-ethyl 2-(4-amino-4-(5-bromo-2-fluorophenyl)-3,3-difluoro-2-methylpentan-2-yloxy)acetate (6.85 g, 16.6 mmol, 88.5% yield) as a light yellow oil.

Intermediate A22A (R)-ethyl 2-(4-amino-4-(5-bromo-2-fluorophenyl)-3,3-difluoro-2-methylpentan-2-yloxy)acetate

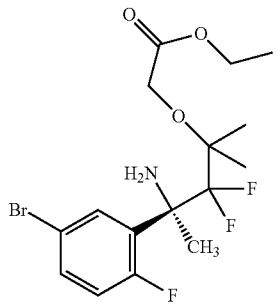 [SMILES: CCOC(=O)COC(C)(C)C(F)(F)[C@](C)(N)c1cc(Br)ccc1F]

The compound was prepared from (R)-ethyl 2-(4-(5-bromo-2-fluorophenyl)-4-(1,1-dimethylethylsulfonamido)-3,3-difluoro-2-methylpentan-2-yloxy)acetate (intermediate A21A) (10.2 g; 18.2 mmol). The (R)-ethyl 2-(4-amino-4-(5-bromo-2-fluorophenyl)-3,3-difluoro-2-methylpentan-2-yloxy)acetate (6.85 g, 16.6 mmol, 88.5% yield) was obtained as a light yellow oil. MS (ISP): m/z=412.1 [(M+H)$^-$] and 414.2 [(M+2+H)$^+$].

Intermediate A22B (R)-ethyl 2-(4-amino-4-(5-bromo-2,4-difluorophenyl)-3,3-difluoro-2-methylpentan-2-yloxy)acetate

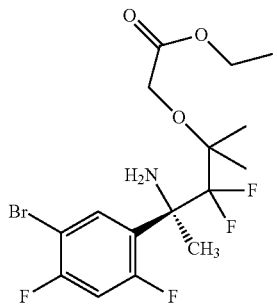 [SMILES: CCOC(=O)COC(C)(C)C(F)(F)[C@](C)(N)c1cc(Br)c(F)cc1F]

The compound was prepared from (R)-ethyl 2-(4-(5-bromo-2,4-difluorophenyl)-4-(1,1-dimethylethylsulfonamido)-3,3-difluoro-2-methylpentan-2-yloxy)acetate (intermediate A21B) (20.55 g; 37.3 mmol). The (R)-ethyl 2-(4-amino-4-(5-bromo-2,4-difluorophenyl)-3,3-difluoro-2-methylpentan-2-yloxy)acetate (16.1 g, 37.4 mmol, 100% yield) was obtained as a light yellow oil. MS (ISP): m/z=430.1 [(M+H)$^+$] and 432.2 [(M+2+H)$^+$].

Intermediate B2A (5-Bromo-2-fluoro-phenyl)-acetyl chloride

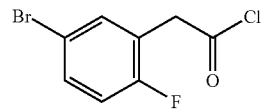

To a mixture of commercially available 5-bromo-2-fluorophenylacetic acid (compound B1A, [CAS No. 883514-21-4], 6.42 g, 26 mmol) in toluene (52 ml) and thionyl chloride (SOCl$_2$) (4.721 ml, 40 mmol) at 23° C. was added a drop of N,N-dimethylformamide (DMF) and the mixture was stirred at 80° C. for 4 hours (reaction checked by HPLC with product+MeOH). All volatiles were removed by rotary evaporation and the residue was dried in high vacuum to give the title compound as a colorless liquid (7.01 g, 105%), which was used without further purification.

Intermediate B2B (3-Bromo-phenyl)-acetyl chloride

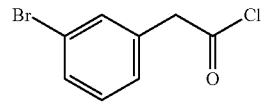 [SMILES: O=C(Cl)Cc1cccc(Br)c1]

The compound was prepared in an analogous manner as described for intermediate B2A from commercially available 3-bromophenylacetic acid (compound B1B, [CAS No. 1878-

Intermediate B3A (5-Bromo-2-fluoro-phenyl)-acetic acid allyl ester

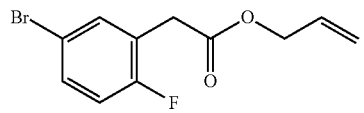

To a mixture of allyl alcohol (22.1 g, 380.5 mmol) and triethylamine (Et₃N) (5.4 ml, 39 mmol) at 0° C. was added over 1 h crude (5-bromo-2-fluoro-phenyl)-acetyl chloride (intermediate B2A) (7.01 g, ca. 26 mmol). Then the reaction was stirred over 1 h from 0° C. to 23° C. The reaction mixture was diluted with ethyl acetate, washed with water, and the organic layer was dried over sodium sulfate. Removal of the solvent in vacuum left the title compound as a yellow oil (7.290 g, 103%), which was used without further purification. MS (ISP): m/z=280.1 [(M+NH$_4$)$^+$] and 282.1 [(M+2+NH$_4$)$^+$]

Intermediate B3B (3-Bromo-phenyl)-acetic acid allyl ester

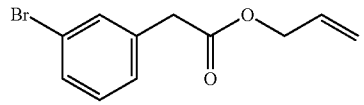

The title compound was prepared in an analogous manner as described for intermediate B3A from (3-bromo-phenyl)-acetyl chloride (intermediate B2B) (12.1 g, ca. 50 mmol). The compound was obtained after silica gel column chromatography with n-heptane/ethyl acetate as a light yellow liquid (7.934 g, 62%). MS (ISP): m/z=272.1 [(M+NH$_4$)$^+$] and 274.1 [(M+2+NH$_4$)$^+$]

Intermediate B4A (5-Bromo-2-fluoro-phenyl)-diazo-acetic acid allyl ester

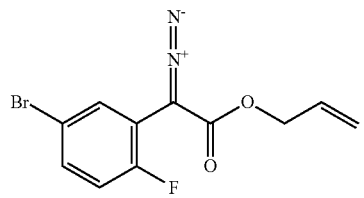 [SMILES: C=CCOC(=O)C(=[N+]=[N-])c1cc(Br)ccc1F]

To a solution of 1,8-diazabicyclo[5.4.0]undec-7-ene (DBU) (4.2 ml, 28 mmol) in THF (24 ml) at 23° C. was added a solution of (5-bromo-2-fluoro-phenyl)-acetic acid allyl ester (intermediate B3A) (7.29 g, 27 mmol) and commercially available p-acetamidobenzenesulfonyl azide ([CAS No. 2158-14-7], 6.94 g, 28 mmol) in THF (48 ml) over 1 h. The mixture was stirred for 5 h at 23° C. Then it was quenched with sat. aqueous ammonium chloride solution, diluted with ethyl acetate, and the organic layer was washed with brine and dried over sodium sulfate. Removal of the solvent in vacuum left a yellow oil, which was purified by silica gel column chromatography with hexane/ethyl acetate to give the title compound as a yellow solid (7.344 g, 92%). MS (ISP): m/z=316.1 [(M+NH$_4$)$^+$] and 318.0 [(M+2+NH$_4$)$^+$].

Intermediate B4B (3-Bromo-phenyl)-diazo-acetic acid allyl ester

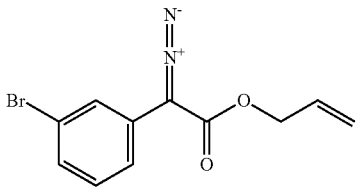 [SMILES: C=CCOC(=O)C(=[N+]=[N-])c1cccc(Br)c1]

The compound was prepared in an analogous manner as described for intermediate B4A from (3-bromo-phenyl)-acetic acid allyl ester (intermediate B3B) (7.93 g, 31 mmol). It was obtained after silica gel column chromatography with n-heptane/ethyl acetate as an orange oil (8.717 g, 100%). MS (ISP): m/z=298.1 [(M+NH$_4$)$^+$] and 300.0 [(M+2+NH$_4$)$^+$].

Intermediate B5A (1SR,5RS)-1-(5-Bromo-2-fluoro-phenyl)-3-oxa-bicyclo[3.1.0]hexan-2-one

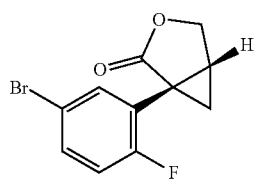 [SMILES: O=C1OC[C@@H]2C[C@]12c1cc(Br)ccc1F]

To a solution of commercially available rhodium(II) octanoate dimer (Rh$_2$(C$_7$H$_{16}$CO$_2$)$_4$) ([CAS No. 73482-96-9], 160 mg, 1 mol %) in DCM (60 ml) at 45° C. was added a solution of (5-bromo-2-fluoro-phenyl)-diazo-acetic acid allyl ester (intermediate B4A) (6.0 g, 20 mmol) in DCM (2×20 ml) via syringe pump within 16 h. Continued refluxing for 1 h, cooled to 23° C., washed with 1 M aqueous hydrochloric acid (HCl) and sat. aqueous sodium hydrogencarbonate solution (NaHCO$_3$-sol.), dried organic layer over sodium sulfate. Removal of the solvent in vacuum left a green solid, which was purified by silica gel column chromatography with n-heptane/ethyl acetate to give the title compound as a light green solid (4.6 g, 85%) [cf. *Adv. Synth. Catal.* 2001, 343, 299, for an enantioselective version of this reaction].

Chiral HPLC (Reprosil Chiral-NR) with n-heptane/ethanol (40 min) showed two peaks: (+) 13.892 min, (−) 16.717 min.

MS (ISP): m/z=272.2 [(M+H)$^+$]. MS (ISP): m/z=271.1 [(M+H)$^-$] and 273.1 [(M+2+H)$^+$].

Intermediate B5B (1S R,5RS)-1-(3-Bromo-phenyl)-3-oxa-bicyclo[3.1.0]hexan-2-one

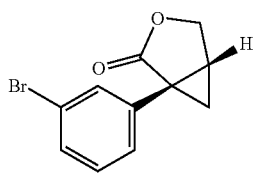

The compound was prepared in an analogous manner as described for intermediate B5A from (3-bromo-phenyl)-diazo-acetic acid allyl ester (intermediate B4B) (8.71 g, 31 mmol). The compound was obtained after silica gel column chromatography with n-heptane/ethyl acetate as light green oil (6.585 g, 84%). MS (ISP): m/z=270.1 [(M+NH$_4$)$^+$] and 272.1 [(M+2+NH$_4$)$^+$].

Intermediate B6A (1S R,2RS)-1-(5-Bromo-2-fluoro-phenyl)-2-hydroxymethyl-cyclopropanecarboxylic acid amide

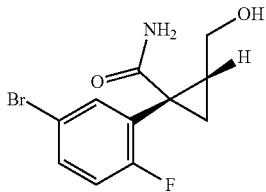 [SMILES: NC(=O)[C@@]1(c2cc(Br)ccc2F)C[C@H]1CO]

To a suspension of (1SR,5RS)-1-(5-bromo-2-fluoro-phenyl)-3-oxa-bicyclo[3.1.0]hexan-2-one (intermediate B5A) (4.6 g, 17 mmol) in dioxane (20 ml) at 23° C. was added ammonia (7 M in MeOH, 40 ml) and the mixture was stirred at 23° C. for 2 days (not complete). Evaporated all volatiles and directly subjected to silica gel chromatography with n-heptane/ethyl acetate to give recovered starting material (0.98 g, 21%) and the title compound as a white solid (3.5 g, 72%). MS (ISP): m/z=287.9 [(M+H)$^+$] and 290.0 [(M+2+H)$^+$].

Intermediate B6B (1SR,2RS)-1-(3-Bromo-phenyl)-2-hydroxymethyl-cyclopropanecarboxylic acid amide

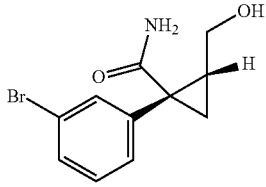 [SMILES: NC(=O)[C@@]1(c2cccc(Br)c2)C[C@H]1CO]

The compound was prepared in an analogous manner as described for intermediate B6A from (1S R,5RS)-1-(3-bromo-phenyl)-3-oxa-bicyclo[3.1.0]hexan-2-one (intermediate B5B) (6.58 g, 26 mmol). The compound was obtained after silica gel column chromatography with n-heptane/ethyl acetate as a white solid (5.54 g, 79%). MS (ISP): m/z=270.2 [(M+H)$^+$] and 272.1 [(M+2+H)$^+$].

Intermediate B7A (1S R,6RS)-1-(5-Bromo-2-fluoro-phenyl)-4-oxa-2-aza-bicyclo[4.1.0]heptan-3-one

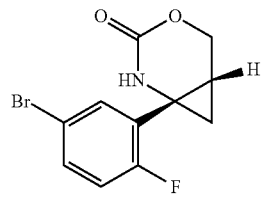 [SMILES: O=C1N[C@@]2(c3cc(Br)ccc3F)C[C@H]2CO1]

Preparation of the oxidizing reagent: Potassium hydroxide (KOH) (85%, 5.62 g, 100 mmol) was dissolved in water (40 ml), cooled to −5° C., N-bromosuccinimide (NBS) (7.16 g, 40 mmol) was added and stirred at −5° C. until all the solid had dissolved. The resulting clear yellow solution was aged at −3 to −5° C. for 2 to 16 h, resulting in a light yellow clear solution of the oxidizing reagent (ca. 1 M).

To a solution of (1SR,2RS)-1-(5-bromo-2-fluoro-phenyl)-2-hydroxymethyl-cyclopropanecarboxylic acid amide (intermediate B6A) (3.04 g, 11 mmol) in THF (95 ml) and MeOH (60 ml) at −20° C. was quickly added the above prepared solution of the oxidizing reagent (40 ml, ca. 40 mmol), stirring was continued at −20 to 0° C. for 2 h, then slowly warmed to 23° C. Stirring was continued at 23° C. for 18 h (reaction not complete). Treated again with the same amount of oxidizing reagent and stirred again at 23° C. for 18 h. Concentrated in vaccum (to remove THF and some MeOH), poured into 1 M HCl+brine+some sat. sodium sulfite (Na$_2$SO$_3$)-sol., extracted with ethyl acetate, washed combined organic layer with sat. NaHCO$_3$-sol. and brine, dried over sodium sulfate. Removal of the solvent in vacuum left a white solid, which was purified by silica gel column chromatography with n-heptane/ethyl acetate to give the title compound as a white solid (2.93 g, 97%). MS (ISP): m/z=285.9 [(M+H)$^+$] and 287.9 [(M+2+H)$^+$].

Intermediate B7B (1SR,6RS)-1-(3-Bromo-phenyl)-4-oxa-2-aza-bicyclo[4.1.0]heptan-3-one

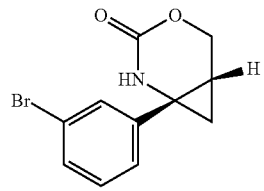 [SMILES: O=C1N[C@@]2(c3cccc(Br)c3)C[C@H]2CO1]

The compound was prepared in an analogous manner as described for intermediate B7A from (1SR,2RS)-1-(3-bromo-phenyl)-2-hydroxymethyl-cyclopropanecarboxylic acid amide (intermediate B6B) (6.41 g, 24 mmol). The title compound was obtained after silica gel column chromatography with n-heptane/ethyl acetate as a white solid (3.49 g, 55%). MS (ISP): m/z=270.2 [(M+H)$^−$] and 272.1 [(M+2+H)$^+$]. Additionally isolated was the ring opened [( SR)-1-(3-bromo-phenyl)-2-((RS)-hydroxymethyl)-cyclopropyl]-carbamic acid methyl ester as a colorless oil (2.49 g, 35%).

Intermediate B8A

[(1RS,2SR)-2-Amino-2-(5-bromo-2-fluoro-phenyl)-cyclopropyl]-methanol

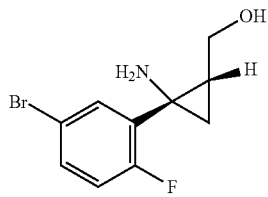 [SMILES: N[C@@]1(c2cc(Br)ccc2F)C[C@H]1CO]

A mixture of (1SR,6RS)-1-(5-bromo-2-fluoro-phenyl)-4-oxa-2-aza-bicyclo[4.1.0]heptan-3-one (intermediate B7A) (1.48 g, 5.17 mmol) and lithium hydroxide monohydrate (LiOH.H$_2$O) (2.17 g, 52 mmol) in ethanol (EtOH) (2.5 ml) and water (12.5 ml) was stirred at 100° C. for 16 h. Poured into ice water, added brine, extracted twice with tert-butyl methyl ether (TBME), washed organic layer with brine, dried over sodium sulfate. Removal of the solvent in vacuum left the title compound as a light brown oil (1.224 g, 91%), which was used without further purification. MS (ISP): m/z=242.2 [(M−NH$_2$)$^+$] and 244.2 [(M+2−NH$_2$)$^+$].

Intermediate B8B

[(1RS,2SR)-2-Amino-2-(3-bromo-phenyl)-cyclopropyl]-methanol

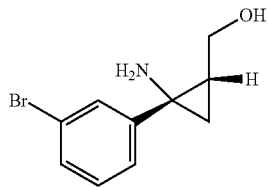 [SMILES: N[C@@]1(c2cccc(Br)c2)C[C@H]1CO]

The compound was prepared in an analogous manner as described for intermediate B8A from a mixture of (1SR,6RS)-1-(3-bromo-phenyl)-4-oxa-2-aza-bicyclo[4.1.0]heptan-3-one (intermediate B7B) and [(SR)-1-(3-bromo-phenyl)-2-((RS)-hydroxymethyl)-cyclopropyl]-carbamic acid methyl ester (side product from intermediate B7B) (together: 5.9 g, 22 mmol). The compound was obtained as light brown oil (5.129 g, 96%). MS (ISP): m/z=242.2 [(M+H)$^+$] and 244.1 [(M+2+H)$^+$].

Intermediate B9A

N-[(1SR,2RS)-1-(5-Bromo-2-fluoro-phenyl)-2-hydroxymethyl-cyclopropyl]-2-chloro-acetamide

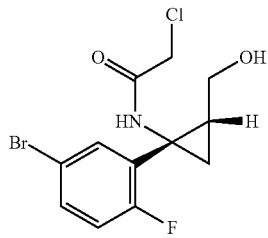 [SMILES: O=C(CCl)N[C@@]1(c2cc(Br)ccc2F)C[C@H]1CO]

To a vigorously stirred mixture of [(1RS,2SR)-2-amino-2-(5-bromo-2-fluoro-phenyl)-cyclopropyl]-methanol (intermediate B8A) (387 mg, 1.49 mmol) in sat. aqueous NaHCO$_3$-sol. (5 ml) and dichloromethane (DCM) (7 ml) at 0° C. was added chloroacetyl chloride (130 ul, 1.64 mmol) and the mixture was stirred at 0° C. for 30 min. Diluted with water, brine and ethyl acetate (EtOAc), separated phases, dried organic layer over sodium sulfate. Removal of the solvent in vacuum left the title compound as an off-white solid (497 mg, 99%), which was used without further purification. MS (ISP): m/z=336.1 [(M+H)$^+$], 338.2 [(M+2+H)$^+$] and 340.1 [(M+4+H)$^+$].

Intermediate B9B

N-[(1SR,2RS)-1-(3-Bromo-phenyl)-2-hydroxymethyl-cyclopropyl]-2-chloro-acetamide

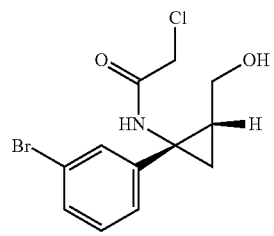 [SMILES: O=C(CCl)N[C@@]1(c2cccc(Br)c2)C[C@H]1CO]

The compound was prepared in an analogous manner as described for intermediate B9A from [(1RS,2SR)-2-amino-2-(3-bromo-phenyl)-cyclopropyl]-methanol (intermediate B8B) (4.12 g, 17 mmol). The compound was obtained as a light brown oil (5.30 g, 98%). MS (ISP): m/z=318.0 [(M+H)$^-$], 320.0 [(M+2+H)$^+$] and 324.0 [(M+4+H)$^+$].

Intermediate B10A (1SR,7RS)-1-(5-Bromo-2-fluoro-phenyl)-5-oxa-2-aza-bicyclo[5.1.0]octan-3-one

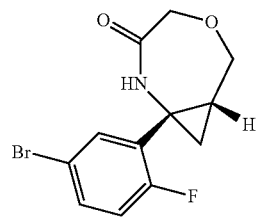 [SMILES: O=C1COC[C@@H]2C[C@]2(c2cc(Br)ccc2F)N1]

To a suspension of N-[(1SR,2RS)-1-(5-bromo-2-fluoro-phenyl)-2-hydroxymethyl-cyclopropyl]-2-chloro-acetamide (intermediate B9A) (495 mg, 1.47 mmol) in tert-butanol (6 ml) at 23° C. was added potassium tert-butoxide (KOBu$^t$) (550 mg, 4.9 mmol) in one portion [exothermic] and the mixture was stirred at 23° C. for 19 h. Poured into 1 M HCl, extracted with ethyl acetate, washed organic layer with brine, dried over sodium sulfate. Removal of the solvent in vacuum left an orange oil, which was purified by silica gel column chromatography with n-heptane/ethyl acetate to give the title compound as a white gum (405 mg, 92%). MS (ISP): m/z=300.1 [(M+H)$^-$] and 302.2 [(M+2+H)$^+$].

Intermediate B10B (1SR,7RS)-1-(3-Bromo-phenyl)-5-oxa-2-aza-bicyclo[5.1.0]octan-3-one

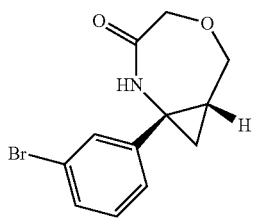 [SMILES: O=C1COC[C@@H]2C[C@]2(c2cccc(Br)c2)N1]

The compound was prepared in an analogous manner as described for intermediate B10A from N-[(1SR,2RS)-1-(3-bromo-phenyl)-2-hydroxymethyl-cyclopropyl]-2-chloro-acetamide (intermediate B9B) (5.3 g, 16.6 mmol). The title compound was obtained as an off-white solid (4.31 g, 92%). MS (ISP): m/z=282.1 [(M+H)$^+$] and 284.1 [(M+2+H)$^+$].

Intermediate B11A (1SR,7RS)-1-[5-(Benzhydrylidene-amino)-2-fluoro-phenyl]-5-oxa-2-aza-bicyclo[5.1.0]octan-3-one

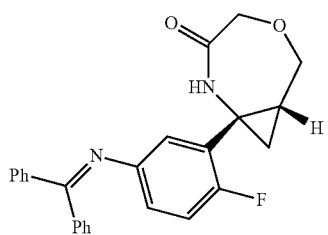 [SMILES: O=C1COC[C@@H]2C[C@]2(c2cc(N=C(c3ccccc3)c3ccccc3)ccc2F)N1]

Under argon in a sealed tube was added to a solution of (1SR,7RS)-1-(5-bromo-2-fluoro-phenyl)-5-oxa-2-aza-bicyclo[5.1.0]octan-3-one (intermediate B10A) (405 mg, 1.349 mmol) in toluene (9 ml), sodium tert-butoxide (NaOBu$^t$) (389 mg, 4.05 mmol), 2-di-tert-butylphosphino-2',4',6'-triisopropylbiphenyl (t-Bu X-phos) (57 mg, 10 mol %) and tris(dibenzylideneacetone)dipalladium chloroform complex (Pd$_2$(dba)$_3$.CHCl$_3$) (42 mg, 3 mol %) followed by benzophenone imine (453 uL, 2.7 mmol). The tube was sealed under argon and the mixture was stirred at 105° C. for 18 h to 2.5 days. The mixture was cooled to 23° C., poured into water, extracted with ethyl acetate, and the organic layer was washed with brine and dried over sodium sulfate. Removal of the solvent in vacuum left a brown oil, which was purified by silica gel column chromatography with n-heptane/ethyl acetate to give the title compound as a yellow foam (460 mg, 85%). MS (ISP): m/z=401.3 [(M+H)$^+$].

Intermediate B11B (1SR,7RS)-1-[3-(Benzhydrylidene-amino)-phenyl]-5-oxa-2-aza-bicyclo[5.1.0]octan-3-one

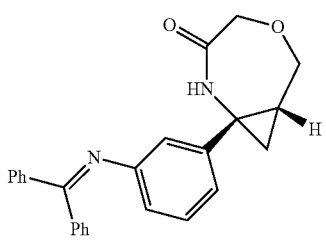 [SMILES: O=C1COC[C@@H]2C[C@]2(c2cccc(N=C(c3ccccc3)c3ccccc3)c2)N1]

The compound was prepared in an analogous manner as described for intermediate B11A from (1SR,7RS)-1-(3-bromo-phenyl)-5-oxa-2-aza-bicyclo[5.1.0]octan-3-one (intermediate B10B) (4.30 g, 15.2 mmol). The compound was obtained as a light brown foam (4.87 g, 84%). MS (ISP): m/z=383.3 [(M+H)$^+$].

Intermediate B12A (1SR,7RS)-1-[5-(Benzhydrylidene-amino)-2-fluoro-phenyl]-5-oxa-2-aza-bicyclo[5.1.0]octane-3-thione

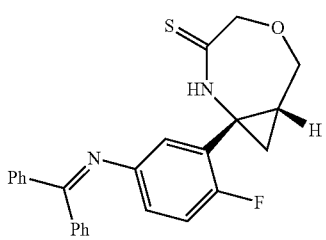 [SMILES: Fc1ccc(N=C(c2ccccc2)c2ccccc2)cc1[C@]12C[C@H]1COCC(=S)N2]

To a solution of (1SR,7RS)-1-[5-(benzhydrylidene-amino)-2-fluoro-phenyl]-5-oxa-2-aza-bicyclo[5.1.0]octan-3-one (intermediate B11A) (460 mg, 1.15 mmol) in dioxane (3 ml) at 23° C. was added 2,4-bis-(4-methoxy-phenyl)-[1,3,2,4]dithiadiphosphetane 2,4-disulfide (Lawesson's reagent) (292 mg, 0.72 mmol) and the mixture was stirred at 80° C. for 2 h. The green solution was poured on sat. NaHCO$_3$ solution, extracted with ethyl acetate, washed the organic layer with brine and dried over sodium sulfate. Removal of the solvent in vacuum left the title compound as a green oil (600 mg, ca. 80% pure, 100%), which was used in the next step without further purification. MS (ISP): m/z=417.3 [(M+H)$^+$].

Intermediate B12B (1SR,7RS)-1-[3-(Benzhydrylidene-amino)-phenyl]-5-oxa-2-aza-bicyclo[5.1.0]octane-3-thione

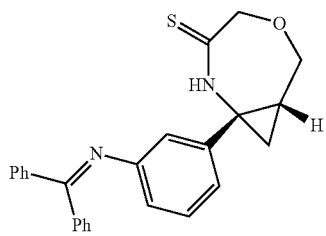 [SMILES: S=C1COC[C@@H]2C[C@]2(c2cccc(N=C(c3ccccc3)c3ccccc3)c2)N1]

The title compound was prepared in an analogous manner as described for intermediate B12A from (1SR,7RS)-1-[3-(benzhydrylidene-amino)-phenyl]-5-oxa-2-aza-bicyclo[5.1.0]octan-3-one (intermediate B11B) (2.30 g, 5.2 mmol). The compound was obtained as a green oil (3.3 g, ca. 70% purity), which was used in the next step without further purification. MS (ISP): m/z=399.2 [(M+H)⁻].

Intermediate B13A (1SR,7RS)-1-(5-Amino-2-fluoro-phenyl)-5-oxa-2-aza-bicyclo[5.1.0]octane-3-thione

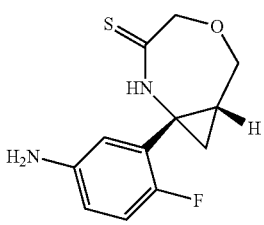 [SMILES: Nc1ccc(F)c([C@]23C[C@H]2COCC(=S)N3)c1]

Crude (1SR,7RS)-1-[5-(benzhydrylidene-amino)-2-fluoro-phenyl]-5-oxa-2-aza-bicyclo[5.1.0]octane-3-thione (intermediate B12A) (600 mg, 1.15 mmol) was dissolved in dioxane (15 ml) and 1 M HCl (1.44 ml, 1.44 mmol) was added at 23° C. After 30 min of stirring, the reaction mixture was poured on sat. NaHCO₃-solution and extracted twice with ethyl acetate. The combined organic layers were washed with brine, dried over sodium sulfate, filtered and evaporated to give a dark green oil (740 mg), which was purified by silica gel column chromatography with dichloromethane/ethyl acetate to give the title compound as a light yellow solid (175 mg, 60%). MS (ISP): m/z=253.2 [(M+H)⁺].

Intermediate B13B (1SR,7RS)-1-(3-Amino-phenyl)-5-oxa-2-aza-bicyclo[5.1.0]octane-3-thione

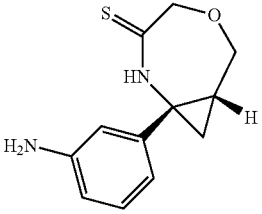 [SMILES: Nc1cccc([C@]23C[C@H]2COCC(=S)N3)c1]

The compound was prepared in an analogous manner as described for intermediate B13A from (1SR,7RS)-1-[3-(benzhydrylidene-amino)-phenyl]-5-oxa-2-aza-bicyclo[5.1.0]octane-3-thione (intermediate B12B) (3.30 g, 70% purity, 6 mmol). The title compound was obtained as a light brown solid (0.955 g, 70%). MS (ISP): m/z=235.1 [(M+H)⁺].

Intermediate B14A

5-Chloro-pyridine-2-carboxylic acid [4-fluoro-3-((1SR,7RS)-3-thioxo-5-oxa-2-aza-bicyclo[5.1.0]oct-1-yl)-phenyl]-amide

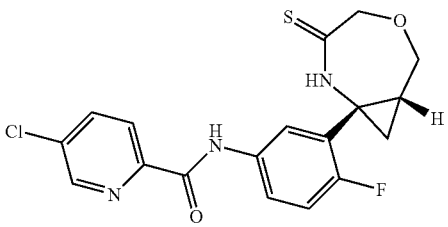 [SMILES: O=C(Nc1ccc(F)c([C@]23C[C@H]2COCC(=S)N3)c1)c1ccc(Cl)cn1]

To a solution of 5-chloro-2-pyridinecarboxylic acid (60 mg, 0.38 mmol) and diisopropylethylamine (0.17 ml, 0.99 mmol) in dichloromethane (20 ml) at 23° C. was added O-(7-azabenzotriazol-1-yl)-N,N,N',N'-tetramethyluronium hexafluorophosphate (HATU) (174 mg, 0.46 mmol), the mixture was stirred for 15 min, then (1SR,7RS)-1-(5-amino-2-fluoro-phenyl)-5-oxa-2-aza-bicyclo[5.1.0]octane-3-thione (intermediate B13A) (91 mg, 0.36 mmol) was added and the resulting light yellow solution was stirred for 1 h at 23° C. The reaction mixture was poured on ice cold sat. NaHCO₃-solution and extracted twice with dichloromethane. The combined organic layers were washed with brine, dried over sodium sulfate, filtered to give a brown solid (280 mg, 168%), which was purified by silica gel column chromatography with dichloromethane/ethyl acetate to give the title compound as a light yellow solid (147 mg, 88%). MS (ISP): m/z=392.1 [(M+H)⁺] and 394 [(M+2H)⁺].

Intermediate B14B 5-(2,2,2-Trifluoro-ethoxy)-pyridine-2-carboxylic acid [4-fluoro-3-((1SR,7RS)-3-thioxo-5-oxa-2-aza-bicyclo[5.1.0]oct-1-yl)-phenyl]-amide

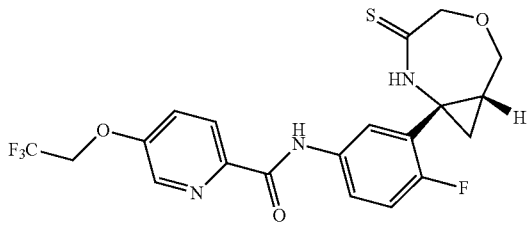 [SMILES: O=C(Nc1ccc(F)c([C@]23C[C@H]2COCC(=S)N3)c1)c1ccc(OCC(F)(F)F)cn1]

Prepared in an analogous manner as described for intermediate B14A from (1SR,7RS)-1-(5-amino-2-fluoro-phenyl)-5-oxa-2-aza-bicyclo[5.1.0]octane-3-thione (intermediate B13A) (87 mg, 0.34 mmol) and 5-(2,2,2-trifluoro-ethoxy)-pyridine-2-carboxylic acid [CAS-no 881409-53-6; described in example 49] (80 mg, 0.36 mmol). The title compound was obtained as a light yellow solid (143 mg, 87%). MS (ISP): m/z=456.1 [(M+H)$^+$].

Intermediate B14C

5-Chloro-pyridine-2-carboxylic acid [3-((1SR,7RS)-3-thioxo-5-oxa-2-aza-bicyclo[5.1.0]oct-1-yl)-phenyl]-amide

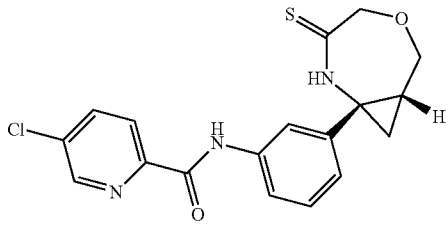 [SMILES: O=C(Nc1cccc([C@]23C[C@H]2COCC(=S)N3)c1)c1ccc(Cl)cn1]

The compound was prepared in an analogous manner as described for intermediate B14A from (1SR,7RS)-1-(3-amino-phenyl)-5-oxa-2-aza-bicyclo[5.1.0]octane-3-thione (intermediate B13B) (230 mg, 0.98 mmol) and commercially available 5-chloro-pyridine-2-carboxylic acid [CAS-no 86873-60-1] (172 mg, 1.09 mmol). The title compound was obtained as a light yellow foam (310 mg, 76%). MS (ISP): m/z=374.1 [(M+H)$^+$] and 376.0 [(M+2+H)$^+$].

Intermediate B14D 5-(2,2,2-Trifluoro-ethoxy)-pyridine-2-carboxylic acid [3-((1SR,7RS)-3-thioxo-5-oxa-2-aza-bicyclo[5.1.0]oct-1-yl)-phenyl]-amide

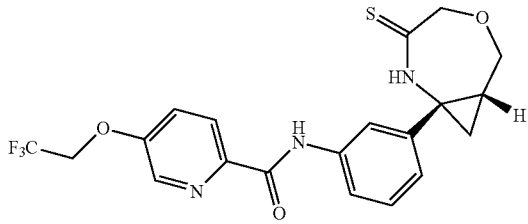 [SMILES: O=C(Nc1cccc([C@]23C[C@H]2COCC(=S)N3)c1)c1ccc(OCC(F)(F)F)cn1]

The compound was prepared in an analogous manner as described for intermediate B14A from (1SR,7RS)-1-(3-amino-phenyl)-5-oxa-2-aza-bicyclo[5.1.0]octane-3-thione (intermediate B13B) (166 mg, 0.712 mmol) and 5-(2,2,2-trifluoro-ethoxy)-pyridine-2-carboxylic acid [CAS No. 881409-53-6; described in example 49] (150 mg, 0.68 mmol). The title compound was obtained as a light yellow gum (266 mg, 90%). MS (ISP): m/z=438.1 [(M+H)$^+$].

Intermediate B14E

3-Chloro-5-trifluoromethyl-pyridine-2-carboxylic acid [3-((6RS,7SR)-3-thioxo-5-oxa-2-aza-bicyclo[5.1.0]oct-1-yl)-phenyl]-amide

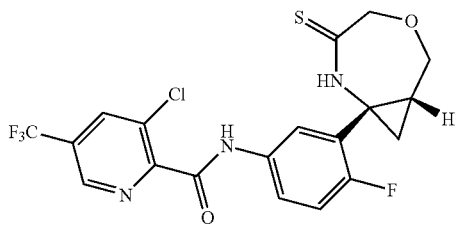 [SMILES: O=C(Nc1ccc(F)c([C@]23C[C@H]2COCC(=S)N3)c1)c1ncc(C(F)(F)F)cc1Cl]

Prepared in an analogous manner as described for intermediate B14A from (1SR,7RS)-1-(3-amino-phenyl)-5-oxa-2-aza-bicyclo[5.1.0]octane-3-thione (intermediate B13B) (345 mg, 1.47 mmol) and commercially available 3-chloro-5-(trifluoromethyl)pyridine-2-carboxylic acid [CAS No. 80194-68-9] (372 mg, 1.65 mmol). The title compound was obtained as a light yellow foam (520 mg, 80%). MS (ISP): m/z=442.1 [(M+H)$^+$] and 444.0 [(M+2+H)$^+$].

Intermediate Olefin C2A

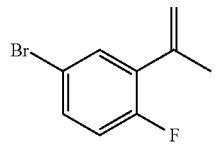

A suspension of methyltriphenylphosphonium bromide (58.92 g, 162 mmol) in tetrahydrofuran (400 ml) was treated at room temperature with potassium tert-butylate (18.51 g, 162 mmol), and the mixture was stirred for 30 minutes. While cooling with ice, a solution of 1-(5-bromo-2-fluoro-phenyl)-ethanone [CAS No. 198477-83-3] (29.23 g, 135 mmol) in tetrahydrofuran (50 ml) was added. Thereafter, the mixture was warmed to room temperature and stirred for 1.5 hours. For the workup, the mixture was treated with ethyl acetate (650 ml) extracted with water (450 ml). The organic layer was separated, washed with brine (220 ml), dried over sodium sulfate and evaporated at reduced pressure. After chromatography on silica gel using a mixture of hexane and ethyl acetate as the eluent, the 4-bromo-1-fluoro-2-isopropenyl-benzene (intermediate C2A) was obtained as a yellow oil (28.49 g, 98% of theory). R$_f$: 0.7 (silica gel; eluent: heptane).

Intermediate Isocyanate C3A

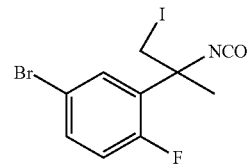

A suspension of 4-bromo-1-fluoro-2-isopropenyl-benzene (28.49 g, 132 mmol) and freshly prepared silver cyanate (24.15 g, 159 mmol) in acetonitrile (175 ml) was treated dropwise under a nitrogen atmosphere in the dark within 45 minutes at 0-5° C. with a solution of iodine (37.0 g, 146 mmol) in ethyl acetate (350 ml). After complete addition, the reaction mixture was left to warm to room temperature and stirring was continued for 16 hours. The precipitate was filtered off on Dicalite, which was washed with ethyl acetate (300 ml). Consecutively the filtrate was washed with an aqueous solution of sodium sulfite (1%, 200 ml) and brine (100 ml), then dried over sodium sulfate, and evaporated at reduced pressure. The (RS)-4-bromo-1-fluoro-2-(2-iodo-1-isocyanato-1-methyl-ethyl)-benzene (intermediate C3A) was obtained as a brown oil (20.13 g) which was used in the next step without further purification and characterisation.

Intermediate Oxazolidinone C4A

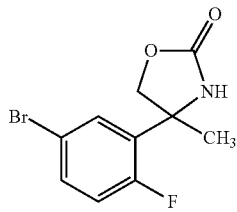

A solution of the crude (RS)-4-bromo-1-fluoro-2-(2-iodo-1-isocyanato-1-methyl-ethyl)-benzene (20.0 g, 52 mmol) in N,N-dimethylformamide (180 ml) and tert-butanol (7.7 ml, 104 mmol) was treated with silver tetrafluoroborate (11.15 g, 57 mmol). The yellow suspension was heated at 80° C. for 16 hours. For the workup, the reaction mixture was evaporated at reduced pressure. After chromatography on silica gel using a using a gradient of heptane and ethyl acetate=100/0 to 40/60 as the eluent, the (RS)-4-(5-bromo-2-fluoro-phenyl) -4-methyl-oxazolidin-2-one (intermediate C4A) was obtained as a white solid (28.49 g, 53.5% of theory).

Intermediate Optically Active Oxazolidinone C5A

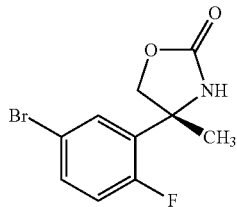

A solution of the (RS)-4-(5-bromo-2-fluoro-phenyl)-4-methyl-oxazolidin-2-one (20.2 g) in ethanol/dichloromethane/heptane (4/2/2) was divided in 1 g aliquots which were separated on chiral HPLC (Chiralpak AD) using a 90:10-mixture of ethanol and heptane as the eluent. The first eluting enantiomer (retention time: 7.98 min), the (R)-(−)-4-(5-bromo-2-fluoro-phenyl)-4-methyl-oxazolidin-2-one (intermediate C5A), was obtained as a brownish crystalline solid (9.154 g, 45.3% of theory), and the second eluting enantiomer (retention time: 12.19 min), the (S)-(+)-N-[1-(5-bromo-2-fluoro-phenyl)-2-hydroxy-1-methyl-ethyl]-2-chloro-acetamide, was also obtained as a light brown crystalline solid (9.25 g, 45.8% of theory), with e.e. >99.5% each.

Intermediate Aminoalcohol C6A

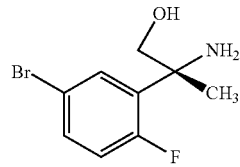

A solution of the (R)-4-(5-bromo-2-fluoro-phenyl)-4-methyl-oxazolidin-2-one (8.94 g, 33 mmol) in ethanol (60 ml) and water (60 ml) was treated with lithium hydroxide monohydrate (6.85 g, 163 mmol) and the reaction mixture was stirred at 100° C. overnight. For the workup, the reaction mixture was evaporated at reduced pressure, and the resulting white residue was dissolved in ethylacetate (90 ml) and hydrochloric acid (2 N, 90 ml). The aqueous layer was treated with sodium hydroxide solution (2 N, 100 ml) and solid sodium chloride was added until saturation was achieved. Thereafter, the aqueous layer was extracted with ethyl acetate (3×200 ml), the organic layers combined and dried over sodium sulfate. After evaporation at reduced pressure the (R)-2-amino-2-(5-bromo-2-fluoro-phenyl)-propan-1-ol (intermediate C6A) was obtained as a crystalline white solid (7.9 g, 97% of theory). $R_f$: 0.6 (silica gel; eluent: dichloromethane/methanol=9:1); e.e. >99% (Chiralpak AD, eluent: heptane/ethanol=85:15; $R_t$: 11.5).

In an analogous manner the (S)-2-amino-2-(5-bromo-2-fluoro-phenyl) -propan-1-ol was obtained as an off-white solid; e.e. >99% (Chiralpak AD, eluent: heptane/ethanol=85:15; $R_t$: 7.2).

Intermediate N-Protected Aminoalcohol C7A

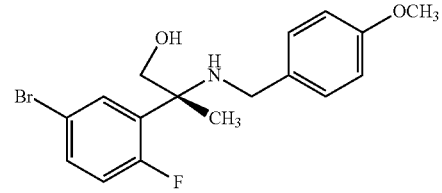 [SMILES: COc1ccc(CN[C@@](C)(CO)c2cc(Br)ccc2F)cc1]

A solution of (R)-2-amino-2-(5-bromo-2-fluoro-phenyl)-propan-1-ol (5.0 g, 20.2 mmol) and 4-methoxybenzaldehyde (2.8 g, 20.2 mmol) in 1,2-dichloroethane (150 ml) was treated with sodium triacetoxyborohydride (8.81 g, 40.3 mmol) at room temperature. TLC check (eluent: heptane:ethyl acetate=1:1) showed complete reaction after 30 minutes. For the workup, to the reaction mixture were added ethyl acetate (250 ml) and saturated sodium hydrogen carbonate solution (100 ml). The aqueous layer was separated, then extracted with ethyl acetate (250 ml). The combined organic layers were washed with saturated sodium chloride solution (100 ml), thereafter dried over sodium sulfate and evaporated at reduced pressure. After chromatography on Silicycle-Si-amine column using a gradient of heptane and ethyl acetate=100/0 to 50/50 as the eluent, (R)-2-(5-bromo-2-fluoro-phenyl)-2-(4-methoxy-benzylamino)-propan-1-ol (intermediate C7A) was obtained as a colourless oil (7.29 g, 98% of theory). MS (ISP): m/z=368.1, 370.1 [M+H]$^+$.

Intermediate N,O-Diprotected Aminoalcohol C8A

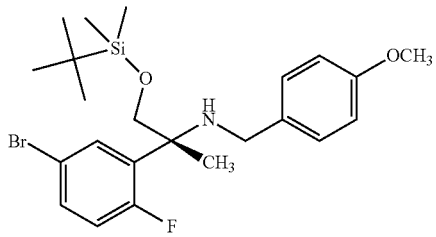 [SMILES: COc1ccc(CN[C@@](C)(CO[Si](C)(C)C(C)(C)C)c2cc(Br)ccc2F)cc1]

A solution of (R)-2-(5-bromo-2-fluoro-phenyl)-2-(4-methoxy-benzylamino)-propan-1-ol (6.95 g, 18.9 mmol) in dichloromethane (170 ml) was treated at room temperature with triethylamine (5.78 ml, 41.5 mmol), 4-dimethylaminopyridine (1.15 g, 9.43 mmol), and tert-butyldimethylchlorosilane (1.15 g, 37.7 mmol). After 16 hours at room temperature the reaction mixture was consecutively extracted with saturated sodium hydrogen carbonate solution (100 ml), water (100 ml), and brine (100 ml). The aqueous layers were re-extracted with dichloromethane (100 ml). The combined organic layers were dried over sodium sulfate and evaporated at reduced pressure. After chromatography on Silicycle-Si-amine column using heptane as the eluent, [(R)-1-(5-bromo-2-fluoro-phenyl)-2-(tert-butyl-dimethyl-silanyloxy)-1-methyl-ethyl]-(4-methoxy-benzyl)-amine (intermediate C8A) was obtained as a colourless oil (8.0 g, 88% of theory). MS (ISP): m/z=482.2, 484.3 [M+H]$^+$.

Intermediate N-Acylated Aminoalcohol C9A

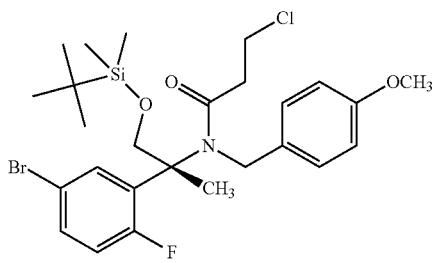 [SMILES: COc1ccc(CN(C(=O)CCCl)[C@@](C)(CO[Si](C)(C)C(C)(C)C)c2cc(Br)ccc2F)cc1]

A suspension of [(R)-1-(5-bromo-2-fluoro-phenyl)-2-(tert-butyl-dimethyl-silanyloxy)-1-methyl-ethyl]-(4-methoxy-benzyl)-amine (7.98 g, 16.5 mmol) in a mixture of chloroform (52 ml) and saturated sodium hydrogen carbonate solution (78 ml) was treated dropwise at 0° C. with 3-chloropropanoyl chloride (2.57 g, 19.8 mmol). The reaction mixture was left to warm to room temperature and vigorous stirring continued for 16 hours. For the workup, the layers were separated, the aqueous layer extracted with chloroform (100 ml), thereupon, the combined organic layers dried over sodium sulfate and evaporated at reduced pressure. After chromatography on Silicycle-Si-amine column using a gradient of heptane and ethyl acetate=100/0 to 60/10 as the eluent, besides recovery of 57% of the starting material, N-[(R)-1-(5-bromo-2-fluoro-phenyl)-2-(tert-butyl-dimethyl-silanyloxy)-1-methyl-ethyl]-3-chloro-N-(4-methoxy-benzyl)-propionamide (intermediate C9A) was obtained as a colourless viscous oil (2.08 g, 22% of theory). MS (ISP): m/z=536.2, 538.3 [M−Cl+H]$^+$.

Intermediate N-Protected Lactam C10A

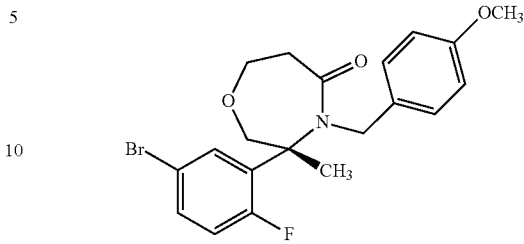

N-[(R)-1-(5-Bromo-2-fluoro-phenyl)-2-(tert-butyl-dimethyl-silanyloxy)-1-methyl-ethyl]-3-chloro-N-(4-methoxy-benzyl)-propionamide (2.08 g, 3.63 mmol) was dissolved in tetrahydrofurane (45 ml) and the solution cooled to 0° C. A solution of tetrabutylammonium fluoride (1 N in tetrahydrofuran, 7.25 ml) was added and the reaction mixture left to warm to room temperature. After 16 hours, the solvent was evaporated at reduced pressure, the residue dissolved in ethyl acetate (25 ml) and water (25 ml) and the mixture stirred for 15 minutes at room temperature. The aqueous layer was separated and extracted with ethyl acetate (50 ml). The organic layers were washed with brine (25 ml), combined, dried over sodium sulfate and evaporated at reduced pressure. After chromatography on Silicycle-Si-amine column using a gradient of heptane and ethyl acetate=100/0 to 20/10 as the eluent, (R)-3-(5-bromo-2-fluoro-phenyl)-4-(4-methoxy-benzyl)-3-methyl-[1,4]oxazepan-5-one (intermediate C10A) was obtained as a white foam (1.34 g, 88% of theory). MS (ISP): m/z=422.1, 424.2 [M+H]$^+$.

Intermediate Lactam C11A

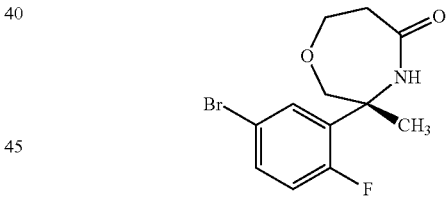

A solution of (R)-3-(5-bromo-2-fluoro-phenyl)-4-(4-methoxy-benzyl)-3-methyl-[1,4]oxazepan-5-one (2.278 g, 5.39 mmol) and anisole (10.7 g, 98.7 mmol) in trifluoroacetic acid (28 ml) was treated dropwise within 6 minutes at room temperature with trifluoromethanesulfonic acid (9.47, 61.9 mmol). After complete addition, the reaction mixture was heated at 73° C. for 24 hours. Following TLC no starting material in a complex mixture of products. For the workup, the cold mixture was poured carefully under stirring into a mixture of saturated sodium hydrogen carbonate solution (200 ml) and ice. The extraction with ethyl acetate (500 ml) and re-extraction of the separated aqueous layer with ethyl acetate (250 ml) was followed by washing the combined organic layers with saturated sodium hydrogen carbonate solution (200 ml) and brine (200 ml). The organic phase was dried over sodium sulfate, then evaporated at reduced pressure. Chromatography on silica gel using a gradient of heptane and ethyl acetate=100/0 to 20/10 as the eluent yielded a product containing fraction of 628 mg which was engaged in the next step without further purification and characterisation. For characterisation of the title compound another fraction of 104 mg was again purified by chromatography on Silicycle-Si-amine column using a gradient of heptane and ethyl acetate=100/0 to 20/10 as the eluent yielding the pure (R)-3-(5-bromo-2-fluoro-phenyl)-3-methyl-[1,4]oxazepan-5-one (intermediate C11A) as a beige foam (56 mg). MS (ISP): m/z=302.2, 304.1 [M+H]$^+$.

Intermediate Benzophenonimine C12A

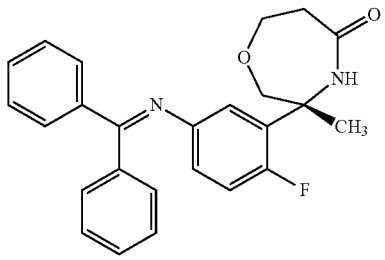 [SMILES: C[C@@]1(c2cc(N=C(c3ccccc3)c3ccccc3)ccc2F)COCCC(=O)N1]

Under an argon atmosphere a mixture of the crude (R)-3-(5-bromo-2-fluoro-phenyl)-3-methyl-[1,4]oxazepan-5-one (626 mg, 1.2 mmol), sodium tert-butoxide (356 mg, 3.59 mmol), 2-di-tert-butylphosphino-2',4',6'-triisopropylbiphenyl (52.4 mg, 0.12 mmol), tris(dibenzylideneacetone)-dipalladium(0) chloroform adduct (38.3 mg, 0.036 mmol), and benzophenonimine (447 mg, 2.4 mmol) in toluene (15 ml) was heated at 105° C. for 16 hours in a sealed vial. For the workup, the reaction mixture was cooled to room temperature, evaporated at reduced pressure, and purified by chromatography on Silicycle-Si-amine column using a gradient of heptane and ethyl acetate=100/0 to 10/20 as the eluent. (R)-3-[5-(Benzhydrylidene-amino)-2-fluoro-phenyl]-3-methyl-[1,4]oxazepan-5-one (intermediate C12A) was obtained as a light yellow foam (348 mg, 69% of theory). MS (ISP): m/z=403.3 [M+H]$^+$.

Intermediate Aniline Derivative C13A

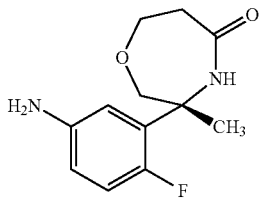 [SMILES: C[C@@]1(c2cc(N)ccc2F)COCCC(=O)N1]

A solution of (R)-3-[5-(benzhydrylidene-amino)-2-fluoro-phenyl]-3-methyl-[1,4]oxazepan-5-one (338 mg, 0.84 mmol) in dioxane (5 ml) was treated with hydrochloric acid (1 N, 1.01 ml) at room temperature for 16 hours. For the workup, the reaction mixture was evaporated at reduced pressure, the resulting residue suspended in hydrochloric acid (1 N, 3 ml) and extracted with diethylether (2×10 ml). The combined organic layers were washed again with hydrochloric acid (1 N, 3 ml), then the aqueous layers were combined and evaporated at reduced pressure to yield the (R)-3-(5-amino-2-fluoro-phenyl)-3-methyl-[1,4]oxazepan-5-one hydrochloride (intermediate C13A) as a light brown foam (225 mg, 97% of theory) which was engaged in the next step without further purification. MS (ISP): m/z=239.3 [M+H]$^+$.

Synthesis of Intermediate Amide Derivatives C14a ($R^7$=COR$^{10}$)

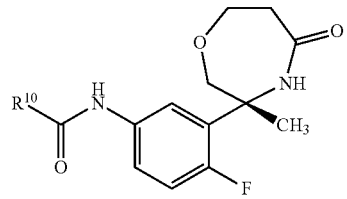

General Procedure

A solution of the carboxylic acid (0.3 mmol) in N,N-dimethylformamide (5 ml) was cooled to 0° C. Consecutively, 1-hydroxybenzotriazole hydrate (52 mg, 0.38 mmol), O-(benzotriazol-1-yl)-N,N,N',N'-tetramethyluronium hexafluorophosphate (143 mg, 0.38 mmol), (R)-3-(5-amino-2-fluoro-phenyl)-3-methyl-[1,4]oxazepan-5-one hydrochloride (intermediate C13A) (74 mg, 0.27 mmol), and N-ethyldiisopropylamine (124 mg, 0.94 mmol) were added, and the mixture was stirred at 0° C. for 10 minutes, then left at room temperature for 16 hours. For the workup, the reaction mixture was evaporated to dryness and the residue directly purified by chromatography on a Silicycle-Si-amine column using a gradient of heptane and ethyl acetate as the eluent.

Intermediate C14A

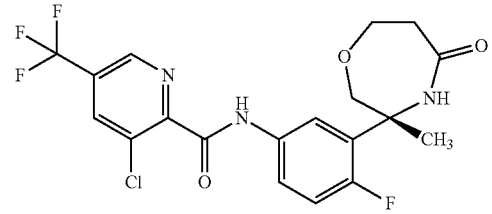 [SMILES: C[C@@]1(c2cc(NC(=O)c3ncc(C(F)(F)F)cc3Cl)ccc2F)COCCC(=O)N1]

Starting from 3-chloro-5-trifluoromethyl-pyridine-2-carboxylic acid and (R) -3-(5-amino-2-fluoro-phenyl)-3-methyl-[1,4]oxazepan-5-one hydrochloride, the 3-chloro-5-trifluoromethyl-pyridine-2-carboxylic acid [4-fluoro-3-((R)-3-methyl-5-oxo-[1,4]oxazepan-3-yl)-phenyl]-amide was obtained as a light yellow foam. MS (ISP): m/z=446.1 [M+H]$^+$.

Intermediate C14B

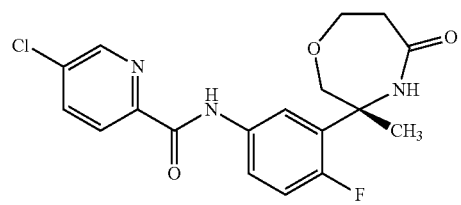 [SMILES: C[C@@]1(c2cc(NC(=O)c3ccc(Cl)cn3)ccc2F)COCCC(=O)N1]

Starting from 5-chloro-pyridine-2-carboxylic acid and (R)-3-(5-amino-2-fluoro-phenyl)-3-methyl-[1,4]oxazepan-5-one hydrochloride, the 5-chloro-pyridine-2-carboxylic acid [4-fluoro-3-((R)-3-methyl-5-oxo-[1,4]oxazepan-3-yl)-phenyl]-amide was obtained as a white solid. MS (ISP): m/z=378.3 [M+H]+.

Intermediate C14C

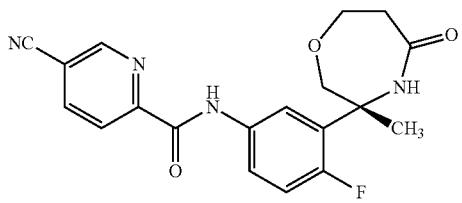 [SMILES: C[C@@]1(c2cc(NC(=O)c3ccc(C#N)cn3)ccc2F)COCCC(=O)N1]

Starting from 5-cyano-pyridine-2-carboxylic acid and (R)-3-(5-amino-2-fluoro-phenyl)-3-methyl-[1,4]oxazepan-5-one hydrochloride, the 5-cyano-pyridine-2-carboxylic acid [4-fluoro-3-((R)-3-methyl-5-oxo-[1,4]oxazepan-3-yl)-phenyl]-amide was obtained as a white solid. MS (ISP): m/z=369.1 [M+H]+.

Synthesis of the Intermediate O-Alkylated Derivatives C15a

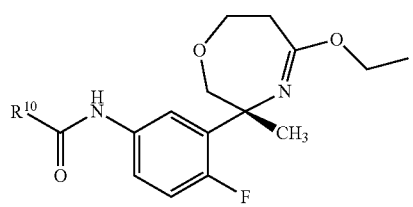

General Procedure

In a dried flask, a dispersion of the intermediate C14 (0.206 mmol) in dichloromethane (8 ml) was treated with triethyloxonium tetrafluoroborate (44 mg, 0.23 mmol) under argon at room temperature during 16 hours. For the workup, the reaction mixture was extracted with a saturated solution of sodium hydrogen carbonate (10 ml), the organic layer separated and dried over sodium sulfate. After evaporation, a mixture of the starting material (intermediate C14a), and the carboxylic acid [3-((R)-5-ethoxy-3-methyl-2,3,6,7-tetrahydro-[1,4]oxazepin-3-yl)-4-fluoro-phenyl]-amide (intermediate C15a) was obtained. The crude product was engaged in the next step without further purification and characterisation.

Intermediate C15A

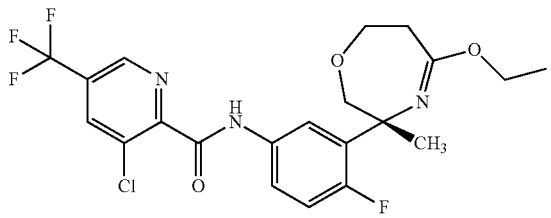 [SMILES: CCOC1=N[C@](C)(c2cc(NC(=O)c3ncc(C(F)(F)F)cc3Cl)ccc2F)COCC1]

Starting from 3-chloro-5-trifluoromethyl-pyridine-2-carboxylic acid [4-fluoro-3-((R)-3-methyl-5-oxo-[1,4]oxazepan-3-yl)-phenyl]-amide, the 3-chloro-5-trifluoromethyl-pyridine-2-carboxylic acid [3-((R)-5-ethoxy-3-methyl-2,3,6,7-tetrahydro-[1,4]oxazepin-3-yl)-4-fluoro-phenyl]-amide was obtained.

Intermediate C15B

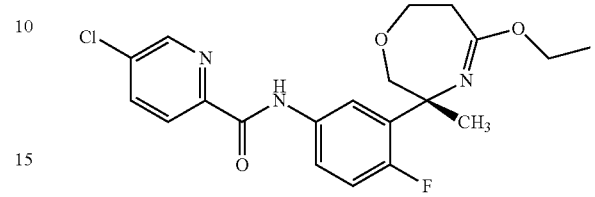

Starting from 5-chloro-pyridine-2-carboxylic acid [4-fluoro-3-((R) -3-methyl-5-oxo-[1,4]oxazepan-3-yl)-phenyl]-amide, the 5-chloro-pyridine-2-carboxylic acid [3-((R)-5-ethoxy-3-methyl-2,3,6,7-tetrahydro-[1,4]oxazepin-3-yl)-4-fluoro-phenyl]-amide was obtained.

Intermediate C15C

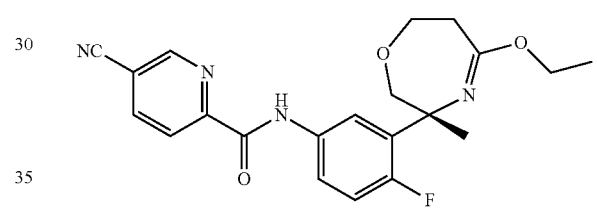

Starting from 5-cyano-pyridine-2-carboxylic acid [4-fluoro-3-((R)-3-methyl-5-oxo-[1,4]oxazepan-3-yl)-phenyl]-amide, the 5-cyano-pyridine-2-carboxylic acid [3-((R)-5-ethoxy-3-methyl-2,3,6,7-tetrahydro-[1,4]oxazepin-3-yl)-4-fluoro-phenyl]-amide was obtained.

Synthesis of Compounds of Formula Id'

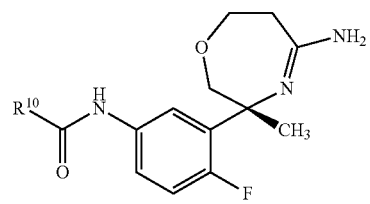

General Procedure

A dried pressure tube was charged under an argon atmosphere with a dispersion of the crude intermediate C15a (0.206 mmol) and ammoniumchloride (69 mg, 1.28 mmol) in methanol (2.6 ml). The sealed pressure tube was heated at 100° C. for 16 hours. After cooling, the reaction mixture was evaporated to dryness and directly purified by two consecutive chromatographies on a Silicycle-Si-amine column using a gradient of dichloromethane and methanol as the eluent.

115

Example 1

5-Chloro-pyridine-2-carboxylic acid [3-((1SR,7RS)-3-amino-5-oxa-2-aza-bicyclo[5.1.0]oct-2-en-1-yl)-4-fluoro-phenyl]-amide

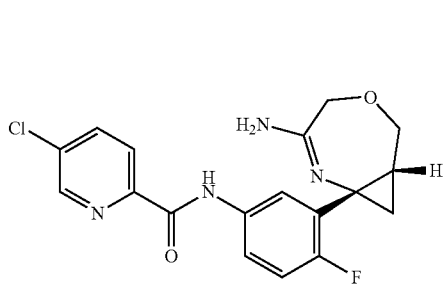 [SMILES: NC1=N[C@@]2(c3cc(NC(=O)c4ccc(Cl)cn4)ccc3F)C[C@H]2COC1]

To mixture of 5-chloro-pyridine-2-carboxylic acid [4-fluoro-3-((1SR,7RS)-3-thioxo-5-oxa-2-aza-bicyclo[5.1.0]oct-1-yl)-phenyl]-amide (intermediate B14A) (142 mg, 0.36 mmol) and 7 N ammonia in methanol (3.1 ml) in methanol (15 ml) at 23° C. was added tert-butylhydroperoxide (70% in water, 0.50 ml, 3.62 mmol) and the mixture was stirred at 23° C. for 20 h. The reaction mixture was extracted with water and dichloromethane. The organic layer was washed with water and brine, the aqueous layers were reextracted with dichloromethane. The combined organic layers were dried over sodium sulfate, filtered and evaporated to give a light yellow oil (180 mg, 132%), which was purified by silica gel column chromatography with dichloromethane to dichloromethane/methanol/ammonium hydroxide 65:10:1 to give the title compound as a white solid (10 mg, 7.4%). MS (ISP): m/z=375.3 [(M+H)$^+$] and 377.3 [(M+2+H)$^+$].

Example 2

5-(2,2,2-Trifluoro-ethoxy)-pyridine-2-carboxylic acid [3-((1SR,7RS)-3-amino-5-oxa-2-aza-bicyclo[5.1.0]oct-2-en-1-yl)-4-fluoro-phenyl]-amide

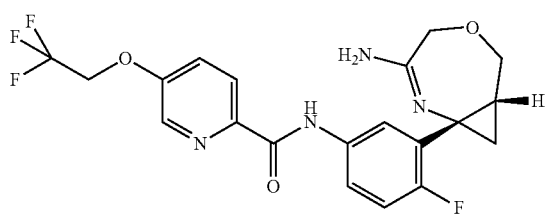 [SMILES: NC1=N[C@@]2(c3cc(NC(=O)c4ccc(OCC(F)(F)F)cn4)ccc3F)C[C@H]2COC1]

The compound was prepared in an analogous manner as described for example 1 from 5-(2,2,2-trifluoro-ethoxy)-pyridine-2-carboxylic acid [4-fluoro-3-((1SR,7RS)-3-thioxo-5-oxa-2-aza-bicyclo[5.1.0]oct-1-yl)-phenyl]-amide (intermediate B14B) (139 mg, 0.31 mmol). The title compound was obtained as a white solid (12 mg, 9%). MS (ISP): m/z=439.3 [(M+H)$^+$].

116

Example 3

5-Chloro-pyridine-2-carboxylic acid [3-((1SR,7RS)-3-amino-5-oxa-2-aza-bicyclo[5.1.0]oct-2-en-1-yl)-phenyl]-amide

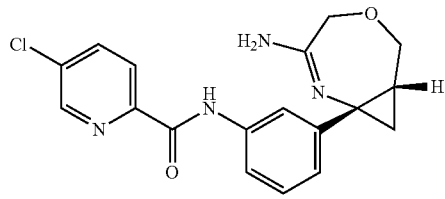 [SMILES: NC1=N[C@@]2(c3cccc(NC(=O)c4ccc(Cl)cn4)c3)C[C@H]2COC1]

The compound was prepared in an analogous manner as described for example 1 from 5-chloro-pyridine-2-carboxylic acid [3-((1SR,7RS)-3-thioxo-5-oxa-2-aza-bicyclo[5.1.0]oct-1-yl)-phenyl]-amide (intermediate B14C) (297 mg, 0.79 mmol). The title compound was obtained as white foam (52 mg, 18%). MS (ISP): m/z=357.1 [(M+H)$^+$] and 359.0 [(M+2+H)$^+$].

Example 4

5-(2,2,2-Trifluoro-ethoxy)-pyridine-2-carboxylic acid [3-((1SR,7RS)-3-amino-5-oxa-2-aza-bicyclo[5.1.0]oct-2-en-1-yl)-phenyl]-amide

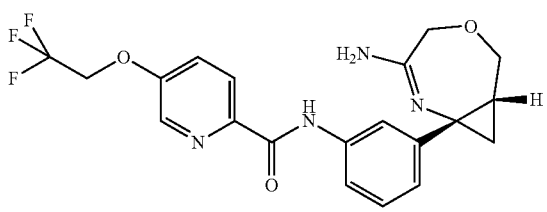 [SMILES: NC1=N[C@@]2(c3cccc(NC(=O)c4ccc(OCC(F)(F)F)cn4)c3)C[C@H]2COC1]

The title compound was prepared in an analogous manner as described for example 1 from 5-(2,2,2-trifluoro-ethoxy)-pyridine-2-carboxylic acid [3-((1SR,7RS)-3-thioxo-5-oxa-2-aza-bicyclo[5.1.0]oct-1-yl)-phenyl]-amide (intermediate B14D) (257 mg, 0.59 mmol). The title compound was obtained as off-white foam (17 mg, 7%). MS (ISP): m/z=421.1 [(M+H)$^+$].

Example 5

5-Chloro-pyridine-2-carboxylic acid [3-((S)-3-amino-5-methyl-2,5,6,7-tetrahydro-[1,4]oxazepin-5-yl)-4-fluoro-phenyl]-amide formate

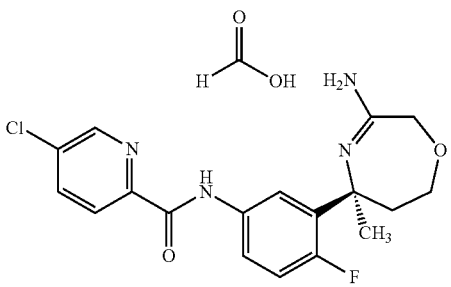 [SMILES: C[C@@]1(c2cc(NC(=O)c3ccc(Cl)cn3)ccc2F)CCOCC(N)=N1 ; O=CO]

The coupling of (S)-5-(5-amino-2-fluoro-phenyl)-5-methyl-2,5,6,7-tetrahydro-[1,4]oxazepin-3-ylamine (intermediate A10C) and 5-chloropyridine-2-carboxylic acid yielded the title compound as a white foam. MS (ISP): m/z=377.1 [M+H]⁺.

Example 6

3-Fluoro-pyridine-2-carboxylic acid [3-((S)-3-amino-5-methyl-2,5,6,7-tetrahydro-[1,4]oxazepin-5-yl)-4-fluoro-phenyl]-amide formate

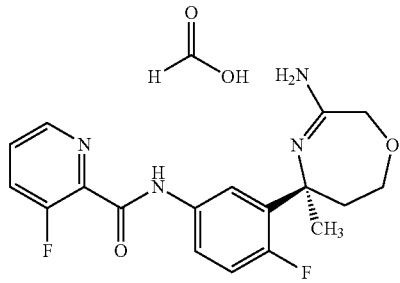 [SMILES: C[C@@]1(c2cc(NC(=O)c3ncccc3F)ccc2F)CCOCC(N)=N1 ; O=CO]

The coupling of (S)-5-(5-amino-2-fluoro-phenyl)-5-methyl-2,5,6,7-tetrahydro-[1,4]oxazepin-3-ylamine (intermediate A10C) and 3-fluoropyridine-2-carboxylic acid yielded the title compound as white foam. MS (ISP): m/z=361.1 [M+H]⁺.

Example 7

Pyridine-2-carboxylic acid [3-((S)-3-amino-5-methyl-2,5,6,7-tetrahydro-[1,4]oxazepin-5-yl)-4-fluoro-phenyl]-amide

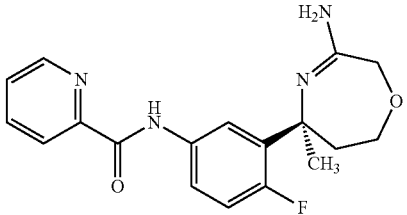 [SMILES: C[C@@]1(c2cc(NC(=O)c3ccccn3)ccc2F)CCOCC(N)=N1]

The coupling of (S)-5-(5-amino-2-fluoro-phenyl)-5-methyl-2,5,6,7-tetrahydro-[1,4]oxazepin-3-ylamine (intermediate A10C) and picolinic acid yielded the title compound as a white foam. MS (ISP): m/z=343.4 [M+H]⁺.

Example 8

3,5-Dichloro-pyridine-2-carboxylic acid [3-((S)-3-amino-5-methyl-2,5,6,7-tetrahydro-[1,4]oxazepin-5-yl)-4-fluoro-phenyl]-amide

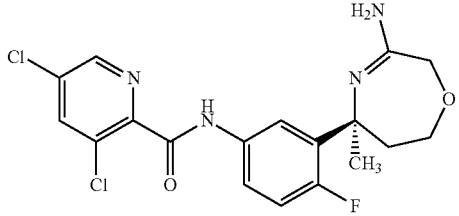 [SMILES: C[C@@]1(c2cc(NC(=O)c3ncc(Cl)cc3Cl)ccc2F)CCOCC(N)=N1]

The coupling of (S)-5-(5-amino-2-fluoro-phenyl)-5-methyl-2,5,6,7-tetrahydro-[1,4]oxazepin-3-ylamine (intermediate A10C) and 3,5-dichloro-2-pyridinecarboxylic acid yielded the title compound as a white foam. MS (ISP): m/z=412.3 [M+H]⁺.

Example 9

[3-((S)-3-amino-5-methyl-2,5,6,7-tetrahydro-[1,4]oxazepin-5-yl)-4-fluoro-phenyl]-amide

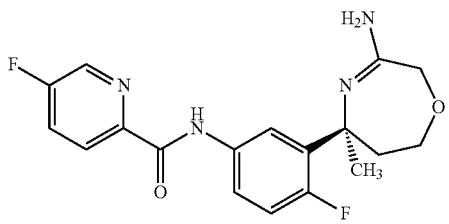 [SMILES: C[C@@]1(c2cc(NC(=O)c3ccc(F)cn3)ccc2F)CCOCC(N)=N1]

The coupling of (S)-5-(5-amino-2-fluoro-phenyl)-5-methyl-2,5,6,7-tetrahydro-[1,4]oxazepin-3-ylamine (intermediate A10C) and 5-fluoropyridine-2-carboxylic acid yielded the title compound as a white foam. MS (ISP): m/z=361.3 [M+H]⁺.

Example 10

5-Chloro-pyridine-2-carboxylic acid [3-((S)-3-amino-5,7,7-trimethyl-2,5,6,7-tetrahydro-[1,4]oxazepin-5-yl)-4-fluoro-phenyl]-amide

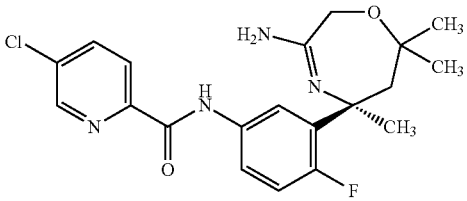 [SMILES: CC1(C)C[C@@](C)(c2cc(NC(=O)c3ccc(Cl)cn3)ccc2F)N=C(N)CO1]

The compound is prepared in an analogous manner as described for example 1 from 5-chloro-pyridine-2-carboxylic acid [4-fluoro-3-((S)-5,7,7-trimethyl-3-thioxo-[1,4]oxazepan-5-yl)-phenyl]-amide (intermediate A18A) (175 mg, 0.42 mmol). The compound was obtained as a white foam (66 mg, 39%). MS (ISP): m/z=405.3 [(M+H)⁺] and 407.3 [(M+2+H)⁺].

Example 11

5-Difluoromethoxy-pyridine-2-carboxylic acid [3-((S)-3-amino-5,7,7-trimethyl-2,5,6,7-tetrahydro-[1,4]oxazepin-5-yl)-4-fluoro-phenyl]-amide

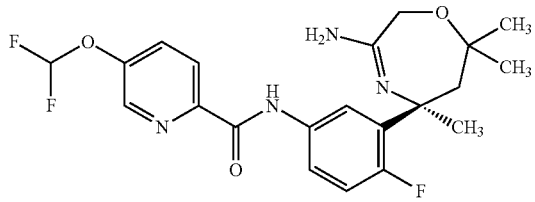 [SMILES: CC1(C)C[C@@](C)(c2cc(NC(=O)c3ccc(OC(F)F)cn3)ccc2F)N=C(N)CO1]

The compounds was prepared in an analogous manner as described for example 1 from 5-difluoromethoxy-pyridine-2-carboxylic acid [4-fluoro-3-((S)-5,7,7-trimethyl-3-thioxo-[1,4]oxazepan-5-yl)-phenyl]-amide (intermediate A18B) (97 mg, 0.21 mmol). The compound was obtained as a white foam (43 mg, 46%). MS (ISP): m/z=437.2 [(M+H)⁺].

Example 12

5-(2,2,2-Trifluoro-ethoxy)-pyridine-2-carboxylic acid [3-((S)-3-amino-5-methyl-2,5,6,7-tetrahydro-[1,4]oxazepin-5-yl)-4-fluoro-phenyl]-amide

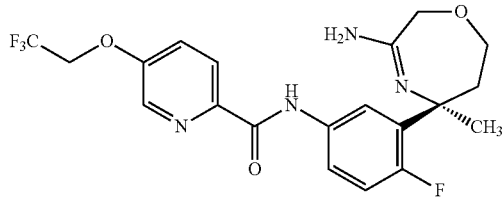 [SMILES: C[C@@]1(c2cc(NC(=O)c3ccc(OCC(F)(F)F)cn3)ccc2F)CCOCC(N)=N1]

The coupling of (S)-5-(5-amino-2-fluoro-phenyl)-5-methyl-2,5,6,7-tetrahydro-[1,4]oxazepin-3-ylamine (intermediate A10C) and 5-(2,2,2-trifluoro-ethoxy)-pyridine-2-carboxylic acid [CAS No. 881409-53-6; described in example 49] yielded the title compound as a white foam. MS (ISP): m/z=441.0 [M+H]$^+$.

Example 13

5-Fluoro-pyridine-2-carboxylic acid [3-((S)-3-amino-5-ethyl-2,5,6,7-tetrahydro-[1,4]oxazepin-5-yl)-4-fluoro-phenyl]-amide

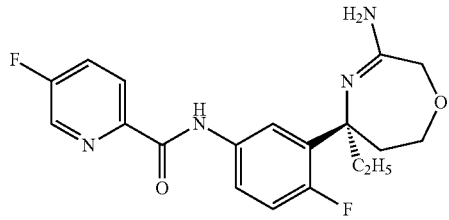 [SMILES: CC[C@@]1(c2cc(NC(=O)c3ccc(F)cn3)ccc2F)CCOCC(N)=N1]

The coupling of (S)-5-(5-amino-2-fluoro-phenyl)-5-ethyl-2,5,6,7-tetrahydro-[1,4]oxazepin-3-ylamine (intermediate A10D) and 5-fluoropyridine-2-carboxylic acid yielded the title compound as a white foam. MS (ISP): m/z=375.0 [M+H]$^+$.

Example 14

5-Chloro-pyridine-2-carboxylic acid [3-((S)-3-amino-5-ethyl-2,5,6,7-tetrahydro-[1,4]oxazepin-5-yl)-4-fluoro-phenyl]-amide

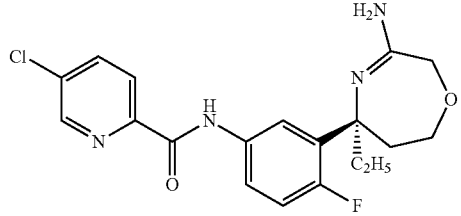 [SMILES: CC[C@@]1(c2cc(NC(=O)c3ccc(Cl)cn3)ccc2F)CCOCC(N)=N1]

The coupling of (S)-5-(5-amino-2-fluoro-phenyl)-5-ethyl-2,5,6,7-tetrahydro-[1,4]oxazepin-5-ylamine (intermediate A10D) and 5-chloropyridine-2-carboxylic acid yielded the title compound as a white foam. MS (ISP): m/z=391.1 [M+H]$^+$.

Example 15

3,5-Dichloro-pyridine-2-carboxylic acid [3-((S)-3-amino-5-ethyl-2,5,6,7-tetrahydro-[1,4]oxazepin-5-yl)-4-fluoro-phenyl]-amide

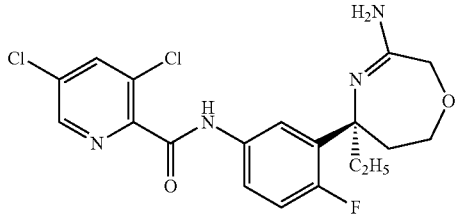 [SMILES: CC[C@@]1(c2cc(NC(=O)c3ncc(Cl)cc3Cl)ccc2F)CCOCC(N)=N1]

The coupling of (S)-5-(5-amino-2-fluoro-phenyl)-5-ethyl-2,5,6,7-tetrahydro-[1,4]oxazepin-3-ylamine (intermediate A10D) and 3,5-dichloro-2-pyridinecarboxylic acid yielded the title compound as a white foam. MS (ISP): m/z=426.9 [M+H]$^+$.

Example 16

3-Chloro-5-trifluoromethyl-pyridine-2-carboxylic acid [3-((S)-3-amino-5-methyl-2,5,6,7-tetrahydro-[1,4]oxazepin-5-yl)-4-fluoro-phenyl]-amide

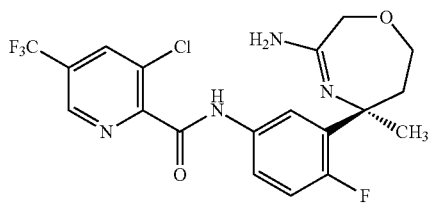 [SMILES: C[C@@]1(c2cc(NC(=O)c3ncc(C(F)(F)F)cc3Cl)ccc2F)CCOCC(N)=N1]

The coupling of (S)-5-(5-amino-2-fluoro-phenyl)-5-methyl-2,5,6,7-tetrahydro-[1,4]oxazepin-3-ylamine (intermediate A10C) and 3-chloro-5-(trifluoromethyl)pyridine-2-carboxylic acid yielded the title compound as a white foam. MS (ISP): m/z=445.1 [M+H]$^+$.

Example 17

1-Trifluoromethyl-cyclopropanecarboxylic acid [3-((S)-3-amino-5-methyl-2,5,6,7-tetrahydro-[1,4]oxazepin-5-yl)-4-fluoro-phenyl]-amide

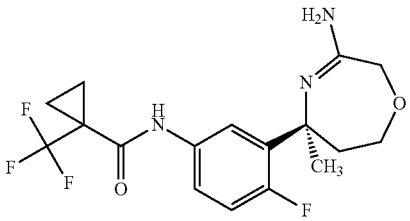 [SMILES: C[C@@]1(c2cc(NC(=O)C3(C(F)(F)F)CC3)ccc2F)CCOCC(N)=N1]

The coupling of (S)-5-(5-amino-2-fluoro-phenyl)-5-methyl-2,5,6,7-tetrahydro-[1,4]oxazepin-3-ylamine (intermediate A10C) and 1-trifluoromethylcyclopropane-1-carboxylic acid yielded the title compound as a white foam. MS (ISP): m/z=374.2 [M+H]$^+$.

Example 18

5-(2,2,2-Trifluoro-ethoxy)-pyridine-2-carboxylic acid [3-((S)-3-amino-5,7,7-trimethyl-2,5,6,7-tetrahydro-[1,4]oxazepin-5-yl)-4-fluoro-phenyl]-amide

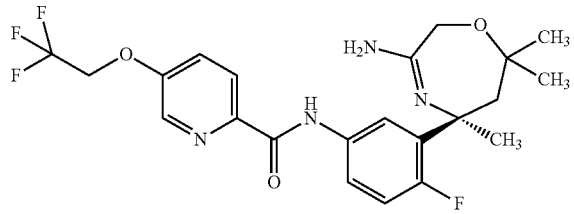 [SMILES: CC1(C)C[C@@](C)(c2cc(NC(=O)c3ccc(OCC(F)(F)F)cn3)ccc2F)N=C(N)CO1]

The compound was prepared in an analogous manner as described for example 1 from 5-(2,2,2-trifluoro-ethoxy)-pyridine-2-carboxylic acid [4-fluoro-3-((S)-5,7,7-trimethyl-3-thioxo-[1,4]oxazepan-5-yl)-phenyl]-amide (intermediate A18C) (151 mg, 0.31 mmol). It was obtained as a white foam (63 mg, 43%). MS (ISP): m/z=469.2 [(M+H)$^+$].

Example 19

2,2-Difluoro-cyclopropanecarboxylic acid [3-((S)-3-amino-5,7,7-trimethyl-2,5,6,7-tetrahydro-[1,4]oxazepin-5-yl)-4-fluoro-phenyl]-amide

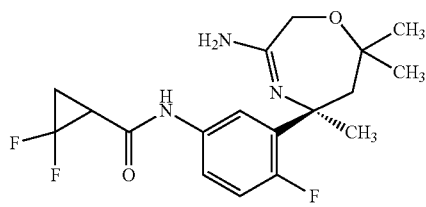 [SMILES: CC1(C)C[C@@](C)(c2cc(NC(=O)C3CC3(F)F)ccc2F)N=C(N)CO1]

The title compound was prepared in an analogous manner as described for example 1 from 2,2-difluoro-cyclopropanecarboxylic acid [4-fluoro-3-((S)-5,7,7-trimethyl-3-thioxo-[1,4]oxazepan-5-yl)-phenyl]-amide (intermediate A18D) (158 mg, 0.41 mmol). Obtained as a white foam (83 mg, 55%). MS (ISP): m/z=370.1 [(M+H)$^+$].

Example 20

1-Trifluoromethyl-cyclopropanecarboxylic acid [3-((S)-3-amino-5,7,7-trimethyl-2,5,6,7-tetrahydro-[1,4]oxazepin-5-yl)-4-fluoro-phenyl]-amide

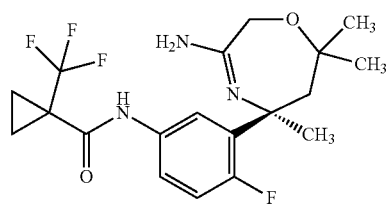 [SMILES: CC1(C)C[C@@](C)(c2cc(NC(=O)C3(C(F)(F)F)CC3)ccc2F)N=C(N)CO1]

The title compound was prepared in an analogous manner as described for example 1 from 1-trifluoromethyl-cyclopropanecarboxylic acid [4-fluoro-3-((S)-5,7,7-trimethyl-3-thioxo-[1,4]oxazepan-5-yl)-phenyl]-amide (intermediate A18E) (165 mg, 0.39 mmol). Obtained as a white foam (88 mg, 55%). MS (ISP): m/z=402.3 [(M+H)$^+$].

Example 21

3-Chloro-5-trifluoromethyl-pyridine-2-carboxylic acid [3-((S)-3-amino-5,7,7-trimethyl-2,5,6,7-tetrahydro-[1,4]oxazepin-5-yl)-4-fluoro-phenyl]-amide

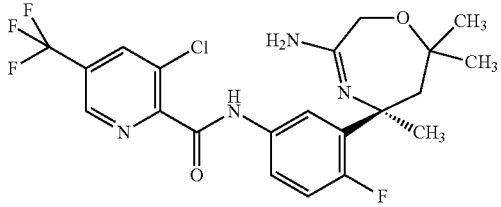 [SMILES: CC1(C)C[C@@](C)(c2cc(NC(=O)c3ncc(C(F)(F)F)cc3Cl)ccc2F)N=C(N)CO1]

The compound was prepared in an analogous manner as described for example 1 from 3-chloro-5-trifluoromethyl-pyridine-2-carboxylic acid [4-fluoro-3-((S)-5,7,7-trimethyl-3-thioxo-[1,4]oxazepan-5-yl)-phenyl]-amide (intermediate A18F) (129 mg, 0.26 mmol). The compound was obtained as a white solid (75 mg, 60%). MS (ISP): m/z=473.2 [(M+H)$^+$] and 475.0 [(M+2+H)$^+$].

Example 22

N-[3-((S)-3-Amino-5,7,7-trimethyl-2,5,6,7-tetrahydro-[1,4]oxazepin-5-yl)-4-fluoro-phenyl]-3,3,3-trifluoro-propionamide

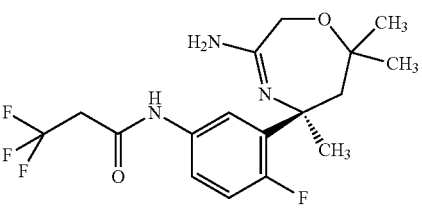 [SMILES: CC1(C)C[C@@](C)(c2cc(NC(=O)CC(F)(F)F)ccc2F)N=C(N)CO1]

The compound was prepared in an analogous manner as described for example 1 from 3,3,3-trifluoro-N-[4-fluoro-3-((S)-5,7,7-trimethyl-3-thioxo-[1,4]oxazepan-5-yl)-phenyl]-propionamide (intermediate A18G) (70 mg, 0.18 mmol). The title compound was obtained as a light yellow solid (33 mg, 49%). MS (ISP): m/z=376.2 [(M+H)$^+$].

Example 23

2,2-Difluoro-cyclopropanecarboxylic acid [3-((S)-3-amino-5-methyl-2,5,6,7-tetrahydro-[1,4]oxazepin-5-yl)-4-fluoro-phenyl]-amide

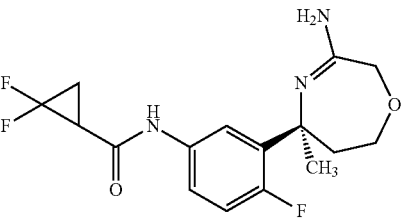 [SMILES: C[C@@]1(c2cc(NC(=O)C3CC3(F)F)ccc2F)CCOCC(N)=N1]

The coupling of (S)-5-(5-amino-2-fluoro-phenyl)-5-methyl-2,5,6,7-tetrahydro-[1,4]oxazepin-3-ylamine (intermediate A10C) and 2,2-difluorocyclopropanecarboxylic acid yielded the title compound as a white foam. MS (ISP): m/z=342.2 [M+H]$^+$.

Example 24

1-Trifluoromethyl-cyclobutanecarboxylic acid [3-((S)-3-amino-5-methyl-2,5,6,7-tetrahydro-[1,4]oxazepin-5-yl)-4-fluoro-phenyl]-amide

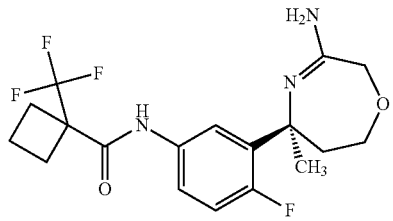 [SMILES: C[C@@]1(c2cc(NC(=O)C3(C(F)(F)F)CCC3)ccc2F)CCOCC(N)=N1]

The coupling of (S)-5-(5-amino-2-fluoro-phenyl)-5-methyl-2,5,6,7-tetrahydro-[1,4]oxazepin-3-ylamine (intermediate A10C) and 1-trifluoromethylcyclobutane-1-carboxylic acid yielded the title compound as a white foam. MS (ISP): m/z=388.2 [M+H]$^+$.

Example 25

3-Chloro-5-trifluoromethyl-pyridine-2-carboxylic acid [3-((R)-3-amino-6,6-difluoro-5-methyl-2,5,6,7-tetrahydro-[1,4]oxazepin-5-yl)-4-fluoro-phenyl]-amide

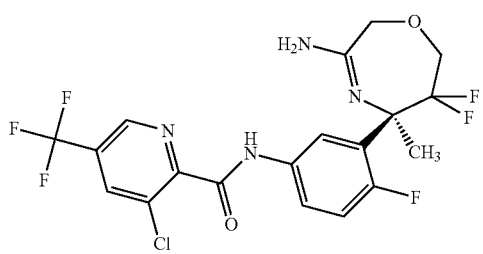 [SMILES: C[C@]1(c2cc(NC(=O)c3ncc(C(F)(F)F)cc3Cl)ccc2F)N=C(N)COCC1(F)F]

The coupling of (R)-5-(5-amino-2-fluorophenyl)-6,6-difluoro-5-methyl-2,5,6,7-tetrahydro-1,4-oxazepin-3-amine (intermediate A10A) and 3-chloro-5-trifluoromethyl-pyridine-2-carboxylic acid yielded the title compound as a white foam. MS (ISP): m/z=481.1 [M+H]$^+$.

Example 26

(R)-N-(3-(3-amino-6,6-difluoro-5-methyl-2,5,6,7-tetrahydro-1,4-oxazepin-5-yl)-4-fluorophenyl)-5-chloropicolinamide

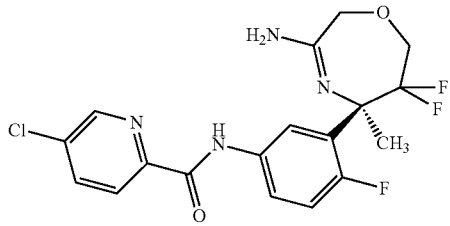 [SMILES: C[C@]1(c2cc(NC(=O)c3ccc(Cl)cn3)ccc2F)N=C(N)COCC1(F)F]

The coupling of (R)-5-(5-amino-2-fluorophenyl)-6,6-difluoro-5-methyl-2,5,6,7-tetrahydro-1,4-oxazepin-3-amine (intermediate A10A) and 5-chloro-pyridine-2-carboxylic acid yielded the title compound as a colorless solid. MS (ISP): m/z=413.3 [M+H]$^+$.

Example 27

(R)-N-(3-(3-amino-6,6-difluoro-5-methyl-2,5,6,7-tetrahydro-1,4-oxazepin-5-yl)-4-fluorophenyl)-3-fluoropicolinamide, salt with formic acid

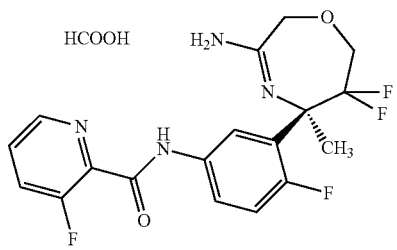 [SMILES: C[C@]1(c2cc(NC(=O)c3ncccc3F)ccc2F)N=C(N)COCC1(F)F ; "HCOOH"]

The coupling of (R)-5-(5-amino-2-fluorophenyl)-6,6-difluoro-5-methyl-2,5,6,7-tetrahydro-1,4-oxazepin-3-amine (intermediate A10A) and 3-fluoro-pyridine-2-carboxylic acid yielded the title compound as a colorless solid. MS (ISP): m/z=397.2 [M+H]$^+$.

Example 28

5-Fluoro-pyridine-2-carboxylic acid [3-(3-amino-2,2,5-trimethyl-2,5,6,7-tetrahydro-[1,4]oxazepin-5-yl)-4-fluoro-phenyl]-amide

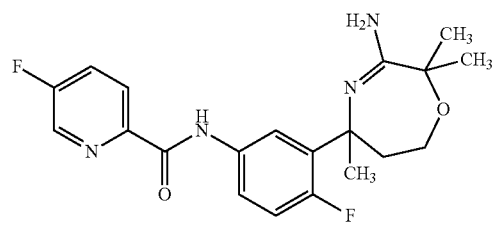 [SMILES: CC1(C)OCCC(C)(c2cc(NC(=O)c3ccc(F)cn3)ccc2F)N=C1N]

The coupling of 5-(5-amino-2-fluoro-phenyl)-2,2,5-trimethyl-2,5,6,7-tetrahydro-[1,4]oxazepin-3-ylamine (intermediate A10E) and 5-fluoropyridine-2-carboxylic acid yielded the title compound as a white foam. MS (ISP): m/z=389.3 [M+H]$^+$.

Example 29

(R)-N-(3-(3-amino-6,6-difluoro-5-methyl-2,5,6,7-tetrahydro-1,4-oxazepin-5-yl)-4-fluorophenyl)-5-fluoropicolinamide formate

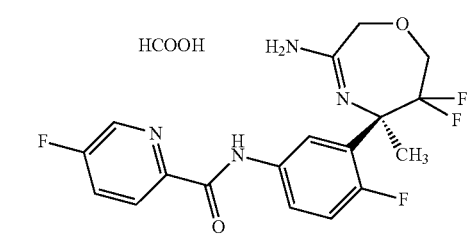 [SMILES: C[C@]1(c2cc(NC(=O)c3ccc(F)cn3)ccc2F)N=C(N)COCC1(F)F ; "HCOOH"]

The coupling of (R)-5-(5-amino-2-fluorophenyl)-6,6-difluoro-5-methyl-2,5,6,7-tetrahydro-1,4-oxazepin-3-amine (intermediate A10A) and 5-fluoro-pyridine-2-carboxylic acid yielded the title compound as a colorless foam. MS (ISP): m/z=397.2 [M+H]⁺.

Example 30

(R)-N-(3-(3-amino-6,6-difluoro-5-methyl-2,5,6,7-tetrahydro-1,4-oxazepin-5-yl)-4-fluorophenyl)-5-cyanopicolinamide formate

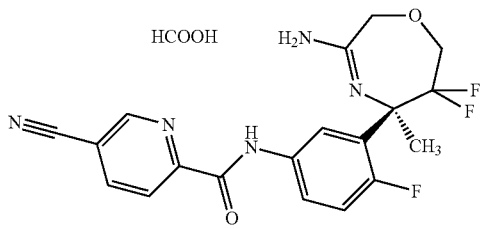 [SMILES: C[C@]1(c2cc(NC(=O)c3ccc(C#N)cn3)ccc2F)N=C(N)COCC1(F)F ; "HCOOH"]

The coupling of (R)-5-(5-amino-2-fluorophenyl)-6,6-difluoro-5-methyl-2,5,6,7-tetrahydro-1,4-oxazepin-3-amine (intermediate A10A) and 5-cyano-pyridine-2-carboxylic acid yielded the title compound as a colorless foam. MS (ISP): m/z=404.3 [M+H]⁺.

Example 31

(R)-N-(3-(3-amino-6,6-difluoro-5-methyl-2,5,6,7-tetrahydro-1,4-oxazepin-5-yl)-4-fluorophenyl)-5-chloro-3-methylpicolinamide formate

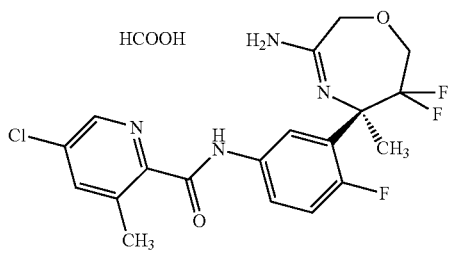 [SMILES: Cc1cc(Cl)cnc1C(=O)Nc1ccc(F)c([C@@]2(C)N=C(N)COCC2(F)F)c1 ; "HCOOH"]

The coupling of (R)-5-(5-amino-2-fluorophenyl)-6,6-difluoro-5-methyl-2,5,6,7-tetrahydro-1,4-oxazepin-3-amine (intermediate A10A) and 5-chloro-3-methyl-pyridine-2-carboxylic acid yielded the title compound as a colorless foam. MS (ISP): m/z=427.1 [M+H]⁺.

Example 32

(R)-N-(3-(3-amino-6,6-difluoro-5-methyl-2,5,6,7-tetrahydro-1,4-oxazepin-5-yl)-4-fluorophenyl)-3,5-difluoropicolinamide formate

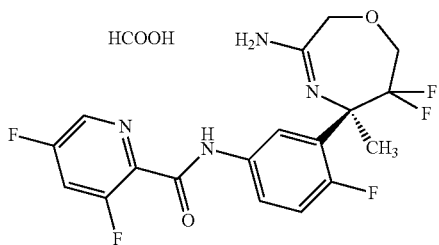 [SMILES: C[C@]1(c2cc(NC(=O)c3ncc(F)cc3F)ccc2F)N=C(N)COCC1(F)F ; "HCOOH"]

The coupling of (R)-5-(5-amino-2-fluorophenyl)-6,6-difluoro-5-methyl-2,5,6,7-tetrahydro-1,4-oxazepin-3-amine (intermediate A10A) and 3,5-difluoro-pyridine-2-carboxylic acid yielded the title compound as a colorless foam. MS (ISP): m/z=415.2 [M+H]⁺.

Example 33

(R)-N-(3-(3-amino-6,6-difluoro-5-methyl-2,5,6,7-tetrahydro-1,4-oxazepin-5-yl)-4-fluorophenyl)-1-(trifluoromethyl)cyclopropanecarboxamide formate

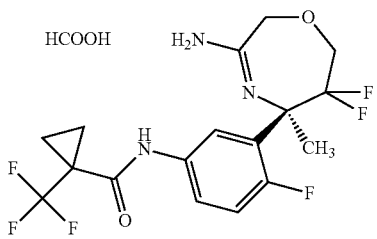 [SMILES: C[C@]1(c2cc(NC(=O)C3(C(F)(F)F)CC3)ccc2F)N=C(N)COCC1(F)F ; "HCOOH"]

The coupling of (R)-5-(5-amino-2-fluorophenyl)-6,6-difluoro-5-methyl-2,5,6,7-tetrahydro-1,4-oxazepin-3-amine (intermediate A10A) and 1-trifluoromethyl-cyclopropanecarboxylic acid yielded the title compound as a colorless foam. MS (ISP): m/z=410.2 [M+H]⁺.

Example 34

N-(3-((R)-3-amino-6,6-difluoro-5-methyl-2,5,6,7-tetrahydro-1,4-oxazepin-5-yl)-4-fluorophenyl)-2,2-difluorocyclopropanecarboxamide formate

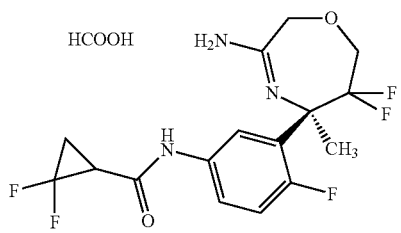 [SMILES: C[C@]1(c2cc(NC(=O)C3CC3(F)F)ccc2F)N=C(N)COCC1(F)F ; "HCOOH"]

The coupling of (R)-5-(5-amino-2-fluorophenyl)-6,6-difluoro-5-methyl-2,5,6,7-tetrahydro-1,4-oxazepin-3-amine (intermediate A10A) and rac-2,2-difluoro-cyclopropanecarboxylic acid yielded the title compound as a colorless foam. MS (ISP): m/z=378.3 [M+H]⁺.

Example 35

(R)-N-(3-(3-amino-6,6-difluoro-5-methyl-2,5,6,7-tetrahydro-1,4-oxazepin-5-yl)-4-fluorophenyl)picolinamide formate

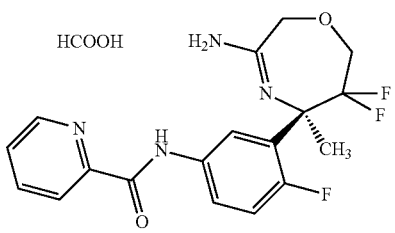 [SMILES: C[C@]1(c2cc(NC(=O)c3ccccn3)ccc2F)N=C(N)COCC1(F)F ; "HCOOH"]

The coupling of (R)-5-(5-amino-2-fluorophenyl)-6,6-difluoro-5-methyl-2,5,6,7-tetrahydro-1,4-oxazepin-3-amine (intermediate A10A) and pyridine-2-carboxylic acid yielded the title compound as a colorless solid. MS (ISP): m/z=379.3 [M+H]⁺.

Example 36

(R)-N-(3-(3-amino-6,6-difluoro-5-methyl-2,5,6,7-tetrahydro-1,4-oxazepin-5-yl)-4-fluorophenyl)-3-chloropicolinamide formate

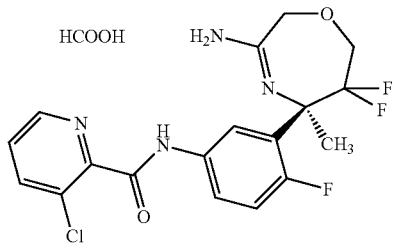 [SMILES: C[C@]1(c2cc(NC(=O)c3ncccc3Cl)ccc2F)N=C(N)COCC1(F)F ; "HCOOH"]

The coupling of (R)-5-(5-amino-2-fluorophenyl)-6,6-difluoro-5-methyl-2,5,6,7-tetrahydro-1,4-oxazepin-3-amine (intermediate A10A) and 3-chloro-pyridine-2-carboxylic acid yielded the title compound as a colorless solid. MS (ISP): m/z=413.3 [M+H]⁺.

Example 37

(R)-N-(3-(3-amino-6,6-difluoro-5-methyl-2,5,6,7-tetrahydro-1,4-oxazepin-5-yl)-4-fluorophenyl)-3-(trifluoromethyl)picolinamide formate

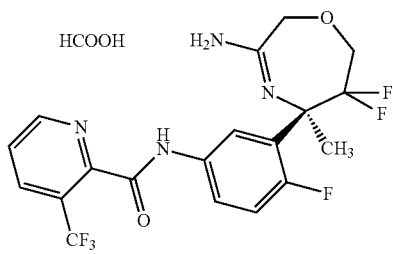 [SMILES: C[C@]1(c2cc(NC(=O)c3ncccc3C(F)(F)F)ccc2F)N=C(N)COCC1(F)F ; "HCOOH"]

The coupling of (R)-5-(5-amino-2-fluorophenyl)-6,6-difluoro-5-methyl-2,5,6,7-tetrahydro-1,4-oxazepin-3-amine (intermediate A10A) and 3-trifluoromethyl-pyridine-2-carboxylic acid yielded the title compound as a colorless solid. MS (ISP): m/z=447.1 [M+H]⁺.

Example 38

(R)-N-(3-(3-amino-6,6-difluoro-5-methyl-2,5,6,7-tetrahydro-1,4-oxazepin-5-yl)-4-fluorophenyl)-5-chloropyrazine-2-carboxamide formate

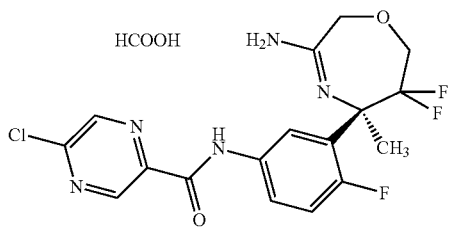 [SMILES: C[C@]1(c2cc(NC(=O)c3cnc(Cl)cn3)ccc2F)N=C(N)COCC1(F)F ; "HCOOH"]

The coupling of (R)-5-(5-amino-2-fluorophenyl)-6,6-difluoro-5-methyl-2,5,6,7-tetrahydro-1,4-oxazepin-3-amine (intermediate A10A) and 5-chloro-pyrazine-2-carboxylic acid yielded the title compound as a colorless solid. MS (ISP): m/z=414.2 [M+H]⁺.

Example 39

(R)-N-(3-(3-amino-6,6-difluoro-5-methyl-2,5,6,7-tetrahydro-1,4-oxazepin-5-yl)-4-fluorophenyl)-3,5-dichloropicolinamide formate

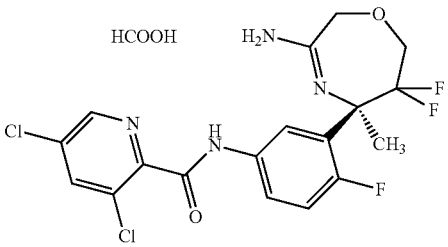 [SMILES: C[C@]1(c2cc(NC(=O)c3ncc(Cl)cc3Cl)ccc2F)N=C(N)COCC1(F)F ; "HCOOH"]

The coupling of (R)-5-(5-amino-2-fluorophenyl)-6,6-difluoro-5-methyl-2,5,6,7-tetrahydro-1,4-oxazepin-3-amine (intermediate A10A) and 3,5-dichloro-pyridine-2-carboxylic acid yielded the title compound as a colorless solid. MS (ISP): m/z=447.1 [M+H]⁺.

Example 40

(R)-N-(3-(3-amino-6,6-difluoro-5-methyl-2,5,6,7-tetrahydro-1,4-oxazepin-5-yl)-4-fluorophenyl)-3-chloro-5-fluoropicolinamide formate

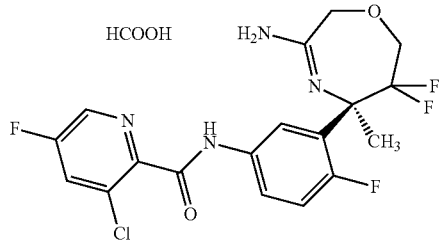 [SMILES: C[C@]1(c2cc(NC(=O)c3ncc(F)cc3Cl)ccc2F)N=C(N)COCC1(F)F ; "HCOOH"]

The coupling of (R)-5-(5-amino-2-fluorophenyl)-6,6-difluoro-5-methyl-2,5,6,7-tetrahydro-1,4-oxazepin-3-amine (intermediate A10A) and 3-chloro-5-fluoro-pyridine-2-carboxylic acid (prepared according to M. Schlosser et al., Eur. J. Org. Chem. 24, 4174 (2002)) yielded the title compound as a colorless solid. MS (ISP): m/z=431.2 [M+H]⁺.

Example 41

(R)-N-(3-(3-amino-6,6-difluoro-5-methyl-2,5,6,7-tetrahydro-1,4-oxazepin-5-yl)-4-fluorophenyl)-4-chloro-1-methyl-1H-pyrazole-3-carboxamide formate

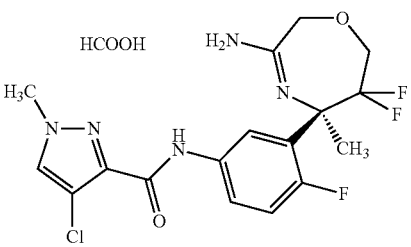 [SMILES: Cn1cc(Cl)c(C(=O)Nc2ccc(F)c([C@@]3(C)N=C(N)COCC3(F)F)c2)n1 ; "HCOOH"]

The coupling of (R)-5-(5-amino-2-fluorophenyl)-6,6-difluoro-5-methyl-2,5,6,7-tetrahydro-1,4-oxazepin-3-amine (intermediate A10A) and 4-chloro-1-methyl-1H-pyrazole-3-carboxylic acid yielded the title compound as a colorless solid. MS (ISP): m/z=416.2 [M+H]⁺.

Example 42

(R)-N-(3-(3-amino-6,6-difluoro-5-methyl-2,5,6,7-tetrahydro-1,4-oxazepin-5-yl)-4-fluorophenyl)-2-methyloxazole-4-carboxamide formate

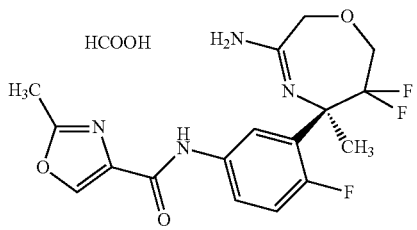 [SMILES: Cc1nc(C(=O)Nc2ccc(F)c([C@@]3(C)N=C(N)COCC3(F)F)c2)co1 ; "HCOOH"]

The coupling of (R)-5-(5-amino-2-fluorophenyl)-6,6-difluoro-5-methyl-2,5,6,7-tetrahydro-1,4-oxazepin-3-amine (intermediate A10A) and 2-methyl-oxazole-4-carboxylic acid yielded the title compound as a colorless solid. MS (ISP): m/z=383.2 [M+H]⁺.

Example 43

(R)-N-(3-(3-amino-6,6-difluoro-5-methyl-2,5,6,7-tetrahydro-1,4-oxazepin-5-yl)-4-fluorophenyl)-1-methyl-1H-pyrazole-3-carboxamide formate

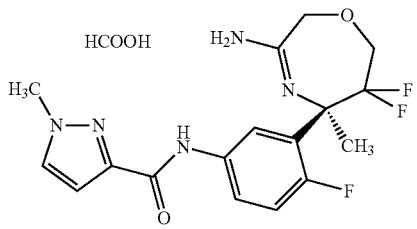 [SMILES: Cn1ccc(C(=O)Nc2ccc(F)c([C@@]3(C)N=C(N)COCC3(F)F)c2)n1 ; "HCOOH"]

The coupling of (R)-5-(5-amino-2-fluorophenyl)-6,6-difluoro-5-methyl-2,5,6,7-tetrahydro-1,4-oxazepin-3-amine (intermediate A10A) and 1-methyl-1H-pyrazole-3-carboxylic acid yielded the title compound as a colorless solid. MS (ISP): m/z=382.3 [M+H]⁺.

Example 44

(R)-N-(3-(3-amino-6,6-difluoro-5-methyl-2,5,6,7-tetrahydro-1,4-oxazepin-5-yl)-4-fluorophenyl)-1-(difluoromethyl)-1H-pyrazole-3-carboxamide formate

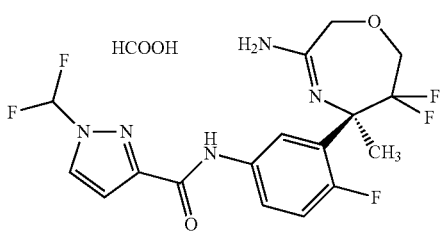 [SMILES: C[C@]1(c2cc(NC(=O)c3ccn(C(F)F)n3)ccc2F)N=C(N)COCC1(F)F ; "HCOOH"]

The coupling of (R)-5-(5-amino-2-fluorophenyl)-6,6-difluoro-5-methyl-2,5,6,7-tetrahydro-1,4-oxazepin-3-amine (intermediate A10A) and 1-difluoromethyl-1H-pyrazole-3-carboxylic acid yielded the title compound as a colorless solid. MS (ISP): m/z=418.2 [M+H]⁺.

Example 45

5-Chloro-pyridine-2-carboxylic acid [3-((R)-5-amino-3-methyl-2,3,6,7-tetrahydro-[1,4]oxazepin-3-yl)-4-fluoro-phenyl]-amide

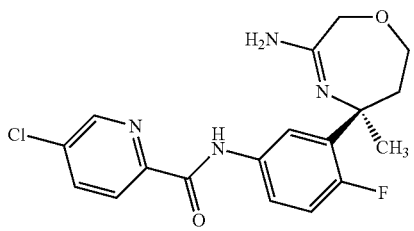 [SMILES: C[C@@]1(c2cc(NC(=O)c3ccc(Cl)cn3)ccc2F)CCOCC(N)=N1]

Treatment of 5-chloro-pyridine-2-carboxylic acid [3-((R)-5-ethoxy-3-methyl-2,3,6,7-tetrahydro-[1,4]oxazepin-3-yl)-4-fluoro-phenyl]-amide (intermediate C15B) with ammonium chloride yielded the title compound as an off-white foam. MS (ISP): m/z=377.3 [M+H]⁺.

Example 46

5-Chloro-pyrimidine-2-carboxylic acid [3-((R)-3-amino-6,6-difluoro-5-methyl-2,5,6,7-tetrahydro-[1,4]oxazepin-5-yl)-4-fluoro-phenyl]-amide

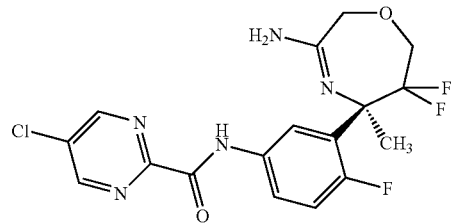

The coupling of (R)-5-(5-amino-2-fluorophenyl)-6,6-difluoro-5-methyl-2,5,6,7-tetrahydro-1,4-oxazepin-3-amine (intermediate A10A) and 5-chloro-pyrimidine-2-carboxylic acid yielded the title compound as a colorless oil. MS (ISP): m/z=414.2 [M+H]⁺.

Example 47

5-Chloro-pyridine-2-carboxylic acid [3-((S)-3-amino-2,2,5-trimethyl-2,5,6,7-tetrahydro-[1,4]oxazepin-5-yl)-4-fluoro-phenyl]-amide

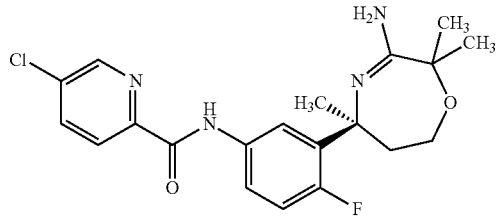 [SMILES: CC1(C)OCC[C@@](C)(c2cc(NC(=O)c3ccc(Cl)cn3)ccc2F)N=C1N]

The coupling of (S)-5-(5-amino-2-fluoro-phenyl)-2,2,5-trimethyl-2,5,6,7-tetrahydro-[1,4]oxazepin-3-ylamine (intermediate A10E) and 5-chloropyridine-2-carboxylic acid yielded the title compound as a white foam. MS (ISP): m/z=405.0 [M+H]⁺.

Example 48

(R)-N-(3-(3-amino-6,6-difluoro-5-methyl-2,5,6,7-tetrahydro-1,4-oxazepin-5-yl)-4-fluorophenyl)-5-(difluoromethoxy)picolinamide formate

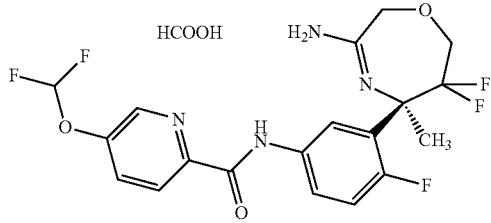 [SMILES: C[C@]1(c2cc(NC(=O)c3ccc(OC(F)F)cn3)ccc2F)N=C(N)COCC1(F)F ; "HCOOH"]

The coupling of (R)-5-(5-amino-2-fluorophenyl)-6,6-difluoro-5-methyl-2,5,6,7-tetrahydro-1,4-oxazepin-3-amine (intermediate A10A) and 5-difluoromethoxy-pyridine-2-carboxylic acid (prepared according to Y. Suzuki et al., Int. Patent Appl. No. WO2009091016) yielded the title compound as a pale yellow solid. MS (ISP): m/z=545.2 [M+H]⁺.

Example 49

(R)-N-(3-(3-amino-6,6-difluoro-5-methyl-2,5,6,7-tetrahydro-1,4-oxazepin-5-yl)-4-fluorophenyl)-5-(2,2,2-trifluoroethoxy)picolinamide formate

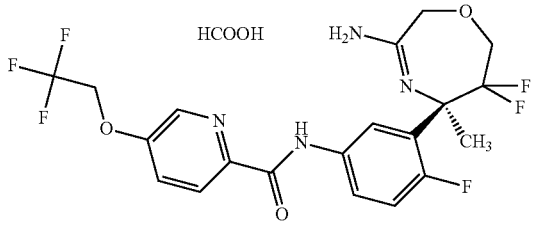 [SMILES: C[C@]1(c2cc(NC(=O)c3ccc(OCC(F)(F)F)cn3)ccc2F)N=C(N)COCC1(F)F ; "HCOOH"]

To a solution of 5-hydroxy-pyridine-2-carboxylic acid methyl ester (200 mg) in DMF (2.0 ml) was added at 22° C. NaH (55% in oil, 64 mg) and stirring was continued until gas evolution ceased. The suspension was cooled to 0° C. and treated with trifluoroethyl trifluormethane sulphonate (728 mg) and stirring was continued at 22° C. for 2 h. The mixture was partitioned between saturated NaHCO₃ and ethyl acetate and the organic layer was dried and evaporated. The residue was purified by chromatography on silica using n-heptane/ethyl acetate (3:1) to give 5-(2,2,2-trifluoro-ethoxy)-pyridine-2-carboxylic acid methyl ester (216 mg) as a white solid. MS (ISP): m/z=236.3 [M+H]⁺.

A solution of 5-(2,2,2-trifluoro-ethoxy)-pyridine-2-carboxylic acid methyl ester (216 mg) in MeOH (1 ml) was treated with a solution of LiOH (78 mg) in water (0.1 ml) and stirring was continued at 22° C. for 2 h. The solution was evaporated and the residue triturated with 1 N aqueous HCl. The suspension was filtered, the residue washed with water and dried to give 5-(2,2,2-trifluoro-ethoxy)-pyridine-2-carboxylic acid (125 mg) as a white solid. MS (ISN): m/z=220.1 [M−H]⁻.

The coupling of (R)-5-(5-amino-2-fluorophenyl)-6,6-difluoro-5-methyl-2,5,6,7-tetrahydro-1,4-oxazepin-3-amine (intermediate A10A) and 5-(2,2,2-trifluoro-ethoxy)-pyridine-2-carboxylic acid yielded the title compound as a white solid. MS (ISP): m/z=477.1 [M+H]⁺.

Example 50

5-Fluoro-pyridine-2-carboxylic acid [3-((S)-3-amino-2,2,5-trimethyl-2,5,6,7-tetrahydro-[1,4]oxazepin-5-yl)-4-fluoro-phenyl]-amide

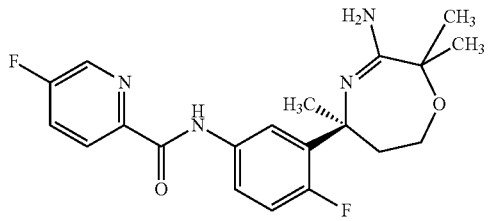 [SMILES: CC1(C)OCC[C@@](C)(c2cc(NC(=O)c3ccc(F)cn3)ccc2F)N=C1N]

The coupling of (S)-5-(5-amino-2-fluoro-phenyl)-2,2,5-trimethyl-2,5,6,7-tetrahydro-[1,4]oxazepin-3-ylamine (intermediate A10E) and 5-fluoropyridine-2-carboxylic acid yielded the title compound as a white foam. MS (ISP): m/z=389.4 [M+H]⁺.

Example 51

3-Chloro-5-trifluoromethyl-pyridine-2-carboxylic acid [3-((R)-3-amino-5-oxa-2-aza-bicyclo[5.1.0]oct-2-en-1-yl)-phenyl]-amide; salt with trifluoroacetic acid

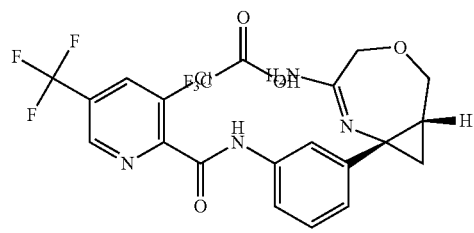

The compounds was prepared in an analogous manner as described for example 1 from 3-chloro-5-trifluoromethyl-pyridine-2-carboxylic acid [3-((6RS,7SR)-3-thioxo-5-oxa-2-aza-bicyclo[5.1.0]oct-1-yl)-phenyl]-amide (intermediate B14E) (520 mg, 1.18 mmol). The compound was obtained as a light brown foam (81 mg, 13%, as trifluoroacetic acid salt). MS (ISP): m/z=425.1 [(M+H)⁺] and 427.2 [(M+2+H)⁺].

Example 52

3-Chloro-5-trifluoromethyl-pyridine-2-carboxylic acid [3-((R)-5-amino-3-methyl-2,3,6,7-tetrahydro-[1,4]oxazepin-3-yl)-4-fluoro-phenyl]-amide

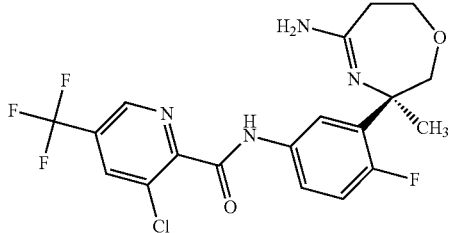 [SMILES: C[C@@]1(c2cc(NC(=O)c3ncc(C(F)(F)F)cc3Cl)ccc2F)COCCC(N)=N1]

Treatment of 3-chloro-5-trifluoromethyl-pyridine-2-carboxylic acid [3-((R)-5-ethoxy-3-methyl-2,3,6,7-tetrahydro-

[1,4]oxazepin-3-yl)-4-fluoro-phenyl]-amide (intermediate C15A) with ammonium chloride yielded the title compound as a yellow solid. MS (ISP): m/z=445.3 [M+H]⁺.

Example 53

5-Cyano-pyridine-2-carboxylic acid [3-((R)-5-amino-3-methyl-2,3,6,7-tetrahydro-[1,4]oxazepin-3-yl)-4-fluoro-phenyl]-amide

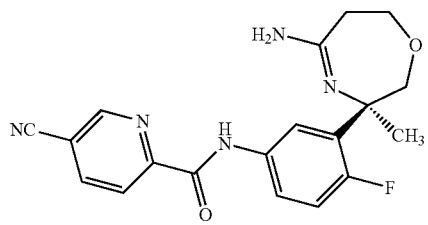 [SMILES: C[C@@]1(c2cc(NC(=O)c3ccc(C#N)cn3)ccc2F)COCCC(N)=N1]

Treatment of 5-cyano-pyridine-2-carboxylic acid [3-((R)-5-ethoxy-3-methyl-2,3,6,7-tetrahydro-[1,4]oxazepin-3-yl)-4-fluoro-phenyl]-amide (intermediate C15C) with ammonium chloride yielded the title compound as an off-white solid. MS (ISP): m/z=368.1 [M+H]⁺.

Example 54

(R)-N-(3-(3-amino-6,6-difluoro-5-methyl-2,5,6,7-tetrahydro-1,4-oxazepin-5-yl)-4-fluorophenyl)-5-(2,2,3,3-tetrafluoropropoxy)picolinamide formate

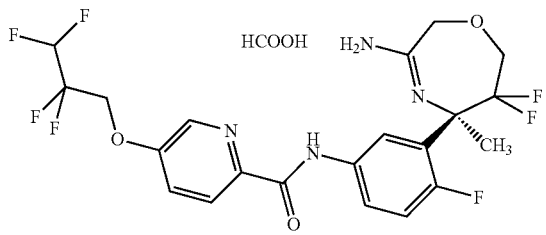 [SMILES: C[C@]1(c2cc(NC(=O)c3ccc(OCC(F)(F)C(F)F)cn3)ccc2F)N=C(N)COCC1(F)F ; "HCOOH"]

Preparation of 5-(2,2,3,3-tetrafluoro-propoxy)-pyridine-2-carboxylic acid: To 5-hydoxy-pyridine-2-carboxylic acid (2.0 g) in acetone (40 ml) was added potassium carbonate (5.4 g) and 2,2,3,3-tetrafluoropropyl trifluoromethanesulfonate (4.3 g) and the reaction mixture was stirred at 22° C. for 4 h. The suspension was diluted with diethyl ether, filtrated, the filtrate was evaporated and the residue purified by chromatography on silica to give 5-(2,2,3,3-tetrafluoro-propoxy)-pyridine-2-carboxylic acid methyl ester (2.65 g).

To a solution of 5-(2,2,3,3-tetrafluoro-propoxy)-pyridine-2-carboxylic acid methyl ester (2.6 g) in THF (20 ml) and water (15 ml) was added lithium hydoxide solution (1 M, 19.4 ml) and the reaction mixture was stirred at 22° C. for 30 min. The reaction mixture was neutralised by addition of aqueous HCl (1 N, 19.4 ml), the organic solvent was evaporated, the suspension obtained still containing water was filtered and the residue was dried to give 5-(2,2,3,3-tetrafluoro-propoxy)-pyridine-2-carboxylic acid (2.3 g) as an off-white solid.

The coupling of (R)-5-(5-amino-2-fluorophenyl)-6,6-difluoro-5-methyl-2,5,6,7-tetrahydro-1,4-oxazepin-3-amine (intermediate A10A) and 5-(2,2,3,3-tetrafluoro-propoxy)-pyridine-2-carboxylic acid yielded the title compound as a white amorphous solid. MS (ISP): m/z=509.3 [M+H]⁺.

Example 55

N-(3-((R)-3-amino-6,6-difluoro-5-methyl-2,5,6,7-tetrahydro-1,4-oxazepin-5-yl)-4-fluorophenyl)-2-methoxypropanamide formate

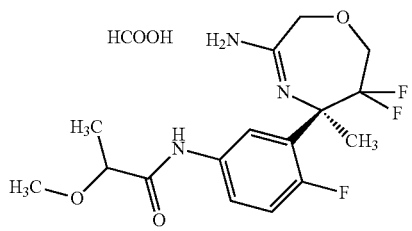 [SMILES: COC(C)C(=O)Nc1ccc(F)c([C@@]2(C)N=C(N)COCC2(F)F)c1 ; "HCOOH"]

The coupling of (R)-5-(5-amino-2-fluorophenyl)-6,6-difluoro-5-methyl-2,5,6,7-tetrahydro-1,4-oxazepin-3-amine (intermediate A10A) and rac-2-methoxy-propionic acid yielded the title compound as a white amorphous solid. MS (ISP): m/z=360.1 [M+H]⁺.

Example 56

(R)-N-(3-(3-amino-6,6-difluoro-5-methyl-2,5,6,7-tetrahydro-1,4-oxazepin-5-yl)-4-fluorophenyl)-3-chloro-5-cyanopicolinamide formate

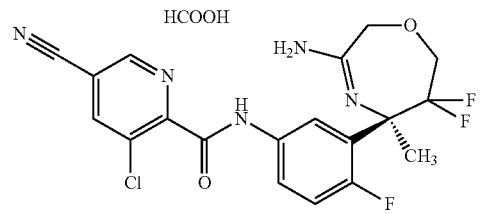 [SMILES: C[C@]1(c2cc(NC(=O)c3ncc(C#N)cc3Cl)ccc2F)N=C(N)COCC1(F)F ; "HCOOH"]

The coupling of (R)-5-(5-amino-2-fluorophenyl)-6,6-difluoro-5-methyl-2,5,6,7-tetrahydro-1,4-oxazepin-3-amine (intermediate A10A) and 3-chloro-5-cyano-pyridine-2-carboxylic acid (prepared according to Hori, A. et al., Int. Patent Application Publ. No. WO2009151098) yielded the title compound as a pale yellow solid. MS (ISP): m/z=438.1 [M+H]⁺.

Example 57

(R)-N-(3-(3-amino-6,6-difluoro-5-methyl-2,5,6,7-tetrahydro-1,4-oxazepin-5-yl)-4-fluorophenyl)-5-(ethoxymethyl)picolinamide formate

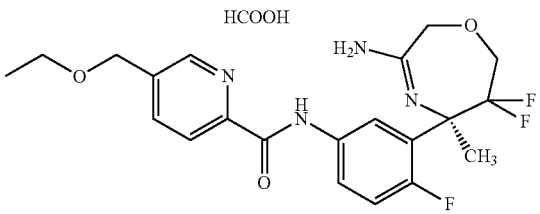 [SMILES: CCOCc1ccc(C(=O)Nc2ccc(F)c([C@@]3(C)N=C(N)COCC3(F)F)c2)nc1 ; "HCOOH"]

The coupling of (R)-5-(5-amino-2-fluorophenyl)-6,6-difluoro-5-methyl-2,5,6,7-tetrahydro-1,4-oxazepin-3-amine (intermediate A10A) and 5-ethoxymethyl-pyridine-2-carboxylic acid (which might be prepared in analogy to the isopropyl ether described by Robert M. et al., Int. Patent Application Publ. No. WO2005007658) yielded the title compound as a white solid. MS (ISP): m/z=437.2 [M+H]$^+$.

Example 58

(R)-ethyl 6-(3-(3-amino-6,6-difluoro-5-methyl-2,5,6,7-tetrahydro-1,4-oxazepin-5-yl)-4-fluorophenylcarbamoyl)nicotinate formate formate

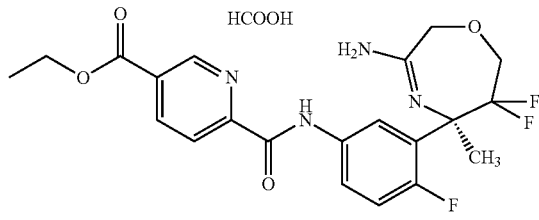 [SMILES: CCOC(=O)c1ccc(C(=O)Nc2ccc(F)c([C@@]3(C)N=C(N)COCC3(F)F)c2)nc1 ; "HCOOH"]

The coupling of (R)-5-(5-amino-2-fluorophenyl)-6,6-difluoro-5-methyl-2,5,6,7-tetrahydro-1,4-oxazepin-3-amine (intermediate A10A) and pyridine-2,5-dicarboxylic acid 5-ethyl ester (prepared according to Gaetjens, J. et al., Chemistry—A European. Journal., 9, 4924 (2003)) yielded the title compound as a white solid. MS (ISP): m/z=451.1 [M+H]$^+$.

Example 59

(R)-N-(3-(3-amino-6,6-difluoro-5-methyl-2,5,6,7-tetrahydro-1,4-oxazepin-5-yl)-4-fluorophenyl)-3-(2,2,2-trifluoroethoxy)picolinamide

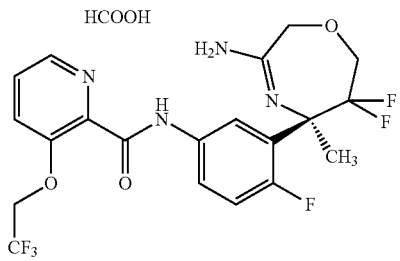 [SMILES: C[C@]1(c2cc(NC(=O)c3ncccc3OCC(F)(F)F)ccc2F)N=C(N)COCC1(F)F ; "HCOOH"]

To a solution of 3-hydroxy-pyridine-2carboxylic acid methyl ester (200 mg) in DMF (2.0 ml) was added at 22° C. NaH (55% in oil, 64 mg) and stirring was continued until gas evolution ceased. The suspension was cooled to 0° C. and treated with trifluoroethyl trifluormethane-sulphonate (728 mg) and stirring was continued at 22° C. for 2 h. The mixture was partitioned between saturated NaHCO$_3$ and ethyl acetate and the organic layer was dried and evaporated. The residue was purified by chromatography on silica using n-heptane/ethyl acetate (3:1) to give 3-(2,2,2-trifluoro-ethoxy)-pyridine-2-carboxylic acid methyl ester as a pale green oil. MS (ISP): m/z=236.2 [M+H]$^+$.

A solution of 3-(2,2,2-trifluoro-ethoxy)-pyridine-2-carboxylic acid methyl ester (216 mg) in MeOH (1 ml) was treated with a solution of LiOH (78 mg) in water (0.1 ml) and stirring was continued at 22° C. for 2 h. The solution was evaporated and the residue triturated with 1N aqueous HCl. The suspension was filtered, the residue washed with water and dried to give 3-(2,2,2-trifluoro-ethoxy)-pyridine-2-carboxylic acid as a colorless solid. MS (ISP): m/z=220.0 [M-H]$^-$.

The coupling of (R)-5-(5-amino-2-fluorophenyl)-6,6-difluoro-5-methyl-2,5,6,7-tetrahydro-1,4-oxazepin-3-amine (intermediate A10A) and 3-(2,2,2-trifluoro-ethoxy)-pyridine-2-carboxylic acid yielded the title compound as a white solid. MS (ISP): m/z=477.1 [M+H]$^+$.

Example 60

(R)-N-(3-(3-amino-6,6-difluoro-5-methyl-2,5,6,7-tetrahydro-1,4-oxazepin-5-yl)-4-fluorophenyl)-5-(2,2-difluoroethoxy)picolinamide formate

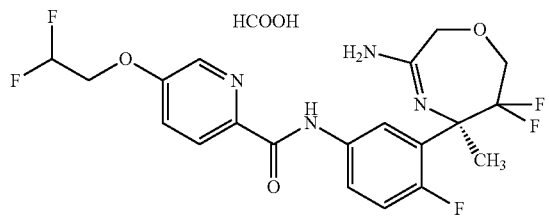 [SMILES: C[C@]1(c2cc(NC(=O)c3ccc(OCC(F)F)cn3)ccc2F)N=C(N)COCC1(F)F ; "HCOOH"]

The coupling of (R)-5-(5-amino-2-fluorophenyl)-6,6-difluoro-5-methyl-2,5,6,7-tetrahydro-1,4-oxazepin-3-amine (intermediate A10A) and 5-(2,2-difluoro-ethoxy)-pyridine-2-carboxylic acid yielded the title compound as an off-white solid. MS (ISP): m/z=459.2 [M+H]$^+$.

Example 61

N-(3-((5R,6R)-3-amino-6-fluoro-5-methyl-2,5,6,7-tetrahydro-1,4-oxazepin-5-yl)-4-fluorophenyl)-5-chloropicolinamide

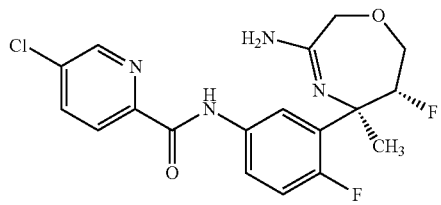 [SMILES: C[C@]1(c2cc(NC(=O)c3ccc(Cl)cn3)ccc2F)N=C(N)COC[C@@H]1F]

The coupling of (5R,6R)-5-(5-amino-2-fluorophenyl)-6-fluoro-5-methyl-2,5,6,7-tetrahydro-1,4-oxazepin-3-amine (intermediate A10B) and 5-chloro-pyridine-2-carboxylic acid yielded the title compound as a pale yellow solid. MS (ISP): m/z=395.1 [M+H]$^+$.

Example 62

N-(3-((5R,6R)-3-amino-6-fluoro-5-methyl-2,5,6,7-tetrahydro-1,4-oxazepin-5-yl)-4-fluorophenyl)-5-fluoropicolinamide

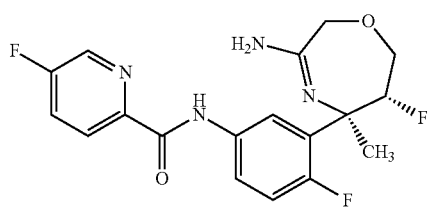 [SMILES: C[C@]1(c2cc(NC(=O)c3ccc(F)cn3)ccc2F)N=C(N)COC[C@@H]1F]

The coupling of (5R,6R)-5-(5-amino-2-fluorophenyl)-6-fluoro-5-methyl-2,5,6,7-tetrahydro-1,4-oxazepin-3-amine (intermediate A10B) and 5-fluoro-pyridine-2-carboxylic acid yielded the title compound as a pale yellow solid. MS (ISP): m/z=379.3 [M+H]+.

Example 63

N-(3-((5R,6R)-3-amino-6-fluoro-5-methyl-2,5,6,7-tetrahydro-1,4-oxazepin-5-yl)-4-fluorophenyl)-5-cyanopicolinamide

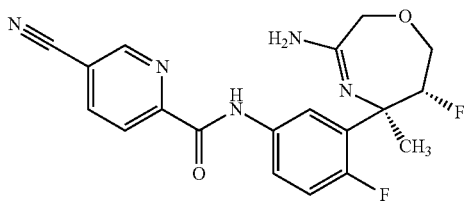 [SMILES: C[C@]1(c2cc(NC(=O)c3ccc(C#N)cn3)ccc2F)N=C(N)COC[C@@H]1F]

The coupling of (5R,6R)-5-(5-amino-2-fluorophenyl)-6-fluoro-5-methyl-2,5,6,7-tetrahydro-1,4-oxazepin-3-amine (intermediate A10B) and 5-cyano-pyridine-2-carboxylic acid yielded the title compound as a colorless solid. MS (ISP): m/z=386.4 [M+H]+.

Example 64

(R)-5-(5-(cyclopentylamino)-2-fluorophenyl)-6,6-difluoro-5-methyl-2,5,6,7-tetrahydro-1,4-oxazepin-3-amine

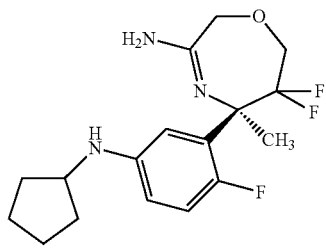 [SMILES: C[C@]1(c2cc(NC3CCCC3)ccc2F)N=C(N)COCC1(F)F]

The reductive amination of (R)-5-(5-amino-2-fluorophenyl)-6,6-difluoro-5-methyl-2,5,6,7-tetrahydro-1,4-oxazepin-3-amine (intermediate A10A) and cyclopentanone yielded the title compound as a white solid. MS (ISP): m/z=342.2 [M+H]+.

Example 65

(5R,6R)-5-(5-(cyclopentylamino)-2-fluorophenyl)-6-fluoro-5-methyl-2,5,6,7-tetrahydro-1,4-oxazepin-3-amine

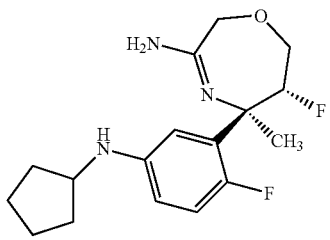 [SMILES: C[C@]1(c2cc(NC3CCCC3)ccc2F)N=C(N)COC[C@@H]1F]

The reductive amination of of (5R,6R)-5-(5-amino-2-fluorophenyl)-6-fluoro-5-methyl-2,5,6,7-tetrahydro-1,4-ox-azepin-3-amine (intermediate A10B) and cyclopentanone yielded the title compound as a pale yellow solid. MS (ISP): m/z=324.3 [M+H]+.

Example 66

(R)-N-(3-(3-Amino-6,6-difluoro-5-methyl-2,5,6,7-tetrahydro-1,4-oxazepin-5-yl)-4-fluorophenyl)-2-chlorothiazole-4-carboxamide formate

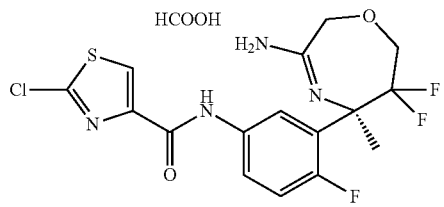 [SMILES: C[C@]1(c2cc(NC(=O)c3csc(Cl)n3)ccc2F)N=C(N)COCC1(F)F ; "HCOOH"]

The coupling of (R)-5-(5-amino-2-fluorophenyl)-6,6-difluoro-5-methyl-2,5,6,7-tetrahydro-1,4-oxazepin-3-amine (intermediate A10A) and 2-chloro-thiazole-4-carboxylic acid yielded the title compound as an off-white amorphous material. MS (ISP): m/z=419.1 [M+H]+.

Example 67

(R)-N-(3-(3-Amino-6,6-difluoro-5-methyl-2,5,6,7-tetrahydro-1,4-oxazepin-5-yl)-4-fluorophenyl)-5-isopropoxypicolinamide formate

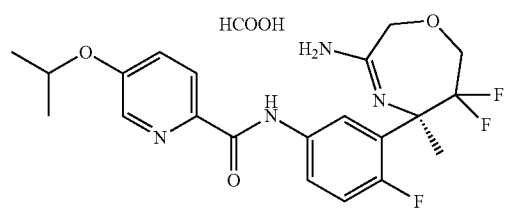 [SMILES: CC(C)Oc1ccc(C(=O)Nc2ccc(F)c([C@@]3(C)N=C(N)COCC3(F)F)c2)nc1 ; "HCOOH"]

The coupling of (R)-5-(5-amino-2-fluorophenyl)-6,6-difluoro-5-methyl-2,5,6,7-tetrahydro-1,4-oxazepin-3-amine (intermediate A10A) and 5-isopropoxy-pyridine-2-carboxylic acid (prepared according to Nagase, T. et al., Patent Application Publ. No. US20100249147) yielded the title compound as an off-white solid. MS (ISP): m/z=437.2 [M+H]+.

Example 68

5-Fluoro-pyridine-2-carboxylic acid [3-((5S,7S)-3-amino-5-methyl-7-phenyl-2,5,6,7-tetrahydro-[1,4]oxazepin-5-yl)-4-fluoro-phenyl]-amide

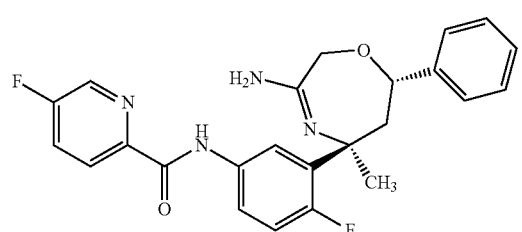

The compound was prepared in an analogous manner as described for the preparation of the amides Ia from (5S,7S)-5-(5-Amino-2-fluoro-phenyl)-5-methyl-7-phenyl-2,5,6,7-tetrahydro-[1,4]oxazepin-3-ylamine (intermediate A10G)

and 5-fluoropyridine-2-carboxylic acid. The title compound was obtained as a white solid. MS (ISP): m/z=437.3 [(M+H)+].

Example 69

5-Fluoro-pyridine-2-carboxylic acid [3-((5S,7S)-3-amino-5-methyl-7-phenyl-2,5,6,7-tetrahydro-[1,4]oxazepin-5-yl)-4-fluoro-phenyl]-amide

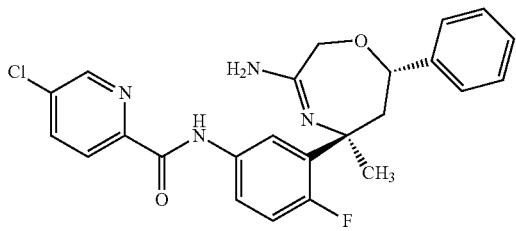 [SMILES: C[C@@]1(c2cc(NC(=O)c3ccc(F)cn3)ccc2F)C[C@@H](c2ccccc2)OCC(N)=N1]

The compound was prepared in an analogous manner as described for the preparation of the amides Ia from (5S,7S)-5-(5-Amino-2-fluoro-phenyl)-5-methyl-7-phenyl-2,5,6,7-tetrahydro-[1,4]oxazepin-3-ylamine (intermediate A10G) and 5-chloropyridine-2-carboxylic acid. The title compound was obtained as a white solid. MS (ISP): m/z=453.1 [(M+H)+].

Example 70

(R)-N-(3-(3-Amino-6,6-difluoro-5-methyl-2,5,6,7-tetrahydro-1,4-oxazepin-5-yl)-4-fluorophenyl)-5-(fluoromethoxy)picolinamide formate

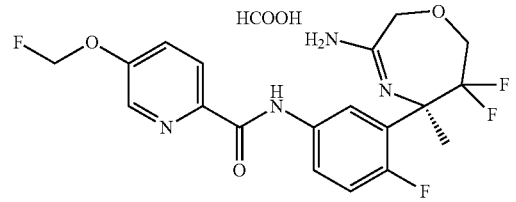 [SMILES: C[C@]1(c2cc(NC(=O)c3ccc(OCF)cn3)ccc2F)N=C(N)COCC1(F)F ; "HCOOH"]

The coupling of (R)-5-(5-amino-2-fluorophenyl)-6,6-difluoro-5-methyl-2,5,6,7-tetrahydro-1,4-oxazepin-3-amine (intermediate A10A) and 5-fluoromethoxy-pyridine-2-carboxylic acid (prepared according to Suzuki, Y. et al., Int. Patent Application Publ. No. WO2009091016) yielded the title compound as an off-white amorphous material. MS (ISP): m/z=427.2 [M+H]+.

Example 71

(R)-N-(3-(3-Amino-6,6-difluoro-5-methyl-2,5,6,7-tetrahydro-1,4-oxazepin-5-yl)-4-fluorophenyl)-5-(2-fluoroethoxy)pyrazine-2-carboxamide formate

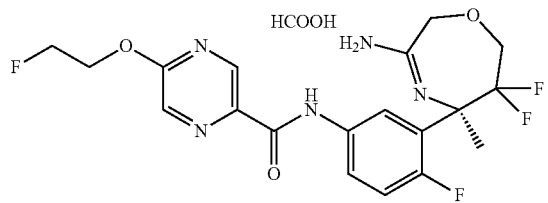 [SMILES: C[C@]1(c2cc(NC(=O)c3cnc(OCCF)cn3)ccc2F)N=C(N)COCC1(F)F ; "HCOOH"]

The coupling of (R)-5-(5-amino-2-fluorophenyl)-6,6-difluoro-5-methyl-2,5,6,7-tetrahydro-1,4-oxazepin-3-amine (intermediate A10A) and 5-(2-fluoro-ethoxy)-pyrazine-2-carboxylic acid (prepared according to Suzuki, Y. et al., Int. Patent Application Publ. No. WO2009091016) yielded the title compound as an off-white amorphous material. MS (ISP): m/z=442.3 [M+H]+.

Example 72

(R)-N-(3-(3-Amino-6,6-difluoro-5-methyl-2,5,6,7-tetrahydro-1,4-oxazepin-5-yl)-4-fluorophenyl)-4,5-dichlorothiophene-2-carboxamide formate,

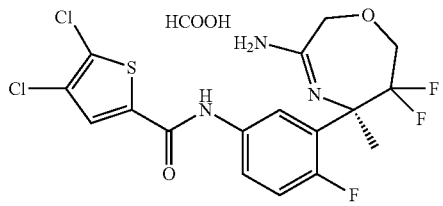 [SMILES: C[C@]1(c2cc(NC(=O)c3cc(Cl)c(Cl)s3)ccc2F)N=C(N)COCC1(F)F ; "HCOOH"]

The coupling of (R)-5-(5-amino-2-fluorophenyl)-6,6-difluoro-5-methyl-2,5,6,7-tetrahydro-1,4-oxazepin-3-amine (intermediate A10A) and 4,5-dichloro-thiophene-2-carboxylic acid yielded the title compound as an off-white amorphous material. MS (ISP): m/z=452.0 [M+H]+.

Example 73

(R)-N-(3-(3-Amino-6,6-difluoro-5-methyl-2,5,6,7-tetrahydro-1,4-oxazepin-5-yl)-4-fluorophenyl)-5-chloro-1,2,4-thiadiazole-3-carboxamide formate

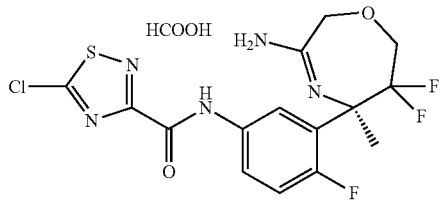 [SMILES: C[C@]1(c2cc(NC(=O)c3nsc(Cl)n3)ccc2F)N=C(N)COCC1(F)F ; "HCOOH"]

The coupling of (R)-5-(5-amino-2-fluorophenyl)-6,6-difluoro-5-methyl-2,5,6,7-tetrahydro-1,4-oxazepin-3-amine (intermediate A10A) and 5-chloro-[1,2,4]thiadiazole-3-carboxylic acid yielded the title compound as an off-white amorphous material. MS (ISP): m/z=420.1 [M+H]+.

The 5-chloro-[1,2,4]thiadiazole-3-carboxylic acid was obtained as follows: A solution of 5-chloro-[1,2,4]thiadiazole-3-carboxylic acid ethyl ester (preparation of the analogous methyl ester see Teraji, T. et al., Patent Application Publ. No. EP 7470) (200 mg, 1.0 mmol) in tetrahydrofuran (3 ml) was treated with a solution of lithium hydroxide in water (1M; 1.25 ml). After stirring at room temperature for 30 minutes the reaction mixture was neutralized by addition of hydrochloric acid (1M; 1.25 ml). The organic layer was separated, and the aqueous layer was extracted with ethyl acetate (3×). The combined organic layers were dried over sodium sulphate, evaporated at reduced pressure and the residue dried at room temperature at 20 mbar. The 5-chloro-[1,2,4]thiadiazole-3-carboxylic acid was obtained as a white solid. MS (ISP): m/z=164 [M]+.

Example 74

(R)-N-(3-(3-Amino-6,6-difluoro-5-methyl-2,5,6,7-tetrahydro-1,4-oxazepin-5-yl)-4-fluorophenyl)-5-(2,2-difluoroethoxy)pyrazine-2-carboxamide formate

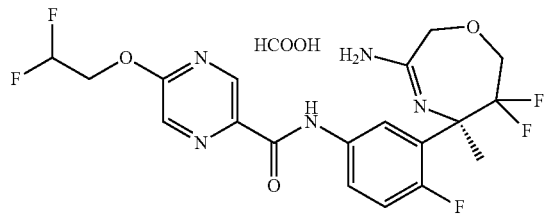 [SMILES: C[C@]1(c2cc(NC(=O)c3cnc(OCC(F)F)cn3)ccc2F)N=C(N)COCC1(F)F ; "HCOOH"]

The coupling of (R)-5-(5-amino-2-fluorophenyl)-6,6-difluoro-5-methyl-2,5,6,7-tetrahydro-1,4-oxazepin-3-amine (intermediate A10A) and 5-(2,2-difluoro-ethoxy)-pyrazine-2-carboxylic acid (prepared according to Suzuki, Y. et al., Int. Patent Application Publ. No. WO2009091016) yielded the title compound as a light yellow solid. MS (ISP): m/z=460.1 [M+H]$^+$.

Example 75

(R)-N-(3-(3-amino-5-ethyl-6,6-difluoro-2,5,6,7-tetrahydro-1,4-oxazepin-5-yl)-4-fluorophenyl)picolinamide

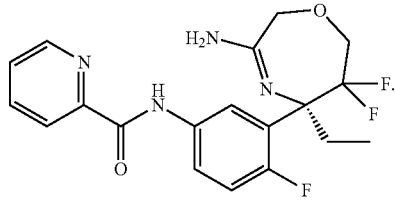 [SMILES: CC[C@]1(c2cc(NC(=O)c3ccccn3)ccc2F)N=C(N)COCC1(F)F]

The coupling of (R)-5-(5-amino-2-fluoro-phenyl)-5-ethyl-6,6-difluoro-2,5,6,7-tetrahydro-[1,4]oxazepin-3-ylamine (intermediate A10F) and pyridine-2-carboxylic acid yielded the title compound as a white solid. MS: m/z=393.1 [M+H]$^+$.

Example 76

(R)-N-(3-(3-Amino-5-ethyl-6,6-difluoro-2,5,6,7-tetrahydro-1,4-oxazepin-5-yl)-4-fluorophenyl)-3-chloropicolinamide

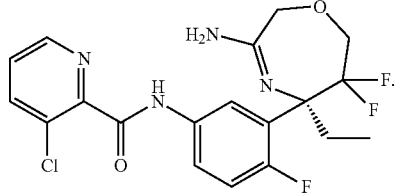 [SMILES: CC[C@]1(c2cc(NC(=O)c3ncccc3Cl)ccc2F)N=C(N)COCC1(F)F]

The coupling of (R)-5-(5-amino-2-fluoro-phenyl)-5-ethyl-6,6-difluoro-2,5,6,7-tetrahydro-[1,4]oxazepin-3-ylamine (intermediate A10F) and 3-chloro-pyridine-2-carboxylic acid yielded the title compound as a white solid. MS: m/z=427.2 [M+H]$^+$.

Example 77

(R)-N-(3-(3-Amino-5-ethyl-6,6-difluoro-2,5,6,7-tetrahydro-1,4-oxazepin-5-yl)-4-fluorophenyl)-3-(trifluoromethyl)picolinamide

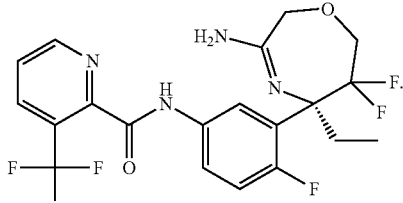

The coupling of (R)-5-(5-amino-2-fluoro-phenyl)-5-ethyl-6,6-difluoro-2,5,6,7-tetrahydro-[1,4]oxazepin-3-ylamine (intermediate A10F) and 3-trifluoromethyl-pyridine-2-carboxylic acid yielded the title compound as a white solid. MS: m/z=461.2 [M+H]$^+$.

Example 78

(R)-N-(3-(3-Amino-5-ethyl-6,6-difluoro-2,5,6,7-tetrahydro-1,4-oxazepin-5-yl)-4-fluorophenyl)-5-fluoropicolinamide

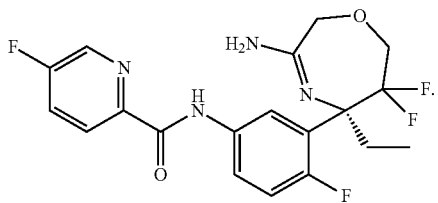 [SMILES: CC[C@]1(c2cc(NC(=O)c3ccc(F)cn3)ccc2F)N=C(N)COCC1(F)F]

The coupling of (R)-5-(5-amino-2-fluoro-phenyl)-5-ethyl-6,6-difluoro-2,5,6,7-tetrahydro-[1,4]oxazepin-3-ylamine (intermediate A10F) and 5-fluoro-pyridine-2-carboxylic acid yielded the title compound as a white solid. MS: m/z=411.2 [M+H]$^+$.

Example 79

(R)-N-(3-(3-Amino-5-ethyl-6,6-difluoro-2,5,6,7-tetrahydro-1,4-oxazepin-5-yl)-4-fluorophenyl)-5-cyanopicolinamide

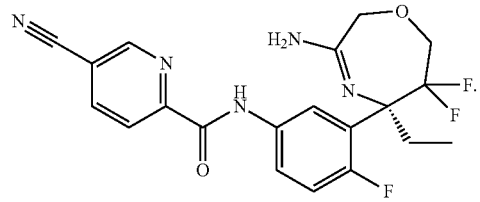 [SMILES: CC[C@]1(c2cc(NC(=O)c3ccc(C#N)cn3)ccc2F)N=C(N)COCC1(F)F]

The coupling of (R)-5-(5-amino-2-fluoro-phenyl)-5-ethyl-6,6-difluoro-2,5,6,7-tetrahydro-[1,4]oxazepin-3-ylamine (intermediate A10F) and 5-cyano-pyridine-2-carboxylic acid yielded the title compound as a white solid. MS: m/z=418.2 [M+H]$^+$.

Example 80

(R)-N-(3-(3-Amino-5-ethyl-6,6-difluoro-2,5,6,7-tetrahydro-1,4-oxazepin-5-yl)-4-fluorophenyl)-5-chloropyrimidine-2-carboxamide

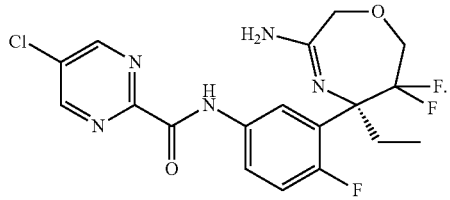 [SMILES: CC[C@]1(c2cc(NC(=O)c3ncc(Cl)cn3)ccc2F)N=C(N)COCC1(F)F]

The coupling of (R)-5-(5-amino-2-fluoro-phenyl)-5-ethyl-6,6-difluoro-2,5,6,7-tetrahydro-[1,4]oxazepin-3-ylamine (intermediate A10F) and 5-chloro-pyrimidine-2-carboxylic acid yielded the title compound as a white solid. MS: m/z=428.2 [M+H]⁻.

Example 81

(R)-N-(3-(3-Amino-5-ethyl-6,6-difluoro-2,5,6,7-tetrahydro-1,4-oxazepin-5-yl)-4-fluorophenyl)pyridazine-3-carboxamide

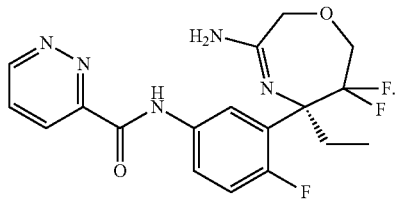 [SMILES: CC[C@]1(c2cc(NC(=O)c3cccnn3)ccc2F)N=C(N)COCC1(F)F]

The coupling of (R)-5-(5-amino-2-fluoro-phenyl)-5-ethyl-6,6-difluoro-2,5,6,7-tetrahydro-[1,4]oxazepin-3-ylamine (intermediate A10F) and pyridazine-3-carboxylic acid yielded the title compound as a white solid. MS: m/z=394.1 [M+H]⁺.

Example 82

(R)-N-(3-(3-Amino-5-ethyl-6,6-difluoro-2,5,6,7-tetrahydro-1,4-oxazepin-5-yl)-4-fluorophenyl)-5-chloropicolinamide

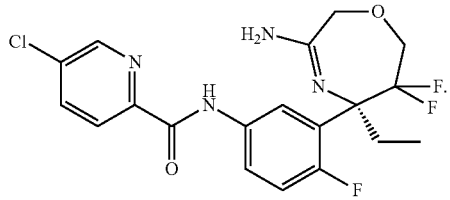 [SMILES: CC[C@]1(c2cc(NC(=O)c3ccc(Cl)cn3)ccc2F)N=C(N)COCC1(F)F]

The coupling of (R)-5-(5-amino-2-fluoro-phenyl)-5-ethyl-6,6-difluoro-2,5,6,7-tetrahydro-[1,4]oxazepin-3-ylamine (intermediate A10F) and 5-chloro-pyridine-2-carboxylic acid yielded the title compound as a white solid. MS: m/z=427.2 [M+H]⁺.

Example 83

(R)-N-(3-(3-Amino-5-ethyl-6,6-difluoro-2,5,6,7-tetrahydro-1,4-oxazepin-5-yl)-4-fluorophenyl)-3,5-dichloropicolinamide

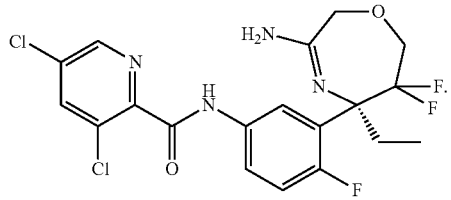 [SMILES: CC[C@]1(c2cc(NC(=O)c3ncc(Cl)cc3Cl)ccc2F)N=C(N)COCC1(F)F]

The coupling of (R)-5-(5-amino-2-fluoro-phenyl)-5-ethyl-6,6-difluoro-2,5,6,7-tetrahydro-[1,4]oxazepin-3-ylamine (intermediate A10F) and 3,5-dichloro-pyridine-2-carboxylic acid yielded the title compound as a white solid. MS: m/z=461.2 & 463.1 [M+H]⁺.

Example 84

(R)-N-(3-(3-Amino-5-ethyl-6,6-difluoro-2,5,6,7-tetrahydro-1,4-oxazepin-5-yl)-4-fluorophenyl)-3-chloro-5-fluoropicolinamide

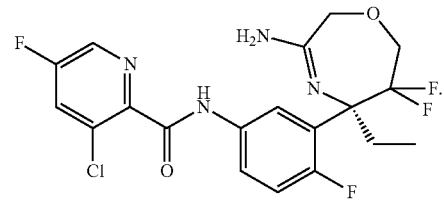 [SMILES: CC[C@]1(c2cc(NC(=O)c3ncc(F)cc3Cl)ccc2F)N=C(N)COCC1(F)F]

The coupling of (R)-5-(5-amino-2-fluoro-phenyl)-5-ethyl-6,6-difluoro-2,5,6,7-tetrahydro-[1,4]oxazepin-3-ylamine (intermediate A10F) and 3-chloro-5-fluoro-pyridine-2-carboxylic acid yielded the title compound as a white solid. MS: m/z=445.2 [M+H]⁺.

Example 85

(R)-N-(3-(3-Amino-5-ethyl-6,6-difluoro-2,5,6,7-tetrahydro-1,4-oxazepin-5-yl)-4-fluorophenyl)-4-chloro-1-methyl-1H-pyrazole-3-carboxamide

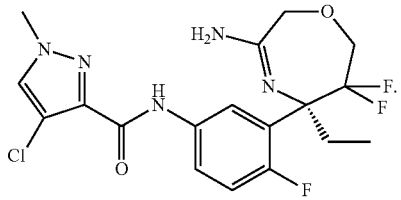 [SMILES: CC[C@]1(c2cc(NC(=O)c3nn(C)cc3Cl)ccc2F)N=C(N)COCC1(F)F]

The coupling of (R)-5-(5-amino-2-fluoro-phenyl)-5-ethyl-6,6-difluoro-2,5,6,7-tetrahydro-[1,4]oxazepin-3-ylamine (intermediate A10F) and 4-chloro-1-methyl-1H-pyrazole-3-carboxylic acid yielded the title compound as a white solid. MS: m/z=430.3 [M+H]⁺.

Example 86

(R)-N-(3-(3-Amino-5-ethyl-6,6-difluoro-2,5,6,7-tetrahydro-1,4-oxazepin-5-yl)-4-fluorophenyl)-4-chloro-1H-pyrazole-3-carboxamide

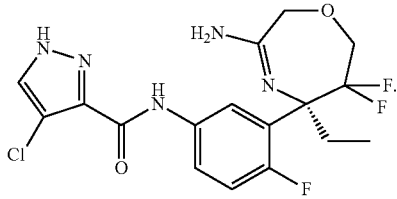 [SMILES: CC[C@]1(c2cc(NC(=O)c3n[nH]cc3Cl)ccc2F)N=C(N)COCC1(F)F]

The coupling of (R)-5-(5-amino-2-fluoro-phenyl)-5-ethyl-6,6-difluoro-2,5,6,7-tetrahydro-[1,4]oxazepin-3-ylamine (intermediate A10F) and 4-chloro-1H-pyrazole-3-carboxylic acid yielded the title compound as a white solid. MS: m/z=416.3 [M+H]$^+$.

Example 87

(R)-N-(3-(3-amino-5-ethyl-6,6-difluoro-2,5,6,7-tetrahydro-1,4-oxazepin-5-yl)-4-fluorophenyl)-5-methyloxazole-4-carboxamide

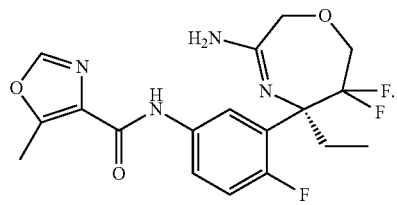 [SMILES: CC[C@]1(c2cc(NC(=O)c3ncoc3C)ccc2F)N=C(N)COCC1(F)F]

The coupling of (R)-5-(5-amino-2-fluoro-phenyl)-5-ethyl-6,6-difluoro-2,5,6,7-tetrahydro-[1,4]oxazepin-3-ylamine (intermediate A10F) and 5-methyl-oxazole-4-carboxylic acid yielded the title compound as a white solid. MS: m/z=397.2 [M+H]$^+$.

Example 88

(R)-N-(3-(3-Amino-6,6-difluoro-5-methyl-2,5,6,7-tetrahydro-1,4-oxazepin-5-yl)-4-fluorophenyl)-3-fluoro-5-(trifluoromethyl)picolinamide formate

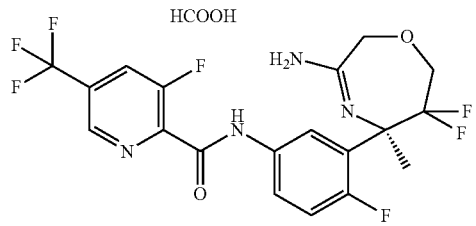 [SMILES: C[C@]1(c2cc(NC(=O)c3ncc(C(F)(F)F)cc3F)ccc2F)N=C(N)COCC1(F)F ; "HCOOH"]

The coupling of (R)-5-(5-amino-2-fluorophenyl)-6,6-difluoro-5-methyl-2,5,6,7-tetrahydro-1,4-oxazepin-3-amine (intermediate A10A) and 3-fluoro-5-trifluoromethyl-pyridine-2-carboxylic acid yielded the title compound as an off-white solid. MS (ISP): m/z=465.3 [M+H]$^+$.

Example 89

(R)-N-(3-(3-Amino-6,6-difluoro-5-methyl-2,5,6,7-tetrahydro-1,4-oxazepin-5-yl)-4-fluorophenyl)-6-(2,2,2-trifluoroethoxy)pyrazine-2-carboxamide formate

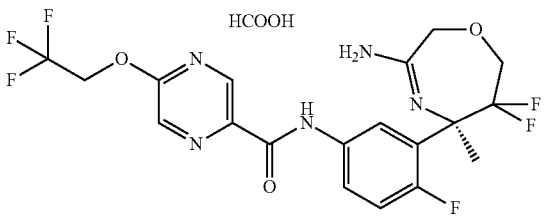 [SMILES: C[C@]1(c2cc(NC(=O)c3cnc(OCC(F)(F)F)cn3)ccc2F)N=C(N)COCC1(F)F ; "HCOOH"]

The coupling of (R)-5-(5-amino-2-fluorophenyl)-6,6-difluoro-5-methyl-2,5,6,7-tetrahydro-1,4-oxazepin-3-amine (intermediate A10A) and 6-(2,2,2-trifluoro-ethoxy)-pyrazine-2-carboxylic acid (prepared according to Suzuki, Y. et al., Int. Patent Application Publ. No. WO2009091016) yielded the title compound as an off-white solid. MS (ISP): m/z=478.1 [M+H]$^+$.

Example 90

(R)-N-(3-(3-Amino-6,6-difluoro-5-methyl-2,5,6,7-tetrahydro-1,4-oxazepin-5-yl)-4-fluorophenyl)-5-methoxypicolinamide formate

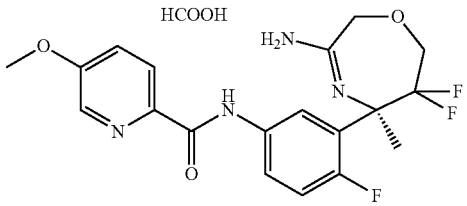 [SMILES: COc1ccc(C(=O)Nc2ccc(F)c([C@@]3(C)N=C(N)COCC3(F)F)c2)nc1 ; "HCOOH"]

The coupling of (R)-5-(5-amino-2-fluorophenyl)-6,6-difluoro-5-methyl-2,5,6,7-tetrahydro-1,4-oxazepin-3-amine (intermediate A10A) and 5-methoxy-pyridine-2-carboxylic acid yielded the title compound as a light brown solid. MS (ISP): m/z=409.2 [M+H]$^+$.

Example 91

(R)-N-(3-(3-Amino-5-ethyl-6,6-difluoro-2,5,6,7-tetrahydro-1,4-oxazepin-5-yl)-4-fluorophenyl)-4-chloro-1-ethyl-1H-pyrazole-3-carboxamide

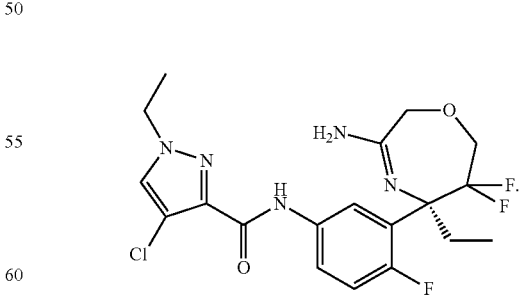

The coupling of (R)-5-(5-amino-2-fluoro-phenyl)-5-ethyl-6,6-difluoro-2,5,6,7-tetrahydro-[1,4]oxazepin-3-ylamine (intermediate A10F) and 4-chloro-1-ethyl-1H-pyrazole-3-carboxylic acid yielded the title compound as a white solid. MS: m/z=444.2 [M+H]$^+$.

Example 92

(R)-N-(3-(3-Amino-5-ethyl-6,6-difluoro-2,5,6,7-tetrahydro-1,4-oxazepin-5-yl)-4-fluorophenyl)-4-methyl-1H-pyrazole-3-carboxamide

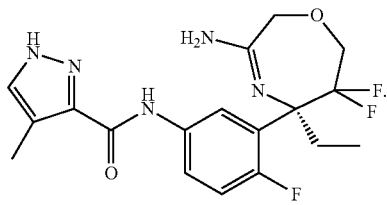 [SMILES: CC[C@]1(c2cc(NC(=O)c3n[nH]cc3C)ccc2F)N=C(N)COCC1(F)F]

The coupling of (R)-5-(5-amino-2-fluoro-phenyl)-5-ethyl-6,6-difluoro-2,5,6,7-tetrahydro-[1,4]oxazepin-3-ylamine (intermediate A10F) and 4-methyl-1H-pyrazole-3-carboxylic acid yielded the title compound as a white solid. MS: m/z=396.2 [M+H]$^+$.

Example 93

(R)-N-(3-(3-Amino-5-ethyl-6,6-difluoro-2,5,6,7-tetrahydro-1,4-oxazepin-5-yl)-4-fluorophenyl)-3-ethyl-4-methyl-1H-pyrazole-5-carboxamide

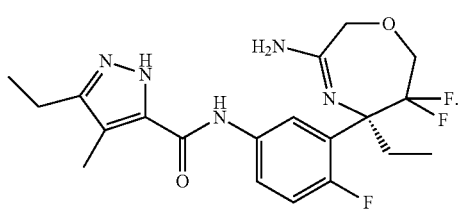 [SMILES: CCc1n[nH]c(C(=O)Nc2ccc(F)c([C@@]3(CC)N=C(N)COCC3(F)F)c2)c1C]

The coupling of (R)-5-(5-amino-2-fluoro-phenyl)-5-ethyl-6,6-difluoro-2,5,6,7-tetrahydro-[1,4]oxazepin-3-ylamine (intermediate A10F) and 5-ethyl-4-methyl-2H-pyrazole-3-carboxylic acid yielded the title compound as a white solid. MS: m/z=424.2 [M+H]$^+$.

Example 94

(R)-N-(3-(3-Amino-6,6-difluoro-5-methyl-2,5,6,7-tetrahydro-1,4-oxazepin-5-yl)-4-fluorophenyl)-5-methylpicolinamide formate

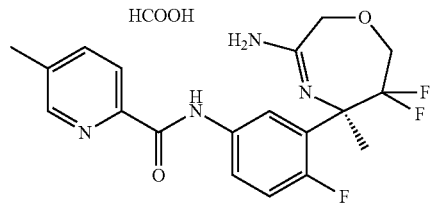 [SMILES: Cc1ccc(C(=O)Nc2ccc(F)c([C@@]3(C)N=C(N)COCC3(F)F)c2)nc1 ; "HCOOH"]

The coupling of (R)-5-(5-amino-2-fluorophenyl)-6,6-difluoro-5-methyl-2,5,6,7-tetrahydro-1,4-oxazepin-3-amine (intermediate A10A) and 5-methyl-pyridine-2-carboxylic acid yielded the title compound as a white solid. MS (ISP): m/z=393.2 [M+H]$^+$.

Example 95

(R)-N-(3-(3-Amino-6,6-difluoro-5-methyl-2,5,6,7-tetrahydro-1,4-oxazepin-5-yl)-4-fluorophenyl)-4-chloro-1-ethyl-1H-pyrazole-3-carboxamide

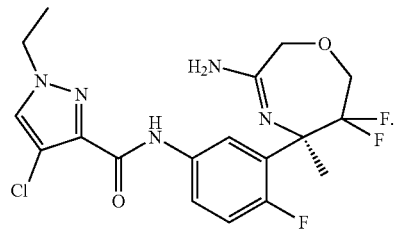 [SMILES: CCn1cc(Cl)c(C(=O)Nc2ccc(F)c([C@@]3(C)N=C(N)COCC3(F)F)c2)n1]

The coupling of (R)-5-(5-amino-2-fluorophenyl)-6,6-difluoro-5-methyl-2,5,6,7-tetrahydro-1,4-oxazepin-3-amine (intermediate A10A) and 4-chloro-1-ethyl-1H-pyrazole-3-carboxylic acid yielded the title compound as a solid. MS: m/z=430.3 [M+H]$^+$.

Example 96

(R)-N-(3-(3-amino-6,6-difluoro-5-methyl-2,5,6,7-tetrahydro-1,4-oxazepin-5-yl)-4-fluorophenyl)-4-chloro-1H-pyrazole-3-carboxamide

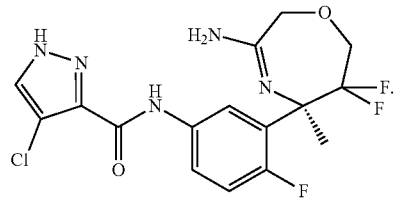 [SMILES: C[C@]1(c2cc(NC(=O)c3n[nH]cc3Cl)ccc2F)N=C(N)COCC1(F)F]

The coupling of (R)-5-(5-amino-2-fluorophenyl)-6,6-difluoro-5-methyl-2,5,6,7-tetrahydro-1,4-oxazepin-3-amine (intermediate A10A) and 4-chloro-1H-pyrazole-3-carboxylic acid yielded the title compound as a solid. MS: m/z=402.3 [M+H]$^+$.

Example 97

(R)-N-(3-(3-Amino-6,6-difluoro-5-methyl-2,5,6,7-tetrahydro-1,4-oxazepin-5-yl)-4-fluorophenyl)-4-methyl-1H-pyrazole-3-carboxamide

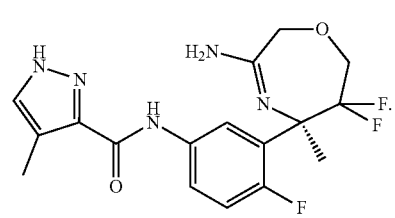 [SMILES: Cc1c[nH]nc1C(=O)Nc1ccc(F)c([C@@]2(C)N=C(N)COCC2(F)F)c1]

The coupling of (R)-5-(5-amino-2-fluorophenyl)-6,6-difluoro-5-methyl-2,5,6,7-tetrahydro-1,4-oxazepin-3-amine (intermediate A10A) and 4-methyl-1H-pyrazole-3-carboxylic acid yielded the title compound as a solid. MS: m/z=382.2 [M+H]⁺.

Example 98

(R)-N-(3-(3-Amino-6,6-difluoro-5-methyl-2,5,6,7-tetrahydro-1,4-oxazepin-5-yl)-4-fluorophenyl)-5-methyloxazole-4-carboxamide

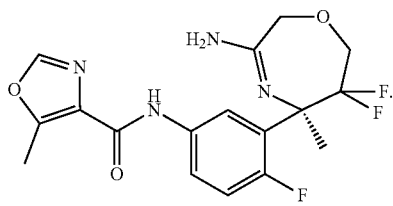 [SMILES: Cc1ocnc1C(=O)Nc1ccc(F)c([C@@]2(C)N=C(N)COCC2(F)F)c1]

The coupling of (R)-5-(5-amino-2-fluorophenyl)-6,6-difluoro-5-methyl-2,5,6,7-tetrahydro-1,4-oxazepin-3-amine (intermediate A10A) and 5-methyl-oxazole-4-carboxylic acid yielded the title compound as a solid. MS: m/z=383.1 [M+H]⁺.

Example 99

(R)-N-(3-(3-Amino-6,6-difluoro-5-methyl-2,5,6,7-tetrahydro-1,4-oxazepin-5-yl)-4-fluorophenyl)-5-ethyloxazole-4-carboxamide

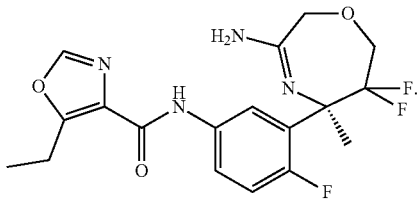 [SMILES: CCc1ocnc1C(=O)Nc1ccc(F)c([C@@]2(C)N=C(N)COCC2(F)F)c1]

The coupling of (R)-5-(5-amino-2-fluorophenyl)-6,6-difluoro-5-methyl-2,5,6,7-tetrahydro-1,4-oxazepin-3-amine (intermediate A10A) and 5-ethyl-oxazole-4-carboxylic acid yielded the title compound as a solid. MS: m/z=397.2 [M+H]⁺.

Example 100

(R)-N-(3-(3-Amino-5-ethyl-6,6-difluoro-2,5,6,7-tetrahydro-1,4-oxazepin-5-yl)-4-fluorophenyl)-5-methyl-1H-imidazole-4-carboxamide

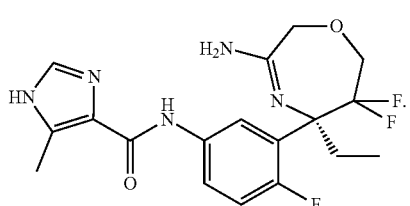

The coupling of (R)-5-(5-amino-2-fluoro-phenyl)-5-ethyl-6,6-difluoro-2,5,6,7-tetrahydro-[1,4]oxazepin-3-ylamine (intermediate A10F) and 5-methyl-1H-imidazole-4-carboxylic acid yielded the title compound as a white solid. MS: m/z=396.2 [M+H]⁺.

Example 101

(R)-N-(3-(3-Amino-6,6-difluoro-5-methyl-2,5,6,7-tetrahydro-1,4-oxazepin-5-yl)-4-fluorophenyl)-5-(trifluoromethyl)pyrazine-2-carboxamide formate

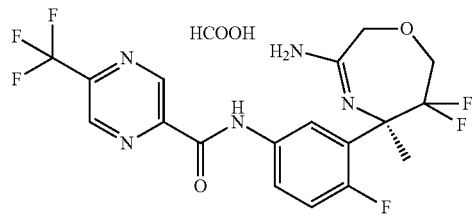 [SMILES: C[C@]1(c2cc(NC(=O)c3cnc(C(F)(F)F)cn3)ccc2F)N=C(N)COCC1(F)F ; "HCOOH"]

The coupling of (R)-5-(5-amino-2-fluorophenyl)-6,6-difluoro-5-methyl-2,5,6,7-tetrahydro-1,4-oxazepin-3-amine (intermediate A10A) and 5-trifluoromethyl-pyrazine-2-carboxylic acid yielded the title compound as a white solid. MS (ISP): m/z=448.1 [M+H]⁺.

Example 102

(R)-N-(3-(3-Amino-5-ethyl-6,6-difluoro-2,5,6,7-tetrahydro-1,4-oxazepin-5-yl)-4-fluorophenyl)-5-fluoro-3-methylpicolinamide

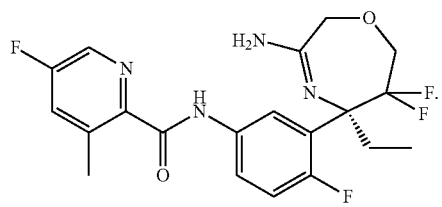 [SMILES: CC[C@]1(c2cc(NC(=O)c3ncc(F)cc3C)ccc2F)N=C(N)COCC1(F)F]

a) 5-Fluoro-3-methyl-pyridine-2-carboxylic acid methyl ester

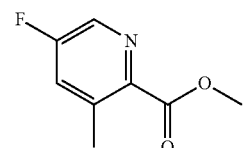

To a solution of 2-bromo-5-fluoro-3-methyl-pyridine (4.90 g) in AcOEt (100 ml) and MeOH (10 ml) was subsequently added NEt3 (5.4 ml) and 1,1'-bis(diphenylphosphino) ferrocene-palladium(II)dichloride dichloromethane adduct (490 mg) and the mixture was carbonylated at 100 bar CO and 110° C. for 20 h. The mixture was evaporated and the residue purified by chromatography on silica gel using n-heptane/AcOEt (7:1) to give the title compound (3.44 g) as a pale red solid. MS: m/z=170.1 [M+H]⁺.

b) 5-Fluoro-3-methyl-pyridine-2-carboxylic acid

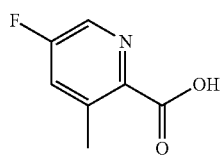

To a solution of 5-fluoro-3-methyl-pyridine-2-carboxylic acid methyl ester (1.28 g) in MeOH (6 ml) was added at 22° C. a solution of lithium hydroxide mono hydrate (636 mg) in water (3 ml) and stiring was continued for 16 h. The mixture was diluted with water, the MeOH was evaporated at reduced pressure and the pH was adjusted to 1 using 1 N aqueous HCl. The aqueous layer was extracted with AcOEt, the organic layer was dried, evaporated and the residue was crystallized from AcOEt/n-heptane to give the title compound (1.02 g) as a pale yellow solid. MS: m/z=153.7 [M−H]−.

The coupling of (R)-5-(5-amino-2-fluoro-phenyl)-5-ethyl-6,6-difluoro-2,5,6,7-tetrahydro-[1,4]oxazepin-3-ylamine (intermediate A10F) and 5-fluoro-3-methyl-pyridine-2-carboxylic acid yielded (R)-N-(3-(3-amino-5-ethyl-6,6-difluoro-2,5,6,7-tetrahydro-1,4-oxazepin-5-yl)-4-fluorophenyl)-5-fluoro-3-methylpicolinamide as a white solid. MS: m/z=425.1 [M+H]+.

Example 103

(R)-N-(3-(3-Amino-6,6-difluoro-5-methyl-2,5,6,7-tetrahydro-1,4-oxazepin-5-yl)-4-fluorophenyl)-5-(fluoromethoxy)pyrazine-2-carboxamide formate

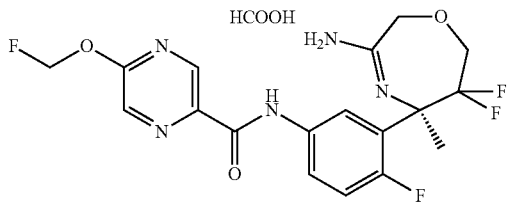 [SMILES: C[C@]1(c2cc(NC(=O)c3cnc(OCF)cn3)ccc2F)N=C(N)COCC1(F)F ; "HCOOH"]

The coupling of (R)-5-(5-amino-2-fluorophenyl)-6,6-difluoro-5-methyl-2,5,6,7-tetrahydro-1,4-oxazepin-3-amine (intermediate A10A) and 5-fluoromethoxy-pyrazine-2-carboxylic acid (prepared according to Suzuki, Y. et al., Int. Patent Application Publ. No. WO2009091016) yielded the title compound as a light brown solid. MS (ISP): m/z=428.3 [M+H]+.

Example 104

(R)-N(R)-N-(3-(3-Amino-6,6-difluoro-5-methyl-2,5,6,7-tetrahydro-1,4-oxazepin-5-yl)-4-fluorophenyl)-4-methylisoxazole-3-carboxamide

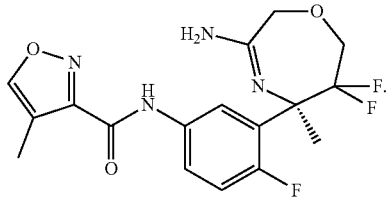 [SMILES: Cc1conc1C(=O)Nc1ccc(F)c([C@@]2(C)N=C(N)COCC2(F)F)c1]

The coupling of (R)-5-(5-amino-2-fluorophenyl)-6,6-difluoro-5-methyl-2,5,6,7-tetrahydro-1,4-oxazepin-3-amine (intermediate A10A) and 4-methyl-isoxazole-3-carboxylic acid yielded the title compound as a white solid. MS: m/z=383.3 [M+H]+.

Example 105

(R)-N-(3-(3-Amino-6,6-difluoro-5-methyl-2,5,6,7-tetrahydro-1,4-oxazepin-5-yl)-4-fluorophenyl)-5-(difluoromethyl)pyrazine-2-carboxamide formate

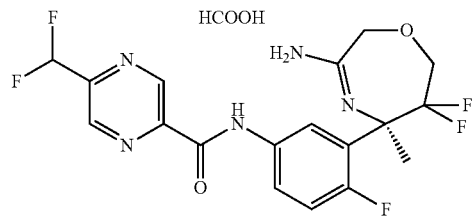 [SMILES: C[C@]1(c2cc(NC(=O)c3cnc(C(F)F)cn3)ccc2F)N=C(N)COCC1(F)F ; "HCOOH"]

The coupling of (R)-5-(5-amino-2-fluorophenyl)-6,6-difluoro-5-methyl-2,5,6,7-tetrahydro-1,4-oxazepin-3-amine (intermediate A10A) and 5-difluoromethyl-pyrazine-2-carboxylic acid (prepared according to Suzuki, Y. et al., Int. Patent Application Publ. No. WO2009091016) yielded the title compound as a white solid. MS (ISP): m/z=430.3 [M+H]+.

Example 106

(R)-N-(3-(3-Amino-6,6-difluoro-5-methyl-2,5,6,7-tetrahydro-1,4-oxazepin-5-yl)-4-fluorophenyl)-4-chloro-1-(2,2,2-trifluoroethyl)-1H-pyrazole-3-carboxamide

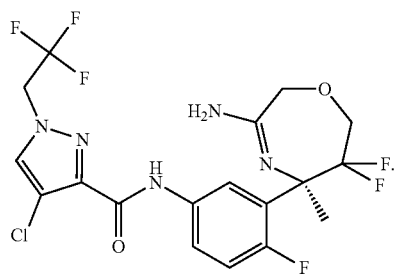 [SMILES: C[C@]1(c2cc(NC(=O)c3nn(CC(F)(F)F)cc3Cl)ccc2F)N=C(N)COCC1(F)F]

The coupling of (R)-5-(5-amino-2-fluorophenyl)-6,6-difluoro-5-methyl-2,5,6,7-tetrahydro-1,4-oxazepin-3-amine (intermediate A10A) and 4-chloro-1-(2,2,2-trifluoro-ethyl)-1H-pyrazole-3-carboxylic acid yielded the title compound as a white amorphous solid. MS: m/z=384.3 [M+H]+.

Example 107

(R)-N-(3-(3-Amino-6,6-difluoro-5-methyl-2,5,6,7-tetrahydro-1,4-oxazepin-5-yl)-4-fluorophenyl)-3-ethyl-4-methyl-1H-pyrazole-5-carboxamide

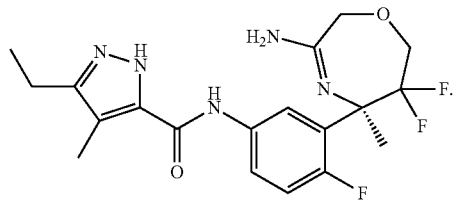 [SMILES: CCc1n[nH]c(C(=O)Nc2ccc(F)c([C@@]3(C)N=C(N)COCC3(F)F)c2)c1C]

The coupling of (R)-5-(5-amino-2-fluorophenyl)-6,6-difluoro-5-methyl-2,5,6,7-tetrahydro-1,4-oxazepin-3-amine (intermediate A10A) and 5-ethyl-4-methyl-2H-pyrazole-3-carboxylic acid yielded the title compound as a white amorphous solid. MS: m/z=410.3 [M+H]⁺.

Example 108

(R)-N-(3-(3-Amino-6,6-difluoro-5-methyl-2,5,6,7-tetrahydro-1,4-oxazepin-5-yl)-4-fluorophenyl)-5-(difluoromethyl)picolinamide formate

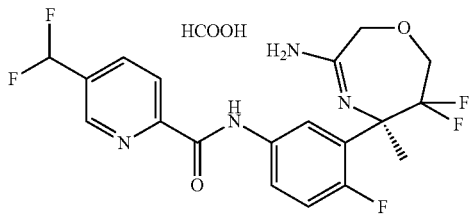 [SMILES: C[C@]1(c2cc(NC(=O)c3ccc(C(F)F)cn3)ccc2F)N=C(N)COCC1(F)F ; "HCOOH"]

The coupling of (R)-5-(5-amino-2-fluorophenyl)-6,6-difluoro-5-methyl-2,5,6,7-tetrahydro-1,4-oxazepin-3-amine (intermediate A10A) and 5-difluoromethyl-pyridine-2-carboxylic acid yielded the title compound as an amorphous light yellow material. MS (ISP): m/z=429.3 [M+H]⁺.

The 5-difluoromethyl-pyridine-2-carboxylic acid was obtained as follows:

a) 5-Difluoromethyl-pyridine-2-carboxylic acid methyl ester

A mixture of 2-bromo-5-difluoromethyl-pyridine (1.8 g, 8.9 mmol) [Lemoine, R. C. et al., Bioorg. Med. Chem. Lett. (2010), 20(16), 4753-56], palladium(II)acetate (19.9 g, 0.089 mmol), triethylamine (9.4 ml, 66.7 mmol) and 1,3-bis(diphenyphosphino)propane (361 mg, 0.89 mmol) in a 2:1-mixture of dry methanol and dimethylsulfoxide (32.5 ml) was heated at 60° C. in an autoclave at 600 psi of carbonmonoxide pressure. After heating for 24 hours, the reaction mixture was cooled and the solid was filtered off. The filtrate was concentrated at reduced pressure to afford the crude product. Ethyl acetate (60 ml) was added and the solution washed successively with water (3×15 ml) to remove the dimethylsulfoxide. After drying over sodium sulphate and concentration at reduced pressure the crude material (5.0 g) was purified by column chromatography using a 1:4-mixture of ethyl acetate and hexane as the eluent. The 5-difluoromethyl-pyridine-2-carboxylic acid methyl ester was obtained as a light yellow oil (1 g, 63% of theory).

b) 5-Difluoromethyl-pyridine-2-carboxylic acid

A solution of 5-difluoromethyl-pyridine-2-carboxylic acid methyl ester (700 mg, 3.7 mmol) in ethanol (8.0 ml) was treated with a solution of sodium hydroxide (5M, 1.5 ml) at 0° C. Then the reaction mixture was allowed to attain room temperature and was stirred for 5 hours. For the workup, ethanol was removed at reduced pressure. The resulting solid was dissolved in water (5 ml) and the solution was washed with ethyl acetate (2×5 ml). The aqueous layer acidified with a solution of citric acid (10%, pH~4), followed by extraction with a 7:3-mixture of dichloromethane and methanol (5×10 ml). The combined organic layers were washed with brine (20 ml), dried over sodium sulphate, and evaporated at reduced pressure. The 5-difluoromethyl-pyridine-2-carboxylic acid was obtained as a white solid (400 mg, 62% of theory).

Example 109

(R)-N-(3-(3-Amino-6,6-difluoro-5-methyl-2,5,6,7-tetrahydro-1,4-oxazepin-5-yl)-4-fluorophenyl)-5-methoxypyrazine-2-carboxamide formate

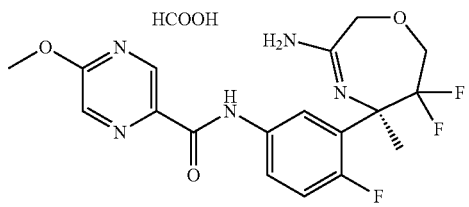 [SMILES: COc1cnc(C(=O)Nc2ccc(F)c([C@@]3(C)N=C(N)COCC3(F)F)c2)cn1 ; "HCOOH"]

The coupling of (R)-5-(5-amino-2-fluorophenyl)-6,6-difluoro-5-methyl-2,5,6,7-tetrahydro-1,4-oxazepin-3-amine (intermediate A10A) and 5-methoxy-pyrazine-2-carboxylic acid yielded the title compound as a white solid. MS (ISP): m/z=410.2 [M+H]⁺.

Example 110

(R)-N-(3-(3-amino-6,6-difluoro-5,7,7-trimethyl-2,5,6,7-tetrahydro-1,4-oxazepin-5-yl)-4-fluorophenyl)-5-chloropicolinamide

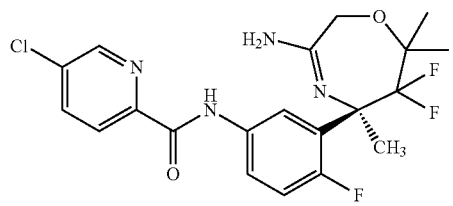 [SMILES: CC1(C)OCC(N)=N[C@](C)(c2cc(NC(=O)c3ccc(Cl)cn3)ccc2F)C1(F)F]

The compound was prepared in an analogous manner as described for example 1 from (R)-5-chloro-N-(3-(6,6-difluoro-5,7,7-trimethyl-3-thioxo-[1,4]oxazepan-5-yl)-4-fluorophenyl)picolinamide (intermediate A18H) (330 mg, 0.468 mmol). The title compound was obtained as a white foam (85 mg, 41%). MS (ISP): m/z=441.2 [(M+H)⁺] and 443.1 [(M+2+H)⁺].

Example 111

(R)-N-(3-(3-amino-6,6-difluoro-5,7,7-trimethyl-2,5,6,7-tetrahydro-1,4-oxazepin-5-yl)-4-fluorophenyl)-5-cyanopicolinamide

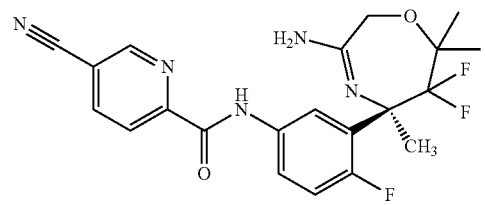 [SMILES: CC1(C)OCC(N)=N[C@](C)(c2cc(NC(=O)c3ccc(C#N)cn3)ccc2F)C1(F)F]

The compound was prepared in an analogous manner as described for example 1 from (R)-5-cyano-N-(3-(6,6-difluoro-5,7,7-trimethyl-3-thioxo-[1,4]oxazepan-5-yl)-4-fluorophenyl)picolinamide(intermediate A18I) (330 mg, 0.468 mmol). The title compound was obtained as a white foam (80 mg, 40%). MS (ISP): m/z=432.3 [(M+H)⁺].

Example 112

N-(3-((5R,6R)-3-amino-6-fluoro-5-methyl-2,5,6,7-tetrahydro-1,4-oxazepin-5-yl)-4-fluorophenyl)-3-(2,2,2-trifluoroethoxy)picolinamide

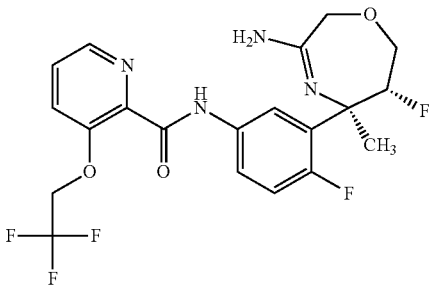 [SMILES: C[C@]1(c2cc(NC(=O)c3ncccc3OCC(F)(F)F)ccc2F)N=C(N)COC[C@@H]1F]

The coupling of (5R,6R)-5-(5-amino-2-fluorophenyl)-6-fluoro-5-methyl-2,5,6,7-tetrahydro-1,4-oxazepin-3-amine (intermediate A10B) and 3-(2,2,2-trifluoro-ethoxy)-pyridine-2-carboxylic acid (prepared as described in example 59) yielded the title compound as a white solid. MS: m/z=459.3 [M+H]⁺.

Example 113

(R)-N-(3-(3-Amino-6,6-difluoro-5-methyl-2,5,6,7-tetrahydro-1,4-oxazepin-5-yl)-4-fluorophenyl)-2-methyl-5-(trifluoromethyl)oxazole-4-carboxamide

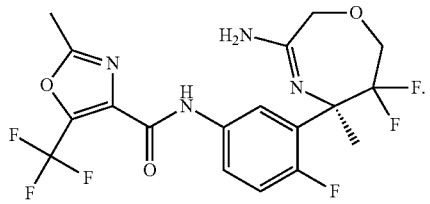 [SMILES: Cc1nc(C(=O)Nc2ccc(F)c([C@@]3(C)N=C(N)COCC3(F)F)c2)c(C(F)(F)F)o1]

The coupling of (R)-5-(5-amino-2-fluorophenyl)-6,6-difluoro-5-methyl-2,5,6,7-tetrahydro-1,4-oxazepin-3-amine (intermediate A10A) and 2-ethyl-5-trifluoromethyl-oxazole-4-carboxylic acid yielded the title compound as a white solid. MS: m/z=451.1 [M+H]⁺.

Example 114

(R)-N-(3-(3-Amino-6,6-difluoro-5-methyl-2,5,6,7-tetrahydro-1,4-oxazepin-5-yl)-4-fluorophenyl)-4-chloro-1-(difluoromethyl)-1H-pyrazole-3-carboxamide

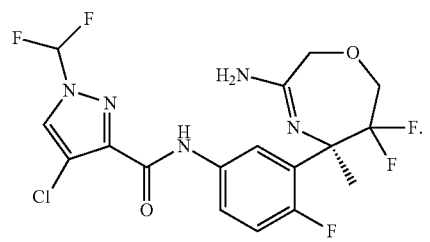 [SMILES: C[C@]1(c2cc(NC(=O)c3nn(C(F)F)cc3Cl)ccc2F)N=C(N)COCC1(F)F]

a) 1-Difluoromethyl-1H-pyrazole-3-carboxylic acid methyl ester

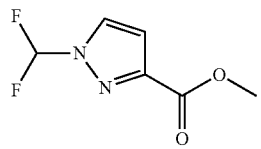

A solution of 1-difluoromethyl-1H-pyrazole-3-carboxylic acid (CAS925179-02-8) (500 mg, 3.1 mmole) in methanol (18 ml) was cooled to 0° C. and treated with sulphuric acid (98%, 0.2 ml, 3.1 mmol). The mixture was heated to reflux for 2 hours, cooled to 22° C. and concentrated at reduced pressure. The residue was partitioned between AcOEt and water, the organic layer was washed with water until the water phase showed a neutral pH, dried and evaporated to give the title compound (535 mg) as a colorless liquid which was used without further purification. MS: m/z=177.1 [M+H]⁺.

b) 4-Chloro-1-difluoromethyl-1H-pyrazole-3-carboxylic acid methyl ester

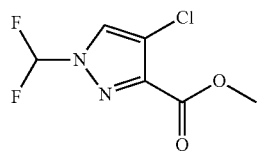

A mixture of 1-difluoromethyl-1H-pyrazole-3-carboxylic acid methyl ester (535 mg, 3 mmole) and N-chloro-succinimide (1.22 g, 9.1 mmole) in DMF (5 ml) was heated at 50° C. overnight. The reaction mixture was cooled, partitioned between AcOEt and water, the organic layer was washed with water, dried, evaporated and the residue was purified by chromatography on silica gel using cyclohexane/AcOEt (3:1) to give the title compound (540 mg) as a white solid. MS: m/z=209.9 [M]⁺.

c) 4-Chloro-1-difluoromethyl-1H-pyrazole-3-carboxylic acid

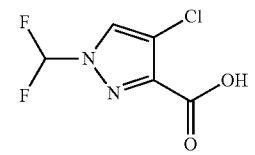

A solution of 4-chloro-1-difluoromethyl-1H-pyrazole-3-carboxylic acid methyl ester (540 mg, 2.6 mmole) in THF (18 ml) was treated at 22° C. with a solution of lithium hydroxide (135 mg, 5.6 mmole) in a 1:1-mixture of water and methanol (12 ml). After 1 hour the reaction was complete, and the solvents were evaporated at reduced pressure. The residue was partitioned between 2 M aqueous HCl and AcOEt, the organic layer was dried, evaporated, the residue was triturated with pentane and the solid was dried to give the title compound (477 mg) as a white solid. MS: m/z=195.0 [M−H]⁻.

The coupling of (R)-5-(5-amino-2-fluorophenyl)-6,6-difluoro-5-methyl-2,5,6,7-tetrahydro-1,4-oxazepin-3-amine (intermediate A10A) and 4-chloro-1-difluoromethyl-1H-pyrazole-3-carboxylic acid yielded (R)-N-(3-(3-amino-6,6-difluoro-5-methyl-2,5,6,7-tetrahydro-1,4-oxazepin-5-yl)-4-fluorophenyl)-4-chloro-1-(difluoromethyl)-1H-pyrazole-3-carboxamide as a white solid. MS: m/z=452.1 [M+H]⁺.

Example 115

N-(3-((5R,6R)-3-Amino-6-fluoro-5-methyl-2,5,6,7-tetrahydro-1,4-oxazepin-5-yl)-4-fluorophenyl)-4-chloro-1-(difluoromethyl)-1H-pyrazole-3-carboxamide

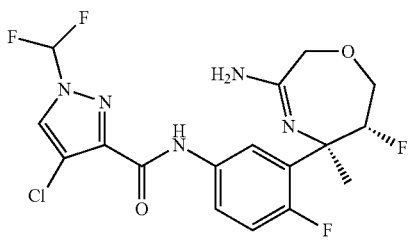 [SMILES: C[C@]1(c2cc(NC(=O)c3nn(C(F)F)cc3Cl)ccc2F)N=C(N)COC[C@@H]1F]

The coupling of (5R,6R)-5-(5-amino-2-fluorophenyl)-6-fluoro-5-methyl-2,5,6,7-tetrahydro-1,4-oxazepin-3-amine (intermediate A10B) and 4-hloro-1-difluoromethyl-1H-pyrazole-3-carboxylic acid (prepared as described in example 125) yielded the title compound as a colorless amorphous solid. MS: m/z=434.3 [M+H]$^+$.

Example 116

(R)-N-(3-(3-Amino-5-ethyl-6,6-difluoro-2,5,6,7-tetrahydro-1,4-oxazepin-5-yl)-4-fluorophenyl)-4-chloro-1-(difluoromethyl)-1H-pyrazole-3-carboxamide

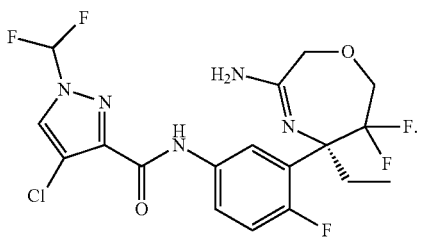

The coupling of (R)-5-(5-amino-2-fluoro-phenyl)-5-ethyl-6,6-difluoro-2,5,6,7-tetrahydro-[1,4]oxazepin-3-ylamine (intermediate A10F) and 4-chloro-1-difluoromethyl-1H-pyrazole-3-carboxylic acid (prepared as described in example 125) yielded the title compound as a colorless solid. MS: m/z=466.2 [M+H]$^+$.

Example 117

(R)-N-(5-(3-amino-6,6-difluoro-5,7,7-trimethyl-2,5,6,7-tetrahydro-1,4-oxazepin-5-yl)-2,4-difluorophenyl)-5-cyanopicolinamide

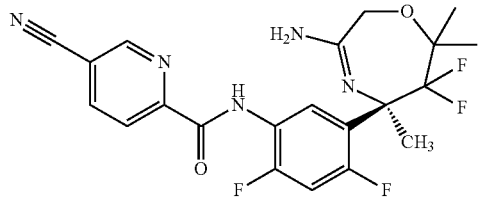 [SMILES: CC1(C)OCC(N)=N[C@](C)(c2cc(NC(=O)c3ccc(C#N)cn3)c(F)cc2F)C1(F)F]

The compound was prepared in an analogous manner as described for example 1 from (R)-5-cyano-N-(5-(6,6-difluoro-5,7,7-trimethyl-3-thioxo-[1,4]oxazepan-5-yl)-2,4-difluorophenyl)picolinamide (intermediate A18K) (80 mg, 0.172 mmol). The title compound was obtained as a white solid (12 mg, 16%). MS (ISP): m/z=450.3 [(M+H)$^+$].

Example 118

(R)-N-(5-(3-amino-6,6-difluoro-5,7,7-trimethyl-2,5,6,7-tetrahydro-1,4-oxazepin-5-yl)-2,4difluorophenyl)-5-chloropicolinamide

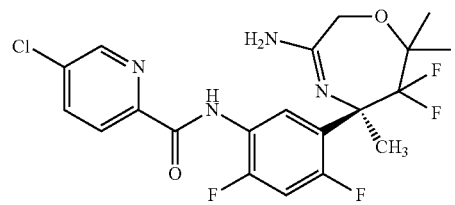 [SMILES: CC1(C)OCC(N)=N[C@](C)(c2cc(NC(=O)c3ccc(Cl)cn3)c(F)cc2F)C1(F)F]

The compound was prepared in an analogous manner as described for example 1 from (R)-5-chloro-N-(5-(6,6-difluoro-5,7,7-trimethyl-3-thioxo-[1,4]oxazepan-5-yl)-2,4-difluorophenyl)picolinamide(intermediate A18J) (90 mg, 0.189 mmol). The title compound was obtained as a white solid (46 mg, 53%). MS (ISP): m/z=459.4 [(M+H)$^{+]\ and}$ 461.2 [(M+2+H)$^+$].

Example 119

(R)-5-(5-(Cyclopentylamino)-2-fluorophenyl)-5-ethyl-6,6-difluoro-2,5,6,7-tetrahydro-1,4-oxazepin-3-amine

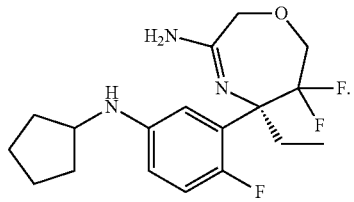 [SMILES: CC[C@]1(c2cc(NC3CCCC3)ccc2F)N=C(N)COCC1(F)F]

The reductive amination of (R)-5-(5-amino-2-fluoro-phenyl)-5-ethyl-6,6-difluoro-2,5,6,7-tetrahydro-[1,4]oxazepin-3-ylamine (intermediate A10F) and cyclopentanone yielded the title compound as a colorless foam. MS: m/z=356.3 [M+H]$^+$.

The invention claimed is:
1. A compound according to formula I,

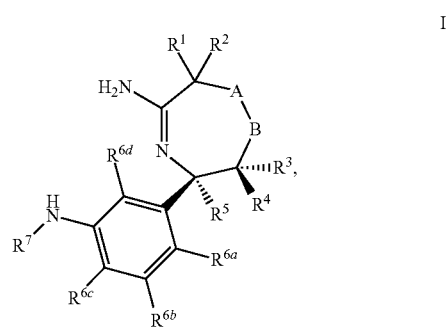

wherein
- A is O and B is —CR$^8$R$^9$—; or
- B is O and A is —CR$^8$R$^9$—;
- R$^1$ is selected from the group consisting of hydrogen, C$_{1-7}$-alkyl and C$_{3-7}$-cycloalkyl;
- R$^2$ is selected from the group consisting of hydrogen, C$_{1-7}$-alkyl and C$_{3-7}$-cycloalkyl;
- R$^3$ is selected from the group consisting of hydrogen, halogen, C$_{1-7}$-alkyl and C$_{3-7}$-cycloalkyl;
- R$^4$ is selected from the group consisting of hydrogen, halogen, C$_{1-7}$-alkyl and C$_{3-7}$-cycloalkyl;
- R$^5$ is C$_{1-7}$-alkyl or C$_{3-7}$-cycloalkyl;
- or R$^3$ and R$^5$ together with the C atom to which they are attached form a cyclopropyl ring;
- R$^{6a}$, R$^{6b}$, R$^{6c}$ and R$^{6d}$ independently from each other are selected from the group consisting of hydrogen, C$_{1-7}$-alkyl, halogen and halogen-C$_{1-7}$-alkyl;
- R$^7$ is —(CO)—R$^{10}$ or R$^{11}$, wherein
- R$^{10}$ is selected from the group consisting of halogen-C$_{1-7}$-alkyl,
- C$_{1-7}$-alkyl and
- R$^{11}$ is selected from the group consisting of
- C$_{1-7}$-alkyl, and
- C$_{3-7}$-cycloalkyl, said cycloalkyl being unsubstituted or substituted by one, two, three or four groups selected from the group consisting of C$_{1-7}$-alkyl, halogen and halogen-C$_{1-7}$-alkyl, and
- R$^8$ and R$^9$ are independently from each other selected from hydrogen, C$_{1-7}$-alkyl and C$_{3-7}$-cycloalkyl;
- or a pharmaceutically acceptable salt thereof.

2. A compound according to claim 1, wherein A is O and B is —CR$^8$R$^9$—.

3. A compound according to claim 1, wherein B is O and A is —CR$^8$R$^9$—.

4. A compound according to claim 1, wherein R$^1$ and R$^2$ are independently from each other hydrogen or C$_{1-7}$-alkyl.

5. A compound according to claim 1, wherein R$^1$ and R$^2$ are hydrogen.

6. A compound according to claim 1, wherein R$^3$ and R$^4$ are independently from each other selected from the group consisting of hydrogen, halogen, and C$_{1-7}$-alkyl.

7. A compound according to claim 1, wherein R$^3$ and R$^4$ are independently from each other hydrogen or fluoro.

8. A compound according to claim 1, wherein R$^3$ and R$^4$ are fluoro.

9. A compound according to claim 1, wherein R$^5$ is methyl or ethyl.

10. A compound according to claim 1, wherein R$^3$ and R$^5$ together with the C atom to which they are attached form a cyclopropyl ring.

11. A compound according to claim 1, wherein R$^{6a}$ is hydrogen or fluoro and R$^{6b}$, R$^{6c}$ and R$^{6d}$ are hydrogen.

12. A compound according to claim 1, wherein R$^7$ is R$^{11}$ and R$^{11}$ is selected from the group consisting of C$_{1-7}$-alkyl and C$_{3-7}$-cycloalkyl, said cycloalkyl being unsubstituted or substituted by one, two, three or four groups selected from the group consisting of C$_{1-7}$-alkyl, halogen and halogen-C$_{1-7}$-alkyl.

13. A compound according to claim 12, wherein R$^{11}$ is C$_{3-7}$-cycloalkyl, said cycloalkyl being unsubstituted or substituted by one, two, three or four groups selected from the group consisting of C$_{1-7}$-alkyl, halogen and halogen-C$_{1-7}$-alkyl.

14. A compound according to claim 1, wherein R$^8$ and R$^9$ are hydrogen.

15. A pharmaceutical composition comprising a compound according to claim 1 and a pharmaceutically acceptable carrier and/or adjuvant.

16. A compound in accordance with claim 1, wherein said compound is selected from the group consisting of:
- N-[3-((S)-3-Amino-5,7,7-trimethyl-2,5,6,7-tetrahydro-[1,4]oxazepin-5-yl)-4-fluoro-phenyl]-3,3,3-trifluoro-propionamide;
- N-[3-((R)-3-Amino-6,6-difluoro-5-methyl-2,5,6,7-tetrahydro-1,4-oxazepin-5-yl)-4-fluorophenyl)-2-methoxypropanamide formate;
- (R)-5-(5-(cyclopentylamino)-2-fluorophenyl)-6,6-difluoro-5-methyl-2,5,6,7-tetrahydro-1,4-oxazepin-3-amine;
- (5R,6R)-5-(5-(cyclopentylamino)-2-fluorophenyl)-6-fluoro-5-methyl-2,5,6,7-tetrahydro-1,4-oxazepin-3-amine; and
- (5R,6R)-5-(5-Cyclopentylamino-2-fluoro-phenyl)-6-fluoro-5-ethyl-2,5,6,7-tetrahydro-[1,4]oxazepin-3-ylamine.

17. A compound according to claim 1, wherein R$^{10}$ is halogen-C$_{1-7}$-alkyl or C$_{1-7}$-alkoxy-C$_{1-7}$-alkyl.

* * * * *